United States Patent
Choi et al.

(10) Patent No.: US 12,433,152 B2
(45) Date of Patent: Sep. 30, 2025

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Eunjeong Choi, Suwon-si (KR); Byungku Kim, Suwon-si (KR); Kipo Jang, Suwon-si (KR); Jiyun Kwon, Suwon-si (KR); Dongyeong Kim, Suwon-si (KR); Namheon Lee, Suwon-si (KR); Jongwoo Choi, Suwon-si (KR); Sung-Hyun Jung, Suwon-si (KR); Ho-Kuk Jung, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 773 days.

(21) Appl. No.: 17/111,766

(22) Filed: Dec. 4, 2020

(65) Prior Publication Data
US 2021/0249607 A1    Aug. 12, 2021

(30) Foreign Application Priority Data
Jan. 30, 2020 (KR) .................... 10-2020-0011150

(51) Int. Cl.
*H10K 85/60* (2023.01)
*C07D 251/24* (2006.01)
(Continued)

(52) U.S. Cl.
CPC ......... *H10K 85/622* (2023.02); *C07D 251/24* (2013.01); *C07D 413/04* (2013.01);
(Continued)

(58) Field of Classification Search
CPC ............... H10K 85/622; H10K 85/654; H10K 85/6574; H10K 50/11; H10K 2101/10;
(Continued)

(56) References Cited

U.S. PATENT DOCUMENTS

| | | | |
|---|---|---|---|
| 5,061,569 A | 10/1991 | Vanslyke et al. | |
| 8,951,647 B2 | 2/2015 | Parham et al. | |

(Continued)

FOREIGN PATENT DOCUMENTS

| | | |
|---|---|---|
| CN | 102282130 A | 12/2011 |
| CN | 103187531 A | 7/2013 |

(Continued)

OTHER PUBLICATIONS

Hung, Wen-Yi, et al. "Balance the carrier mobility to achieve high performance exciplex OLED using a triazine-based acceptor." ACS Applied Materials & Interfaces 8.7 (2016): 4811-4818. (Year: 2016).*

(Continued)

*Primary Examiner* — Dawn L Garrett
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:

(Continued)

[Chemical Formula 1]

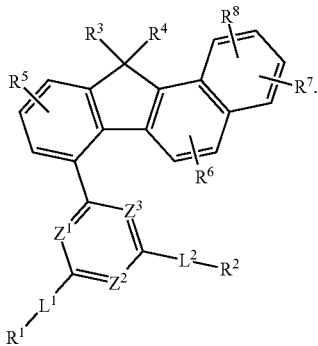

14 Claims, 1 Drawing Sheet

(51) Int. Cl.
C07D 413/04 (2006.01)
C09K 11/06 (2006.01)
H10K 50/11 (2023.01)
H10K 101/00 (2023.01)
H10K 101/10 (2023.01)

(52) U.S. Cl.
CPC ............ C09K 11/06 (2013.01); H10K 85/654 (2023.02); H10K 85/6574 (2023.02); *C09K 2211/1018* (2013.01); *H10K 50/11* (2023.02); *H10K 2101/10* (2023.02); *H10K 2101/90* (2023.02)

(58) Field of Classification Search
CPC ............. H10K 2101/90; H10K 85/342; H10K 85/615; H10K 85/626; H10K 85/6576; H10K 85/657; C07D 251/24; C07D 13/04; C07D 239/26; C07D 405/04; C07D 405/10; C07D 405/14; C07D 409/04; C09K 11/06; C09K 2211/1018
See application file for complete search history.

(56) References Cited

U.S. PATENT DOCUMENTS

| 2011/0121274 | A1* | 5/2011 | Parham | C09B 57/00 |
| | | | | 252/301.16 |
| 2011/0168992 | A1 | 7/2011 | Bae et al. | |
| 2011/0272684 | A1 | 11/2011 | Parham et al. | |
| 2016/0164005 | A1* | 6/2016 | Feldman | H05B 33/14 |
| | | | | 252/301.16 |

FOREIGN PATENT DOCUMENTS

| CN | 104650029 A | 5/2015 |
| CN | 105938877 A | 9/2016 |
| CN | 110364632 A | 10/2019 |
| CN | 111848501 A | 10/2020 |
| CN | 115397816 A | 11/2022 |
| JP | 1993-009471 A | 1/1993 |
| JP | 1995-126615 A | 5/1995 |
| JP | 1998-095973 A | 4/1998 |
| JP | 4250370 B2 | 4/2009 |
| KR | 10-2013-0025190 A | 3/2013 |
| KR | 10-1262443 B1 | 5/2013 |
| KR | 10-2014-0057439 A | 5/2014 |
| KR | 10-1399636 B1 | 5/2014 |
| KR | 10-1537499 B1 | 7/2015 |
| KR | 10-1542714 B1 | 8/2015 |
| KR | 10-2015-0115648 A | 10/2015 |
| KR | 10-1591286 B1 | 2/2016 |
| KR | 10-1638071 B1 | 7/2016 |
| KR | 10-2017-0097820 A | 8/2017 |
| KR | 10-2017-0134264 A | 12/2017 |
| KR | 10-1804630 B1 | 12/2017 |
| KR | 10-2018-0094349 A | 8/2018 |
| KR | 10-2018-0099547 A | 9/2018 |
| KR | 10-2019-0009994 A | 1/2019 |
| KR | 10-2019-0108935 A | 9/2019 |
| KR | 10-2021-0089524 A | 7/2021 |
| WO | WO 1995-009147 A1 | 4/1995 |
| WO | WO 2010/021524 A2 | 2/2010 |
| WO | WO 2010/114264 A2 | 10/2010 |
| WO | WO 2011/068204 A1 | 6/2011 |
| WO | WO 2013/035275 A1 | 3/2013 |
| WO | WO 2013/077352 A1 | 5/2013 |
| WO | WO 2013/077362 A1 | 5/2013 |
| WO | WO 2014/002871 A1 | 1/2014 |
| WO | WO 2016/105141 A3 | 6/2016 |

OTHER PUBLICATIONS

Machine translation of KR 10-2019-0009994 A (publication date Jan. 2019). (Year: 2019).*
Chinese Office Action (including a search report) dated Jun. 12, 2023, of the corresponding Chinese Patent Application No. 202011418119.2.

* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2020-0011150, filed on Jan. 30, 2020, in the Korean Intellectual Property Office, and entitled: "Compound for Organic Optoelectronic Device, Composition for Organic Optoelectronic Device, Organic Optoelectronic Device and Display Device," is incorporated by reference herein in its entirety.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One includes a photoelectric device where excitons generated by photoenergy are separated into electrons and holes and the electrons and holes are transferred to different electrodes respectively and electrical energy is generated, and another includes a light emitting device to generate photoenergy from electrical energy by supplying a voltage or a current to electrodes.

Examples of the organic optoelectronic device include an organic photoelectric device, an organic light emitting diode, an organic solar cell, and an organic photo conductor drum.

Among them, the organic light emitting diode (OLED) has recently drawn attention due to an increase in demand for flat panel displays. The organic light emitting diode converts electrical energy into light, and the performance of organic light emitting diode is greatly influenced by the organic materials disposed between electrodes.

SUMMARY

The embodiments may be realized by providing a compound for an organic optoelectronic device, the compound being represented by Chemical Formula 1:

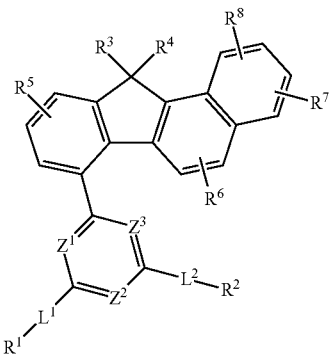

[Chemical Formula 1]

wherein, in Chemical Formula 1, $Z^1$ to $Z^3$ are independently N or $CR^a$, at least two of $Z^1$ to $Z^3$ are N, $L^1$ and $L^2$ are independently a single bond, a substituted or unsubstituted C6 to C30 arylene group, a substituted or unsubstituted dibenzofuranylene group, or a substituted or unsubstituted dibenzothiophenylene group, $R^1$ and $R^2$ are independently a substituted or unsubstituted C6 to C30 aryl group, a substituted or unsubstituted dibenzofuranyl group, or a substituted or unsubstituted dibenzothiophenyl group, $R^3$ and $R^4$ are independently a substituted or unsubstituted C1 to C30 alkyl group, a substituted or unsubstituted C6 to C30 aryl group, or a combination thereof, $R^3$ and $R^4$ being separate or being a combination of substituted or unsubstituted C1 to C9 alkyl groups linked to each other to form a substituted or unsubstituted C3 to C10 cycloalkyl group, and $R^a$ and $R^5$ to $R^8$ are independently hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof.

The embodiments may be realized by providing a composition for an organic optoelectronic device, the composition including a first compound for an organic optoelectronic device; and a second compound for an organic optoelectronic device, wherein the first compound is the compound for an organic optoelectronic device according to an embodiment, and the second compound is represented by Chemical Formula 2; a combination of Chemical Formula 3 and Chemical Formula 4; a combination of Chemical Formula 5 and Chemical Formula 6; or a combination of Chemical Formula 7 and Chemical Formula 8,

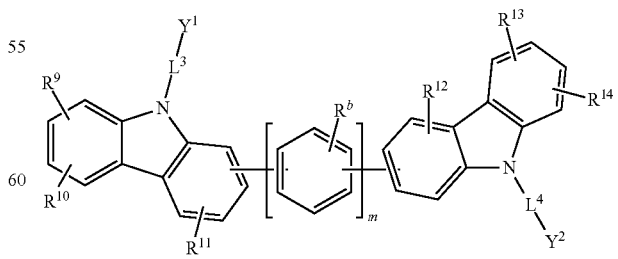

[Chemical Formula 2]

in Chemical Formula 2, $Y^1$ and $Y^2$ are independently a substituted or unsubstituted C6 to C20 aryl group, or a substituted or unsubstituted C2 to C30 heterocyclic group, $L^3$ and $L^4$ are independently a single bond, or a substituted or unsubstituted C6 to C20 arylene group, Rb and $R^9$ to $R^{14}$ are independently hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, and m is an integer of 0 to 2;

[Chemical Formula 3]

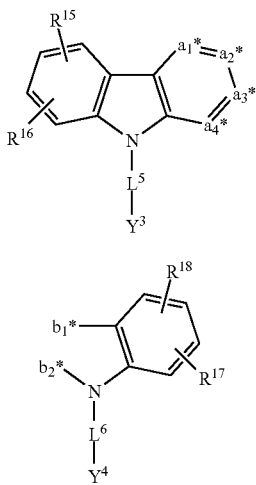

[Chemical Formula 4]

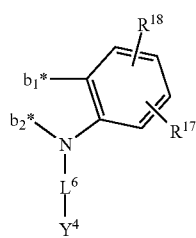

in Chemical Formulae 3 and 4, $Y^3$ and $Y^4$ are independently a substituted or unsubstituted C6 to C20 aryl group, or a substituted or unsubstituted C2 to C30 heterocyclic group, adjacent two of $a_1^*$ to $a_4^*$ are linked to $b_1^*$ and $b_2^*$, respectively, remaining two of $a_1^*$ to $a_4^*$ not linked to $b_1^*$ and $b_2^*$ are independently C-$L^a$-$R^c$, $L^a$, $L^5$, and $L^6$ are independently a single bond, or a substituted or unsubstituted C6 to C20 arylene group, and $R^c$ and $R^{15}$ to $R^{18}$ are independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group;

[Chemical Formula 5]

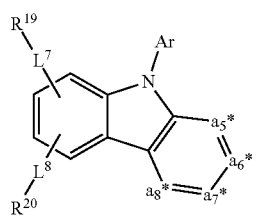

[Chemical Formula 6]

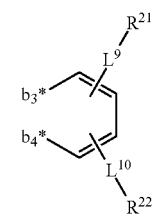

in Chemical Formulae 5 and 6, Ar is a substituted or unsubstituted C6 to C30 aryl group, a substituted or unsubstituted C2 to C30 heterocyclic group, or a combination thereof, adjacent two of $a_5^*$ to $a_8^*$ are linked to $b_3^*$ and $b_4^*$, respectively, remaining two of $a_5^*$ to $a_8^*$ not linked to $b_3^*$ and $b_4^*$ are independently C-$L^b$-$R^d$, $L^b$ and $L^7$ to $L^{10}$ are independently a single bond, a substituted or unsubstituted C6 to C20 arylene group, a substituted or unsubstituted C2 to C20 heterocyclic group, or a combination thereof, $R^d$ and $R^{19}$ to $R^{22}$ are independently hydrogen, deuterium, a cyano group, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^d$ and $R^{19}$ to $R^{22}$ is a group represented by Chemical Formula A,

[Chemical Formula A]

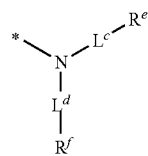

in Chemical Formula A, $L^c$ and $L^d$ are independently a single bond or a substituted or unsubstituted C6 to C20 arylene group, $R^e$ and $R^f$ are independently a substituted or unsubstituted C6 to C30 aryl group, a substituted or unsubstituted C2 to C30 heterocyclic group, or a combination thereof, and * is a linking point with one of $L^b$ and $L^7$ to $L^{10}$;

[Chemical Formula 7]

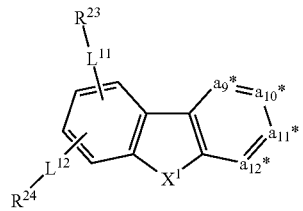

[Chemical Formula 8]

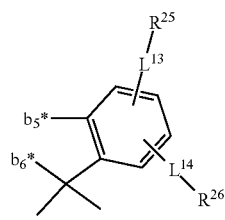

in Chemical Formulae 7 and 8, $X^1$ is O or S, adjacent two of $a_9^*$ to $a_{12}^*$ are linked to $b_5^*$ and $b_6^*$, respectively, remaining two of $a_9^*$ to $a_{12}^*$ not linked to $b_5^*$ and $b_6^*$ are independently C-$L^e$-$R^8$, $L^e$, and $L^{11}$ to $L^{14}$ are independently a single bond, or a substituted or unsubstituted C6 to C20 arylene group, $R^g$ and $R^{23}$ to $R^{26}$ are independently hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^g$ and $R^{23}$ to $R^{26}$ is a group represented by Chemical Formula B,

[Chemical Formula B]

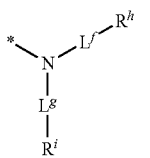

in Chemical Formula B, $L^f$ and $L^g$ are independently a single bond or a substituted or unsubstituted C6 to C20 arylene group, $R^h$ and $R^i$ are independently a substituted or unsubstituted C6 to C30 aryl group, a substituted or unsubstituted C2 to C30 heterocyclic group, or a combination thereof, and * is a linking point with one of $L^e$ and $L^{11}$ to $L^{14}$.

The embodiments may be realized by providing an organic optoelectronic device including an anode and a cathode facing each other; and at least one organic layer between the anode and the cathode, wherein the at least one organic layer includes the compound for an organic optoelectronic device according to an embodiment.

The embodiments may be realized by providing an organic optoelectronic device including an anode and a cathode facing each other; and at least one organic layer between the anode and the cathode, wherein the at least one organic layer includes the composition for an organic optoelectronic device according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
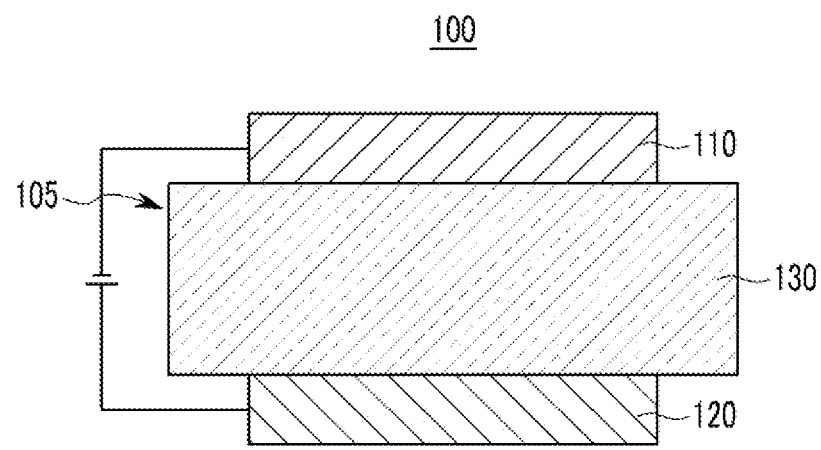
FIGS. 1 and 2 are cross-sectional views of an organic light emitting diode according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers or elements may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples, "substituted" refers to replacement of at least one hydrogen of a substituent or a compound by deuterium, a C1 to C20 alkyl group, a C6 to C30 aryl group, or a cyano group. In addition, in specific examples, "substituted" refers to replacement of at least one hydrogen of a substituent or a compound by deuterium, a C1 to C5 alkyl group, a C6 to C18 aryl group, or a cyano group. In addition, in specific examples, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic device according to an embodiment is described.

Hereinafter, a compound for an organic optoelectronic device according to an embodiment may be, e.g., represented by Chemical Formula 1.

[Chemical Formula 1]

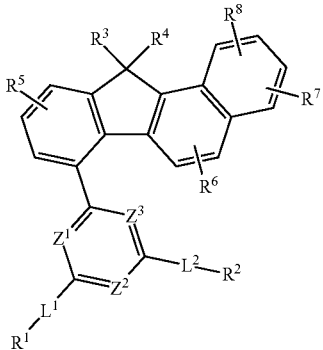

In Chemical Formula 1, $Z^1$ to $Z^3$ may each independently be, e.g., N or $CR^a$. In an implementation, at least two of $Z^1$ to $Z^3$ are N.

$L^1$ and $L^2$ may each independently be or include, e.g., a single bond, a substituted or unsubstituted C6 to C30 arylene group, a substituted or unsubstituted dibenzofuranylene group, or a substituted or unsubstituted dibenzothiophenylene group.

$R^1$ and $R^2$ may each independently be or include, e.g., a substituted or unsubstituted C6 to C30 aryl group, a substituted or unsubstituted dibenzofuranyl group, or a substituted or unsubstituted dibenzothiophenyl group.

$R^3$ and $R^4$ may each independently be or include, e.g., a substituted or unsubstituted C1 to C30 alkyl group, a substituted or unsubstituted C6 to C30 aryl group, or a combination thereof.

In an implementation, $R^3$ and $R^4$ may be separate or may be (e.g., a combination of substituted or unsubstituted C1 to C9 alkyl groups) linked to each other to form a substituted or unsubstituted C3 to C10 cycloalkyl group.

$R^a$ and $R^5$ to $R^8$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof.

The compound represented by Chemical Formula 1 may include a backbone or core in which a benzene ring is further fused at positions 1 and 2 of one benzene ring of a fluorene moiety. A nitrogen-containing six-membered (e.g., hexagonal) ring may be present at the position 4 of the other benzene ring of the fluorene moiety.

By including a backbone in which the benzene ring is further fused at positions 1 and 2 of the one benzene ring of the fluorene moiety, the compound may have a high glass transition temperature, and may be deposited at a relatively low temperature to provide an organic light emitting diode having low process temperature and heat resistance properties.

In addition, by having a structure in which a nitrogen-containing six-membered ring is present at the position 4 of the other benzene ring of the fluorene moiety, an organic light emitting device having efficient spectral characteristics may be provided.

In an implementation, the nitrogen-containing six-membered ring including $Z^1$ to $Z^3$ may be pyrimidine or triazine.

In an implementation, $Z^1$ and $Z^2$ may each be N, and $Z^3$ may be CH.

In an implementation, $Z^1$ and $Z^3$ may each be N, and $Z^2$ may be CH.

In an implementation, $Z^2$ and $Z^3$ may each be N, and $Z^1$ may be CH.

In an implementation, $Z^1$ to $Z^3$ may each be N.

In an implementation, $L^1$ and $L^2$ may each independently be or include, e.g., a single bond, a substituted or unsubstituted C6 to C30 arylene group, a substituted or unsubstituted dibenzofuranylene group, or a substituted or unsubstituted dibenzothiophenylene group.

In an implementation, $R^1$ and $R^2$ may each independently be or include, e.g., a substituted or unsubstituted C6 to C30 aryl group, a substituted or unsubstituted dibenzofuranyl group, or a substituted or unsubstituted dibenzothiophenyl group.

In an implementation, $R^1$ and $R^2$ may each independently be or include, e.g., a C6 to C30 aryl group that is unsubstituted or substituted with a C6 to C12 aryl group, a dibenzofuranyl group or a dibenzothiophenyl group, a dibenzofuranyl group that is unsubstituted or substituted with a C6 to C12 aryl group, a dibenzofuranyl group or a dibenzothiophenyl group, or a dibenzothiophenyl group that is unsubstituted or substituted with a C6 to C12 aryl group, a dibenzofuranyl group or a dibenzothiophenyl group.

In an implementation, $R^1$ and $R^2$ may each independently be or include, e.g., a C6 to C12 aryl group that is unsubstituted or substituted with a phenyl group, a biphenyl group, or a naphthyl group, a dibenzofuranyl group that is unsubstituted or substituted with a phenyl group, a biphenyl group, or a naphthyl group, or a dibenzothiophenyl group that is unsubstituted or substituted with a phenyl group, a biphenyl group, or a naphthyl group.

In an implementation, moieties *-$L^1$-$R^1$ and *-$L^2$-$R^2$ of Chemical Formula 1 may each independently be a moiety of Group I.

[Group I]

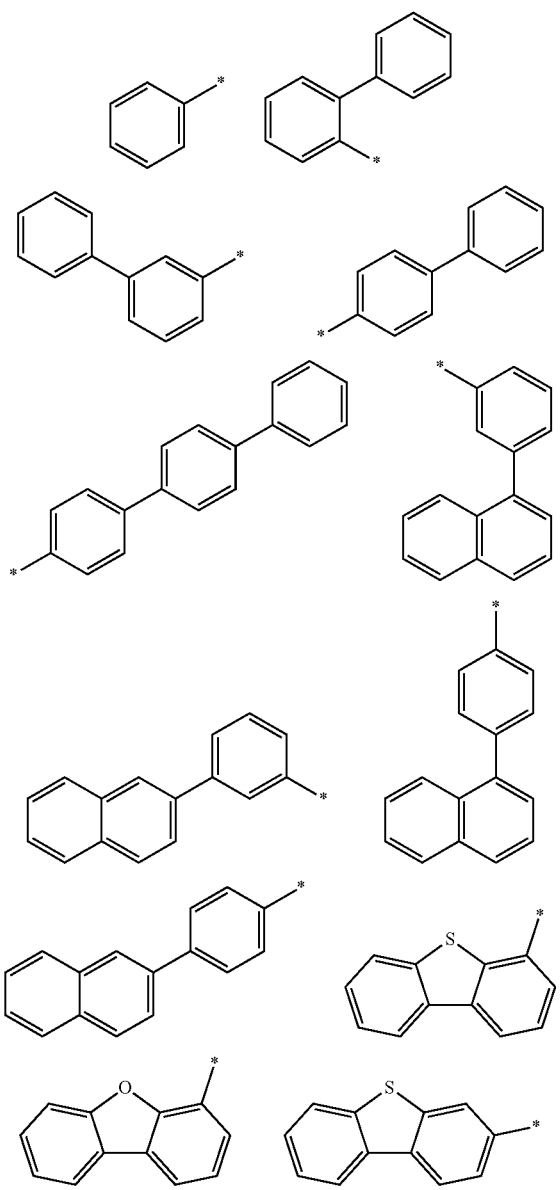

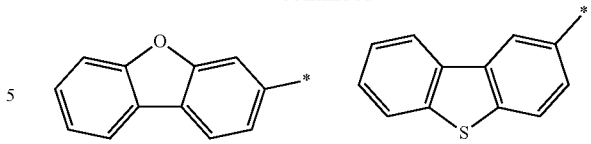

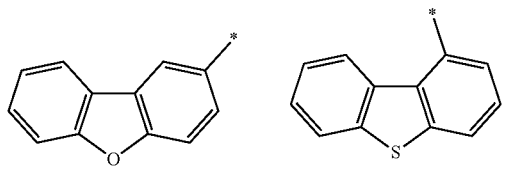

In Group I, * is a linking point with the nitrogen-containing six-membered ring.

In an implementation, $L^1$ and $L^2$ may each independently be or include, e.g., a single bond, a substituted or unsubstituted C6 to C30 arylene group, a substituted or unsubstituted dibenzofuranylene group, or a substituted or unsubstituted dibenzothiophenylene group. In an implementation, $L^1$ and $L^2$ may each independently be or include, e.g., a single bond, a substituted or unsubstituted phenylene group, a substituted or unsubstituted naphthylene group, or a substituted or unsubstituted biphenylene group.

In an implementation, $R^1$ and $R^2$ may each independently be or include, e.g., a substituted or unsubstituted C6 to C30 aryl group, a substituted or unsubstituted dibenzofuranyl group, or a substituted or unsubstituted dibenzothiophenyl group. In an implementation, $R^1$ and $R^2$ may each independently be or include, e.g., a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

In an implementation, $R^3$ and $R^4$ may each independently be or include, e.g., a substituted or unsubstituted C1 to C30 alkyl group, a substituted or unsubstituted C6 to C30 aryl group, or a combination thereof.

In an implementation, $R^3$ and $R^4$ may be linked to each other to form a substituted or unsubstituted C3 to C10 cycloalkyl group.

In an implementation, $R^3$ and $R^4$ may each independently be, e.g., a methyl group, an ethyl group, or a phenyl group. In an implementation, $R^3$ and $R^4$ may each independently be (e.g., a combination of a C1 to C4 alkyl group) linked to each other to form a cyclopentyl group.

In an implementation, the compound represented by Chemical Formula 1 may be, e.g., a compound of Group 1.

[Group 1]
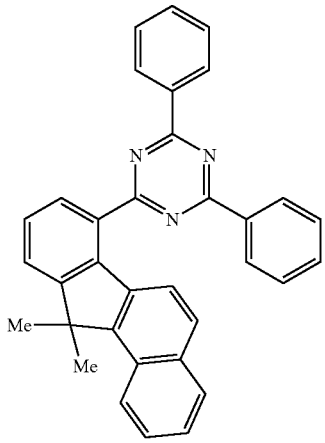 [1]
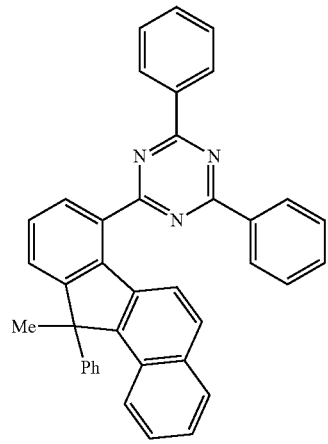 [4]
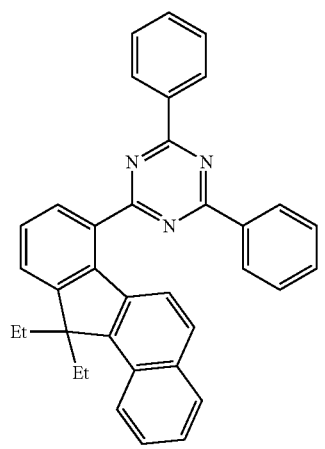 [2]
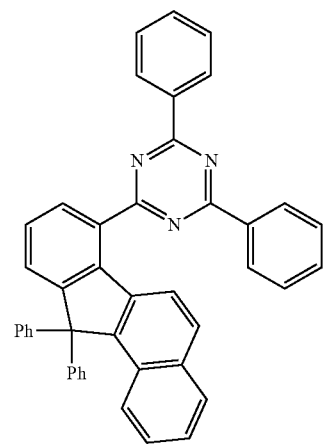 [5]
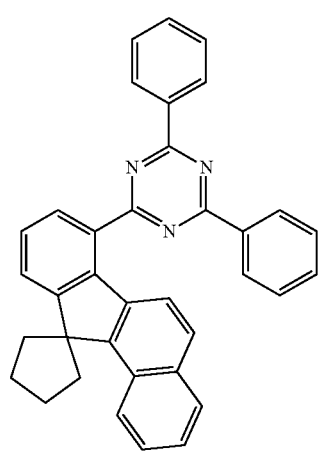 [3]
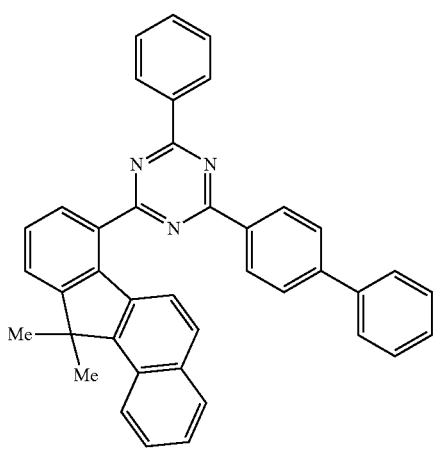 [6]

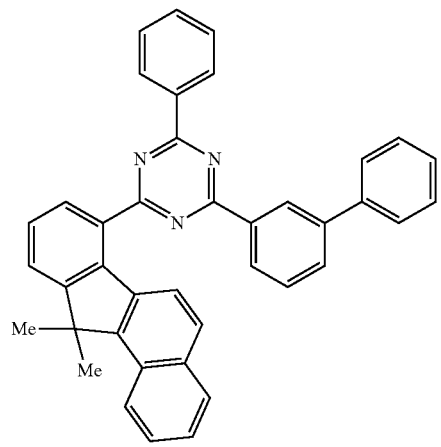
[7]
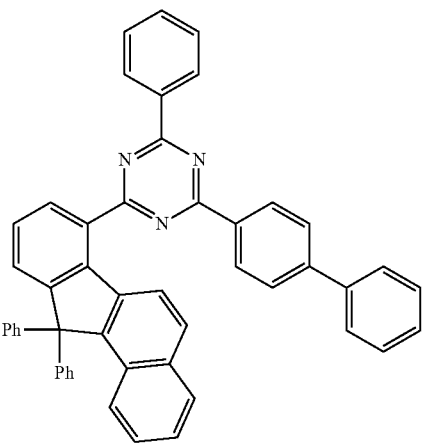
[10]
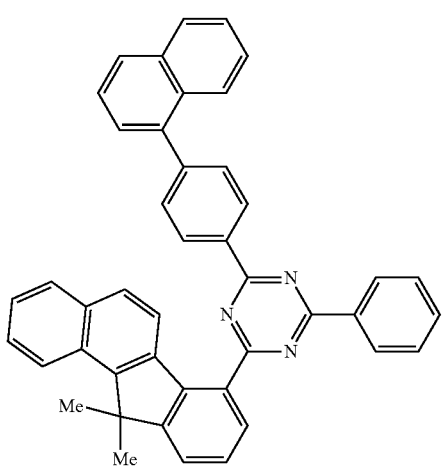
[8]
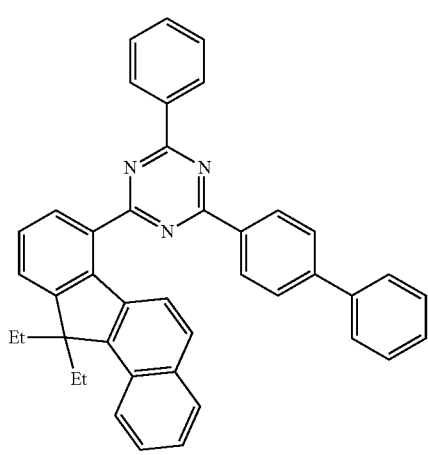
[11]
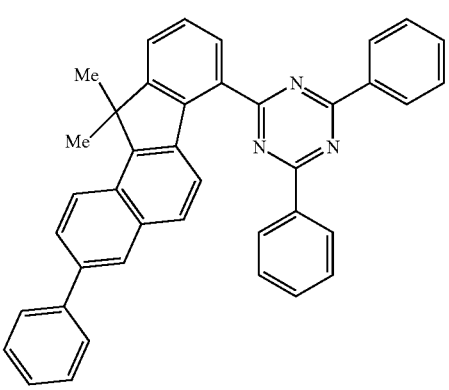
[9]
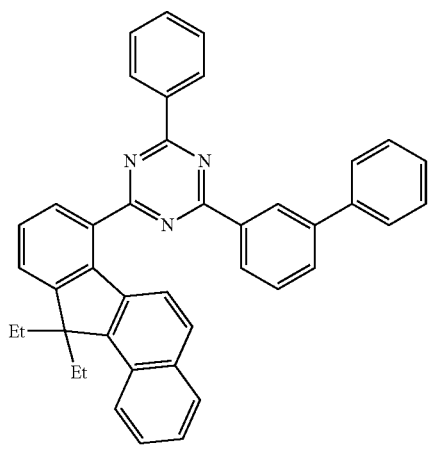
[12]

[13]
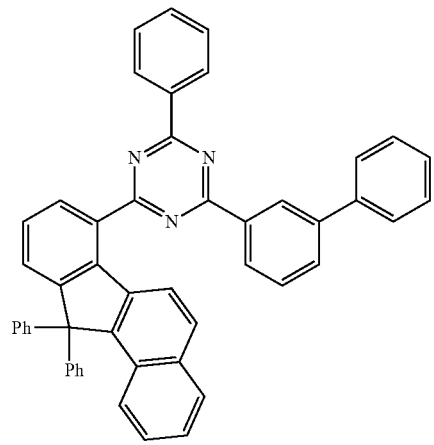
[14]
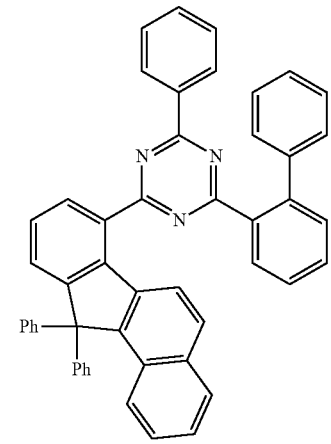
[15]
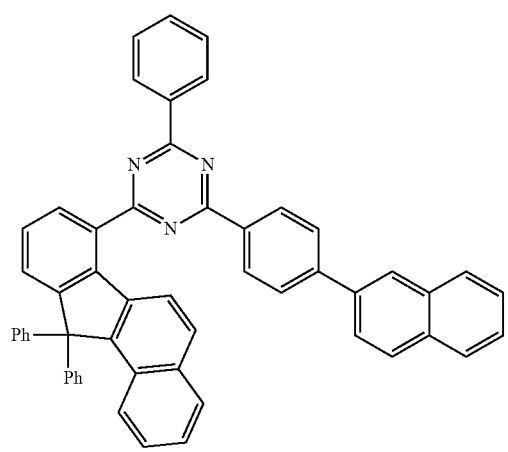
[16]
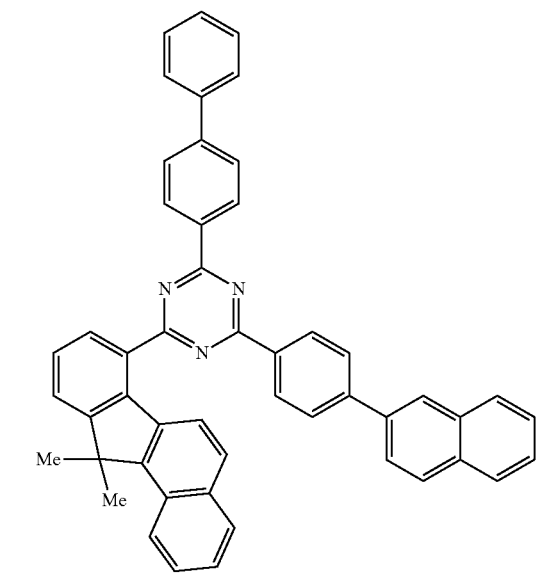
[17]
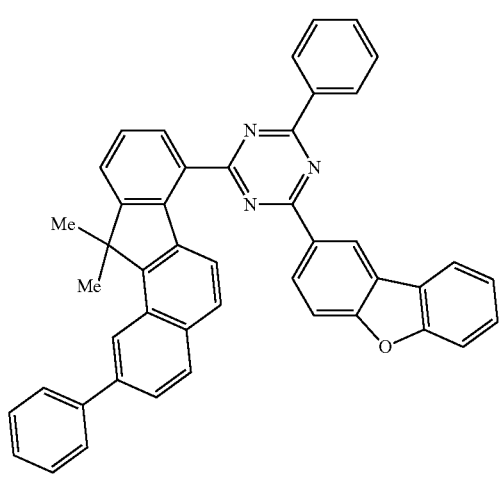
[18]
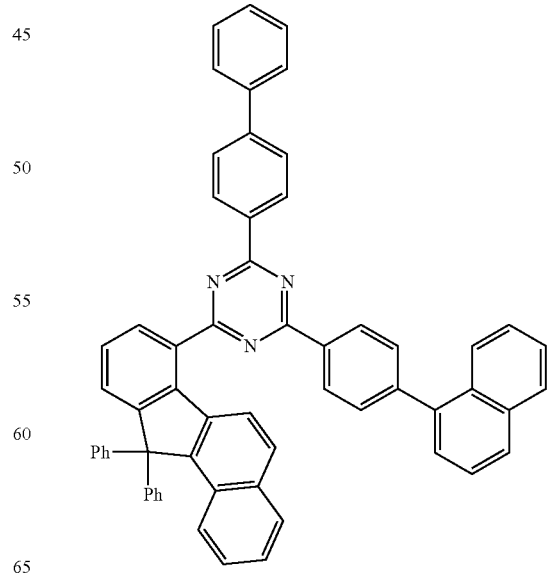

[19]
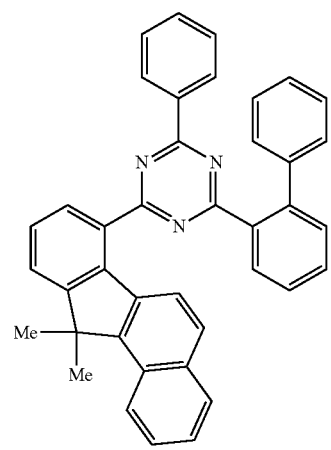
[20]
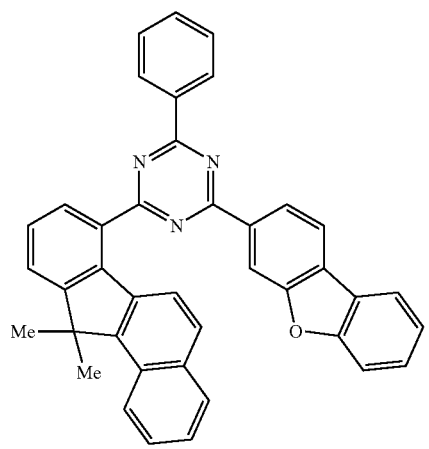
[21]
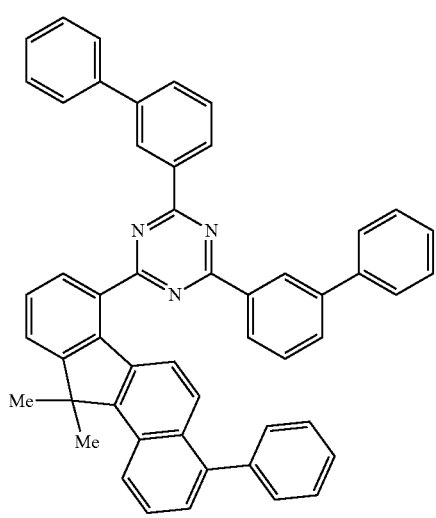
[22]
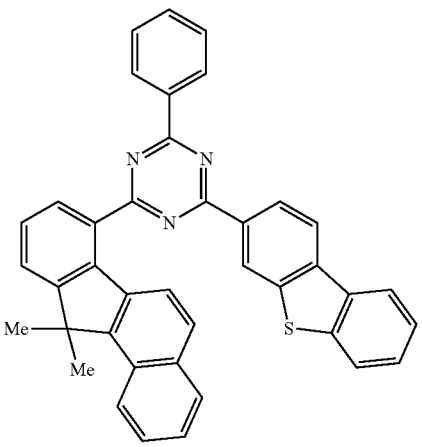
[23]
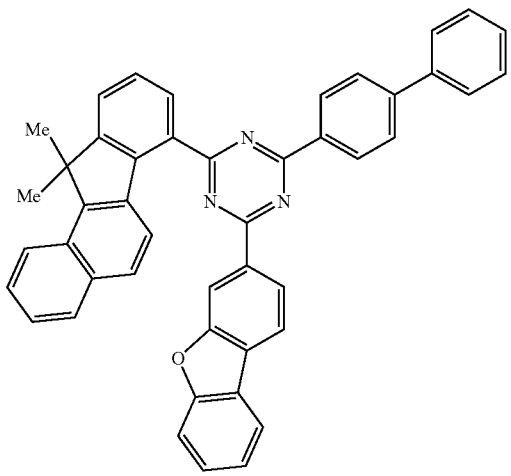
[24]
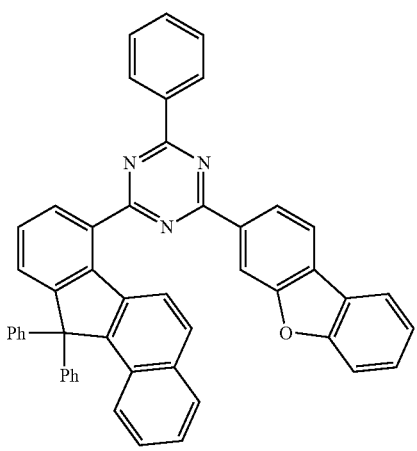

[25]
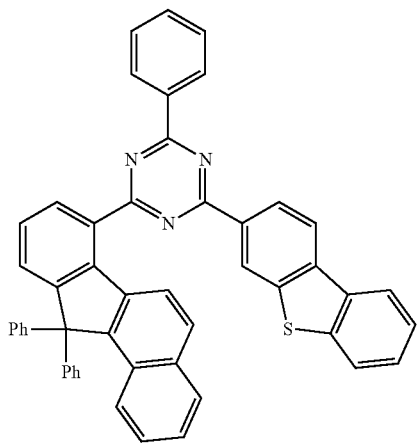
[26]
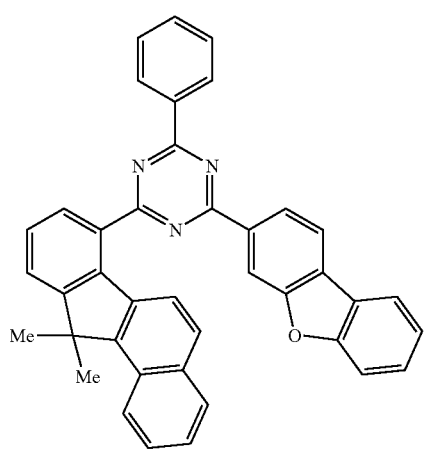
[27]
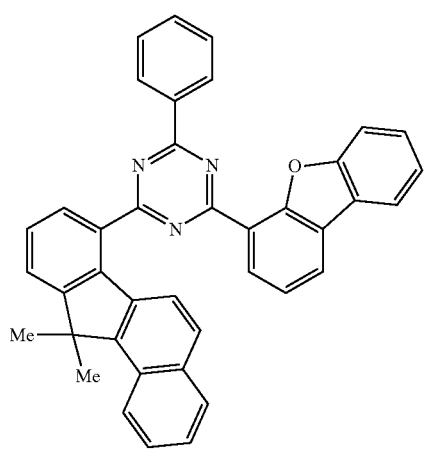
[28]
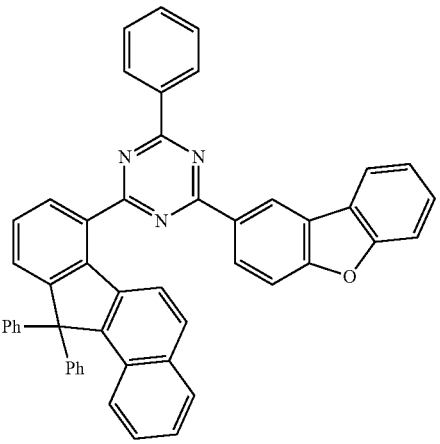
[29]
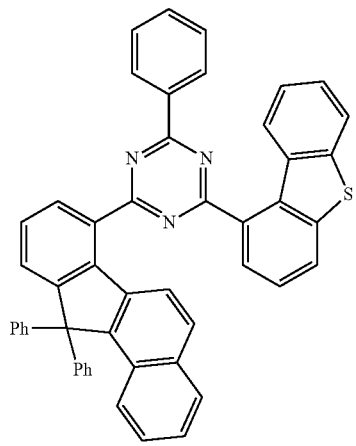
[30]
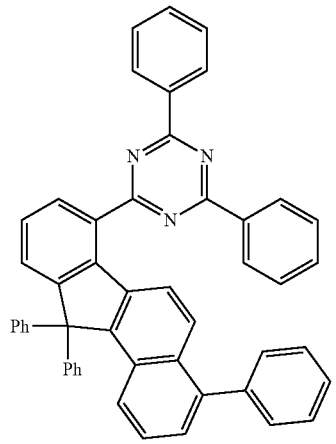

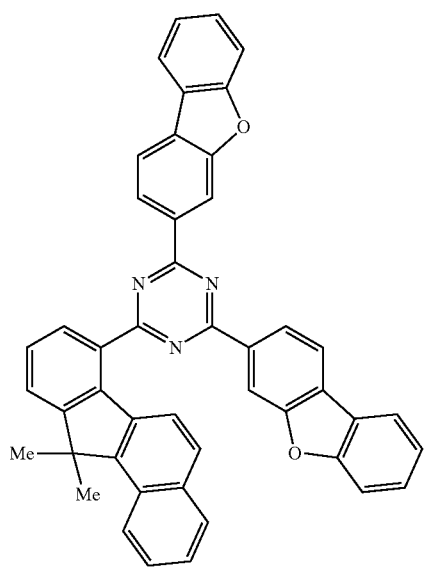
[31]
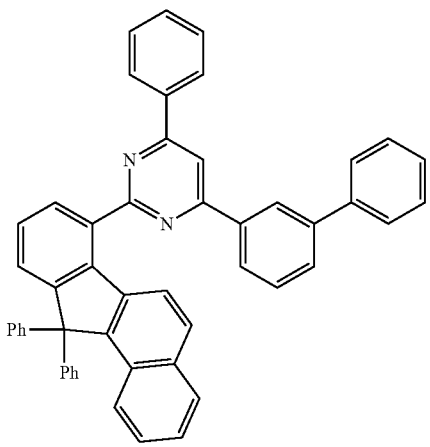
[32]
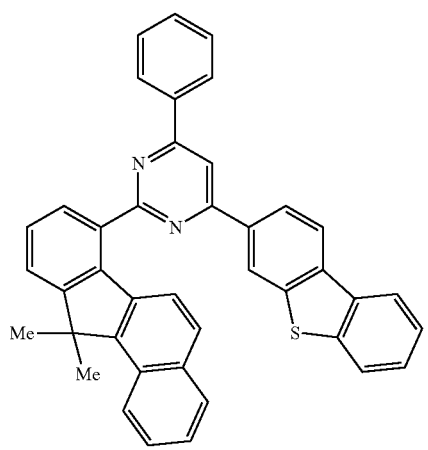
[33]
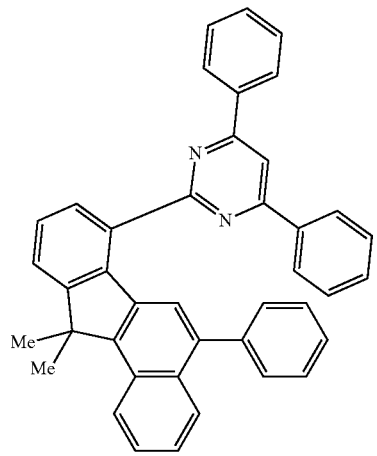
[34]
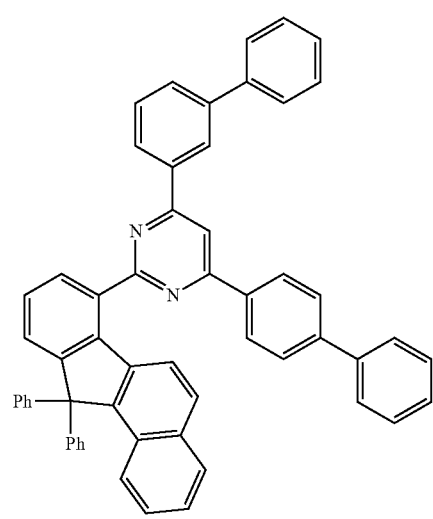
[35]
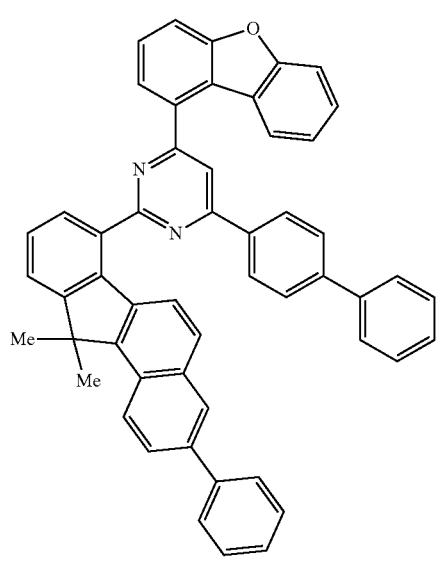
[36]

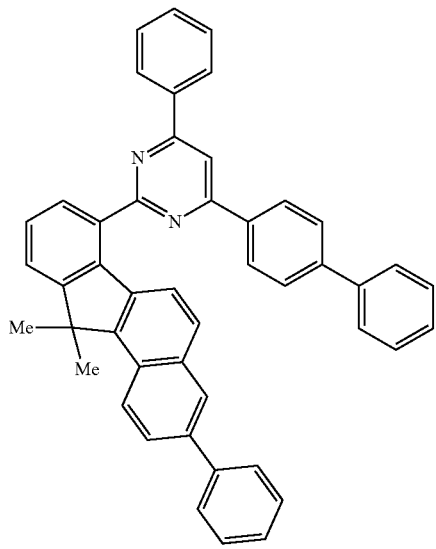
[37]
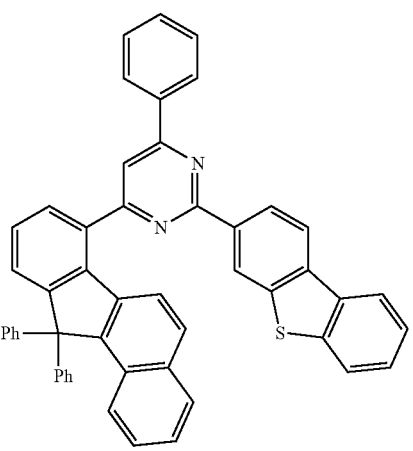
[40]
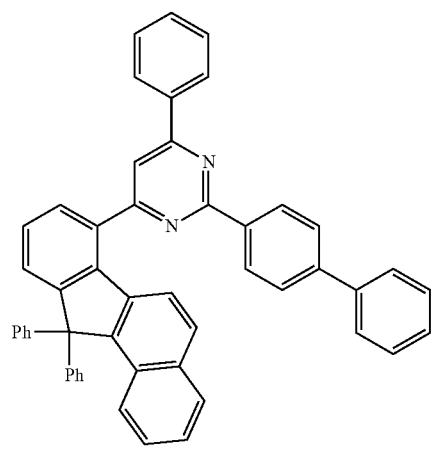
[38]
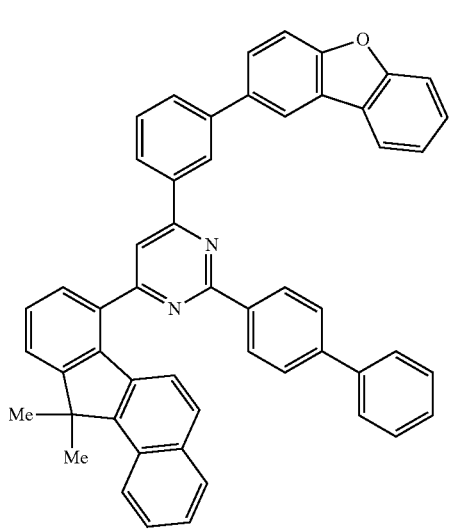
[41]
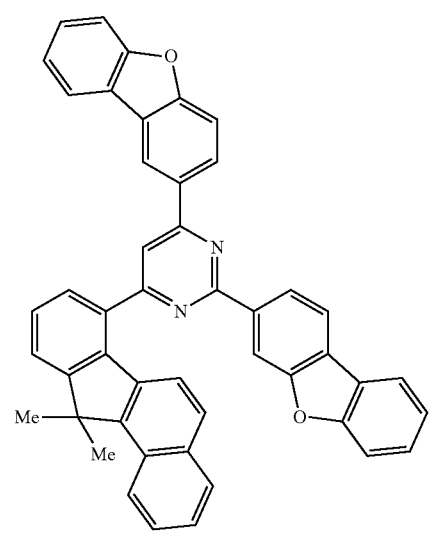
[39]
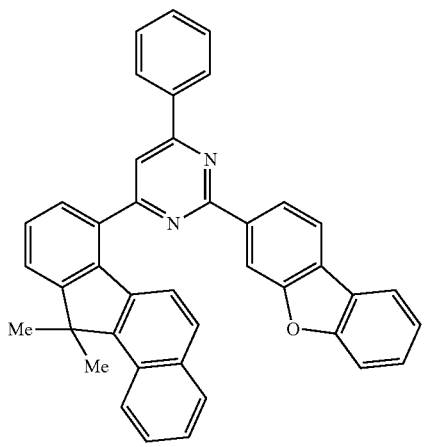
[42]

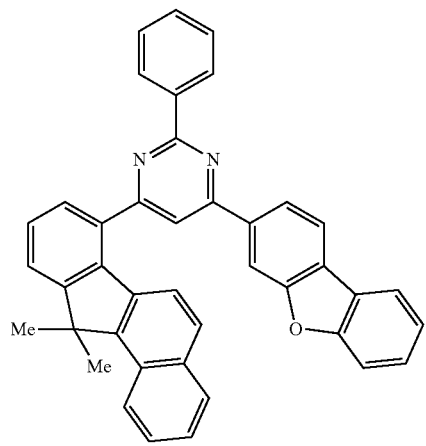
[43]
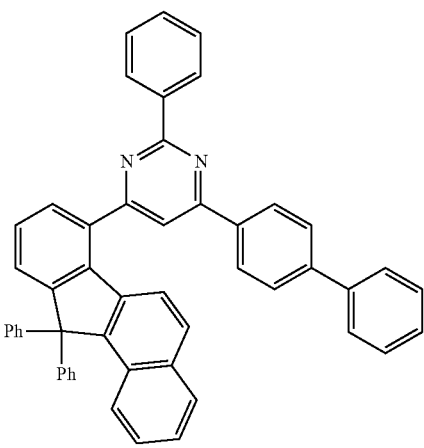
[46]
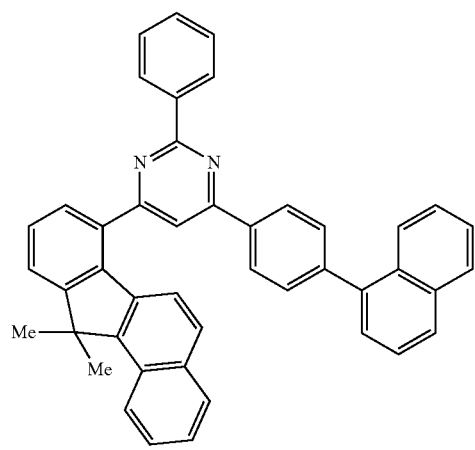
[44]
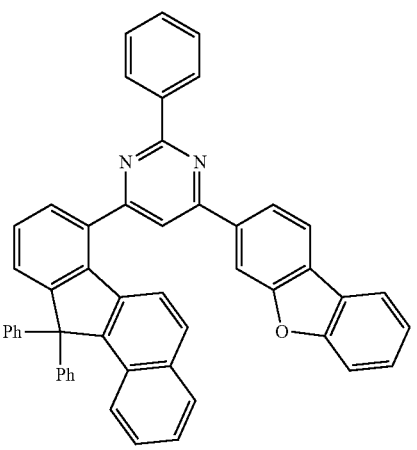
[47]
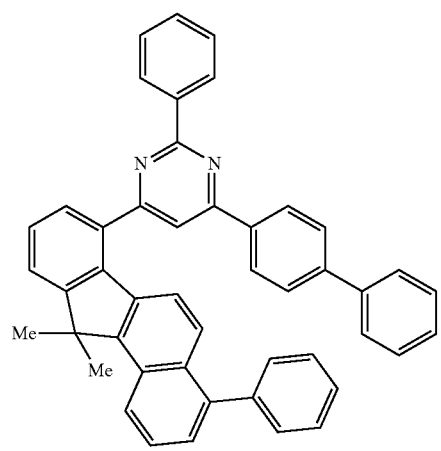
[45]
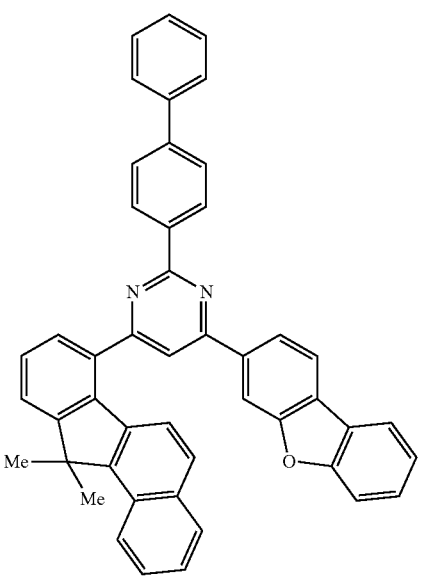
[48]

-continued

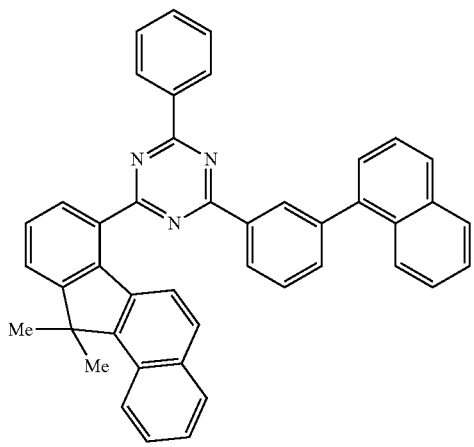

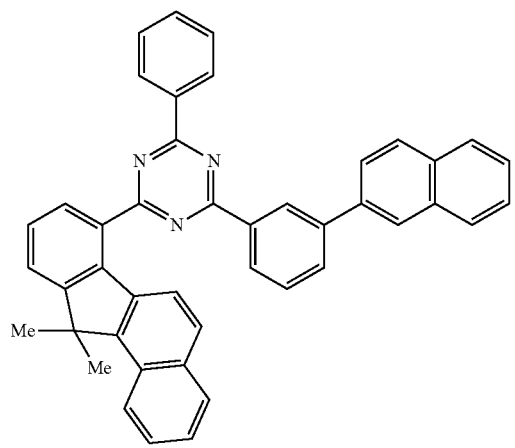

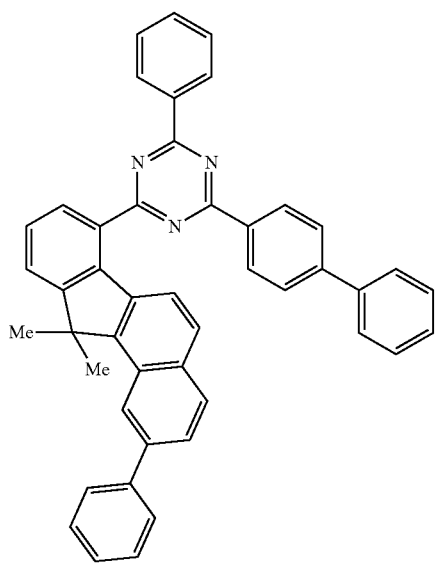

A composition for an organic optoelectronic device according to another embodiment may include, e.g., a first compound for an organic optoelectronic device and a second compound for an organic optoelectronic device. In an implementation, the first compound may be, e.g., the aforementioned compound represented by Chemical Formula 1, and the second compound may be, e.g., represented by Chemical Formula 2; a combination of Chemical Formula 3 and Chemical Formula 4; a combination of Chemical Formula 5 and Chemical Formula 6; or a combination of Chemical Formula 7 and Chemical Formula 8. In an implementation, the composition may include a mixture of the first compound and the second compound.

[Chemical Formula 2]

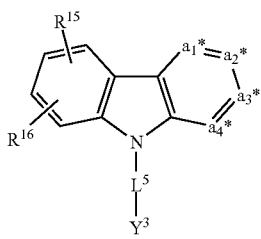

In Chemical Formula 2, $Y^1$ and $Y^2$ may each independently be or include, e.g., a substituted or unsubstituted C6 to C20 aryl group or a substituted or unsubstituted C2 to C30 heterocyclic group, $L^3$ and $L^4$ may each independently be or include, e.g., a single bond, or a substituted or unsubstituted C6 to C20 arylene group, $R^b$ and $R^9$ to $R^{14}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, and m may be, e.g., an integer of 0 to 2.

[Chemical Formula 3]

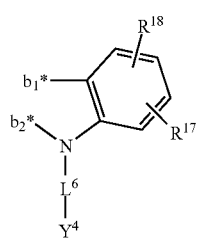

[Chemical Formula 4]

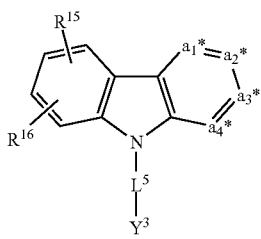

In Chemical Formulae 3 and 4, $Y^3$ and $Y^4$ may each independently be or include, e.g., a substituted or unsubstituted C6 to C20 aryl group, or a substituted or unsubstituted C2 to C30 heterocyclic group, adjacent two of $a_1^*$ to $a_4^*$ may be linked to $b_1^*$ and $b_2^*$, respectively, remaining two of $a_1^*$ to $a_4^*$ not linked to $b_1^*$ and $b_2^*$ may independently be C-$L^a$-$R^c$, $L^a$, $L^5$, and $L^6$ may each independently be or include, e.g., a single bond or a substituted or unsubstituted C6 to C20 arylene group, and $R^e$ and $R^{15}$ to $R^{18}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

[Chemical Formula 5]

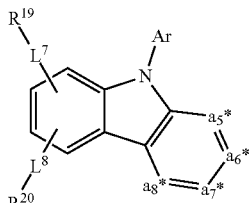

[Chemical Formula 6]

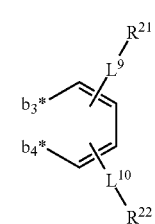

In Chemical Formulas 5 and 6,

Ar may be or may include, e.g., a substituted or unsubstituted C6 to C30 aryl group, a substituted or unsubstituted C2 to C30 heterocyclic group, or a combination thereof, adjacent two of $a_5^*$ to $a_8^*$ may be linked to $b_3^*$ and $b_4^*$, respectively, remaining two of $a_5^*$ to $a_8^*$ not linked to $b_3^*$ and $b_4^*$ may independently be $C\text{-}L^b\text{-}R^d$, $L^b$ and $L^7$ to $L^{10}$ may each independently be or include, e.g., a single bond, a substituted or unsubstituted C6 to C20 arylene group, a substituted or unsubstituted C2 to C20 heterocyclic group, or a combination thereof, $R^d$ and $R^{19}$ to $R^{22}$ may each independently be or include, e.g., hydrogen, deuterium, a cyano group, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^d$ and $R^{19}$ to $R^{22}$ may be, e.g., a group represented by Chemical Formula A.

[Chemical Formula A]

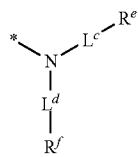

In Chemical Formula A, $L^c$ and $L^d$ may each independently be or include, e.g., a single bond or a substituted or unsubstituted C6 to C20 arylene group, $R^e$ and $R^f$ may each independently be or include, e.g., a substituted or unsubstituted C6 to C30 aryl group, a substituted or unsubstituted C2 to C30 heterocyclic group, or a combination thereof, and

* is a linking point with one of $L^b$ and $L^7$ to $L^{10}$.

[Chemical Formula 7]

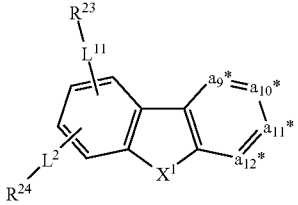

[Chemical Formula 8]

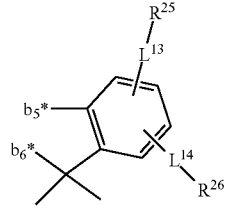

In Chemical Formulae 7 and 8, $X^1$ may be, e.g., O or S, adjacent two of $a_9^*$ to $a_{12}^*$ may be linked to $b_5^*$ and $b_6^*$, respectively, remaining two of $a_9^*$ to $a_{12}^*$ not linked to $b_5^*$ and $b_6^*$ may independently be $C\text{-}L^e\text{-}R^g$, $L^e$ and $L^{11}$ to $L^{14}$ may each independently be or include, e.g., a single bond or a substituted or unsubstituted C6 to C20 arylene group, $R^g$ and $R^{23}$ to $R^{26}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^g$ and $R^{23}$ to $R^{26}$ may be a group represented by Chemical Formula B.

[Chemical Formula B]

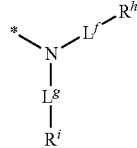

In Chemical Formula B, $L^f$ and $L^g$ may each independently be or include, e.g., a single bond or a substituted or unsubstituted C6 to C20 arylene group, $R^h$ and $R^i$ may each independently be or include, e.g., a substituted or unsubstituted C6 to C30 aryl group, a substituted or unsubstituted C2 to C30 heterocyclic group, or a combination thereof, and

* is a linking point with one of $L^e$ and $L^{11}$ to $L^{14}$.

The second compound may be used in a light emitting layer together with the compound for the organic optoelectronic device to help improve charge mobility and stability, thereby improving luminous efficiency and life-span characteristics.

In an implementation, $Y^1$ and $Y^2$ of Chemical Formula 2 may each independently be or include, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, $L^3$ and $L^4$ of Chemical Formula 2 may each independently be or include, e.g., a single bond, a substituted or unsubstituted phenylene group, or a substituted or unsubstituted biphenylene group, $R^9$ to $R^{14}$ of Chemical Formula 2 may each independently be or include, e.g., hydrogen, deuterium, or a substituted or unsubstituted C6 to C12 aryl group, and m may be, e.g., 0 or 1.

In an implementation, "substituted" of Chemical Formula 2 refers to replacement of at least one hydrogen by deuterium, a C1 to C4 alkyl group, a C6 to C18 aryl group, or a C2 to C30 heteroaryl group.

In an implementation, the compound represented by Chemical Formula 2 may be represented by, e.g., one of Chemical Formulae 2-1 to 2-15.

[Chemical Formula 2-1]

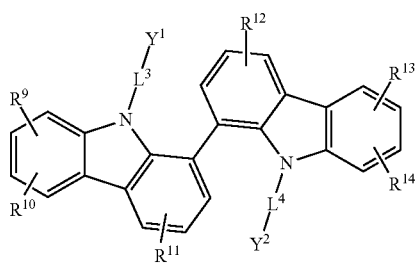

[Chemical Formula 2-2]

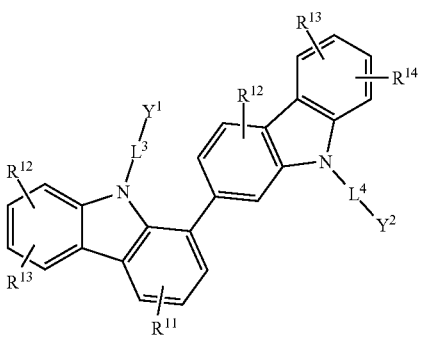

[Chemical Formula 2-3]

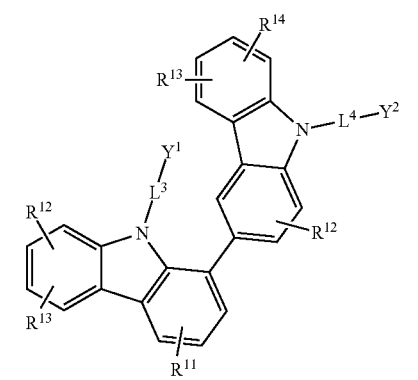

[Chemical Formula 2-4]

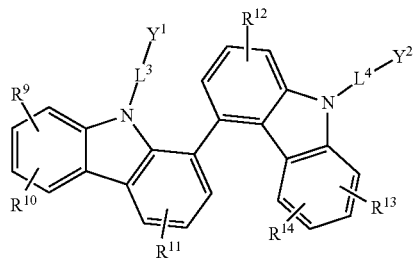

[Chemical Formula 2-5]

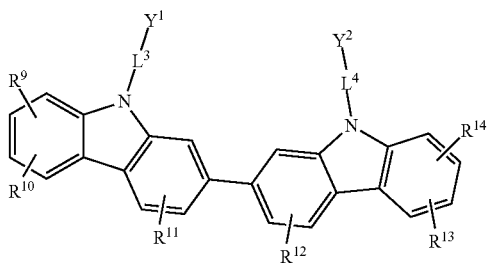

[Chemical Formula 2-6]

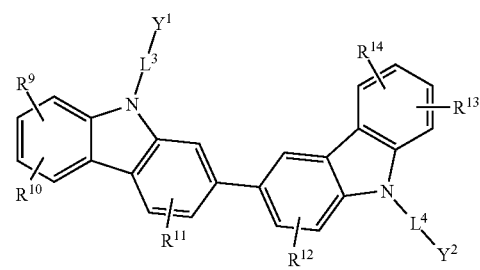

[Chemical Formula 2-7]

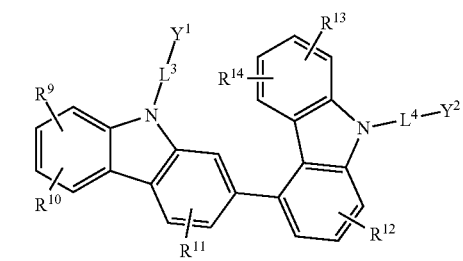

[Chemical Formula 2-8]

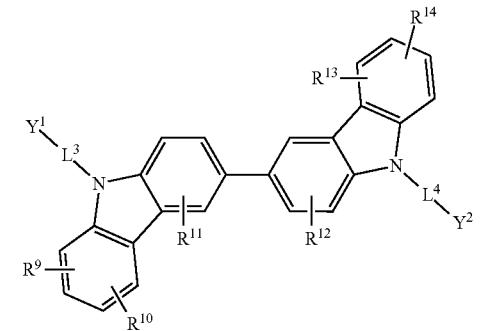

[Chemical Formula 2-9]
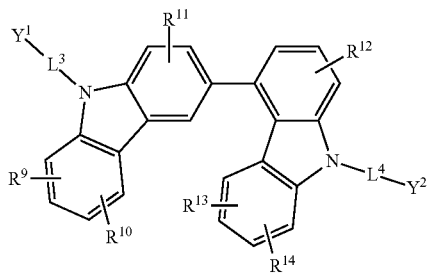
[Chemical Formula 2-10]
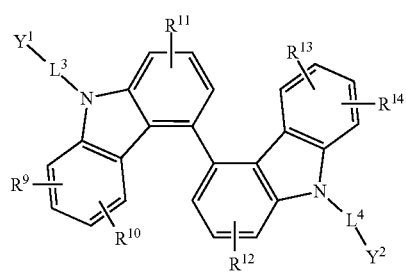
[Chemical Formula 2-11]
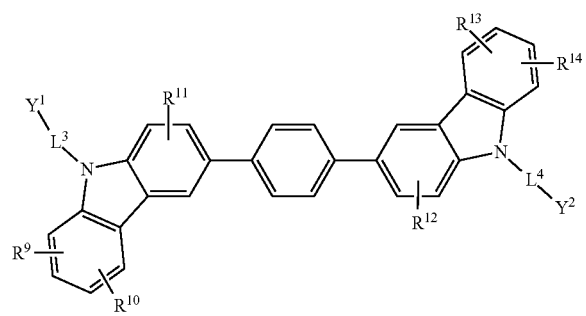
[Chemical Formula 2-12]
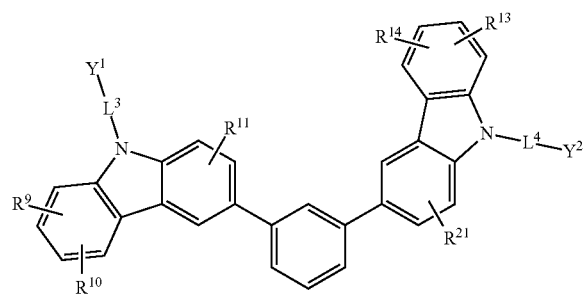
[Chemical Formula 2-13]
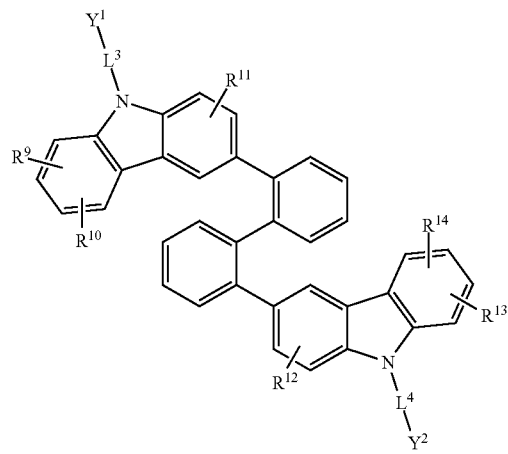
[Chemical Formula 2-14]
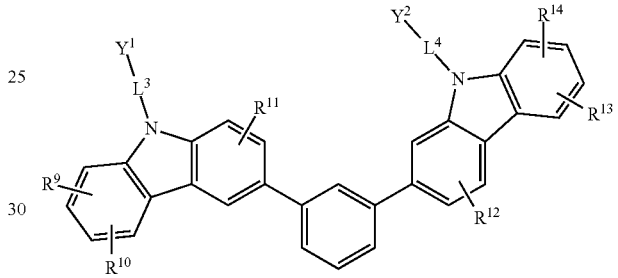
[Chemical Formula 2-15]
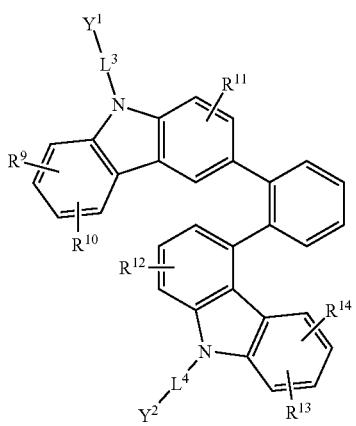
In Chemical Formulae 2-1 to 2-15, $R^9$ to $R^{14}$ may each independently be or include, e.g., hydrogen or a substituted or unsubstituted C6 to C12 aryl group, and moieties *-$L^3$-$Y^1$ and *-$L^4$-$Y^2$ may each independently be a moiety of Group II.
[Group II]
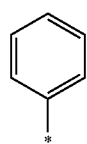
C-1

-continued
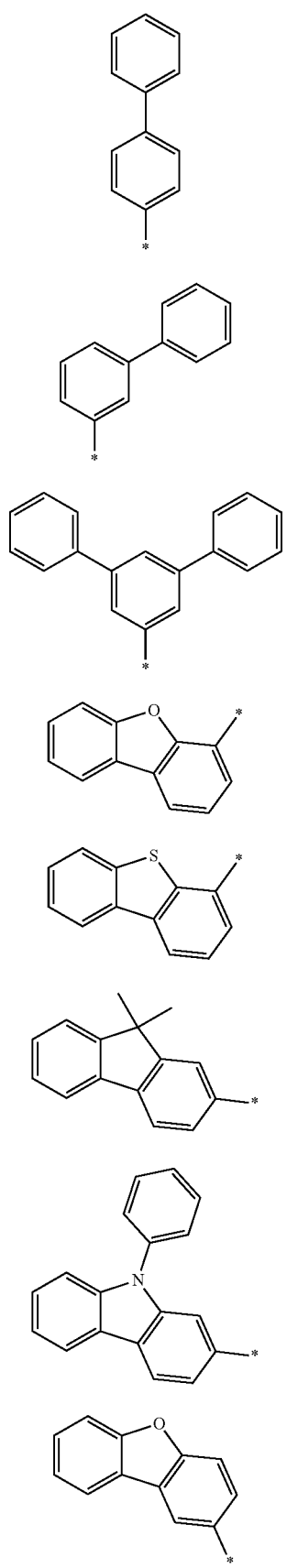
C-2
C-3
C-4
C-5
C-6
C-7
C-8
C-9
-continued
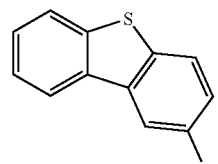
C-10
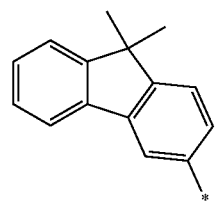
C-11
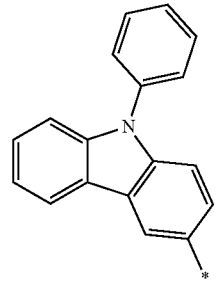
C-12
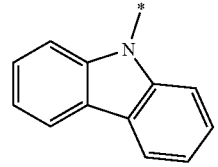
C-13
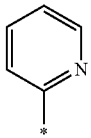
C-14
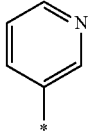
C-15
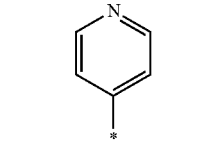
C-16
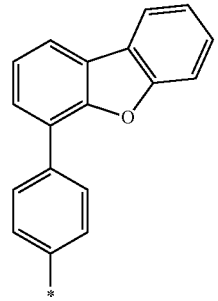
C-17

-continued
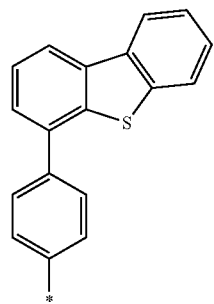
C-18
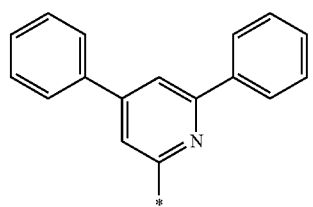
C-19
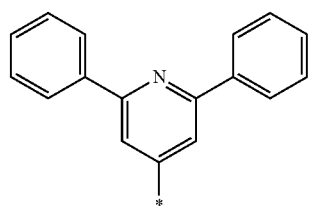
C-20
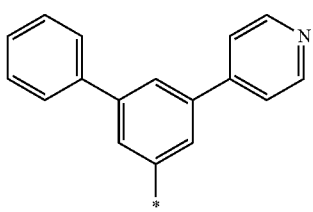
C-21
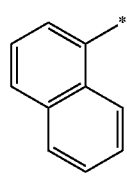
C-22
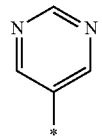
C-23
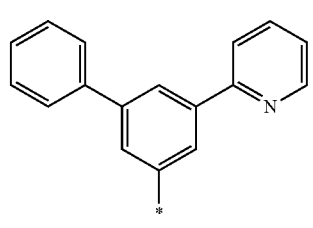
C-24
-continued
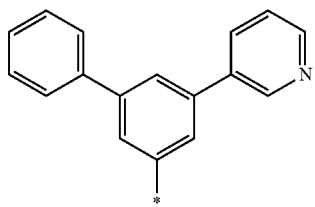
C-25
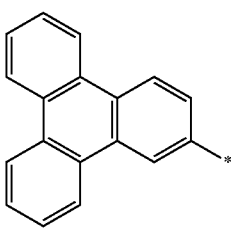
C-26
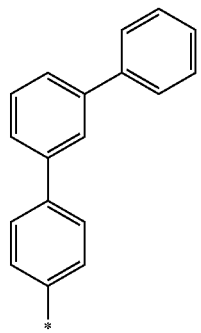
C-27
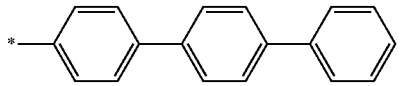
C-28
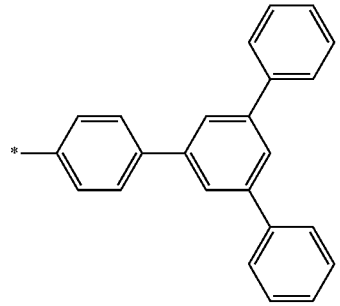
C-29
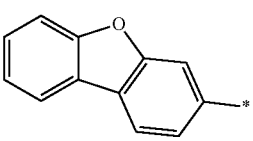
C-30
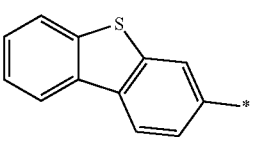
C-31

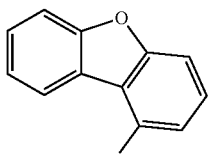

C-32

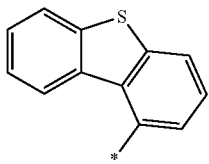

C-33

In Group II, * is a linking point.

In an implementation, Chemical Formula 2 may be represented by Chemical Formula 2-8.

In an implementation, moieties *-$L^3$-$Y^1$ and *-$L^4$-$Y^2$ of Chemical Formula 2-8 may each independently be a moiety of Group II, e.g., one of C-1, C-2, C-3, C-19 and C-26.

In an implementation, both moieties *-$L^3$-$Y^1$ and *-$L^4$-$Y^2$ may be represented by C-1, C-2, or C-3 of Group II.

In an implementation, the second compound represented by the combination of Chemical Formulae 3 and 4 may be represented by one of Chemical Formulae 3A, 3B, 3C, 3D, and 3E.

[Chemical Formula 3A]

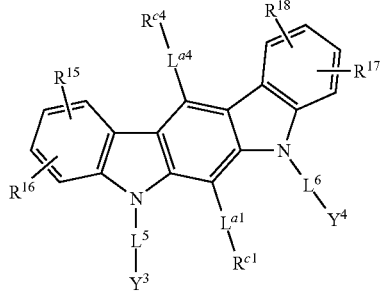

[Chemical Formula 3B]

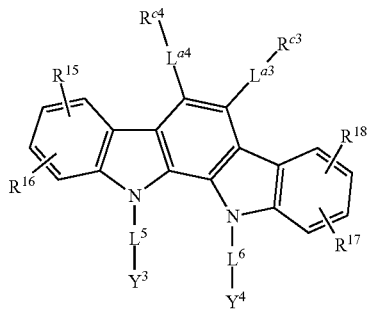

[Chemical Formula 3C]

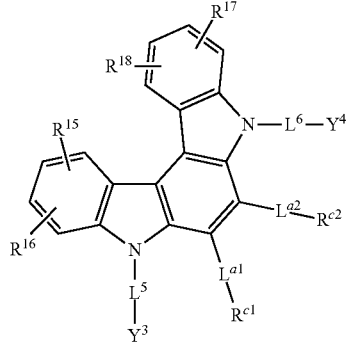

[Chemical Formula 3D]

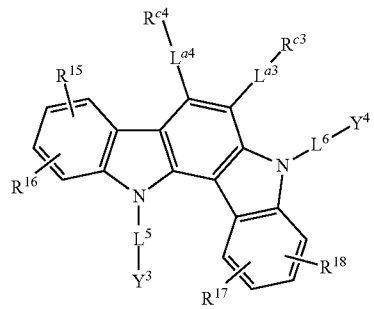

[Chemical Formula 3E]

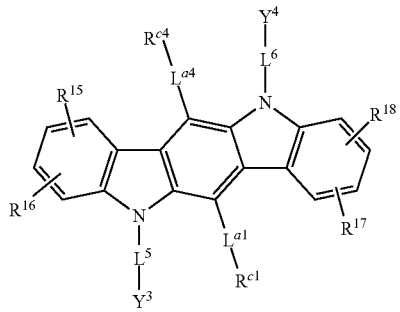

In Chemical Formulas 3A to 3E, $Y^3$ and $Y^4$, $L^5$ and $L^6$, and $R^{15}$ to $R^{18}$ may be defined the same as those described above, $L^{a1}$ to $L^{a4}$ may be defined the same as $L^5$ and $L^6$ described above, and $R^{c1}$ to $R^{c4}$ may be defined the same as $R^{15}$ to $R^{18}$ In an implementation, $Y^3$ and $Y^4$ of Chemical Formulae 3 and 4 may each independently be or include, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, and $R^{c1}$ to $R^{c4}$ and $R^{15}$ to $R^{18}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Y^3$ and $Y^4$ of Chemical Formulae 3 and 4 may each independently be a group of Group III.

[Group III]

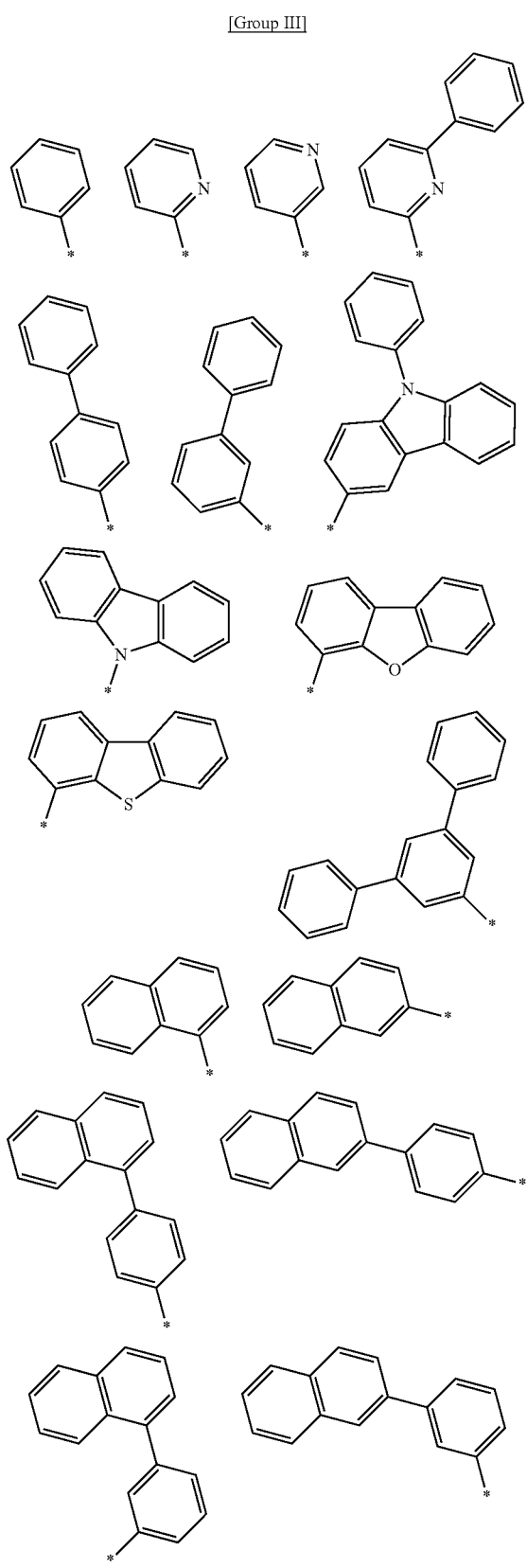

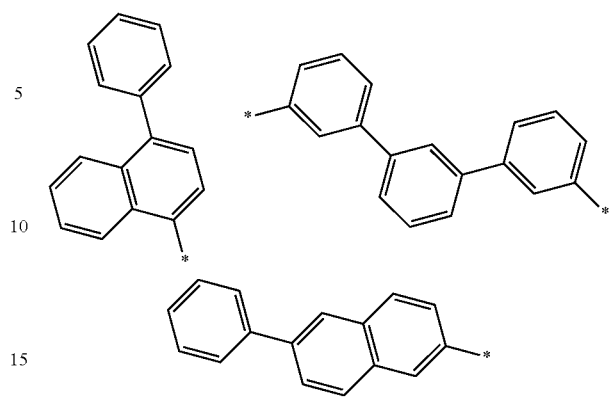

In Group III, * is a linking point with $L^5$ and $L^6$, respectively.

In an implementation, $R^{c1}$ to $R^{c4}$ and $R^{15}$ to $R^{18}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{c1}$ to $R^{c4}$ and $R^{15}$ to $R^{18}$ may each independently be or include, e.g., hydrogen, deuterium, a cyano group, or a substituted or unsubstituted phenyl group.

In an implementation, $R^{c1}$ to $R^{c4}$ may each be hydrogen, and $R^{15}$ to $R^{18}$ may each independently be or include, e.g., hydrogen or a substituted or unsubstituted phenyl group.

In an implementation, the second compound represented by the combination of Chemical Formulae 5 and 6 may be represented by, e.g., one of Chemical Formulae 5A, 5B, and 5C.

[Chemical Formula 5A]

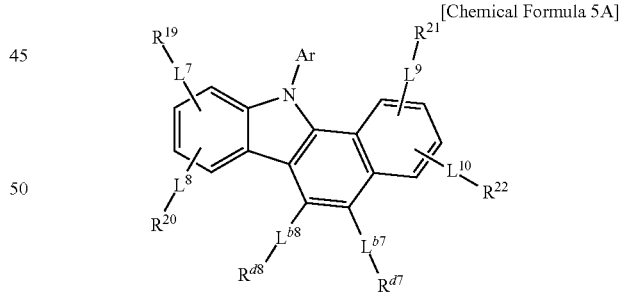

[Chemical Formula 5B]

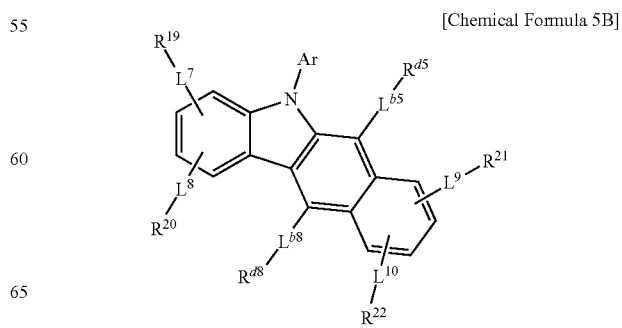

[Chemical Formula 5C]

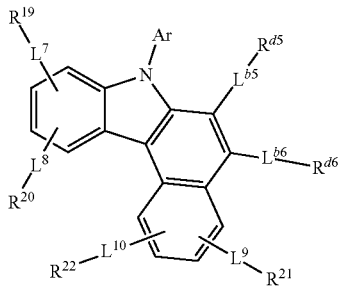

[Chemical Formula 5A-4]

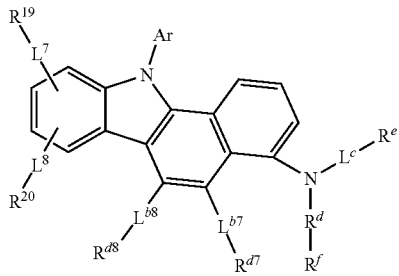

In Chemical Formulae 5A to 5C, Ar, $L^7$ to $L^{10}$, and $R^{19}$ to $R^{22}$ may be defined the same as those described above, $L^{b5}$ to $L^{b8}$ may be defined the same as $L^b$, and $R^{d5}$ to $R^{d8}$ may be defined the same as $R^d$.

In an implementation, the second compound represented by the combination of Chemical Formulae 5 and 6 may be represented by Chemical Formula 5A, e.g., one of Chemical Formulae 5A-1 to 5A-4 depending on the substitution position of the amino group.

In Chemical Formulae 5A-1 to 5A-4, Ar, $L^7$, $L^8$, $L^{b5}$ to $L^{b8}$, $L^c$, $L^d$, $R^{19}$, $R^{20}$, $R^{d5}$ to $R^{d8}$, $R^e$, and $R^f$ may be defined the same as those described above.

In an implementation, the second compound represented by the combination of Chemical Formulae 7 and 8 may be represented by, e.g., one of Chemical Formulae 7A, 7B, 7C, 7D, 7E, and 7F.

[Chemical Formula 5A-1]

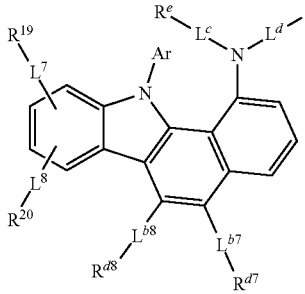

[Chemical Formula 7A]

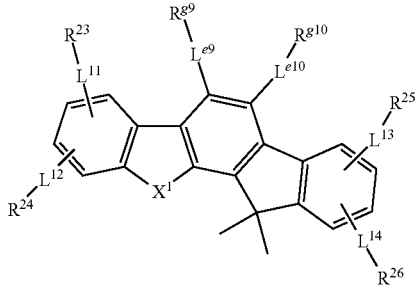

[Chemical Formula 5A-2]

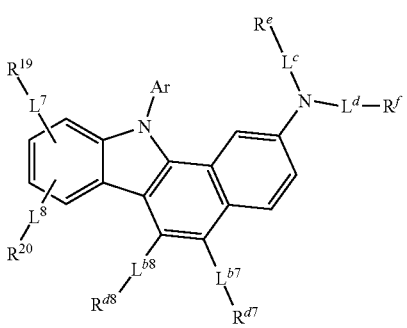

[Chemical Formula 7B]

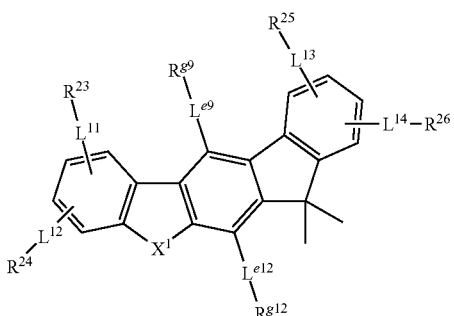

[Chemical Formula 5A-3]

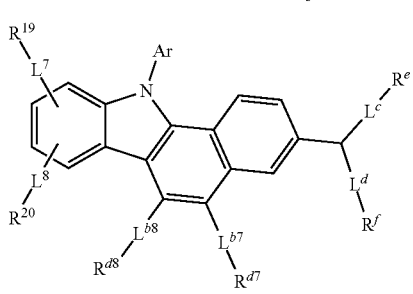

[Chemical Formula 7C]

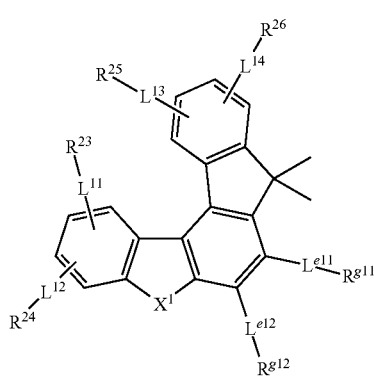

[Chemical Formula 7D]

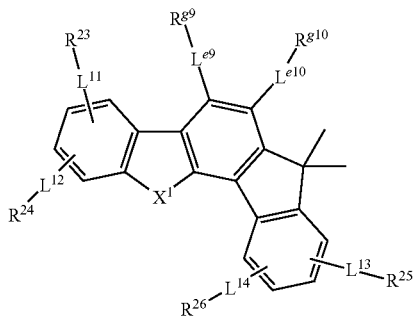

[Chemical Formula 7E]

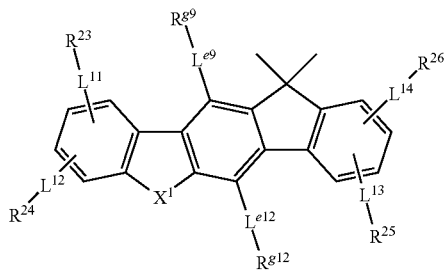

[Chemical Formula 7F]

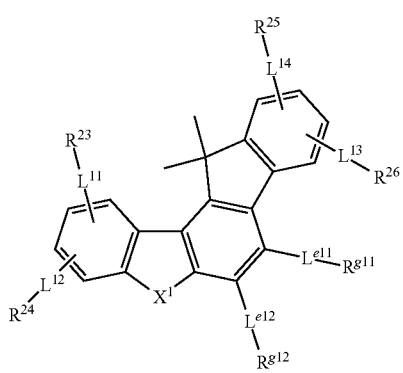

In Chemical Formulas 7A to 7F, $X^1$, $L^{11}$ to $L^{14}$, and $R^{23}$ to $R^{26}$ may be defined the same as those described above, $L^{e9}$ to $L^{e12}$ may be defined the same as $L^e$, and $R^{g9}$ to $R^{g12}$ may be defined the same as $R^e$.

In an implementation, the second compound represented by the combination of Chemical Formulae 7 and 8 may be represented by Chemical Formula 7F, e.g., one of Chemical Formulae 7F-1 to 7F-4 depending on the substitution position of the amino group.

[Chemical Formula 7F-1]

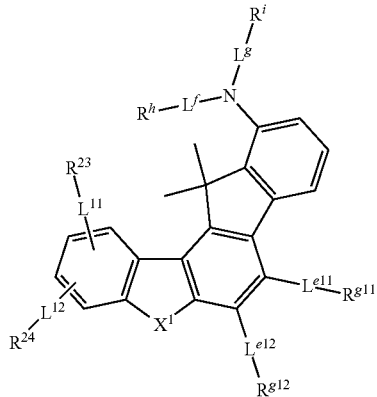

[Chemical Formula 7F-2]

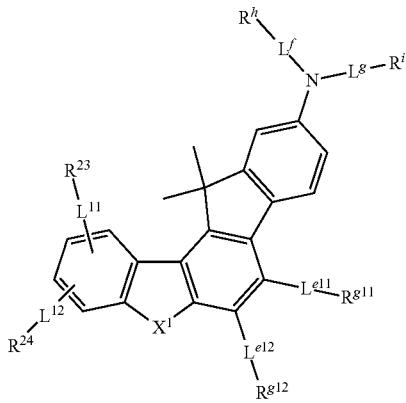

[Chemical Formula 7F-3]

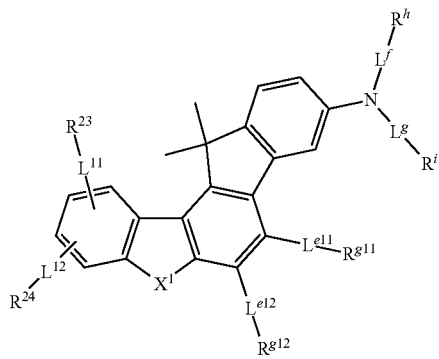

[Chemical Formula 7F-4]

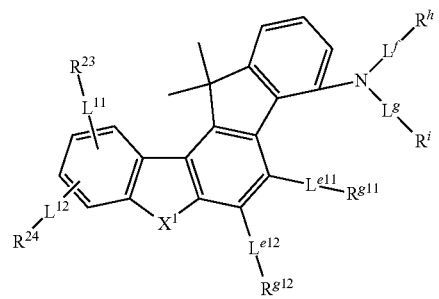

In Chemical Formulas 7F-1 to 7F-4, $X^1$, $L^{11}$, $L^{12}$, $L^{e9}$ to $L^{e12}$, $L^f$, $L^g$, $R^{23}$, $R^{24}$, $R^{g9}$ to $R^{g12}$, $R^h$, and $R^i$ may be defined the same as those described above.

In an implementation, the second compound may be represented by Chemical Formula 2-8, and $Y^1$ and $Y^2$ of Chemical Formula 2-8 may each independently be or include, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^3$ and $L^4$ may each independently be or include, e.g., a single bond, or a substituted or unsubstituted C6 to C20 arylene group, and $R^9$ to $R^{14}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In implementation, the second compound may be represented by Chemical Formula 3C, and $L^{a1}$ and $L^{a2}$ of Chemical Formula 3C may each be a single bond, $L^5$ and $L^6$ may each independently be or include, e.g., a single bond or a substituted or unsubstituted C6 to C12 arylene group, $R^{15}$ to $R^{18}$, $R^{c1}$ and $R^{e2}$ may each be hydrogen, and $Y^3$ and $Y^4$ may each independently be or include, e.g., a substituted or unsubstituted phenyl group, a substituted or unsubstituted naphthyl group, or a substituted or unsubstituted biphenyl group.

In an implementation, the second compound may be represented by Chemical Formula 5A-2, and Ar of Chemical Formula 5A-2 may be or may include, e.g., a substituted or unsubstituted C6 to C12 aryl group, $L^7$, $L^8$, $L^{b7}$, and $L^{b8}$ may each be a single bond, $L^e$ and $L^d$ may each independently be or include, e.g., a single bond or a substituted or unsubstituted C6 to C12 arylene group, $R^{19}$, $R^{20}$, $R^{d7}$, and $R^{d8}$ may each be hydrogen, and $R^e$ and $R^f$ may each independently be or include, e.g., a substituted or unsubstituted phenyl group or a substituted or unsubstituted biphenyl group.

In an implementation, the second compound may be represented by Chemical Formula 7F-2, and $L^{11}$, $L^{12}$, $L^{e11}$, and $L^{e12}$ of Chemical Formula 7F-2 may each be a single bond, $L^g$ and $L^f$ may each independently be or include, e.g., a single bond or a substituted or unsubstituted C6 to C12 arylene group, $R^{23}$, $R^{24}$, $R^{g11}$, and $R^{g12}$ may each independently be or include, e.g., hydrogen, and $R^h$ and $R^i$ may independently be a substituted or unsubstituted phenyl group, a substituted or unsubstituted biphenyl group, or a substituted or unsubstituted naphthyl group.

In an implementation, the second compound may be a compound of Group 2.

[Group 2]

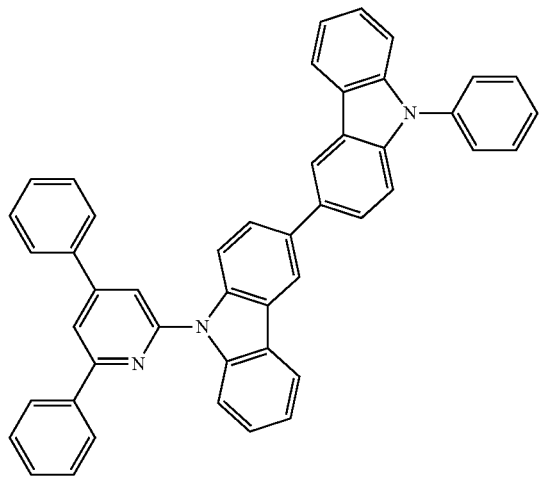

[A-1]

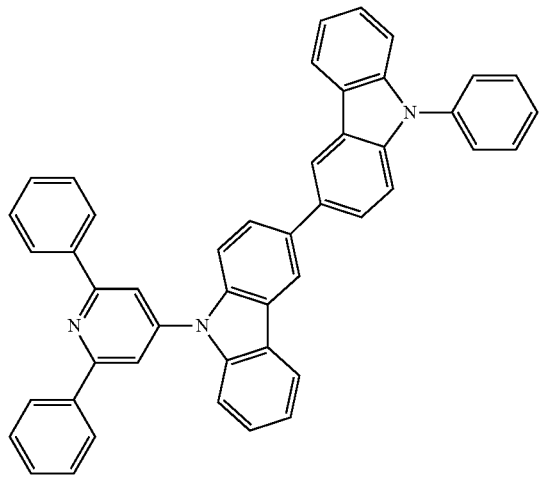

[A-2]

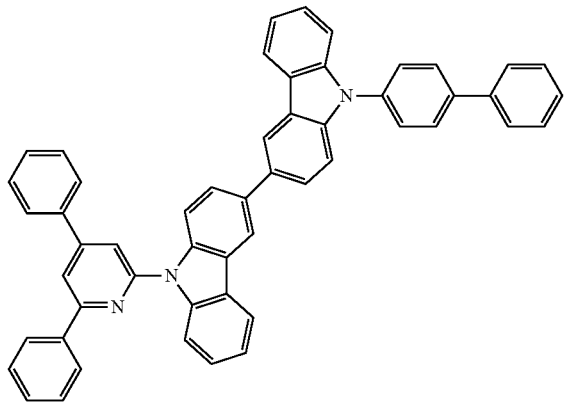

[A-3]

-continued
[A-4]
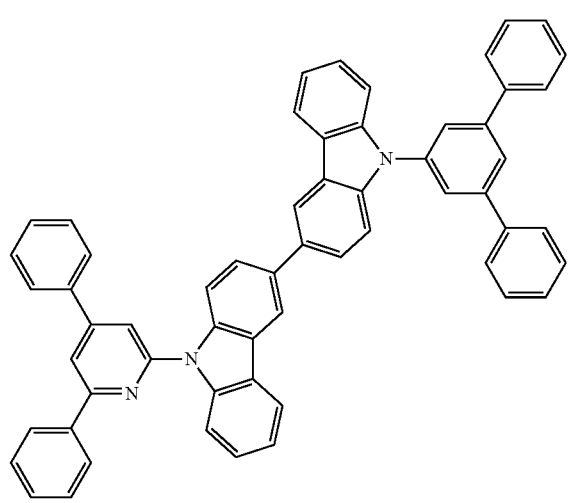
[A-5]
[A-6]
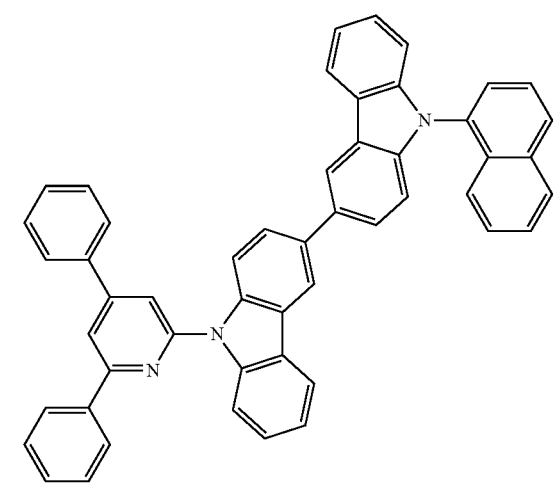
[A-7]
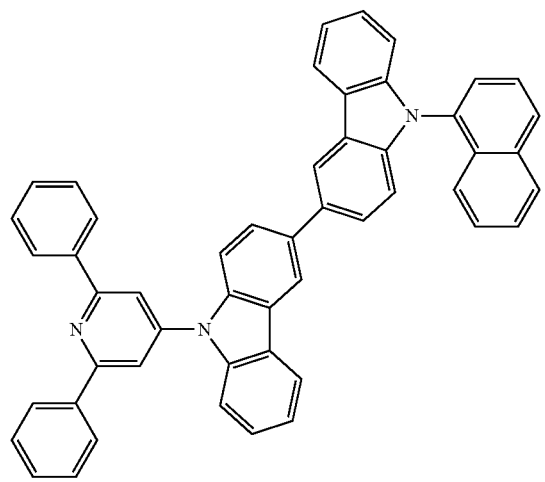
[A-8]
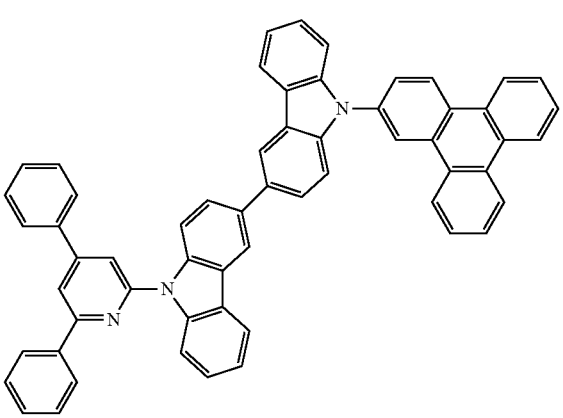
[A-9]
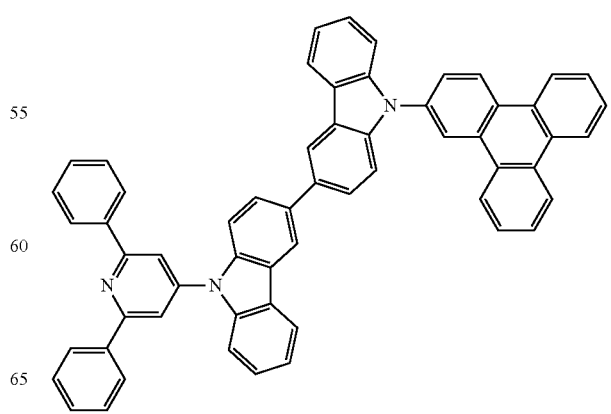

[A-10]
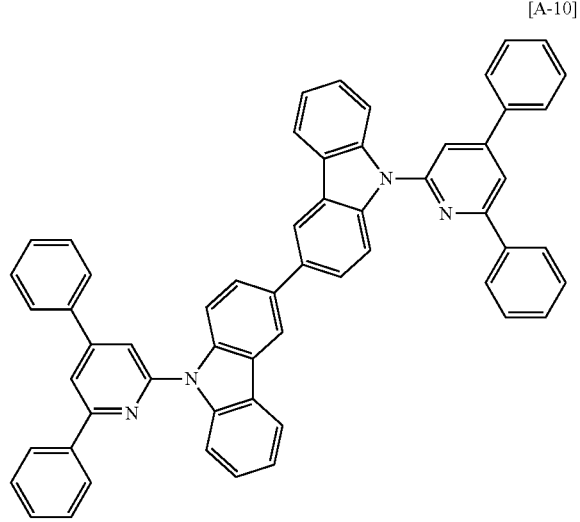
[A-13]
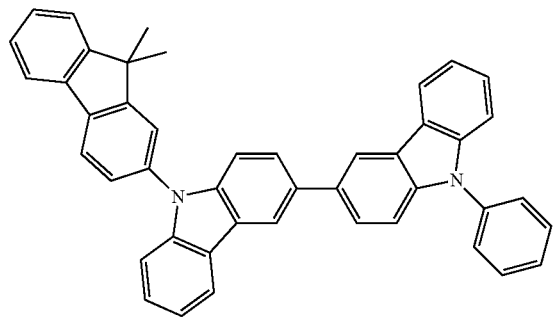
[A-11]
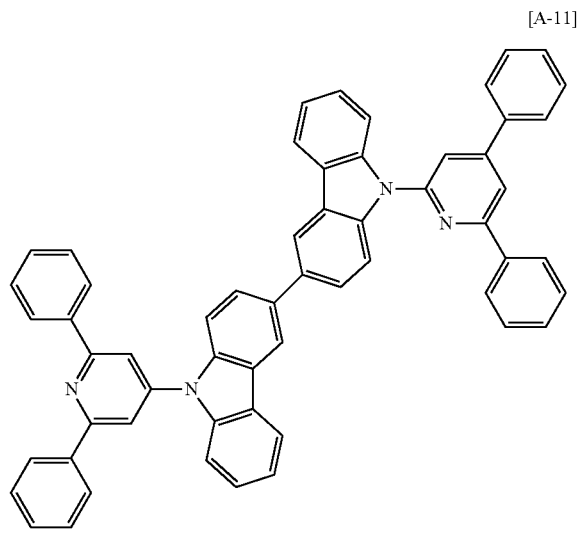
[A-14]
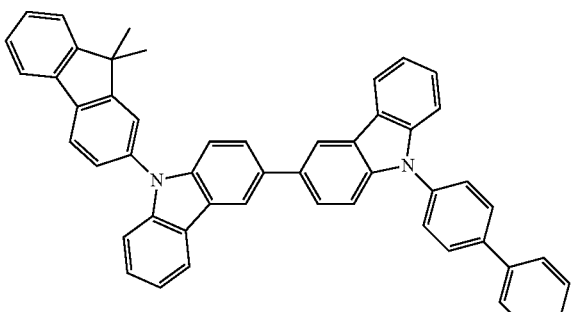
[A-15]
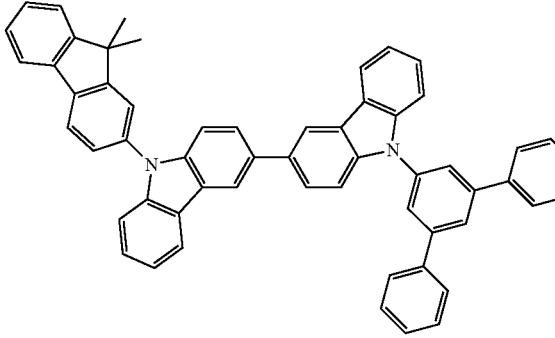
[A-12]
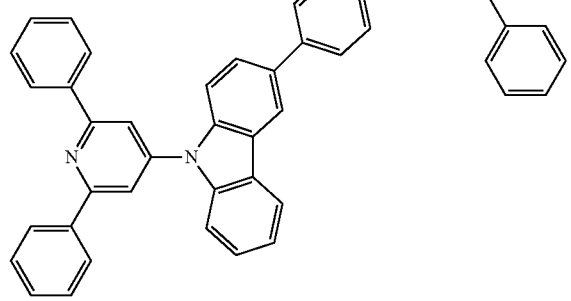
[A-16]
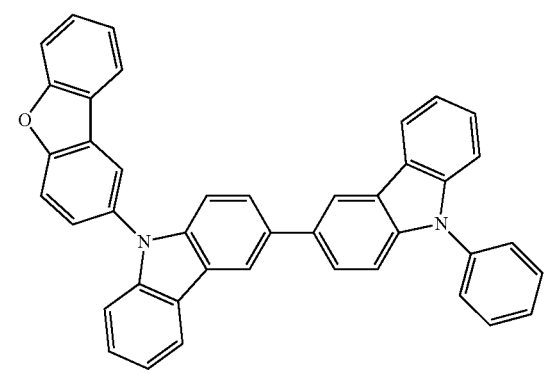

[A-17]
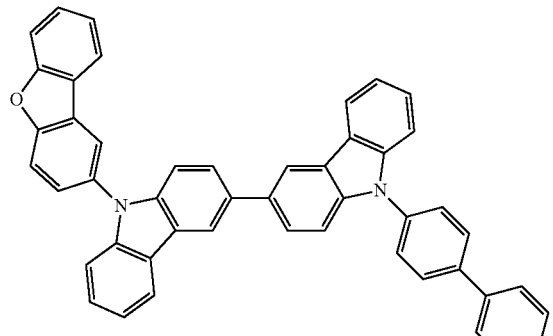
[A-18]
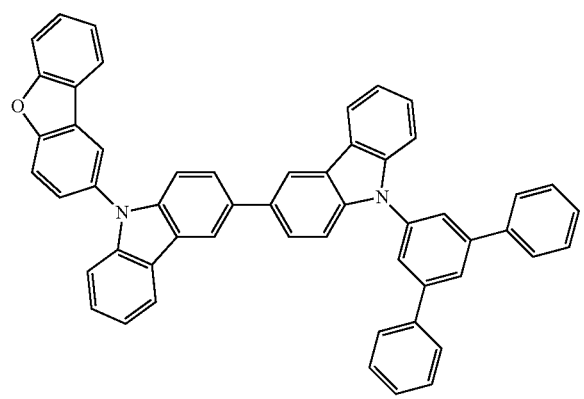
[A-19]
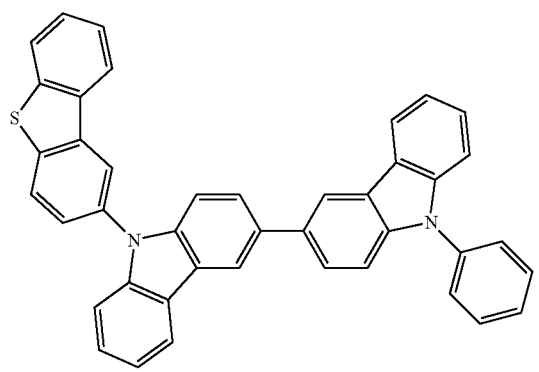
[A-20]
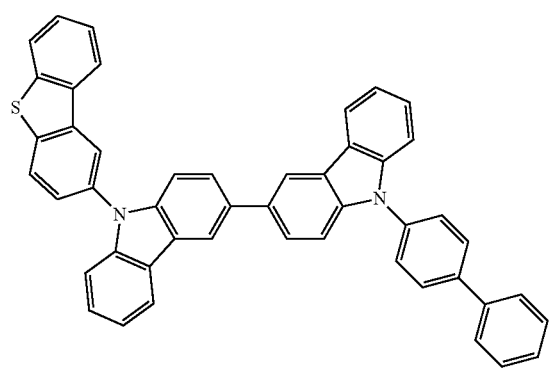
[A-21]
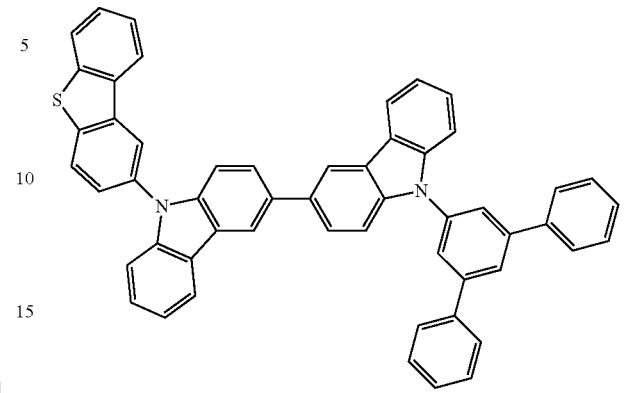
[A-22]
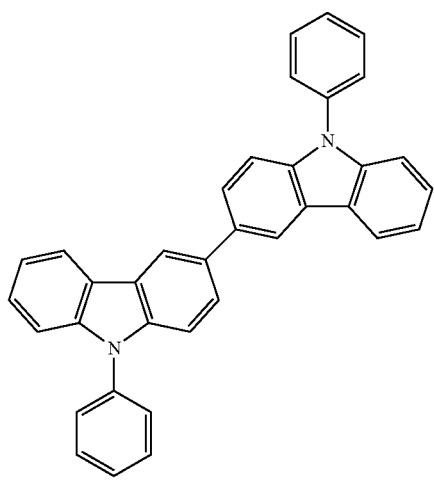
[A-23]
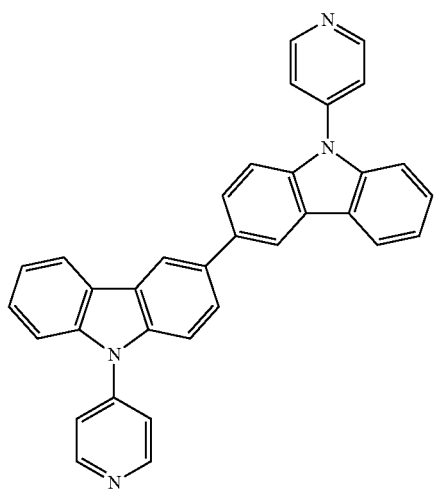

[A-24]
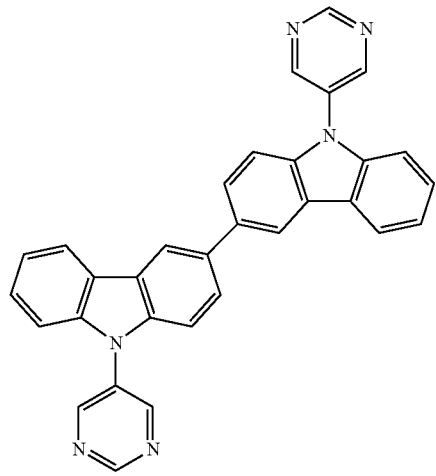
[A-25]
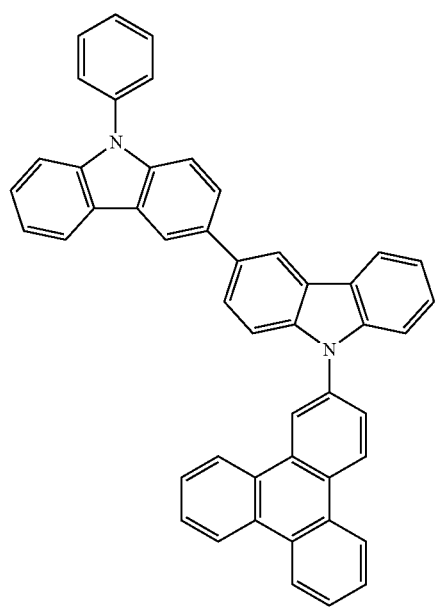
[A-26]
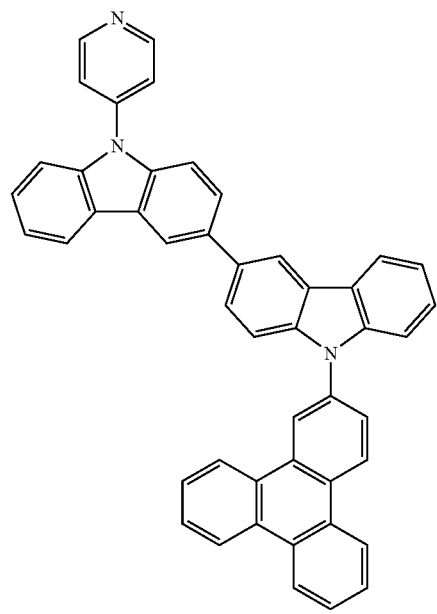
[A-27]
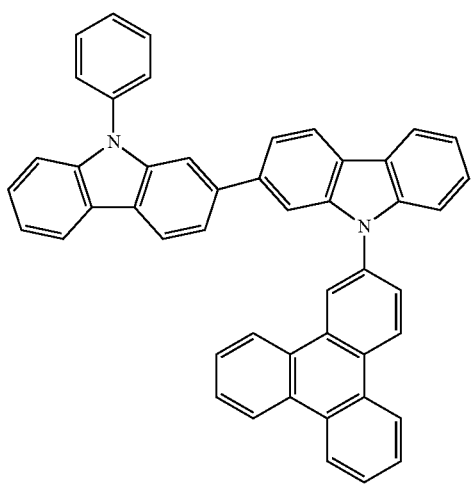
[A-28]
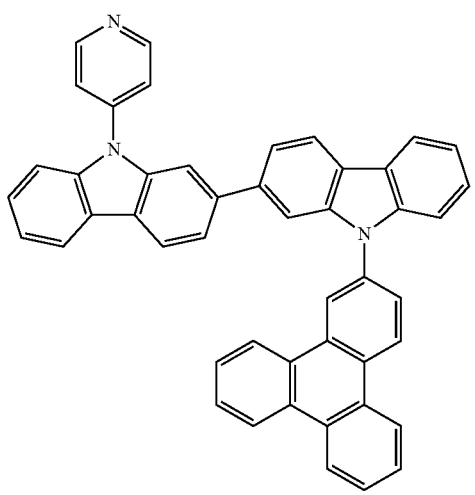

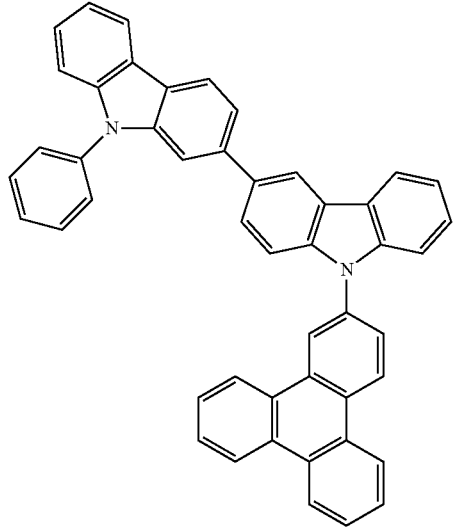
[A-29]
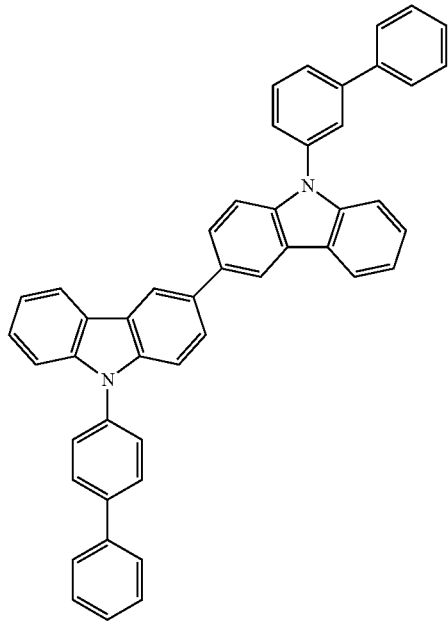
[A-31]
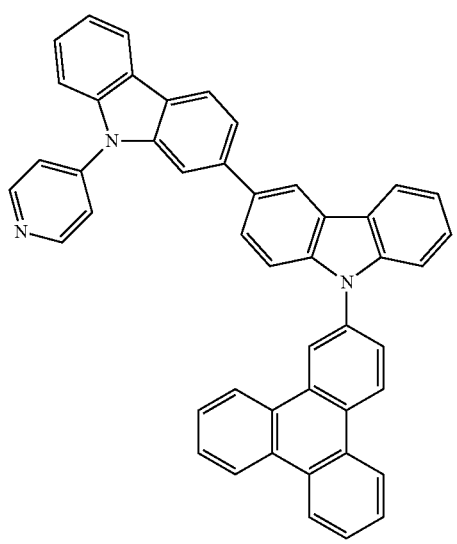
[A-30]
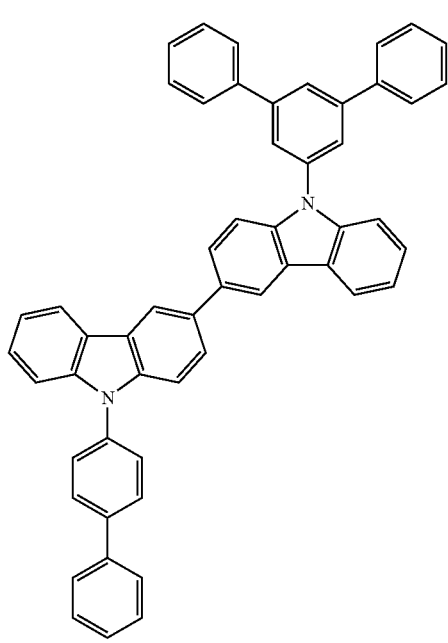
[A-32]

[A-33]
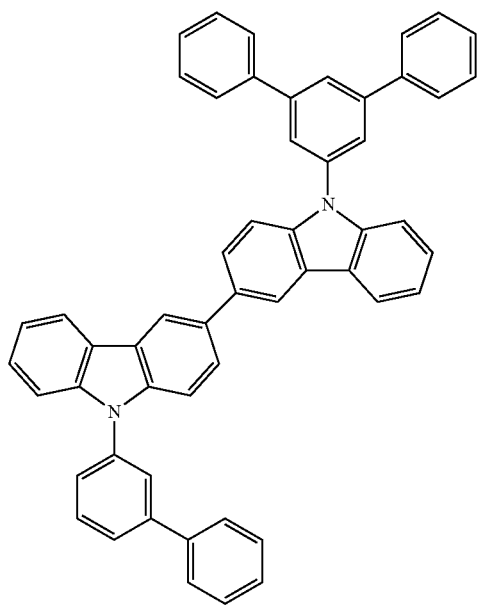
[A-35]
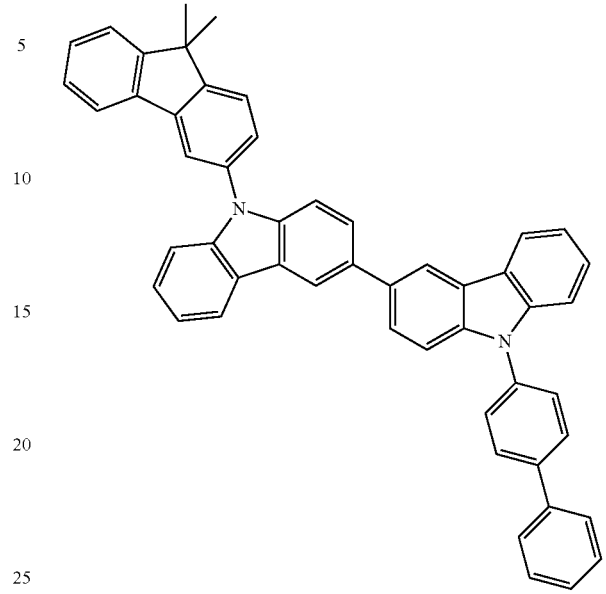
[A-36]
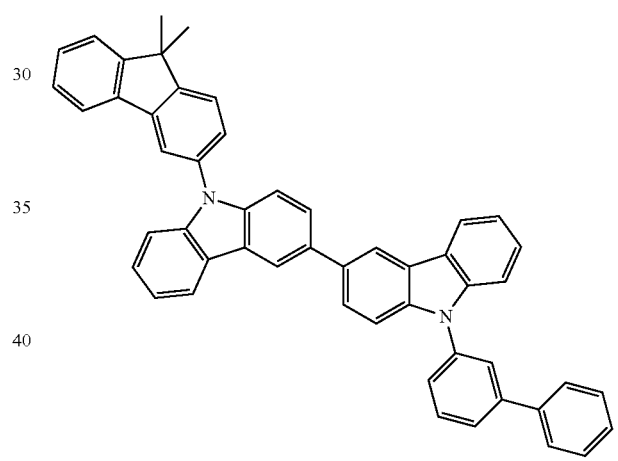
[A-34]
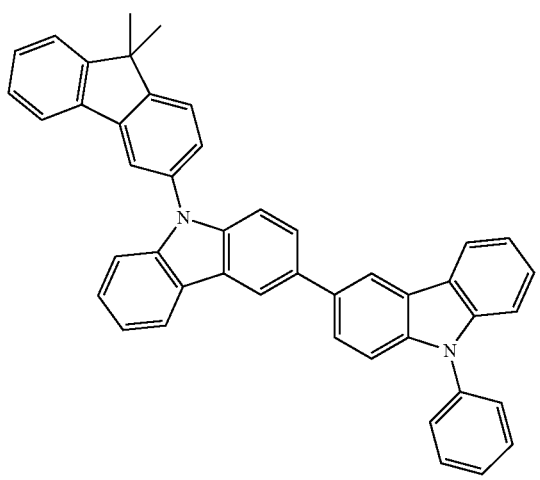
[A-37]

-continued
[A-38]
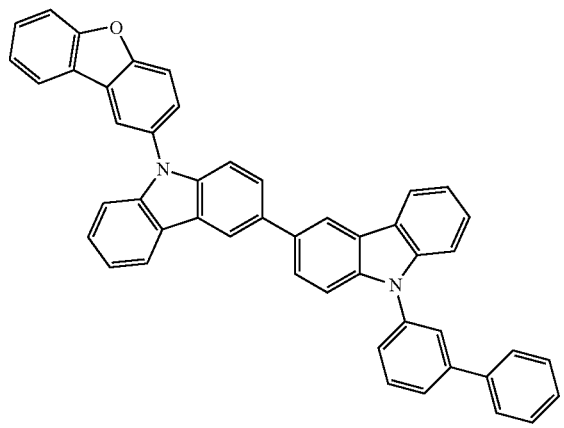
[A-39]
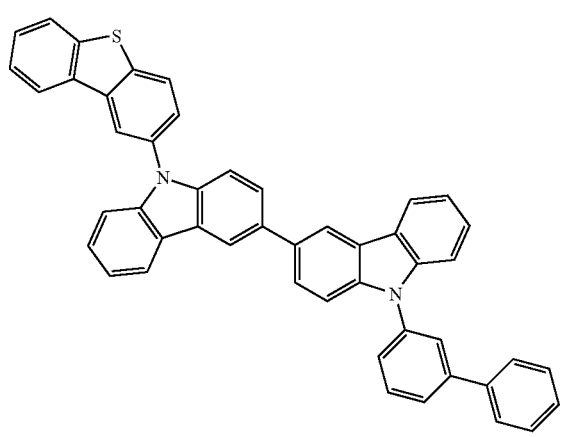
[A-40]
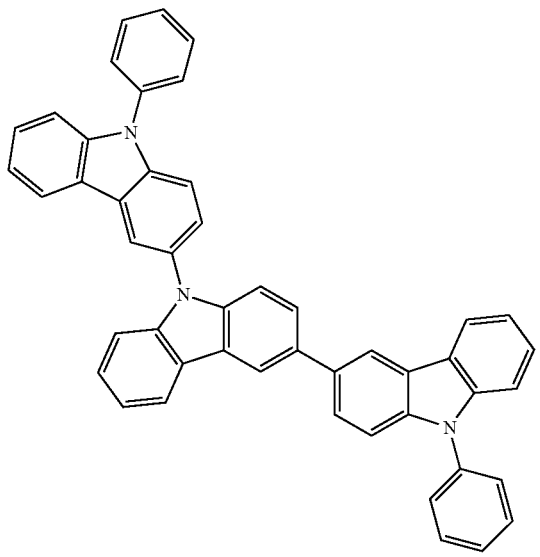
-continued
[A-41]
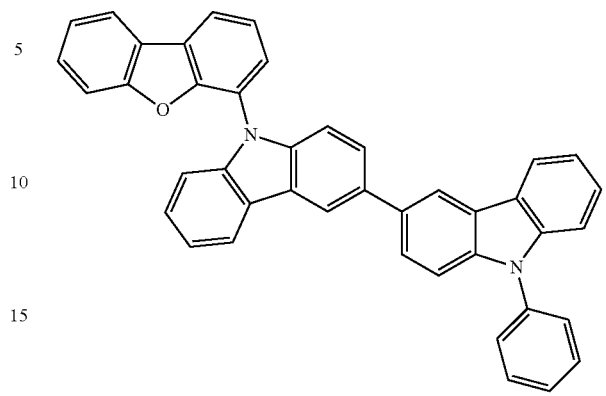
[A-42]
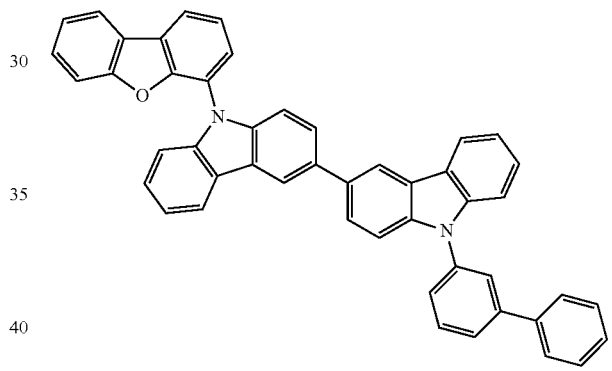
[A-43]
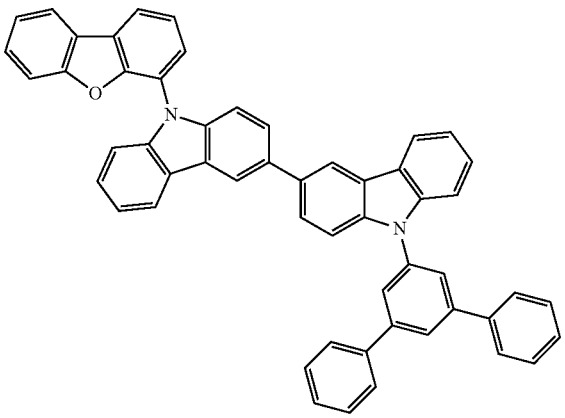

[A-44]
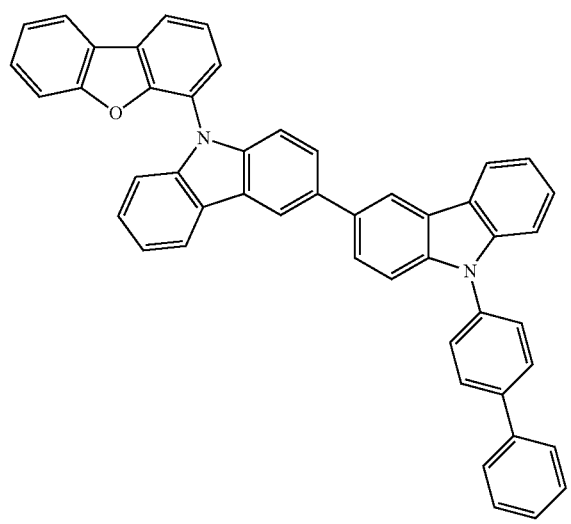
[A-45]
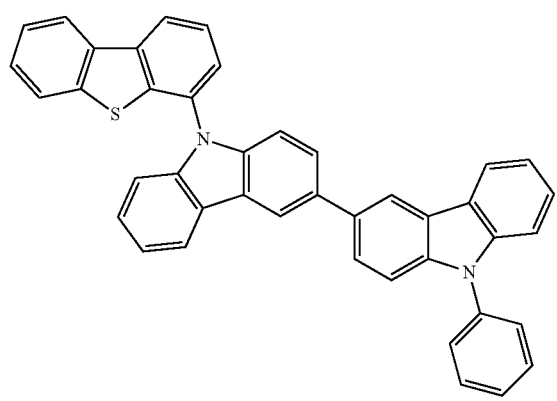
[A-46]
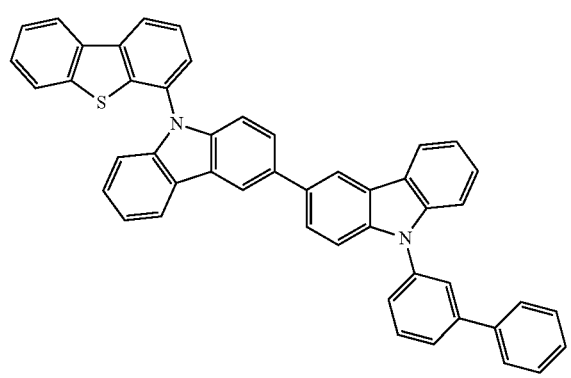
[A-47]
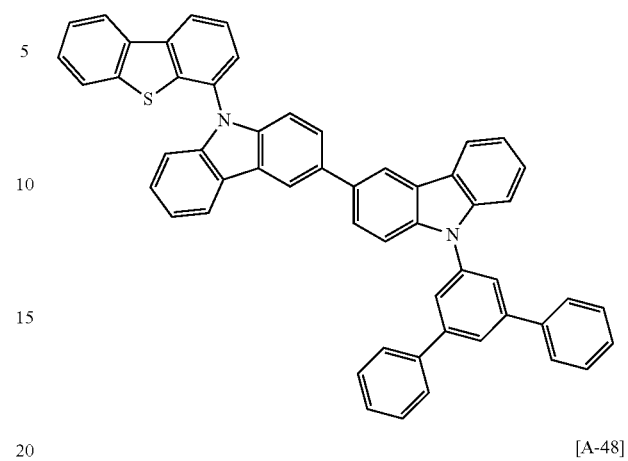
[A-48]
[A-49]
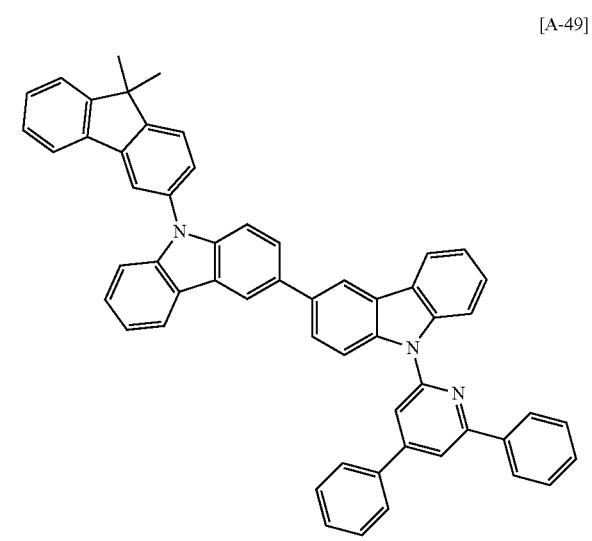

[A-50]
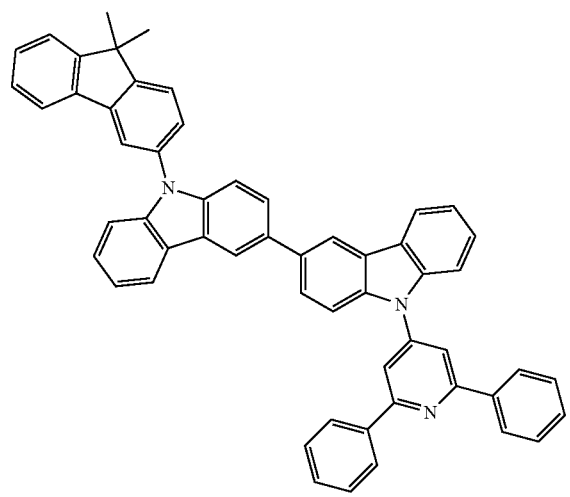
[A-51]
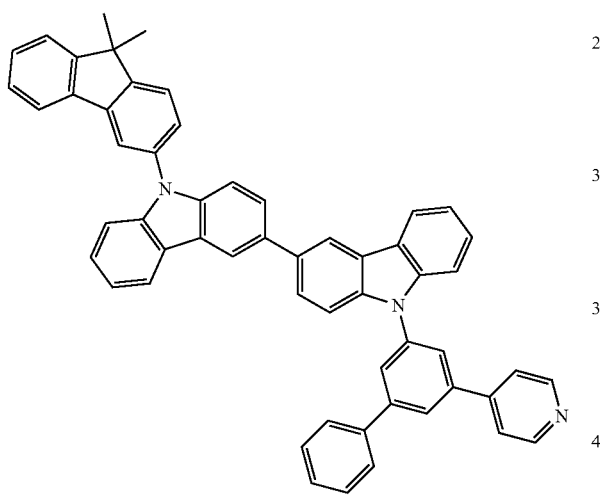
[A-52]
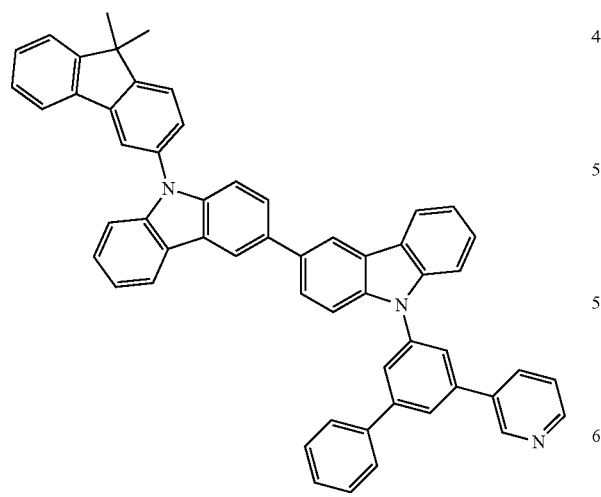
[A-53]
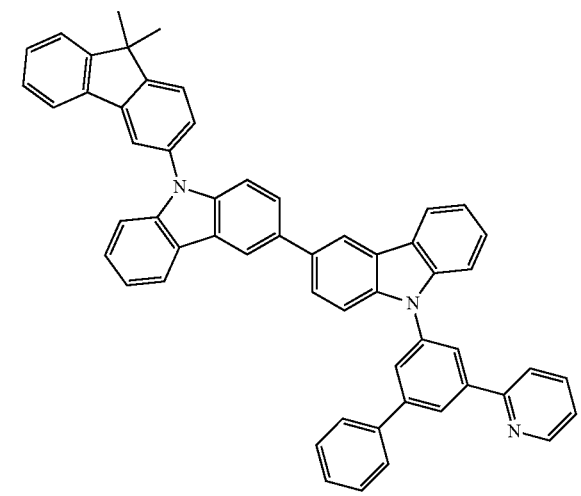
[A-54]
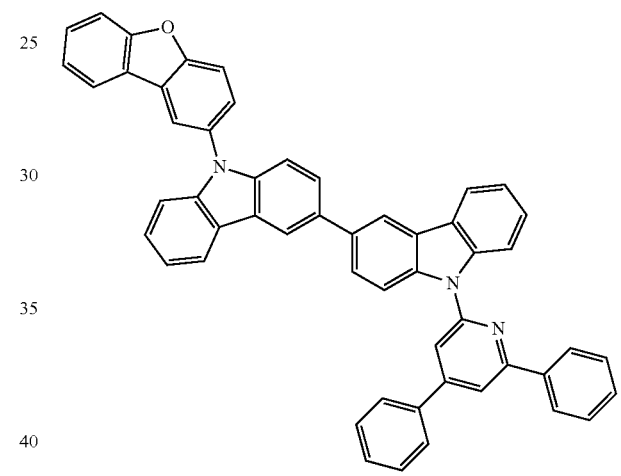
[A-55]
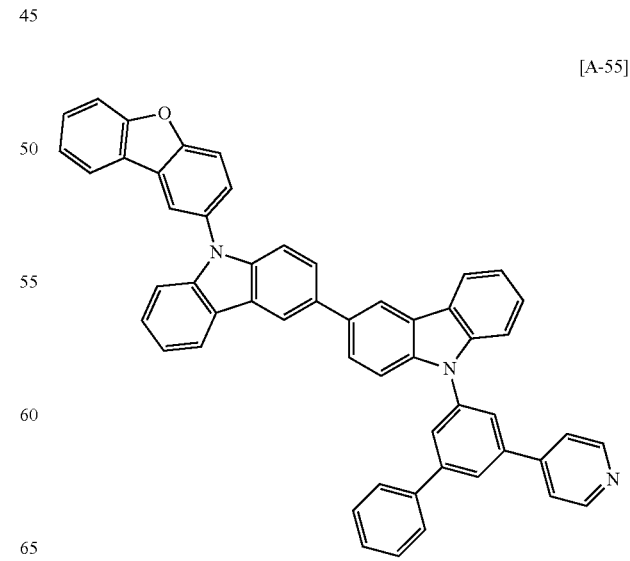

[A-56]
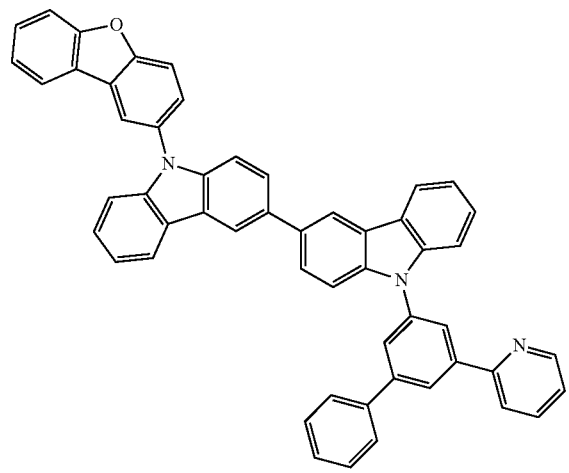
[A-57]
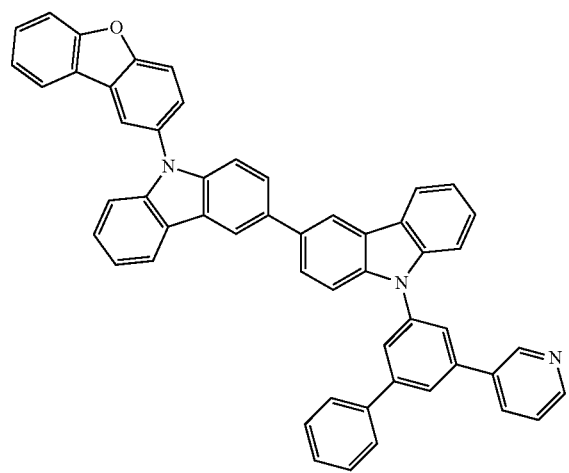
[A-58]
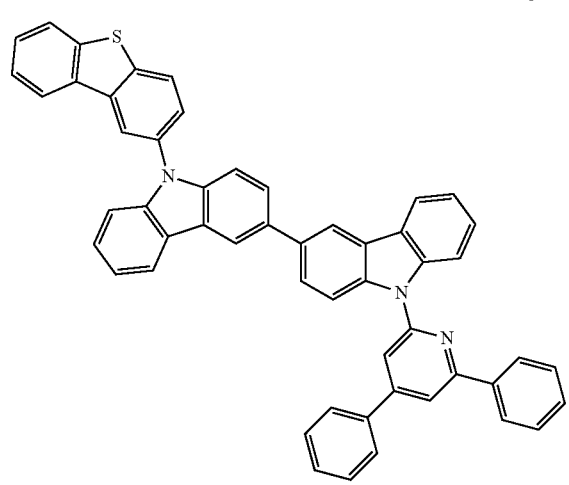
[A-59]
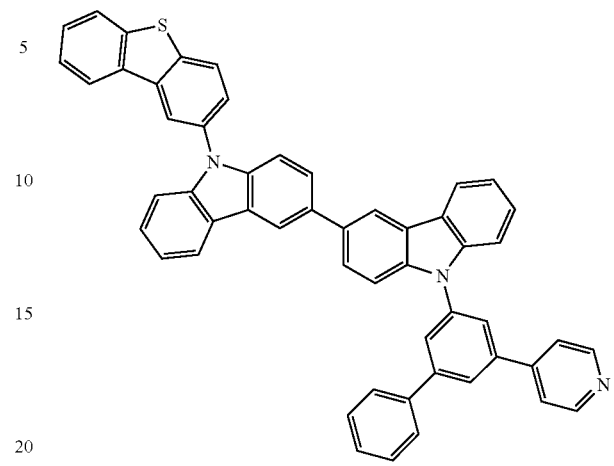
[A-60]
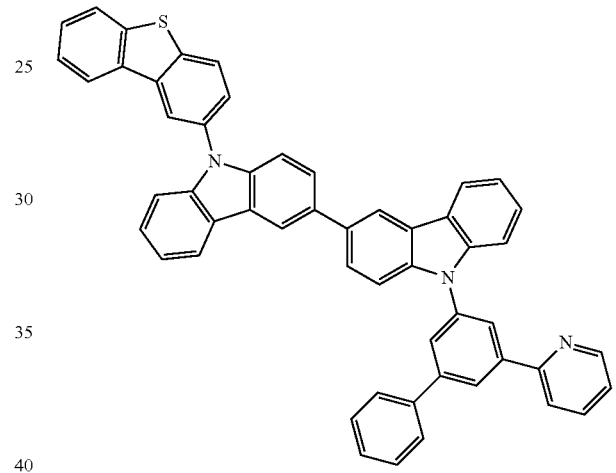
[A-61]
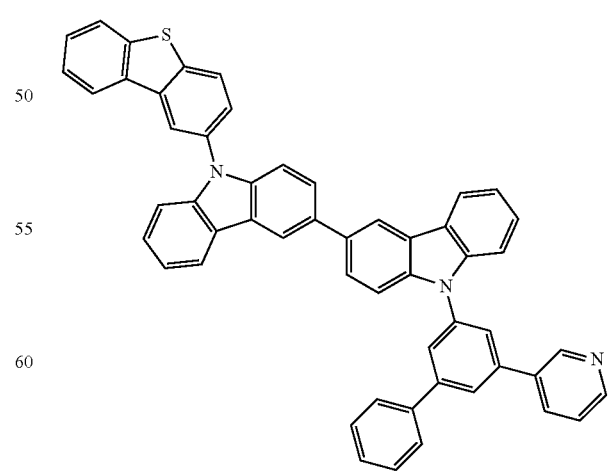

[A-62]
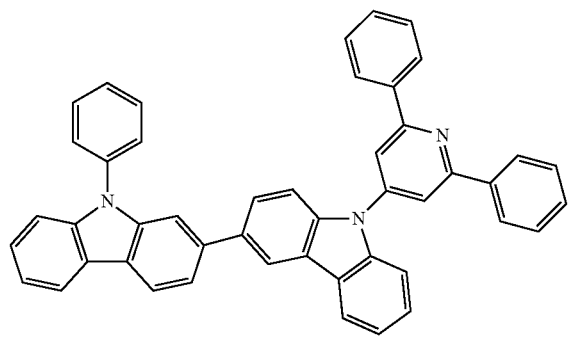
[A-66]
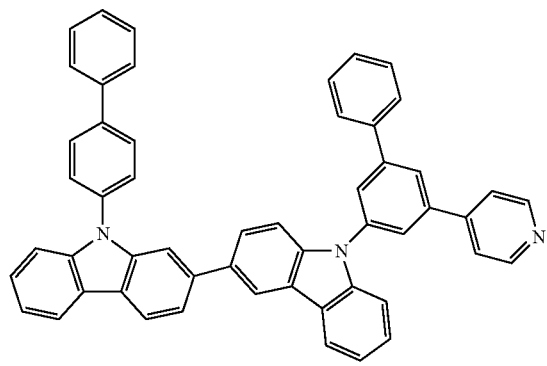
[A-63]
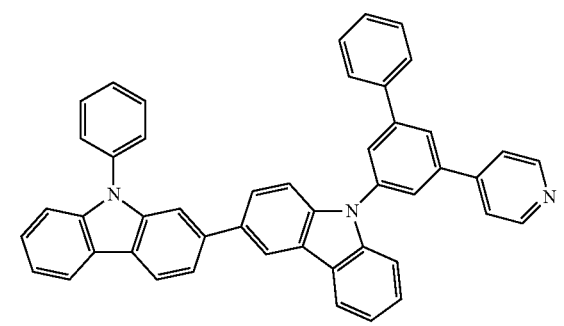
[A-67]
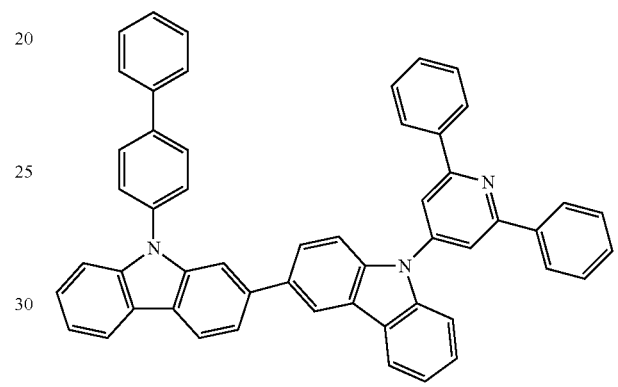
[A-64]
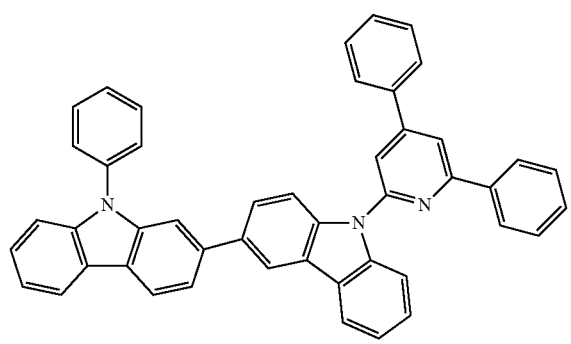
[A-68]
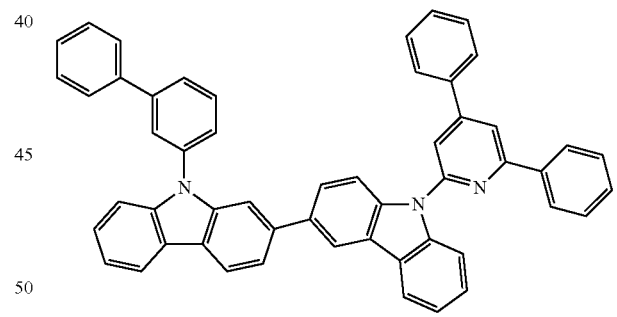
[A-65]
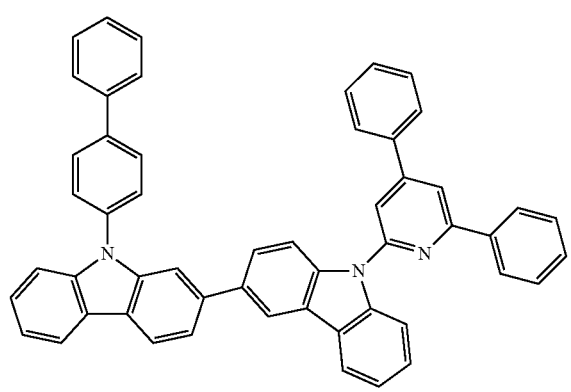
[A-69]
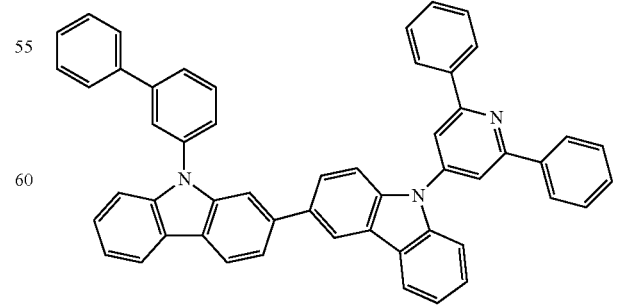

[A-70]
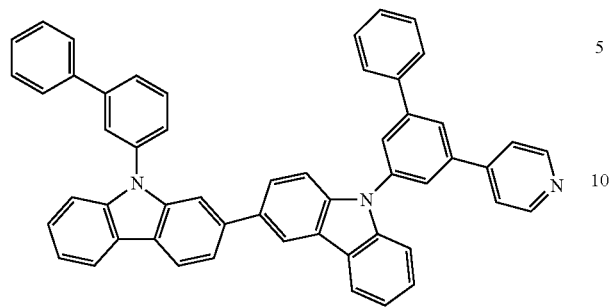
[A-71]
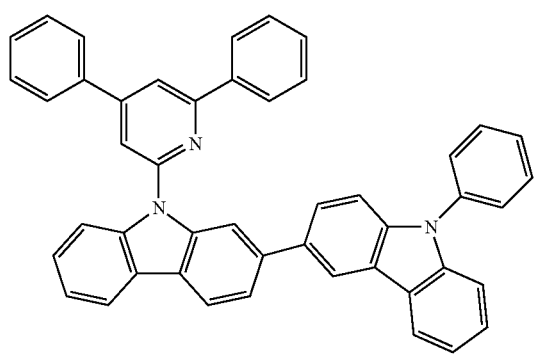
[A-72]
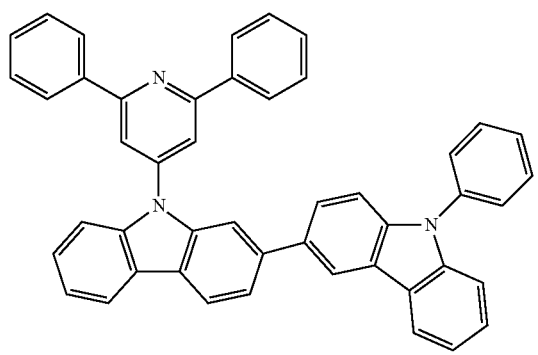
[A-73]
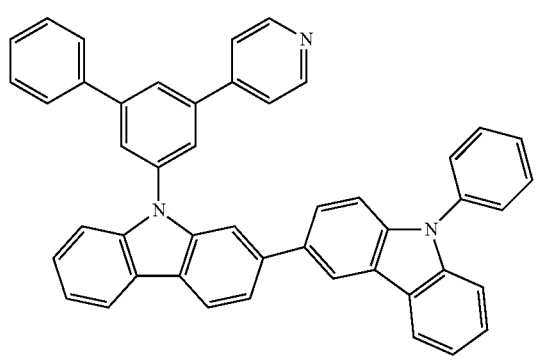
[A-74]
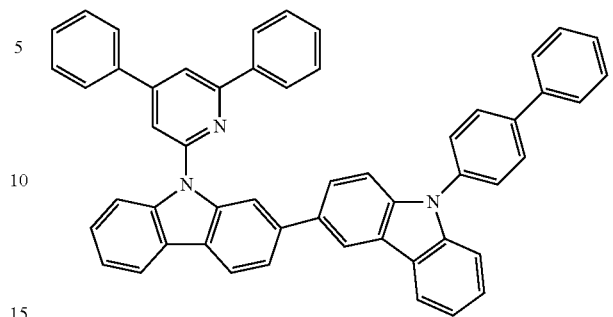
[A-75]
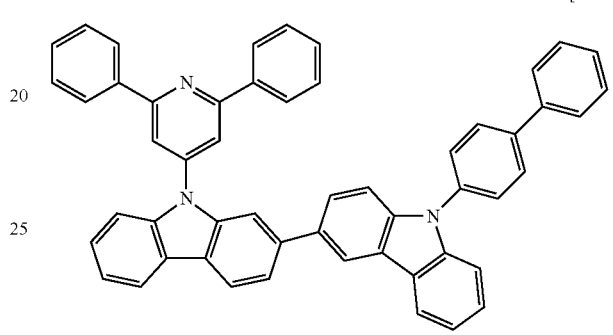
[A-76]
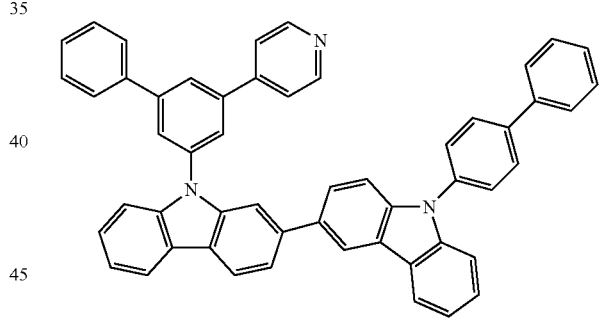
[A-77]
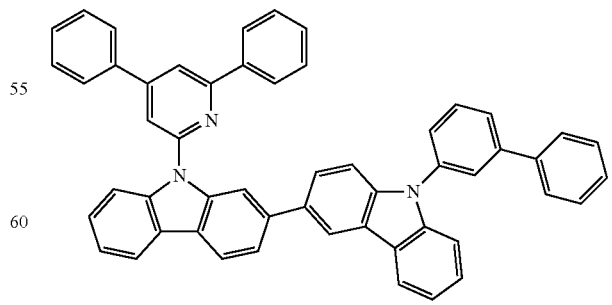

[A-78]
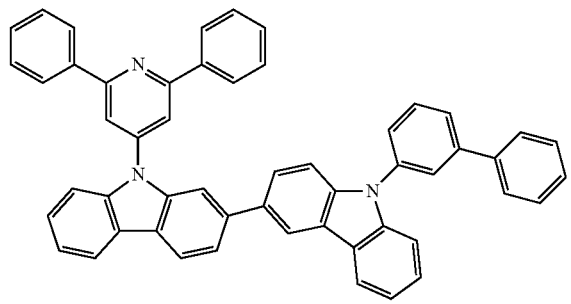
[A-79]
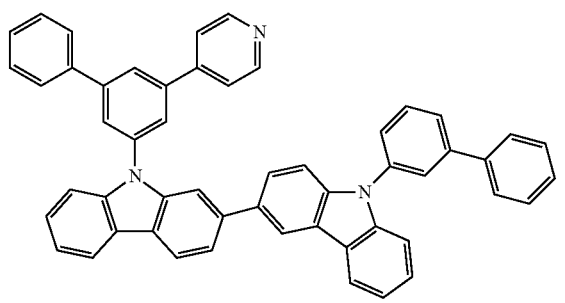
[A-80]
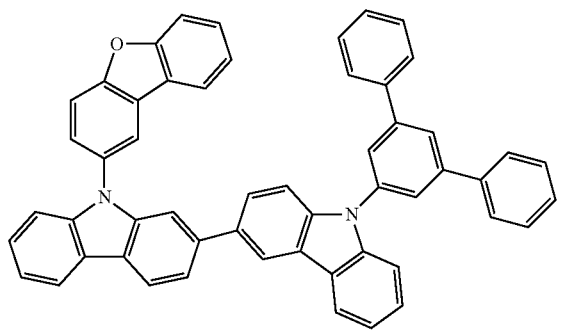
[A-81]
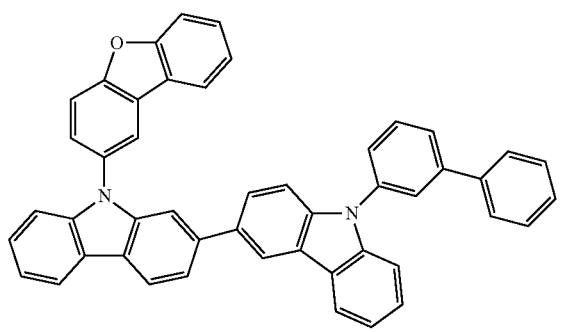
[A-82]
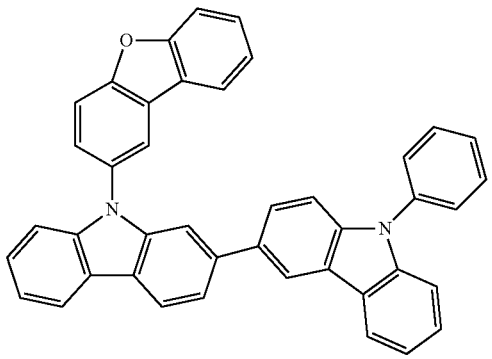
[A-83]
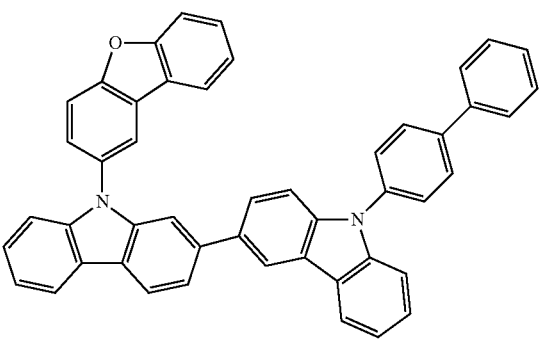
[A-84]
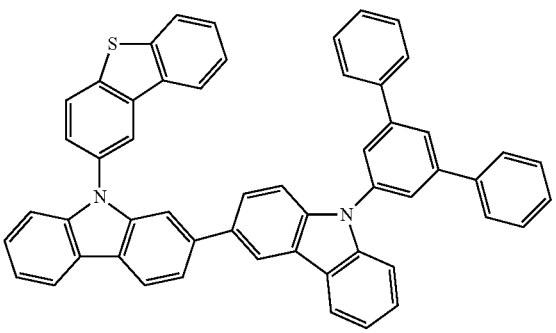
[A-85]
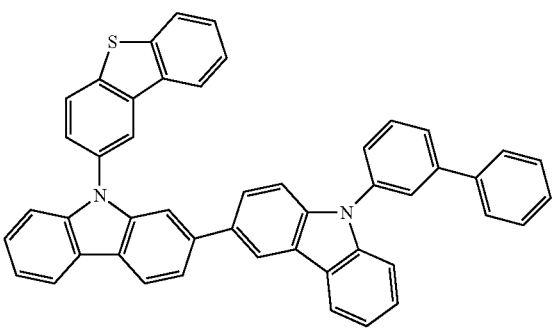

[A-86]
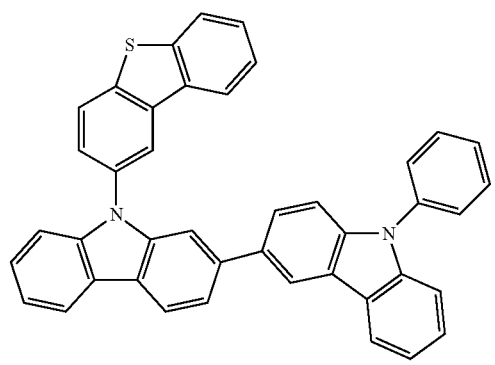
[A-87]
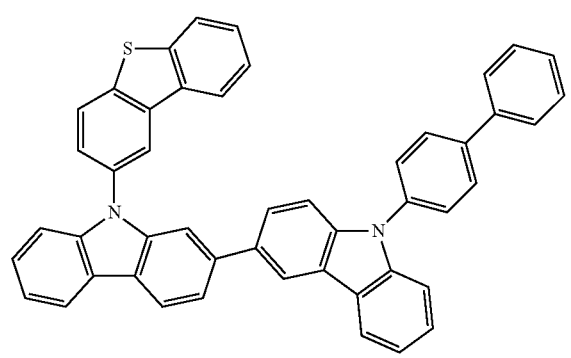
[A-88]
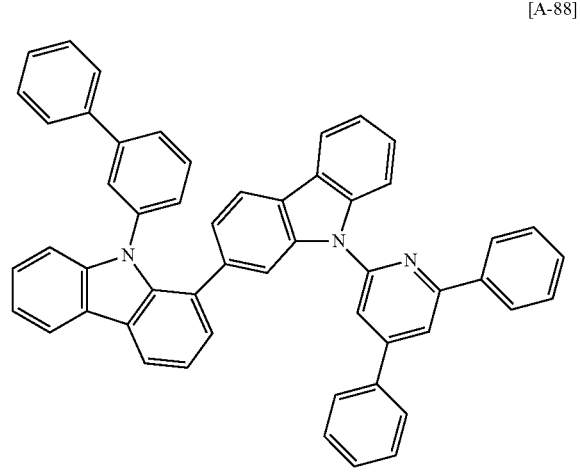
[A-89]
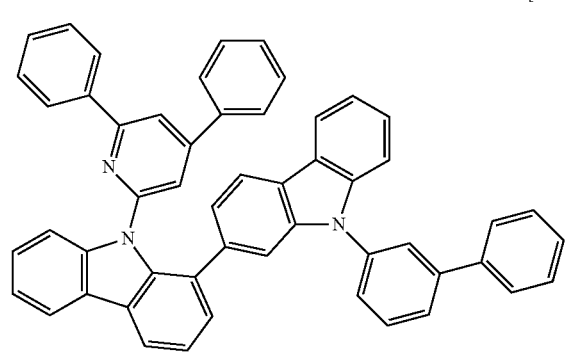
[A-90]
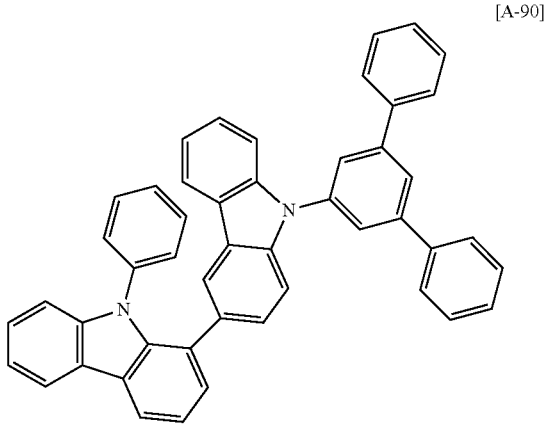
[A-91]
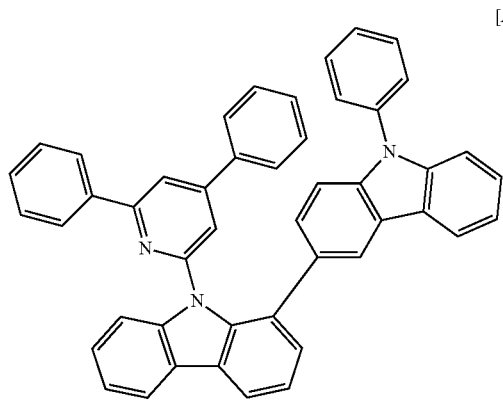
[A-92]
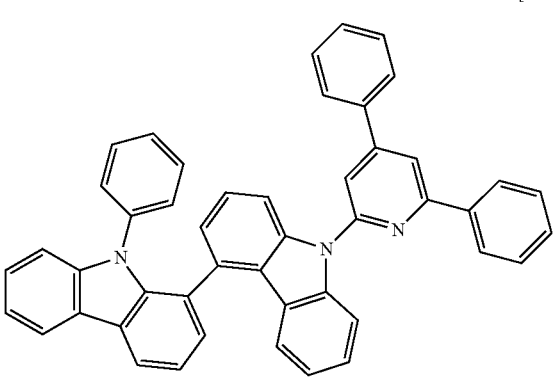
[A-93]
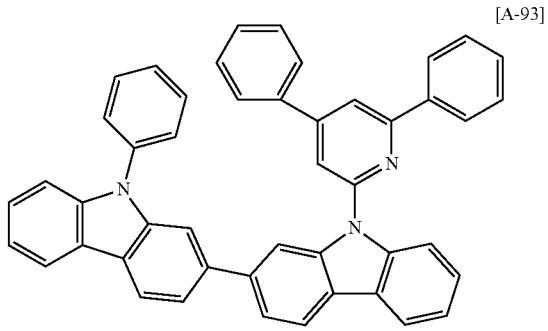

[A-94]
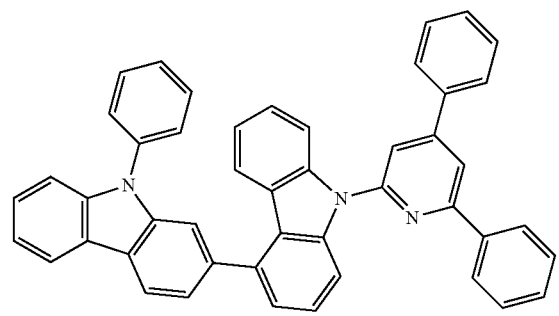
[A-98]
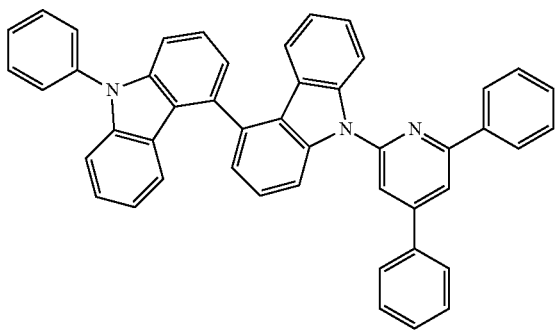
[A-95]
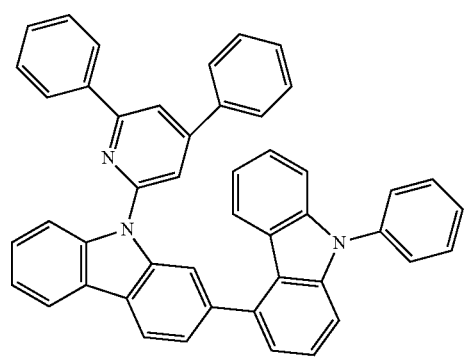
[A-99]
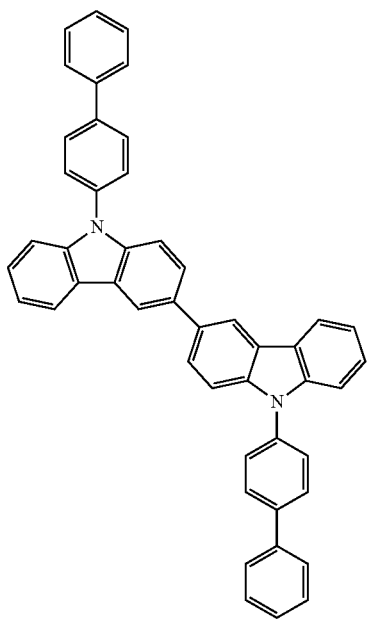
[A-96]
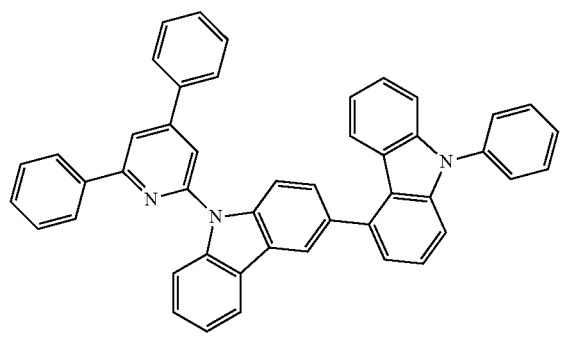
[A-100]
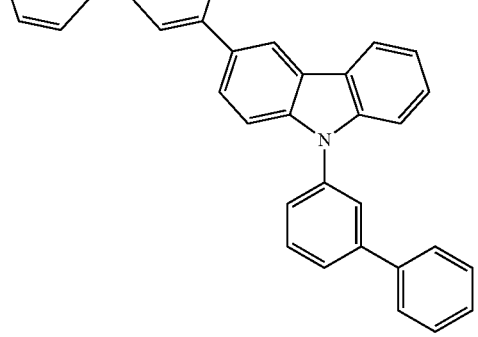
[A-97]
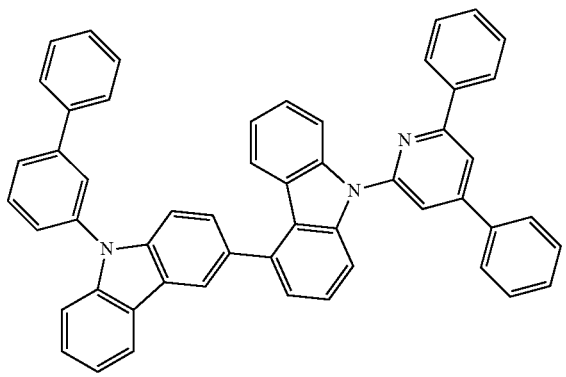

[A-101]
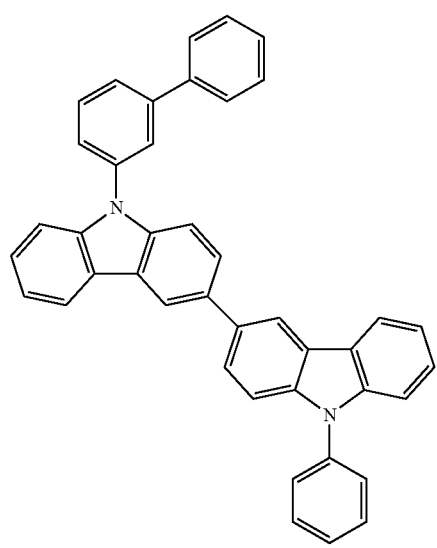
[A-102]
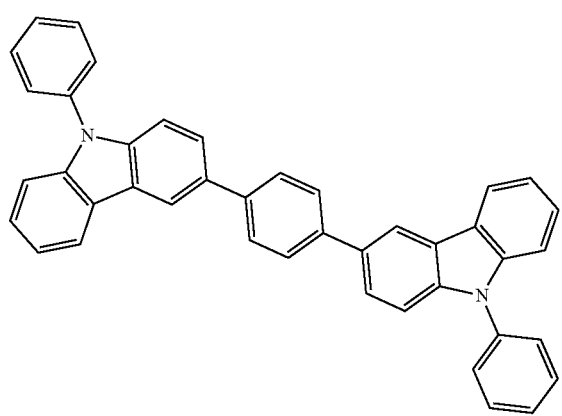
[A-103]
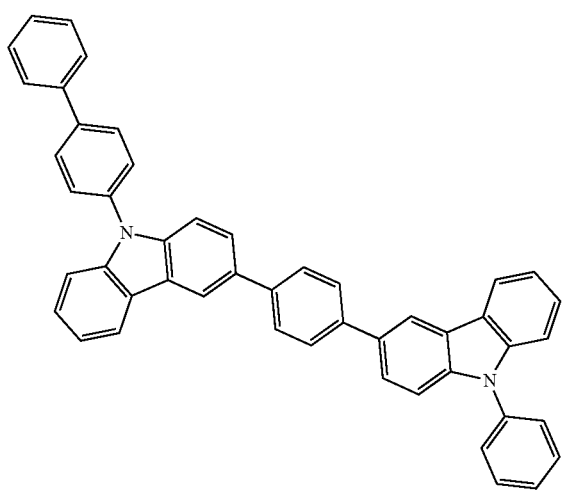
[A-104]
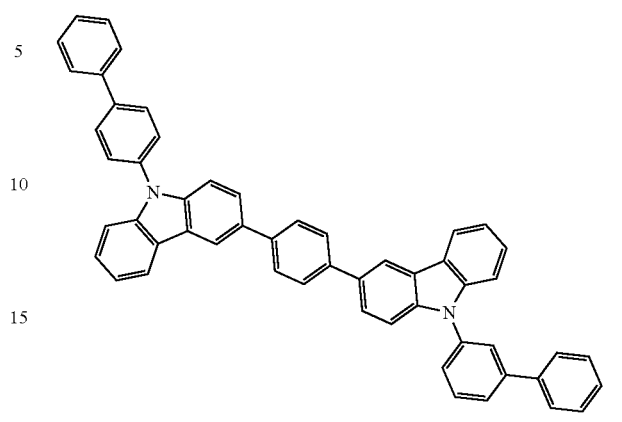
[A-105]
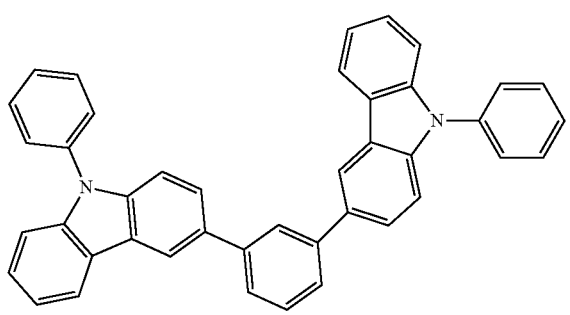
[A-106]
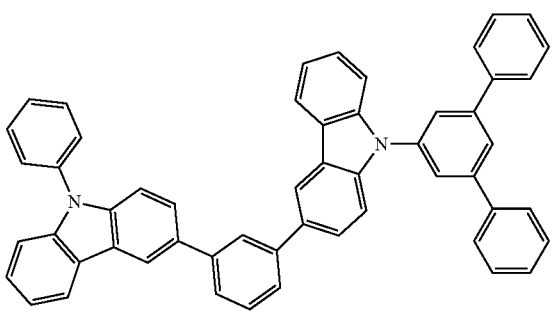
[A-107]
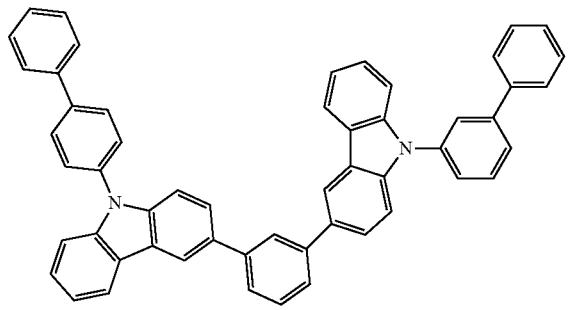

[A-108]
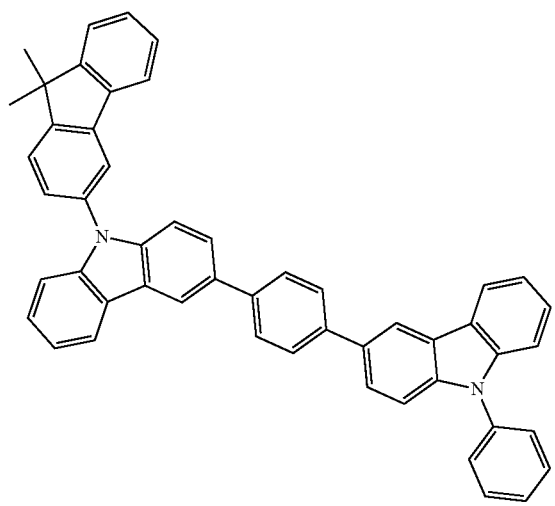
[A-111]
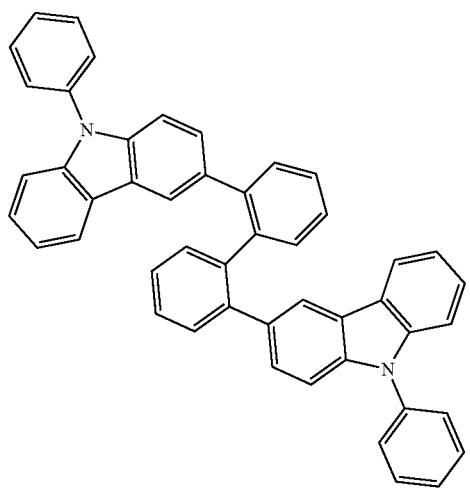
[A-109]
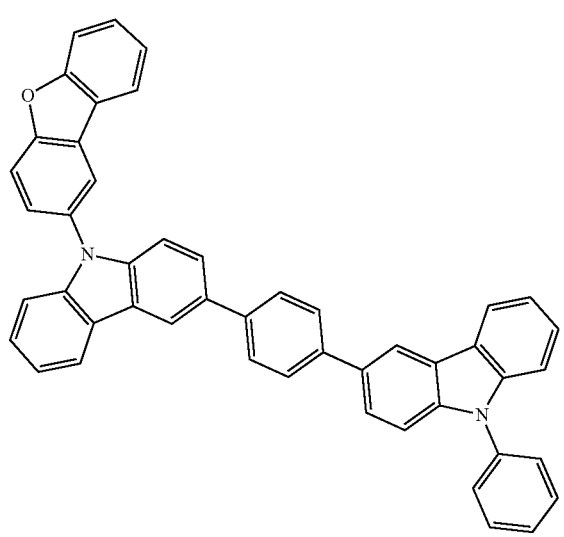
[A-112]
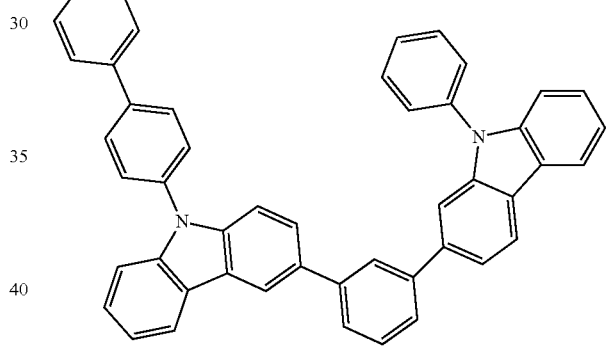
[A-110]
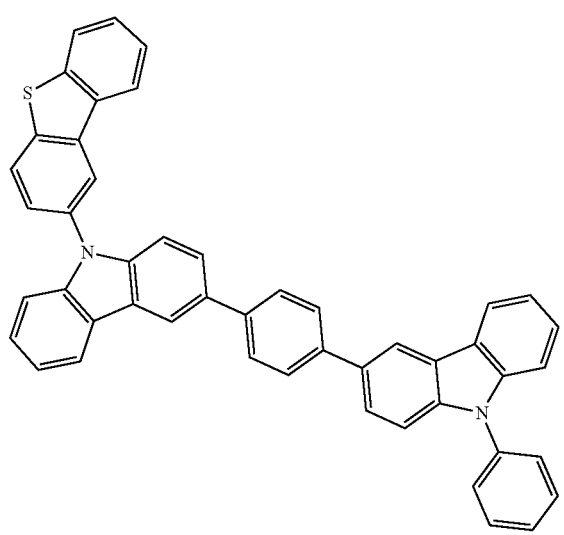
[A-113]
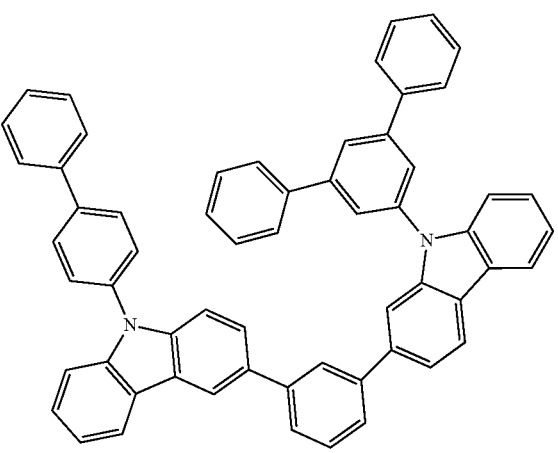

[A-114]
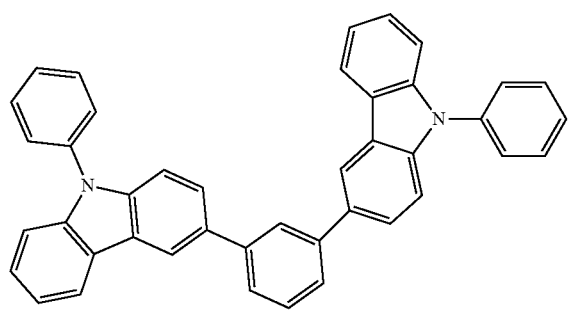
[A-118]
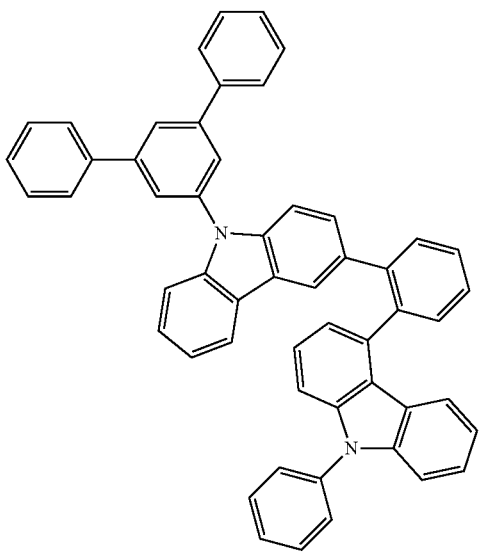
[A-115]
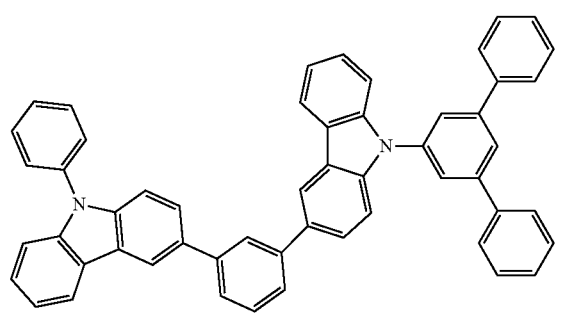
[A-119]
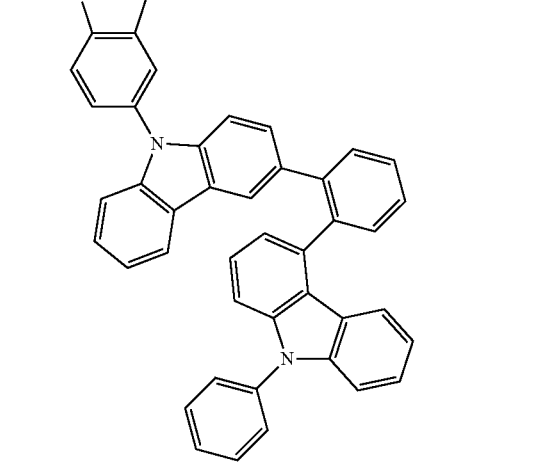
[A-116]
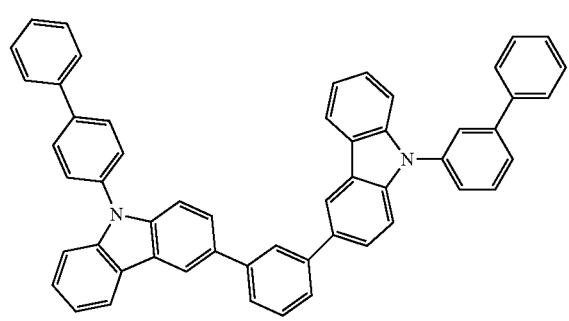
[A-117]
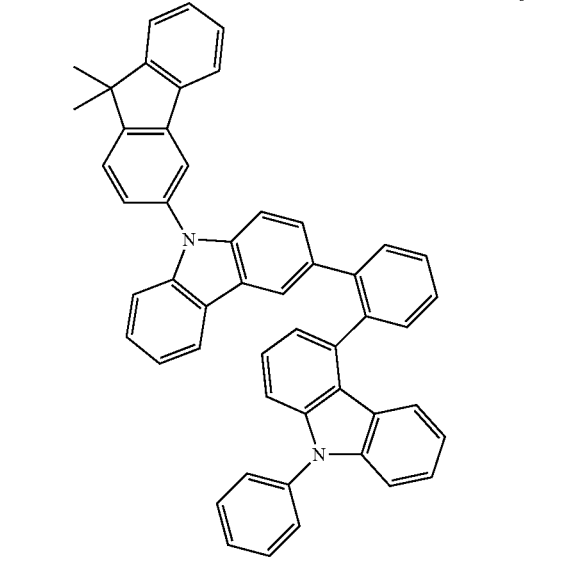
[A-120]
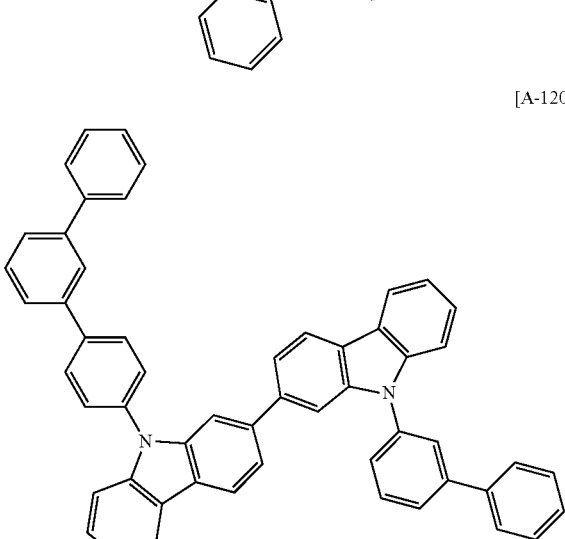

[A-121]
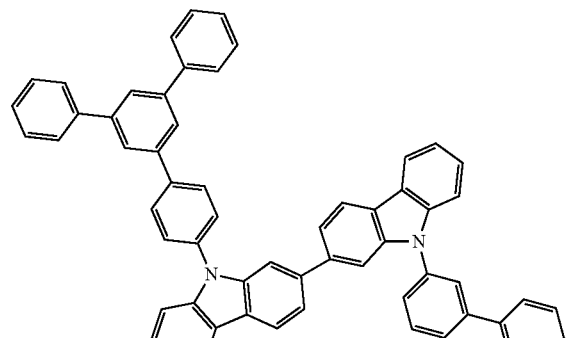
[A-122]
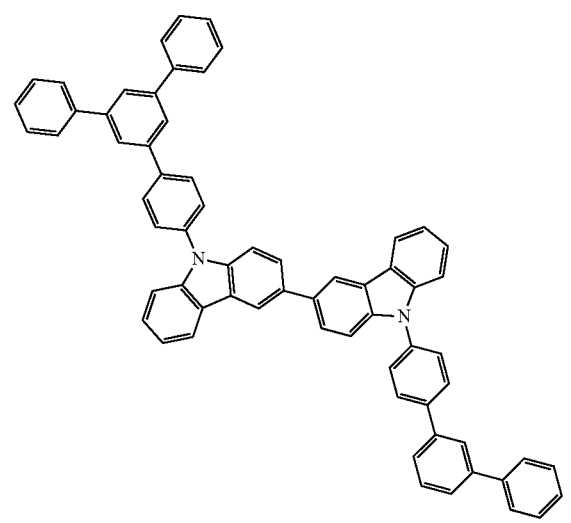
[A-123]
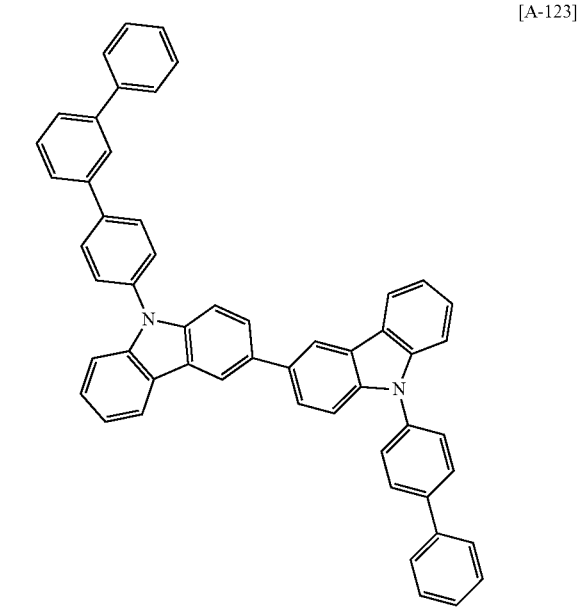
[A-124]
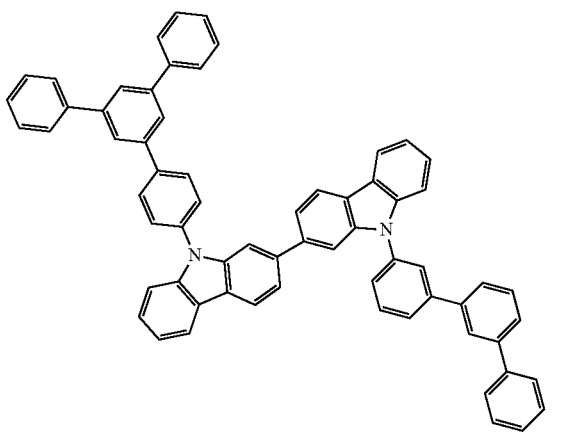
[A-125]
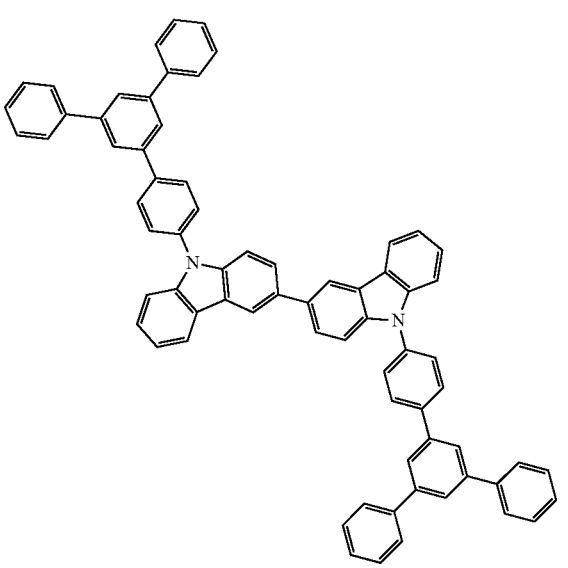
[A-126]
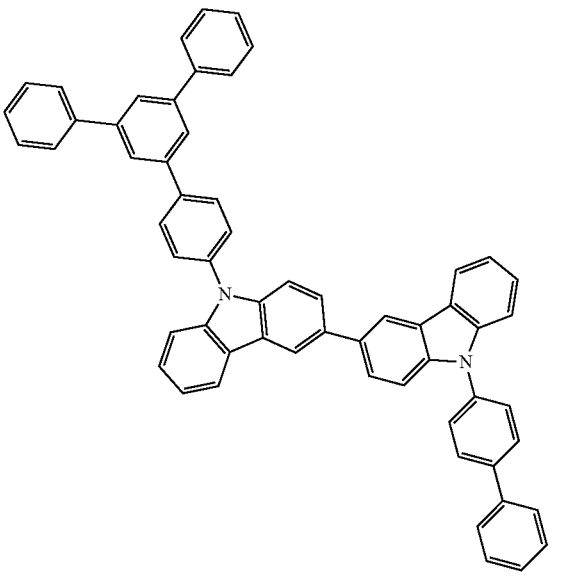

[A-127]
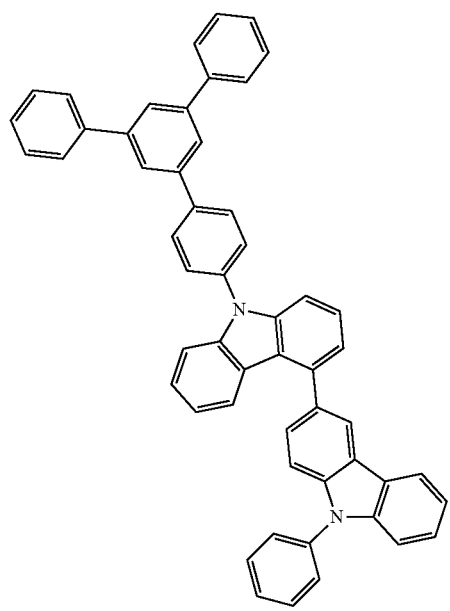
[A-128]
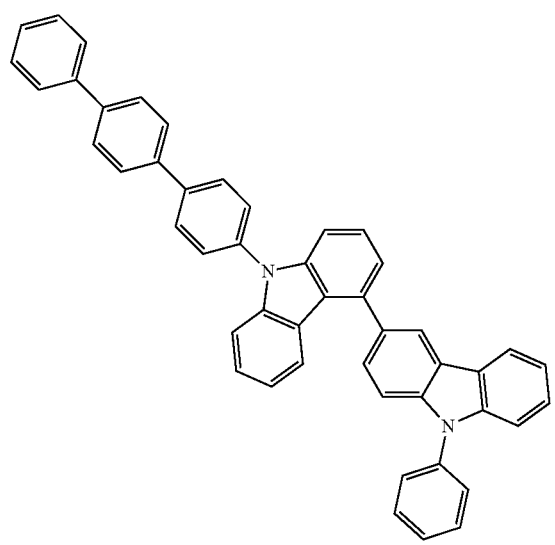
[A-129]
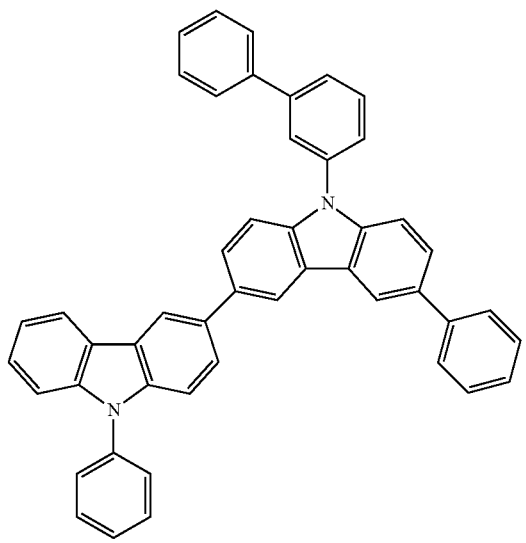
[A-130]
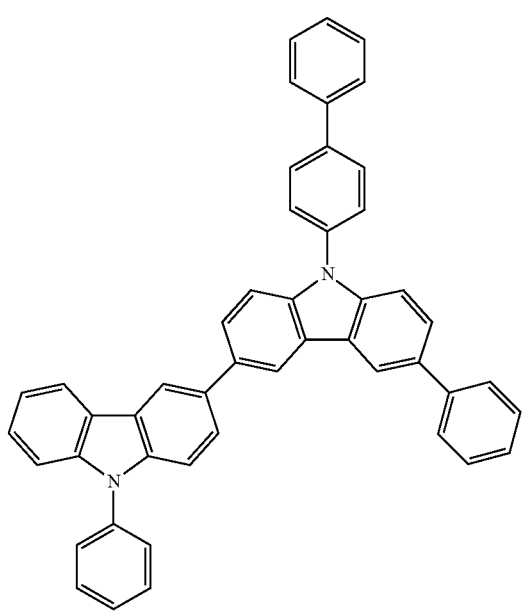

[A-131]
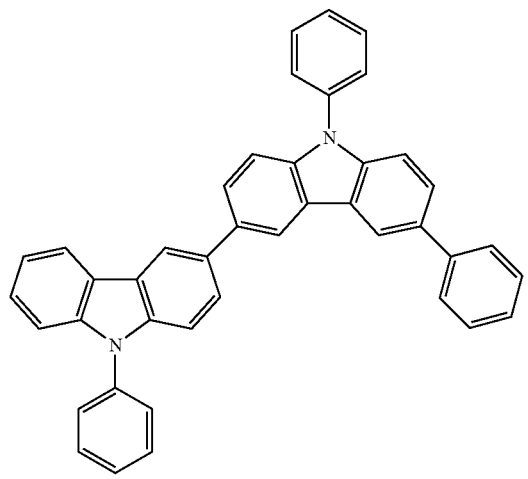
[A-132]
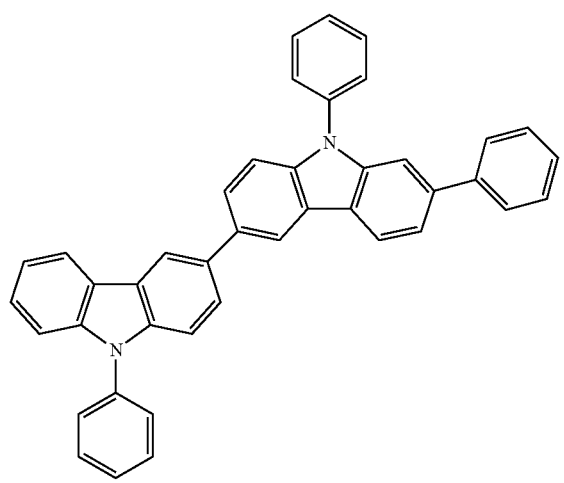
[A-133]
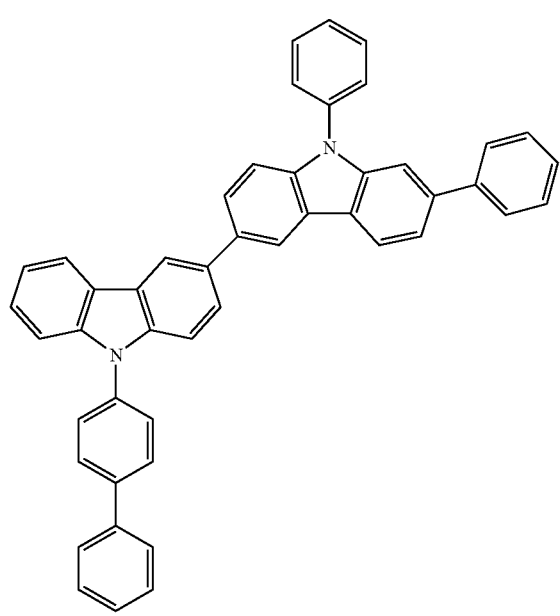
[A-134]
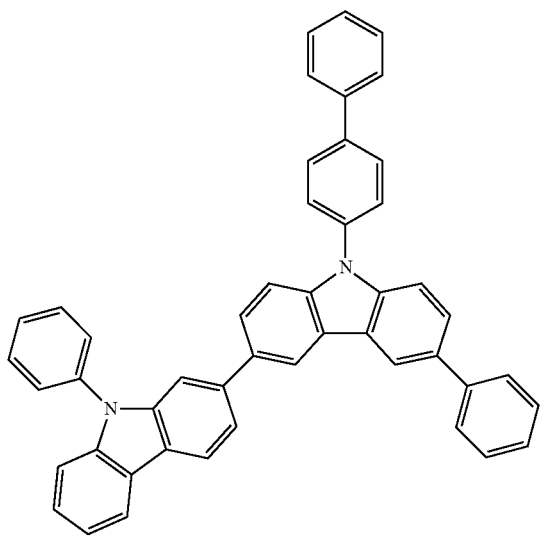
[A-135]
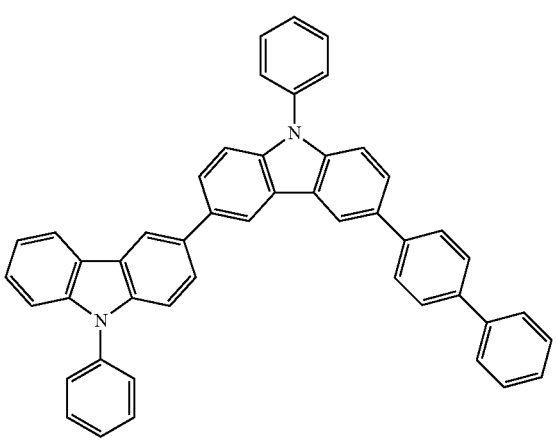
[A-136]

[A-137]
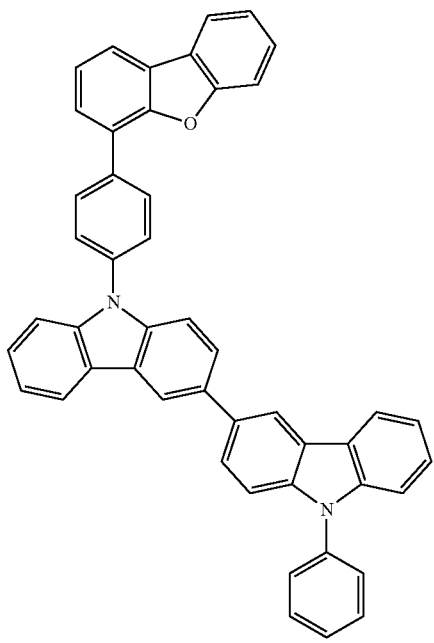
[A-138]
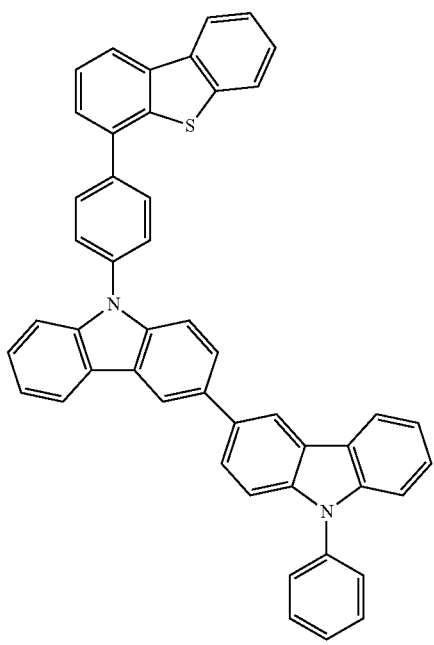
[B-1]
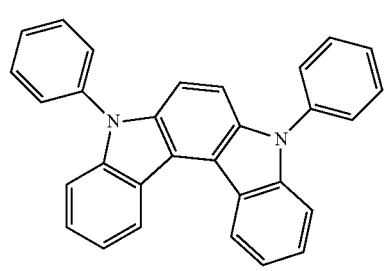
[B-2]
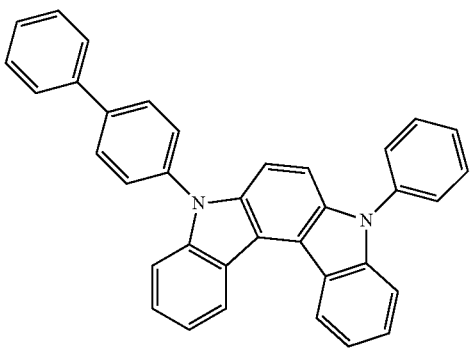
[B-3]
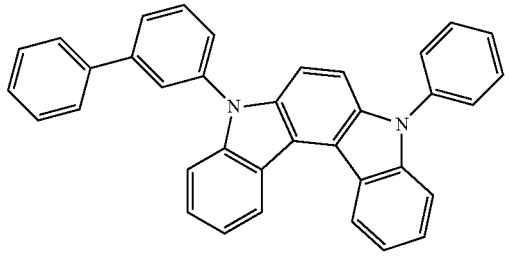
[B-4]
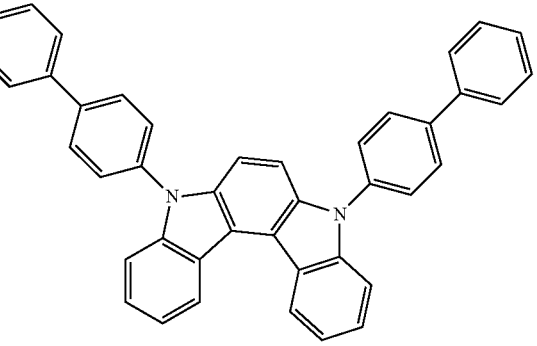
[B-5]
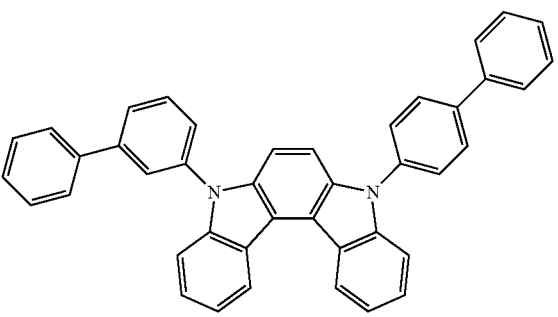

-continued
[B-6]
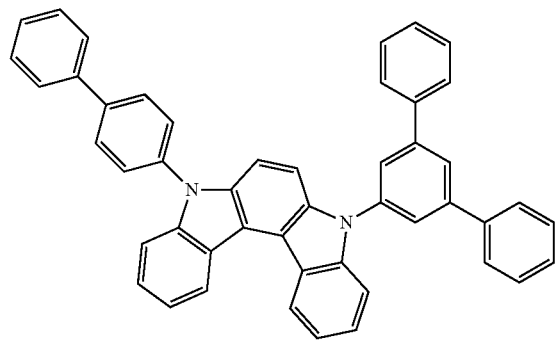
[B-7]
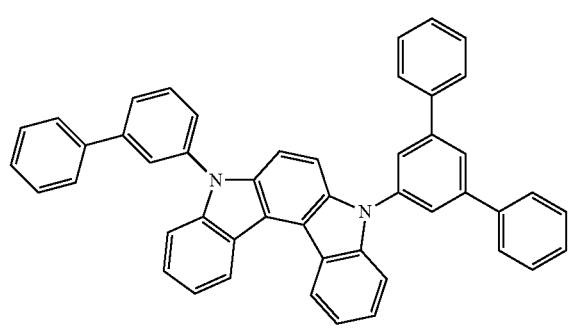
[B-8]
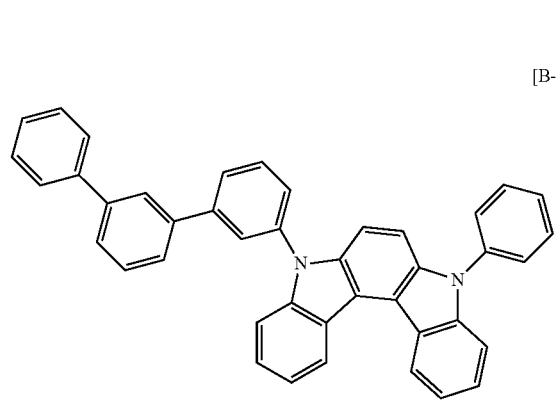
[B-9]
-continued
[B-10]
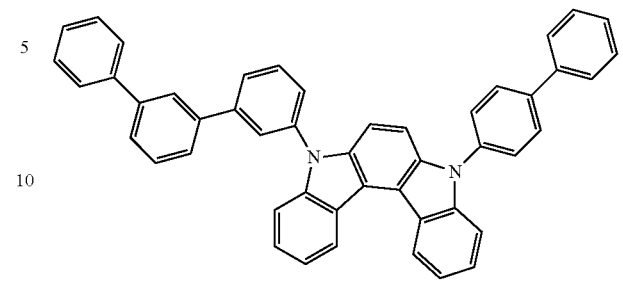
[B-11]
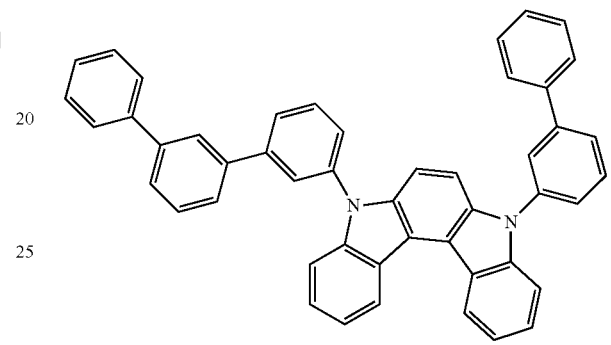
[B-12]
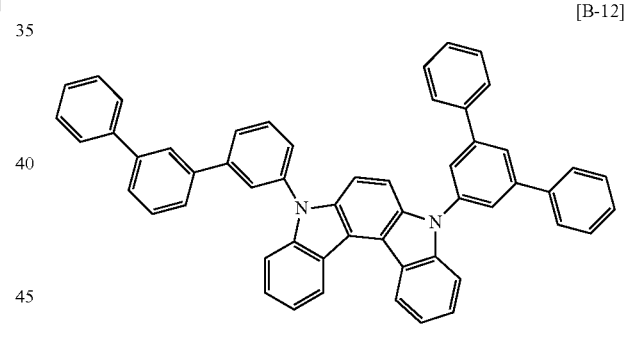
[B-13]
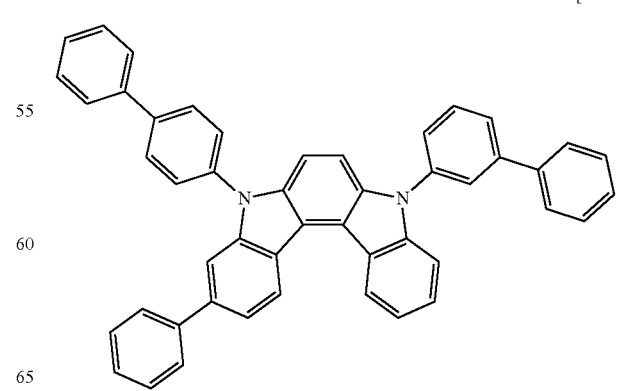

[B-14]
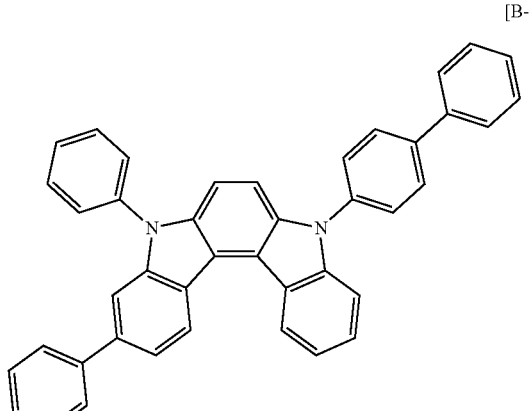
[B-17]
[B-15]
[B-18]
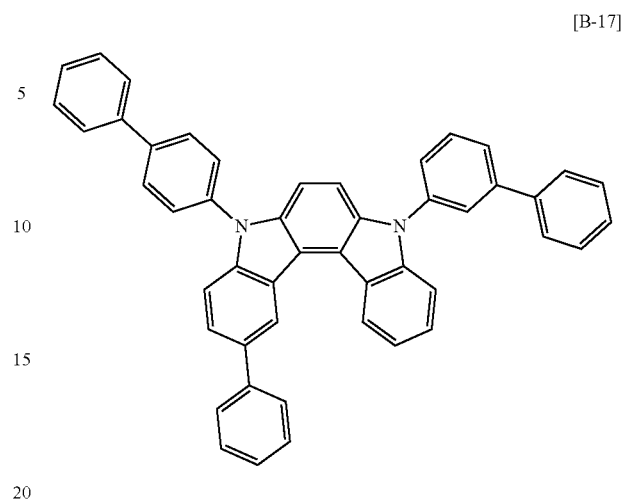
[B-16]
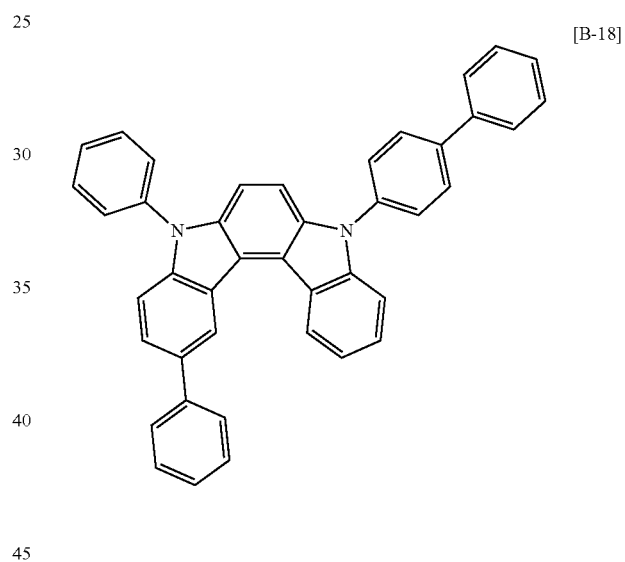
[B-19]
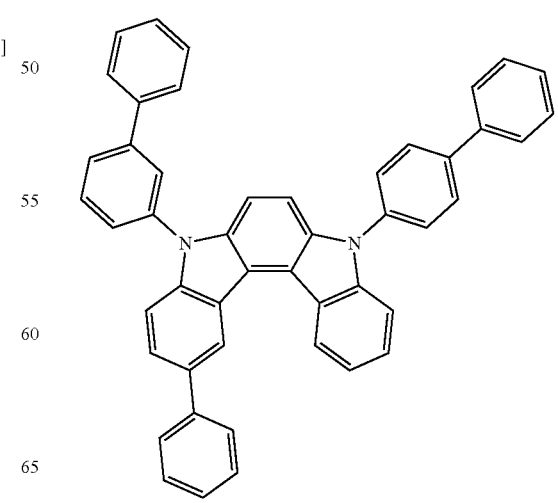

[B-20]
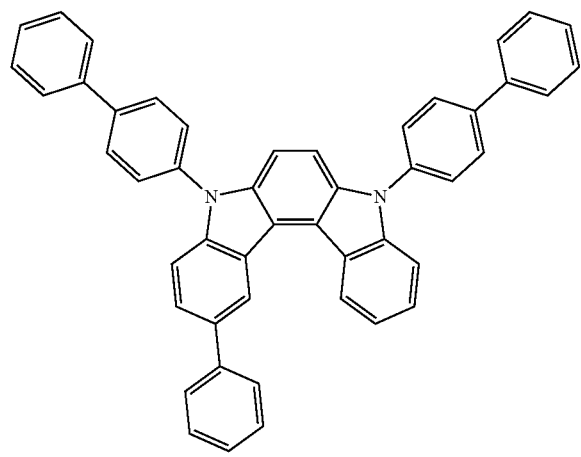
[B-21]
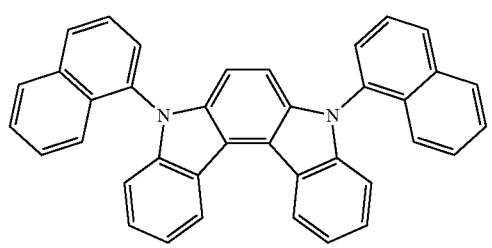
[B-22]
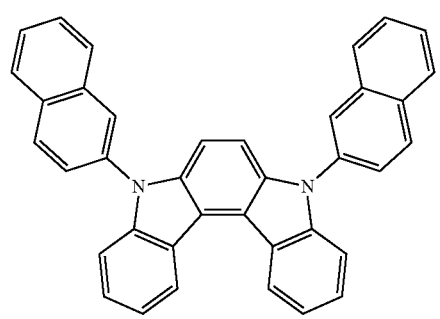
[B-23]
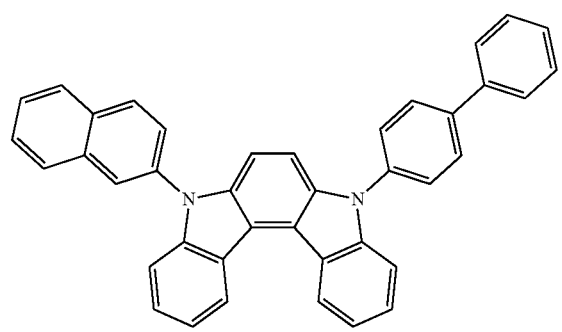
[B-24]
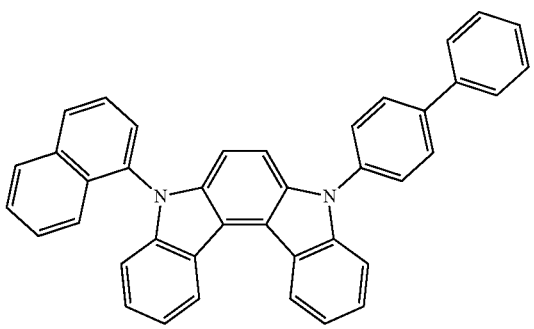
[B-25]
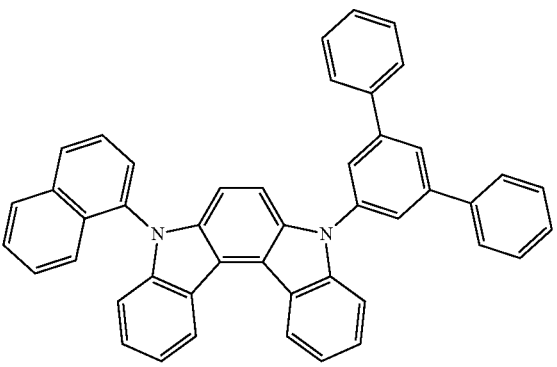
[B-26]
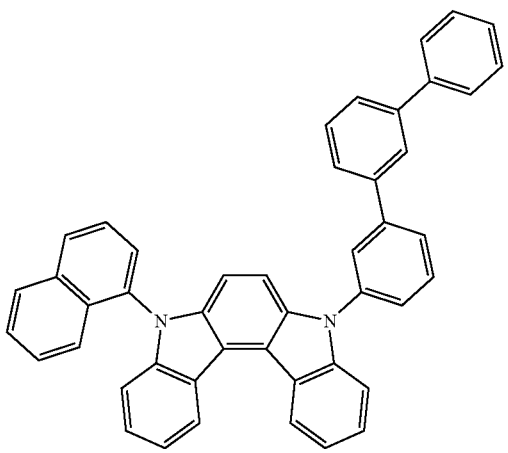

[B-27]
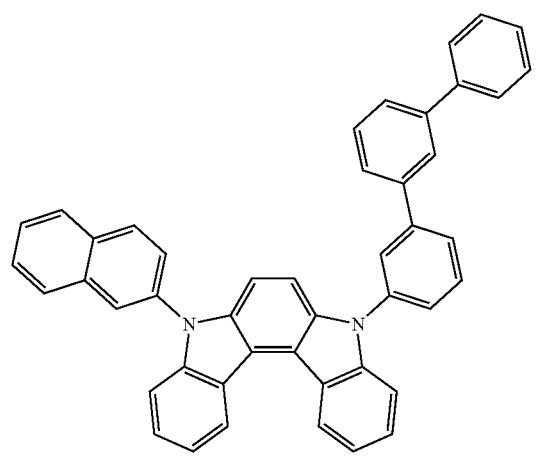
[B-28]
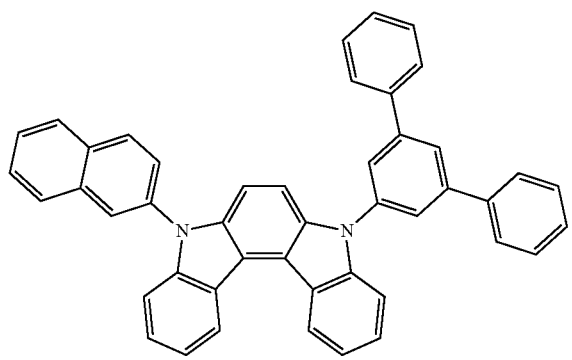
[B-29]
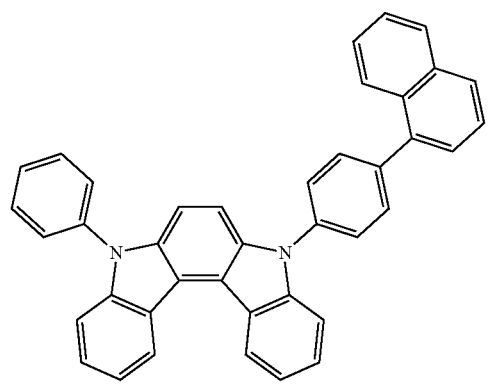
[B-30]
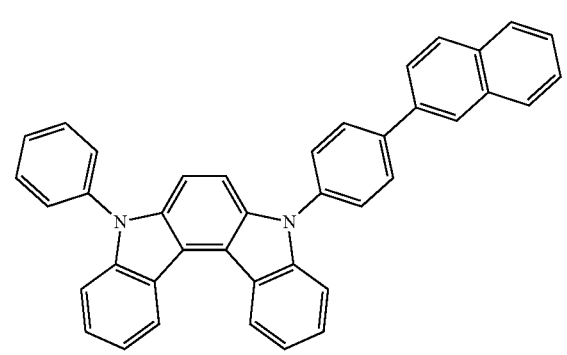
[B-31]
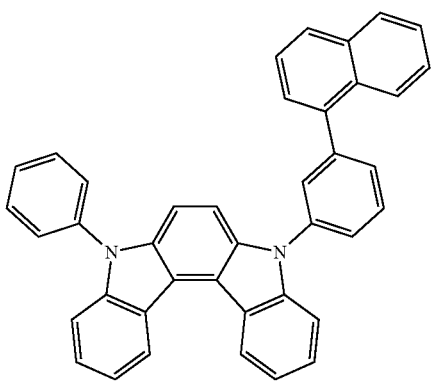
[B-32]
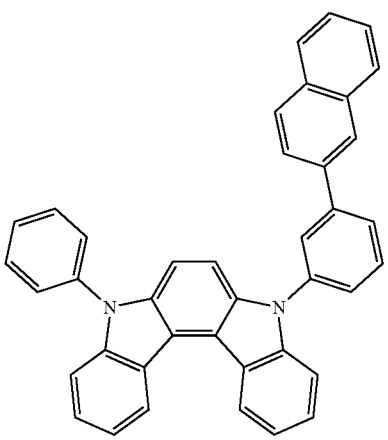
[B-33]
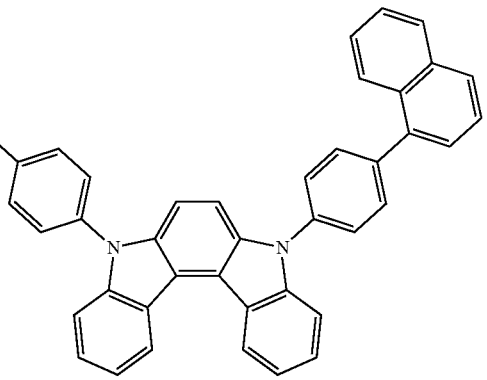
[B-34]
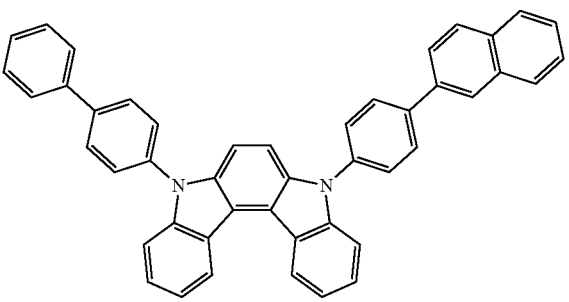

[B-35]
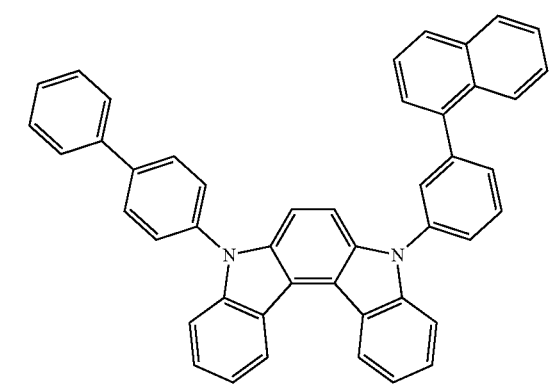
[B-36]
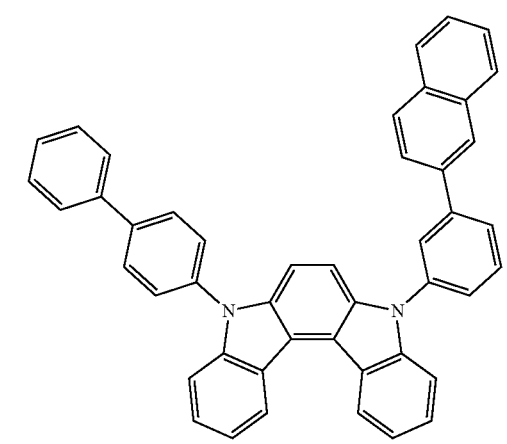
[B-37]
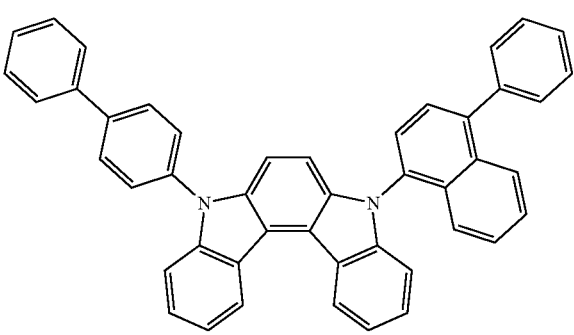
[B-38]
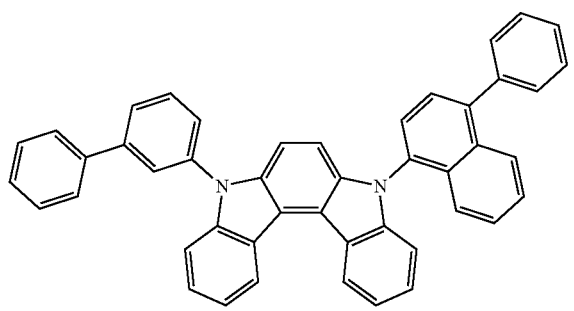
[B-39]
[B-40]
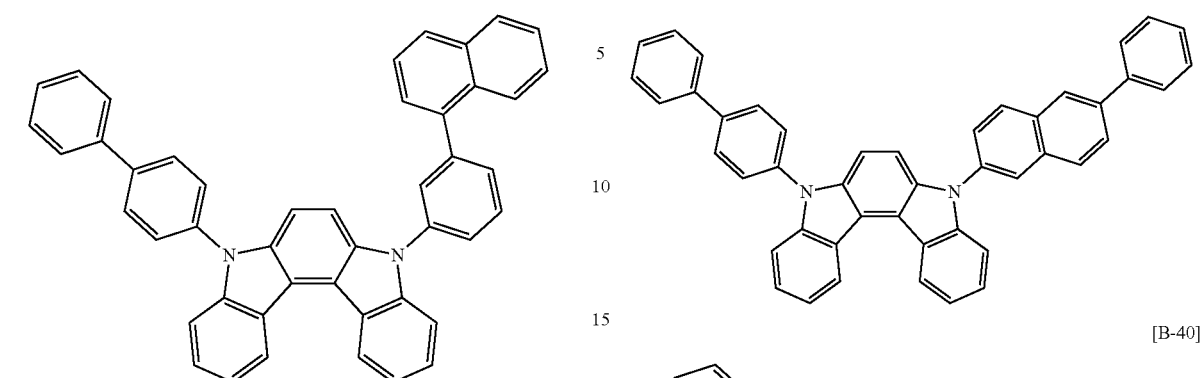
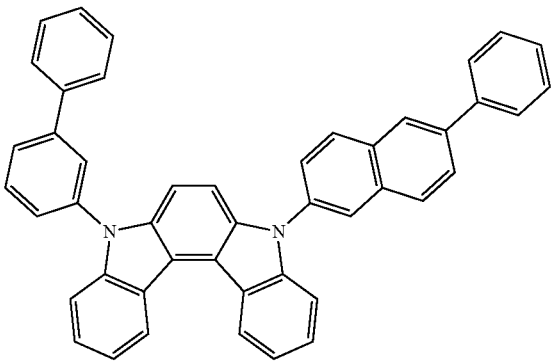
[B-41]
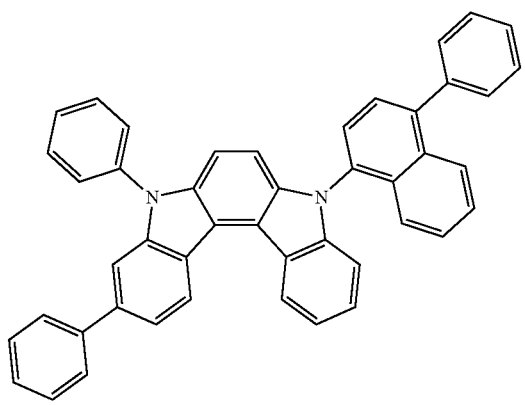
[B-42]
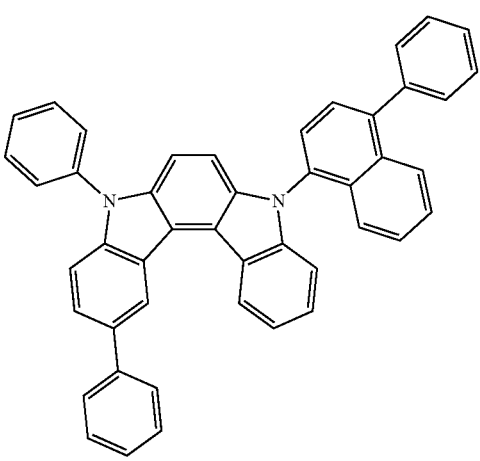

[B-43]
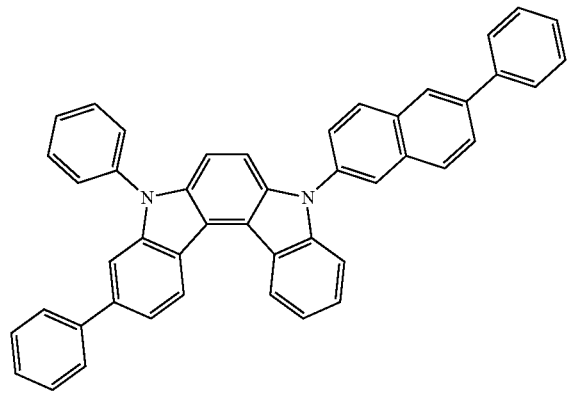
[B-44]
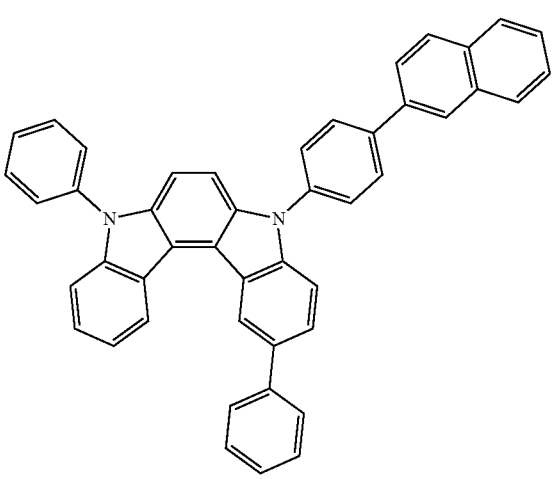
[B-45]
[B-46]
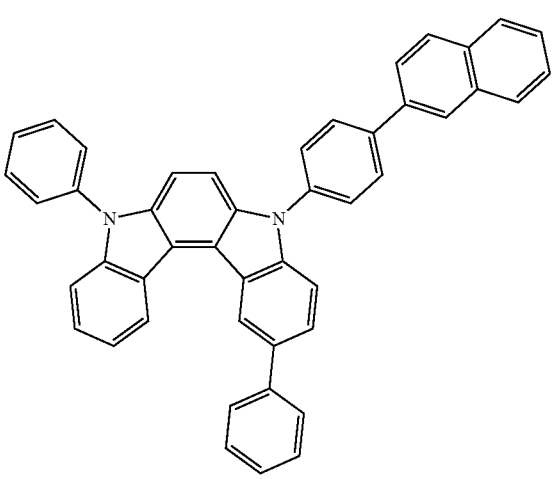
[B-47]
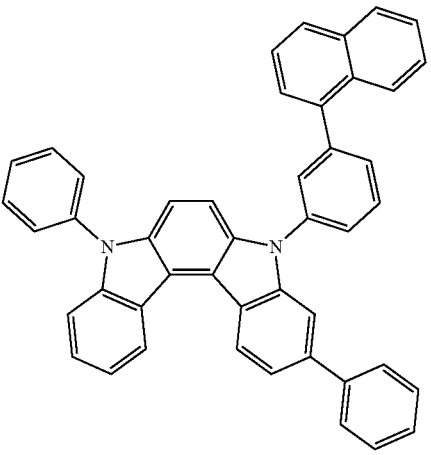
[B-48]
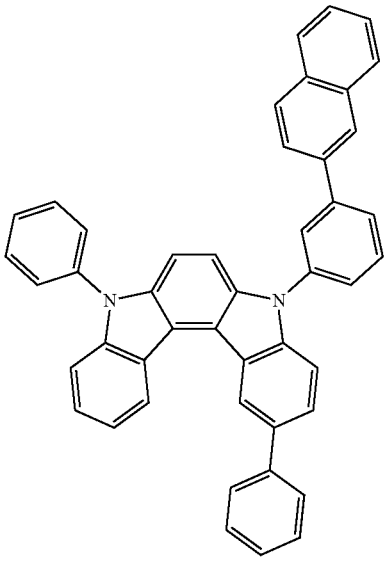

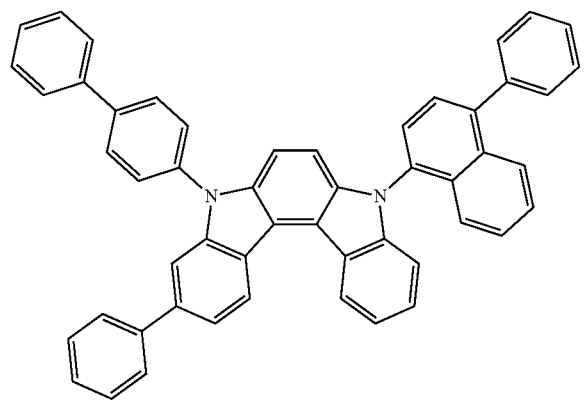
[B-49]
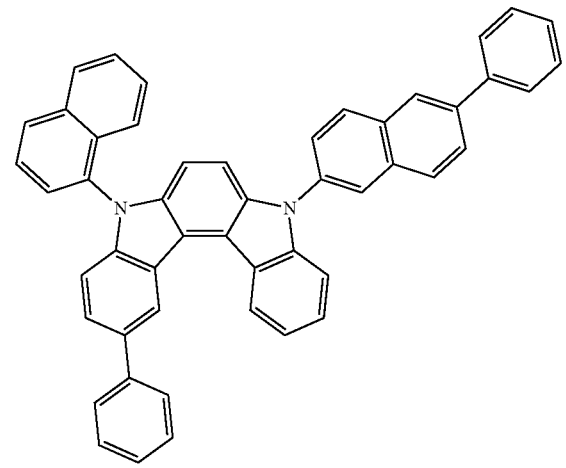
[B-52]
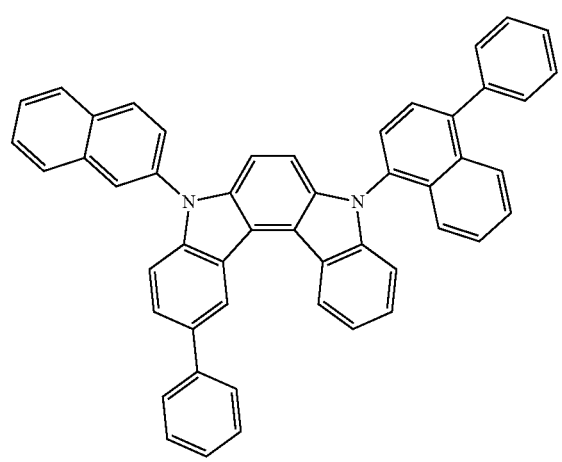
[B-50]
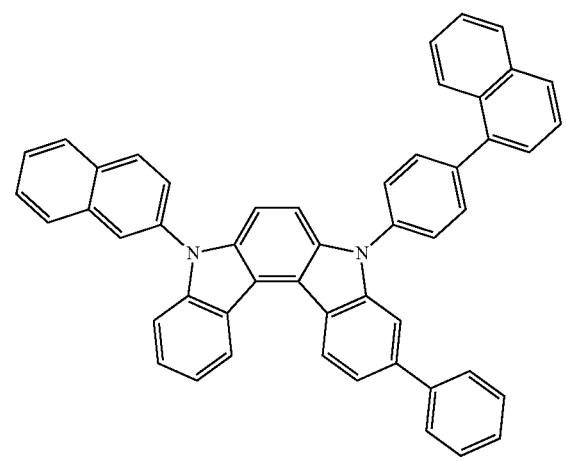
[B-53]
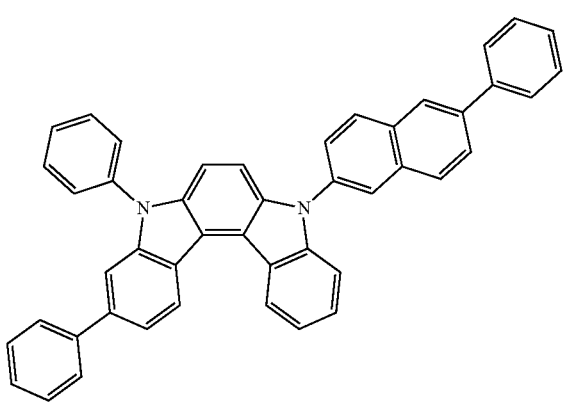
[B-51]
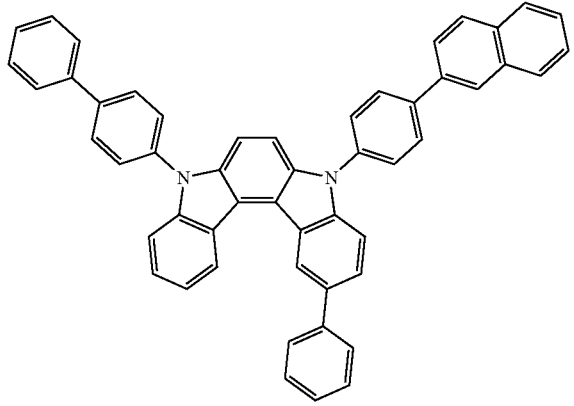
[B-54]

[B-55]
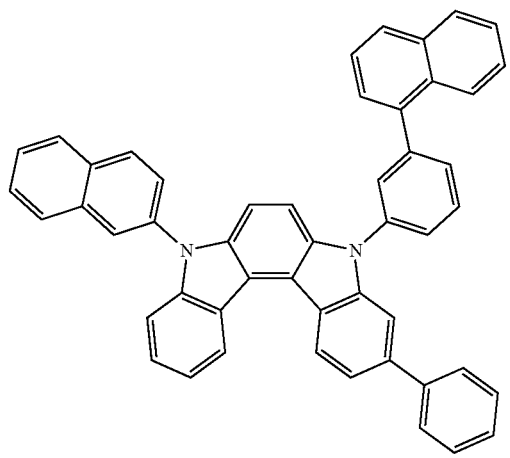
[B-56]
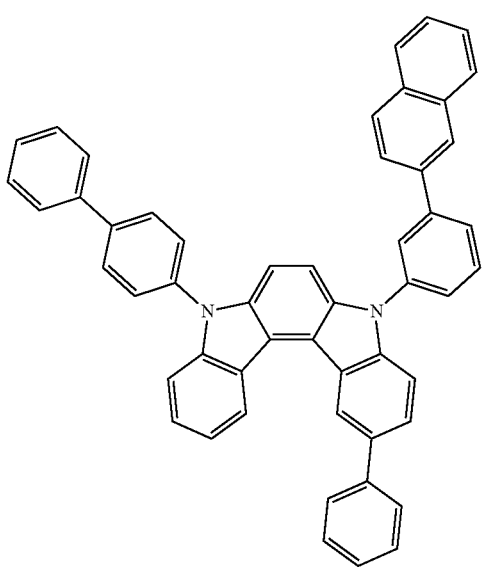
[C-1]
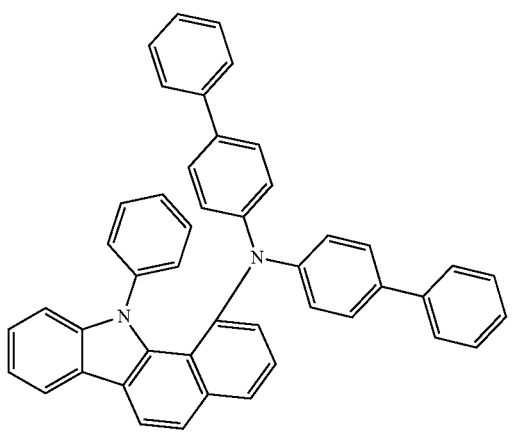
[C-2]
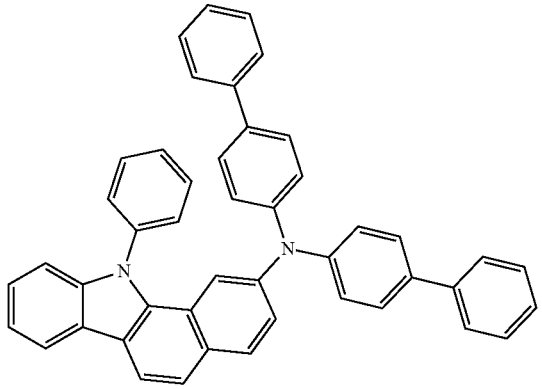
[C-3]
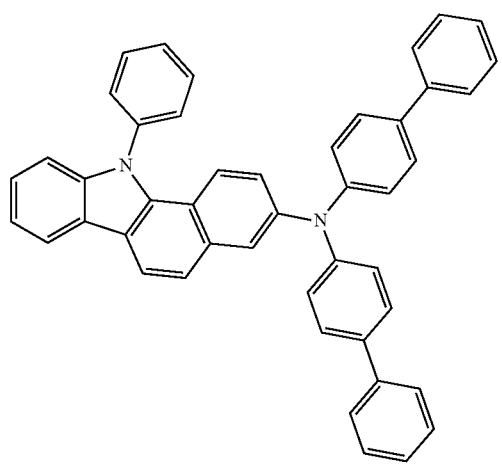
[C-4]
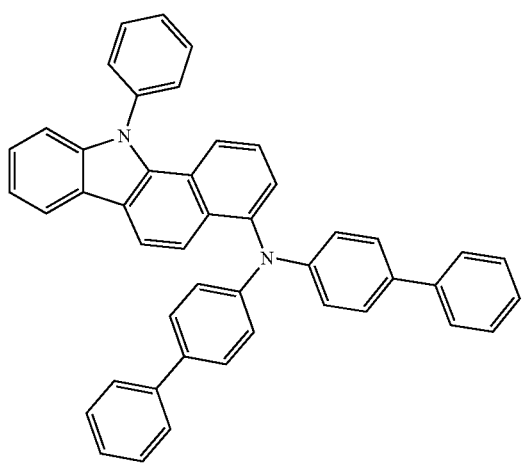

[C-5]
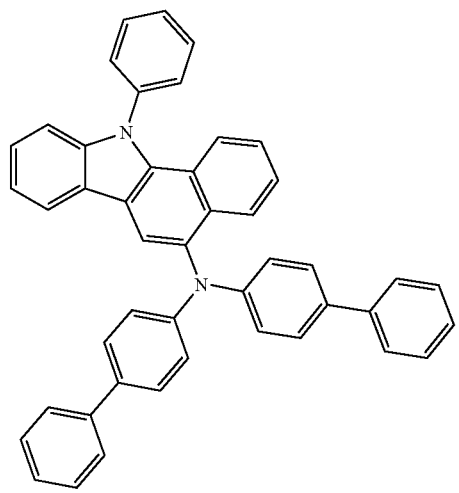
[C-6]
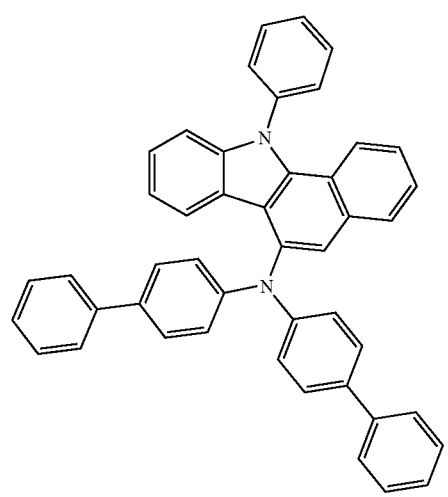
[C-7]
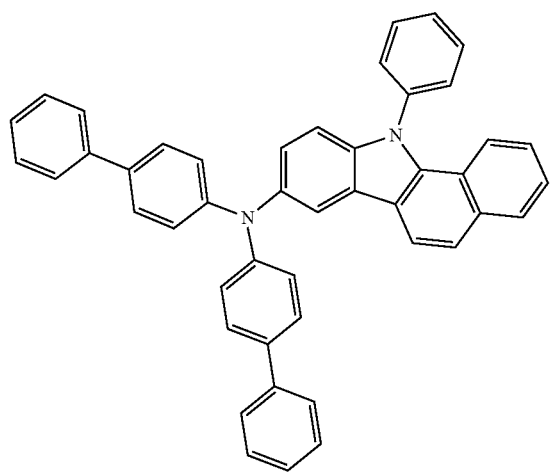
[C-8]
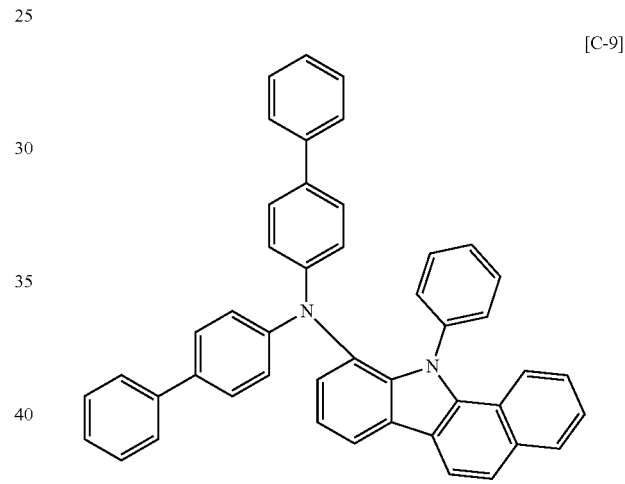
[C-9]
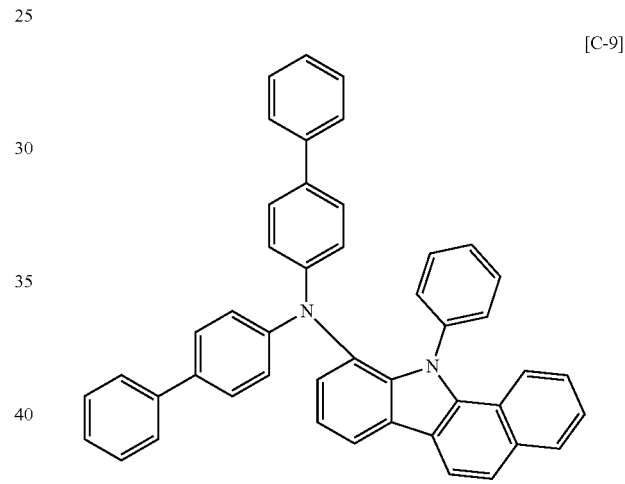
[C-10]
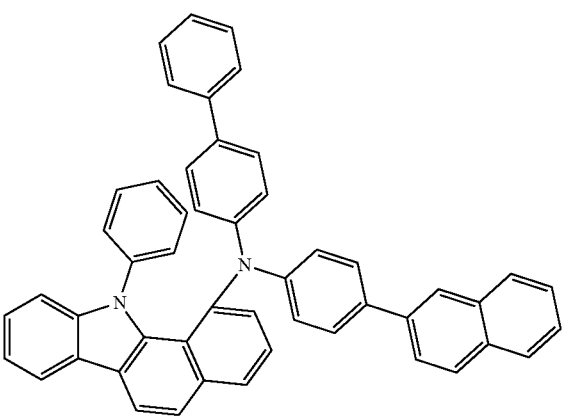

[C-11]
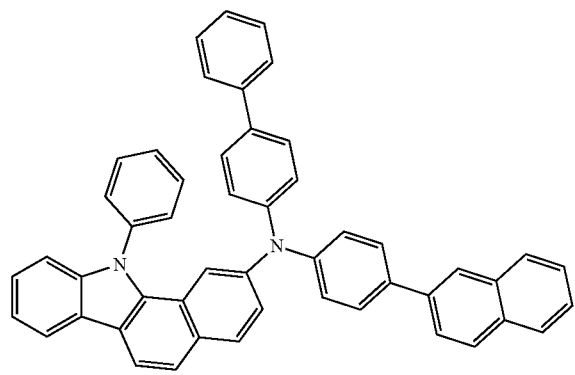
[C-12]
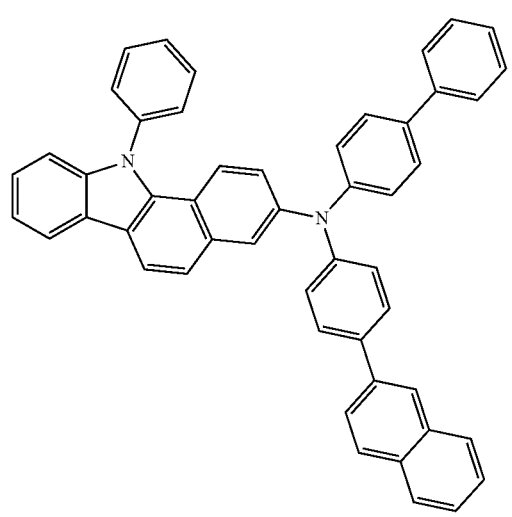
[C-13]
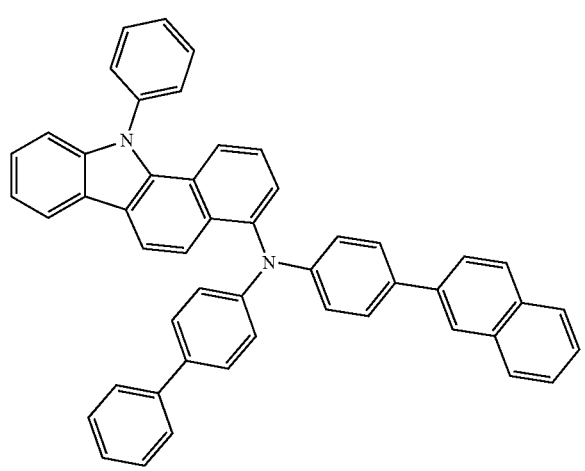
[C-14]
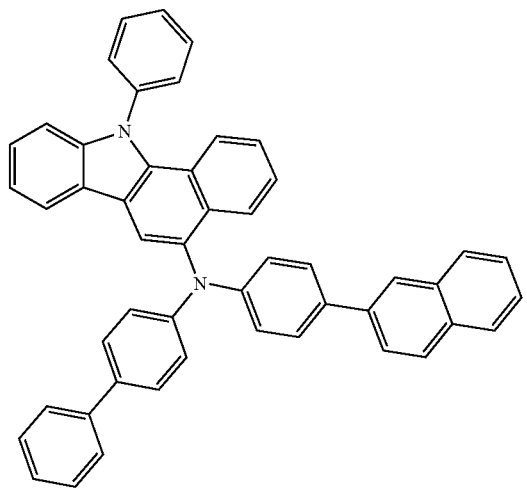
[C-15]
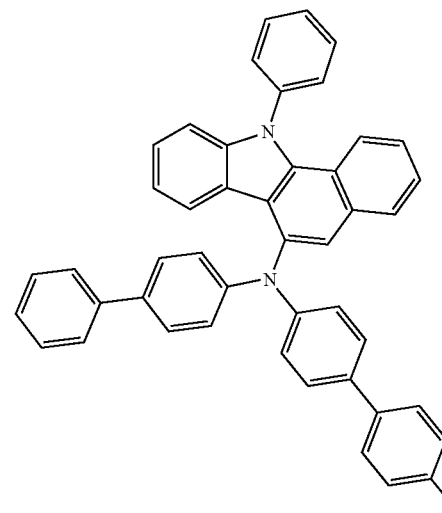
[C-16]
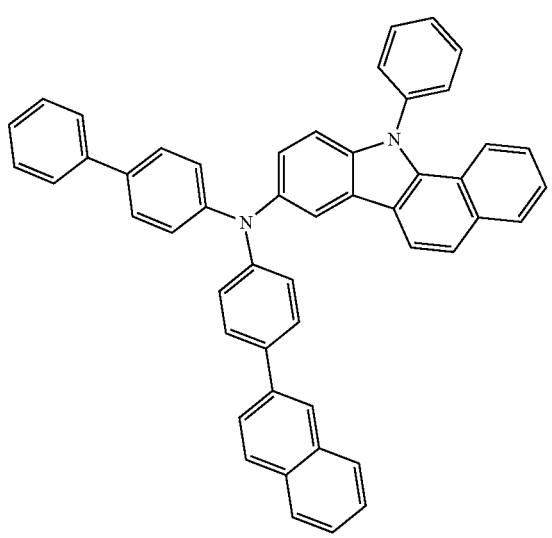

[C-17]
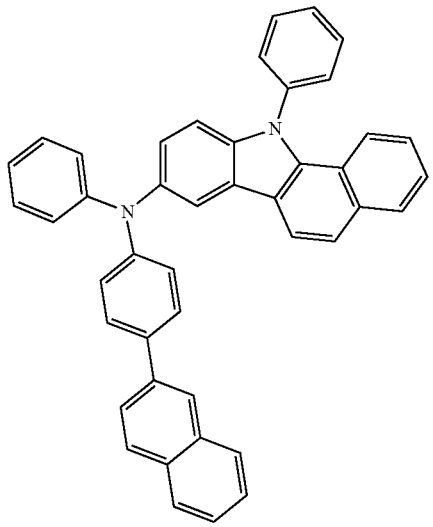
[C-18]
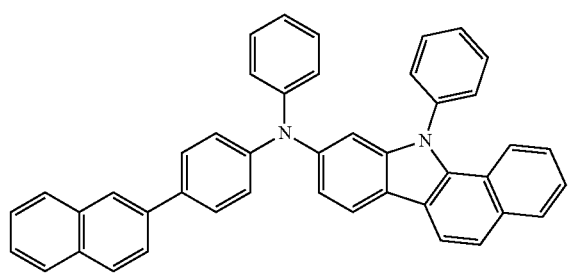
[C-19]
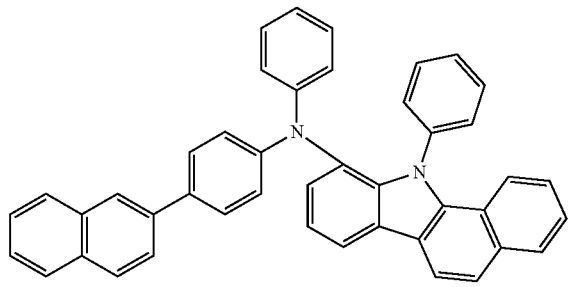
[C-20]
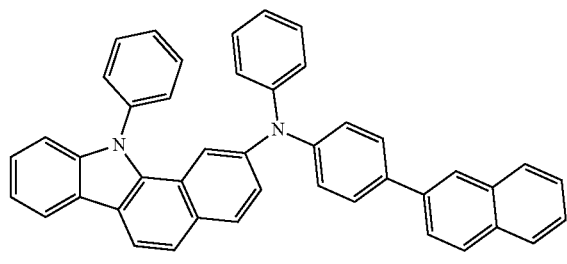
[C-21]
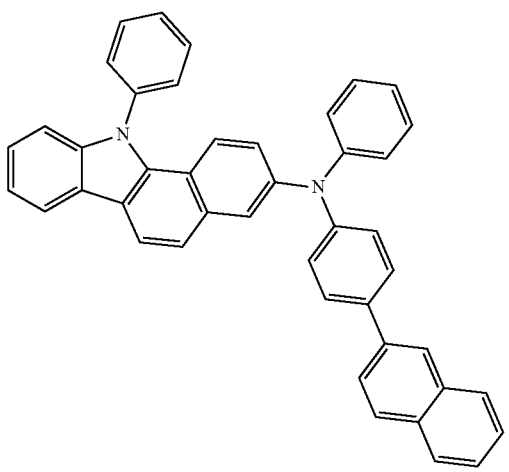
[C-22]
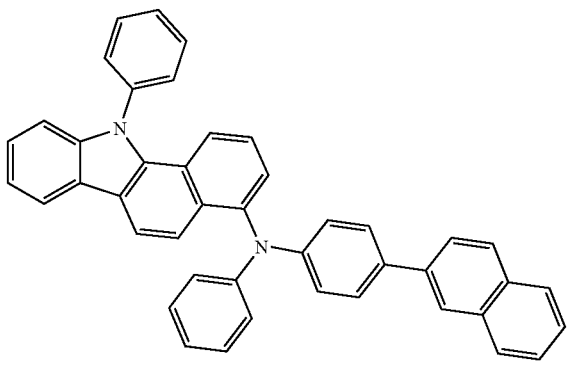
[C-23]
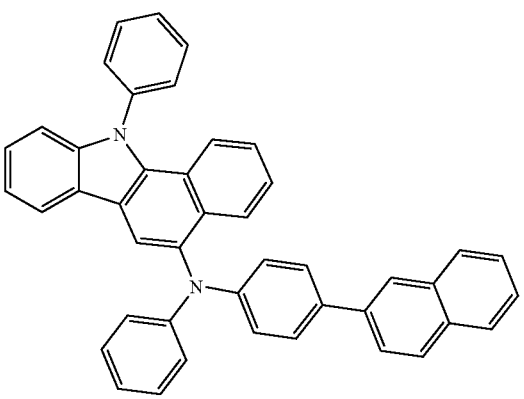

[C-24]
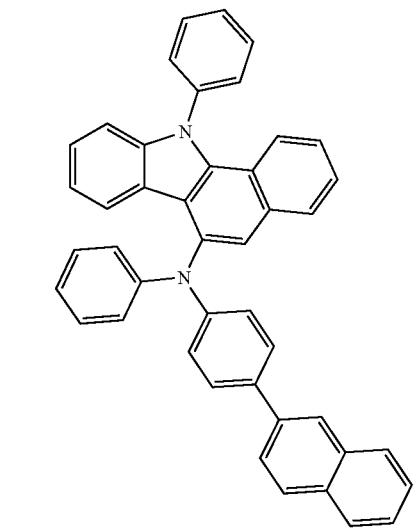
[C-25]
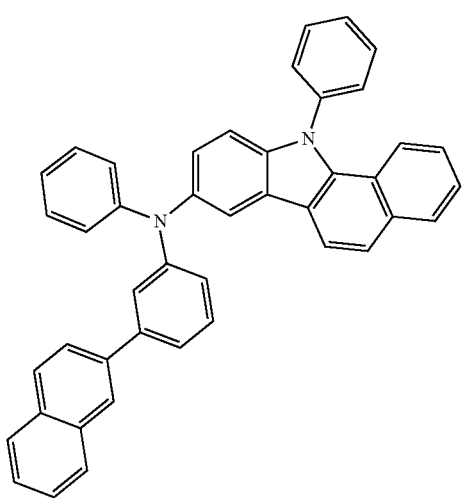
[C-26]
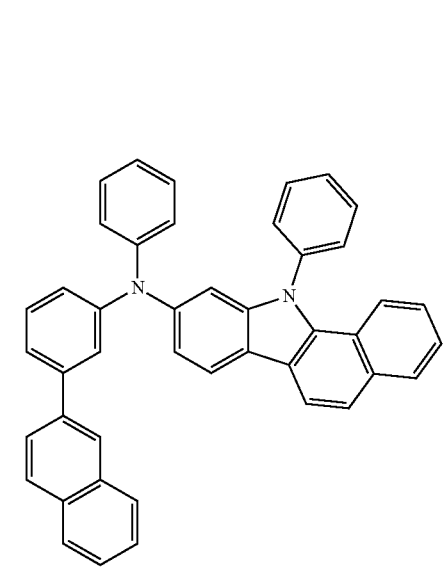
[C-27]
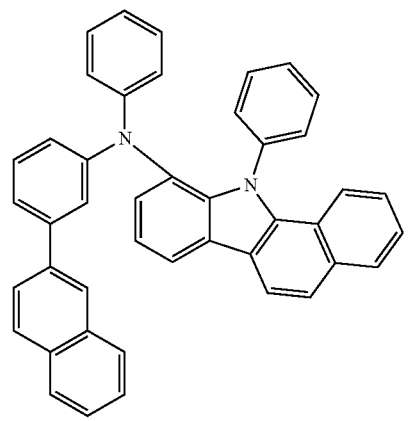
[C-28]
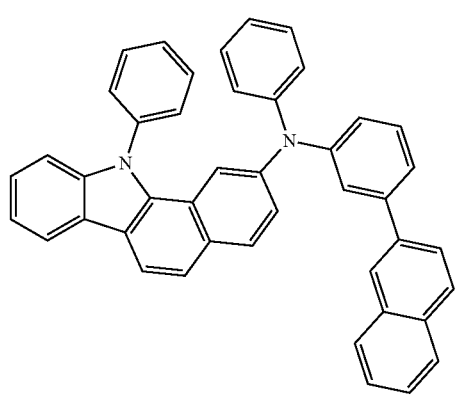
[C-29]
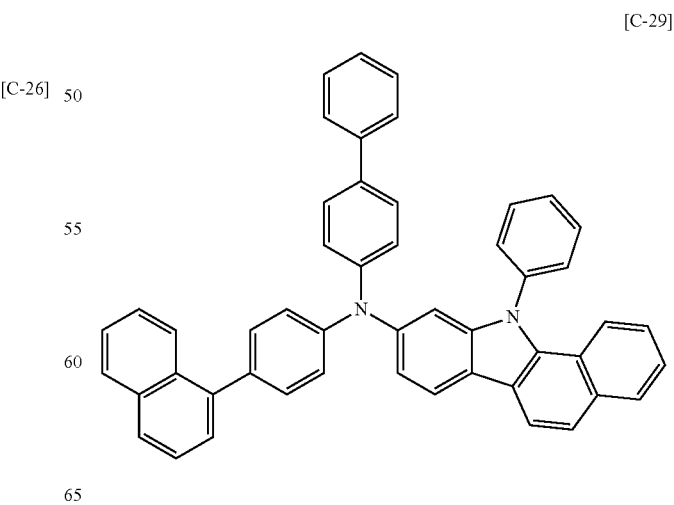

[C-30]
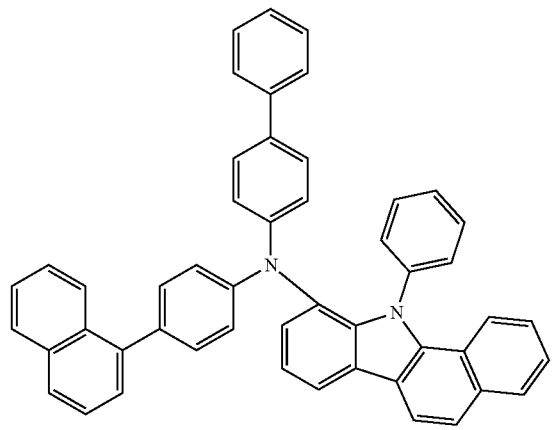
[C-31]
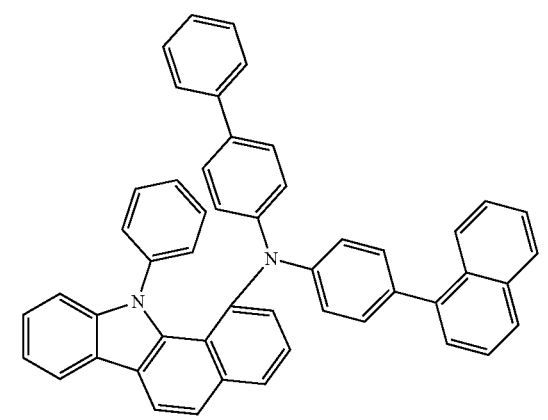
[C-32]
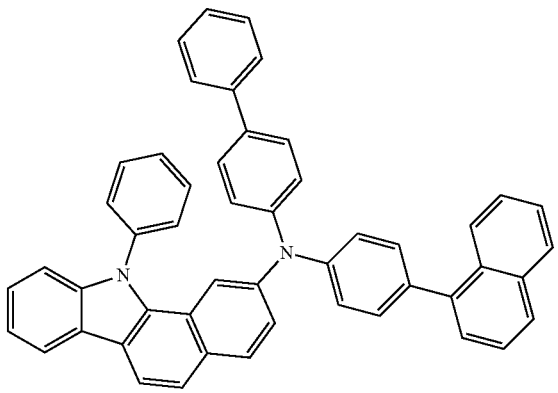
[C-33]
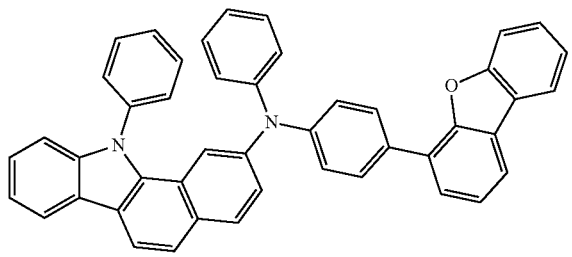
[C-34]
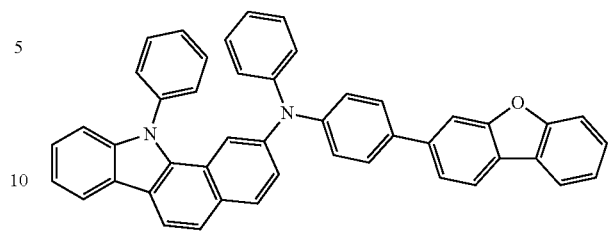
[C-35]
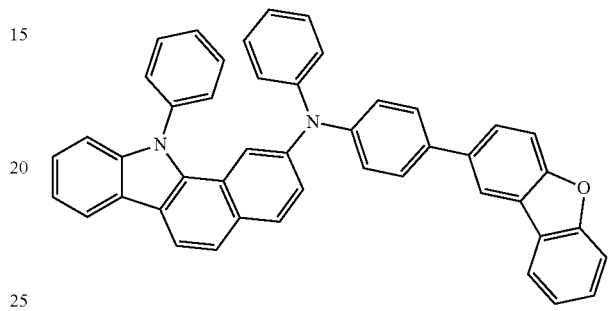
[C-36]
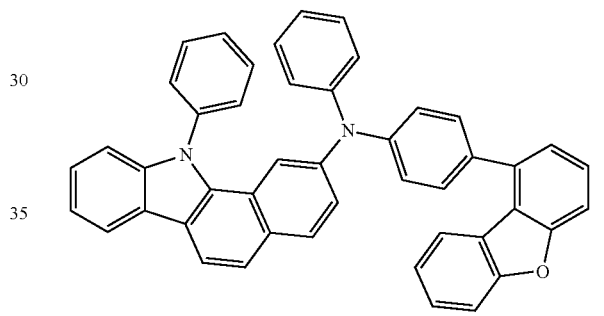
[C-37]
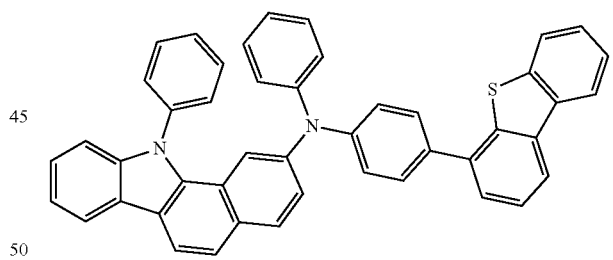
[C-38]
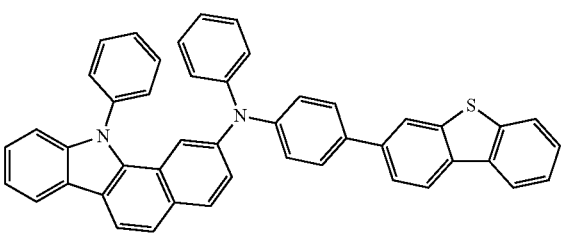

[C-39]
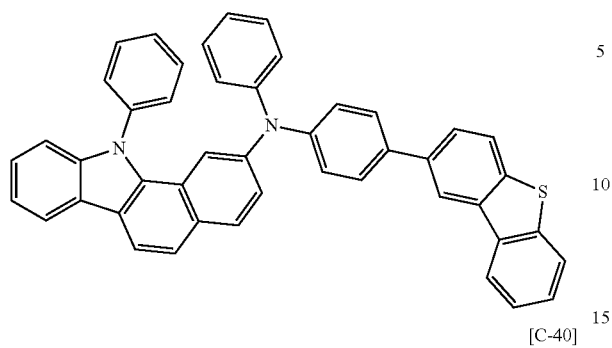
[C-40]
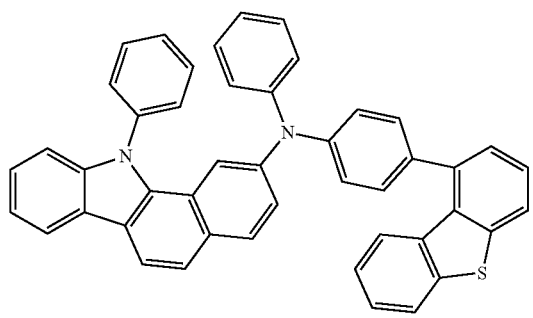
[C-41]
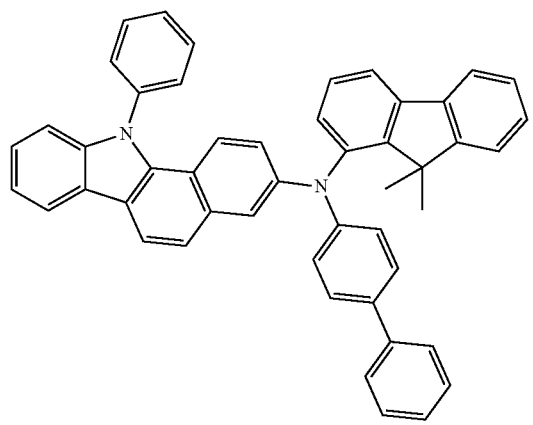
[C-42]
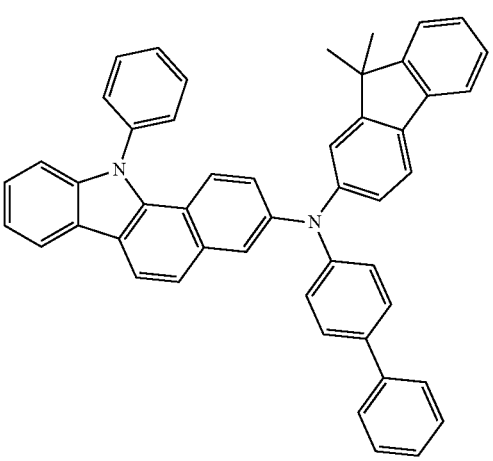
[C-43]
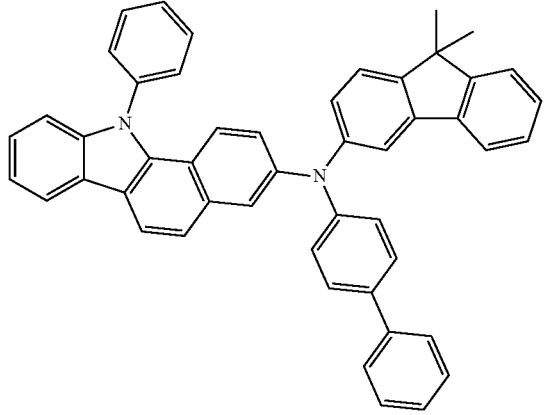
[C-44]
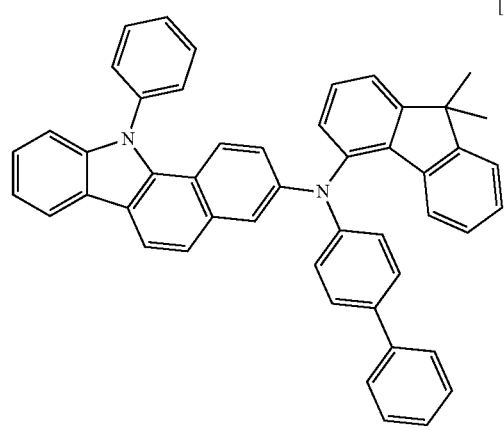
[C-45]
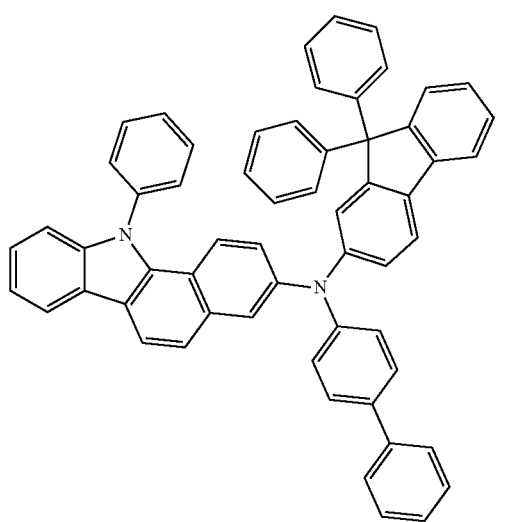

-continued
[C-46]
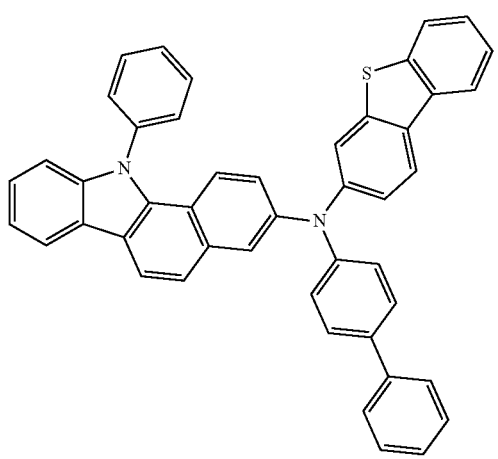
[C-47]
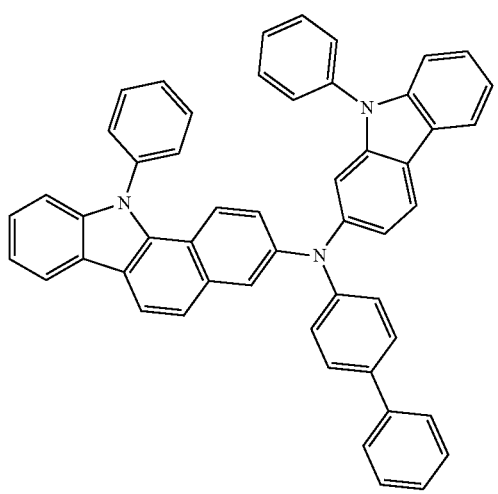
[C-48]
-continued
[C-49]
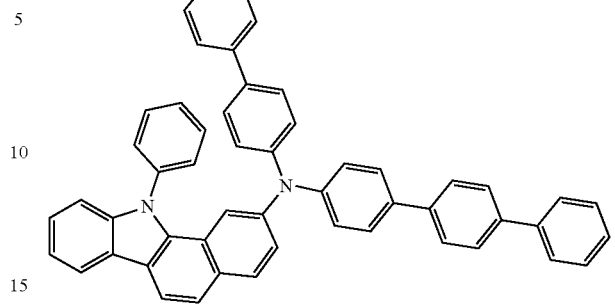
[C-50]
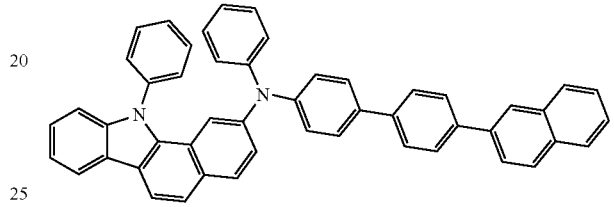
[C-51]
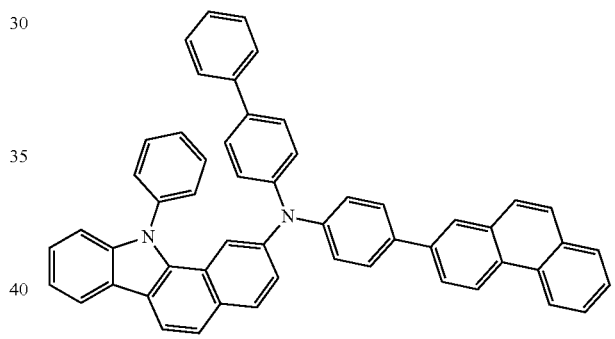
[C-52]
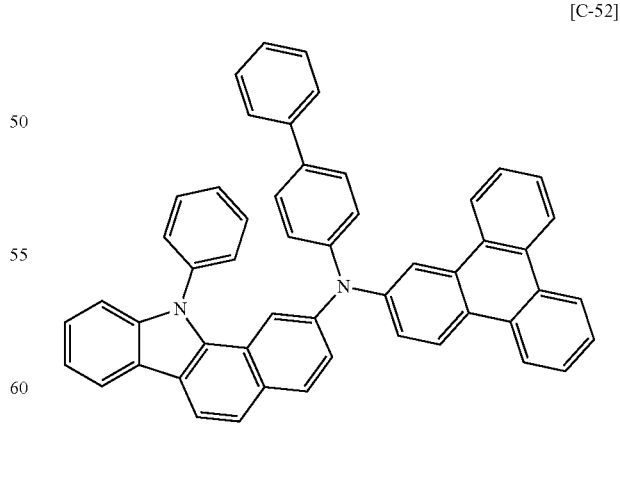

[C-53]
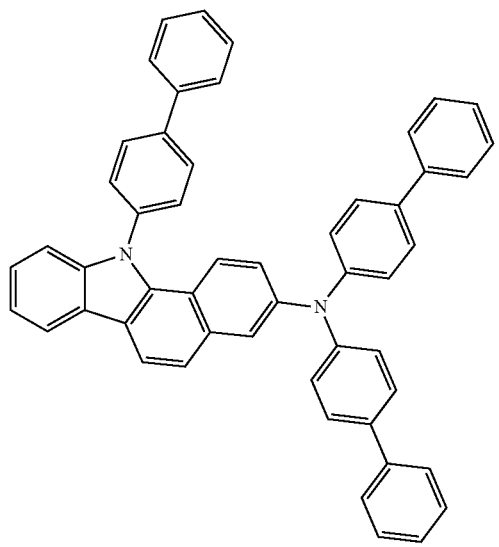
[C-54]
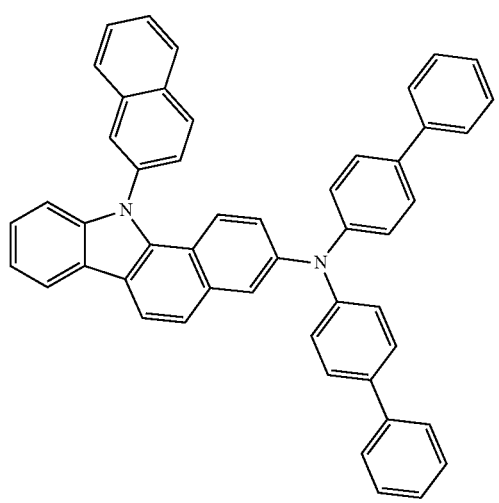
[C-55]
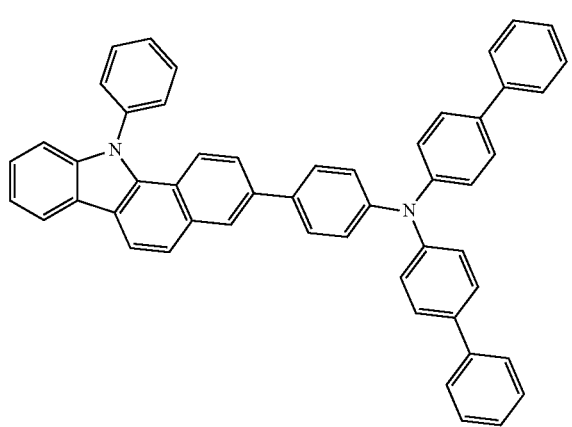
[C-56]
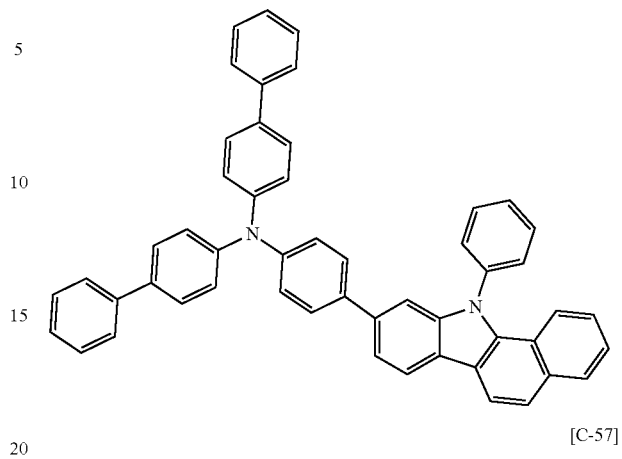
[C-57]
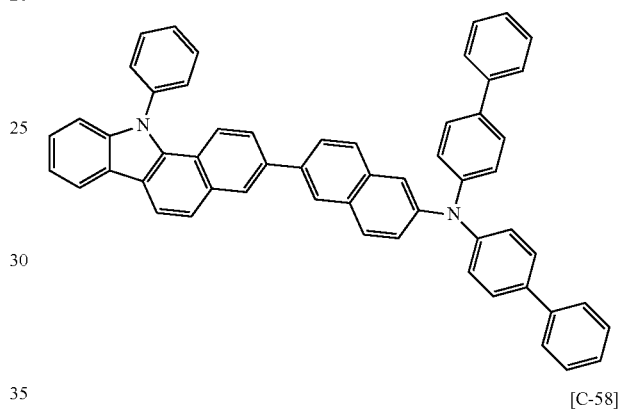
[C-58]
[C-59]
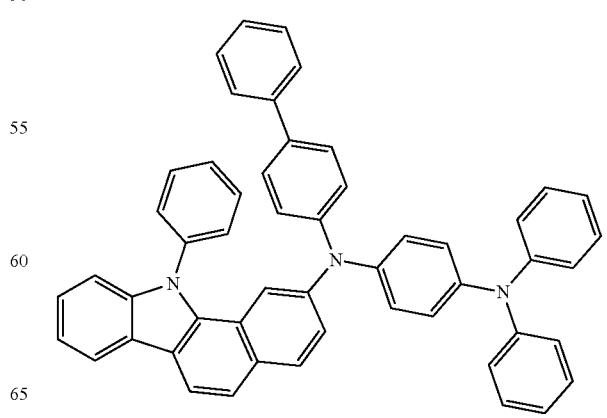

-continued
[C-60]
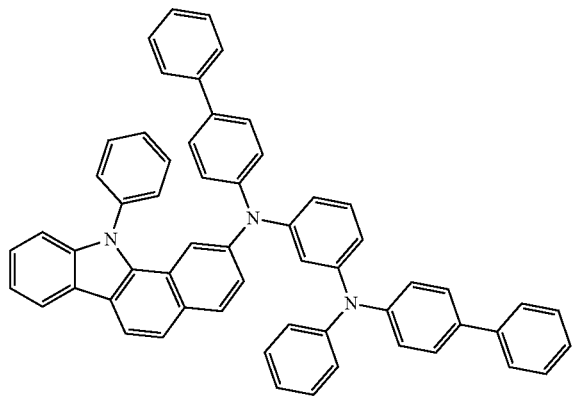
[C-61]
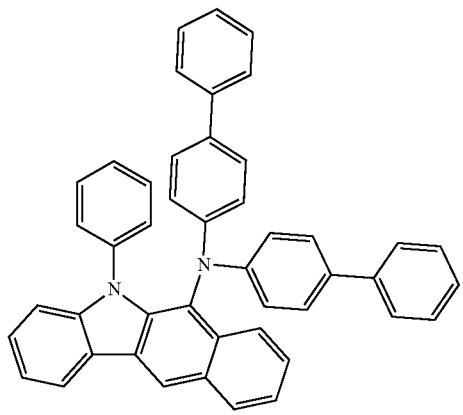
[C-62]
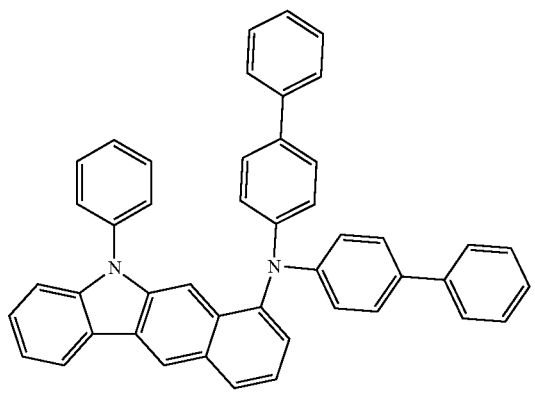
[C-63]
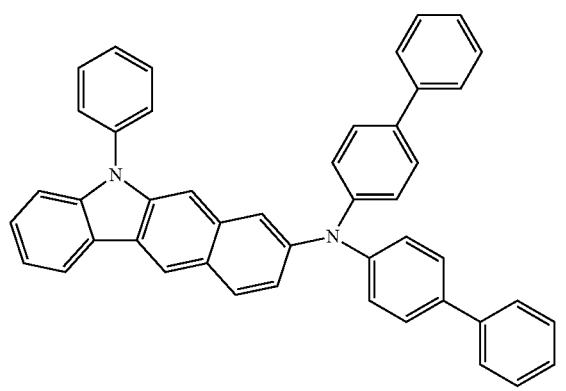
-continued
[C-64]
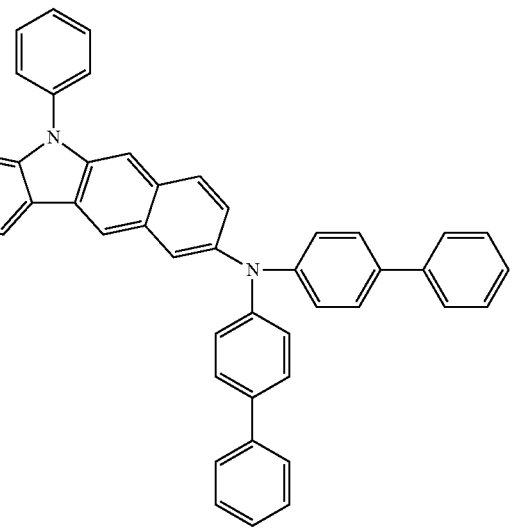
[C-65]
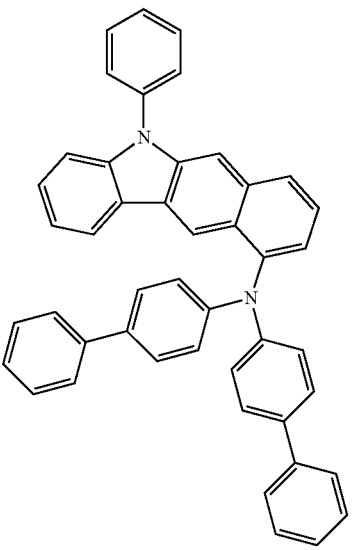
[C-66]
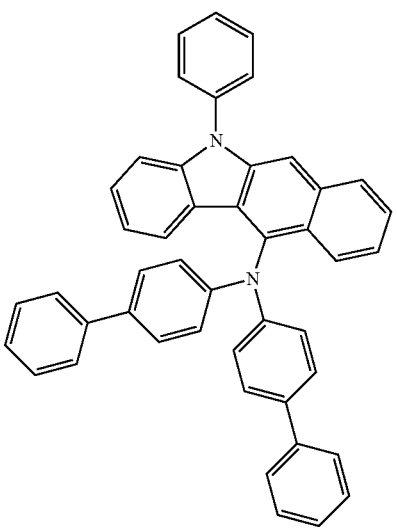

[C-67]
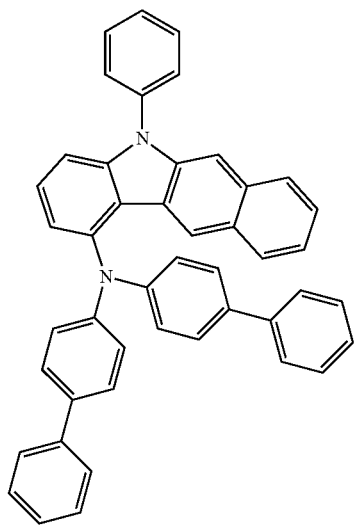
[C-70]
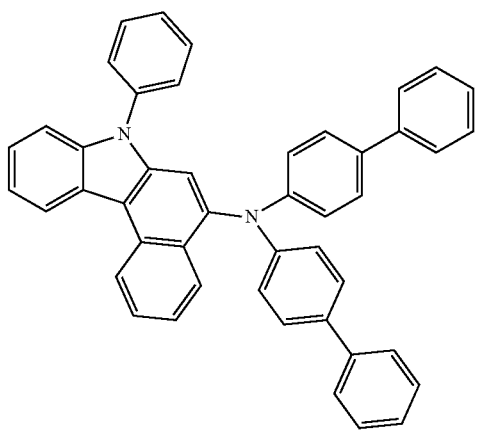
[C-68]
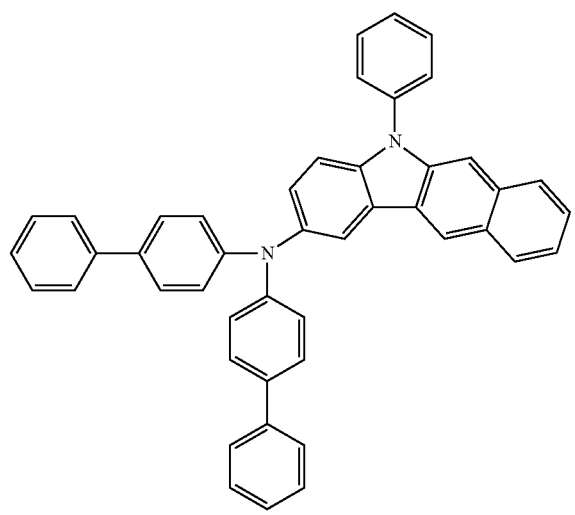
[C-71]
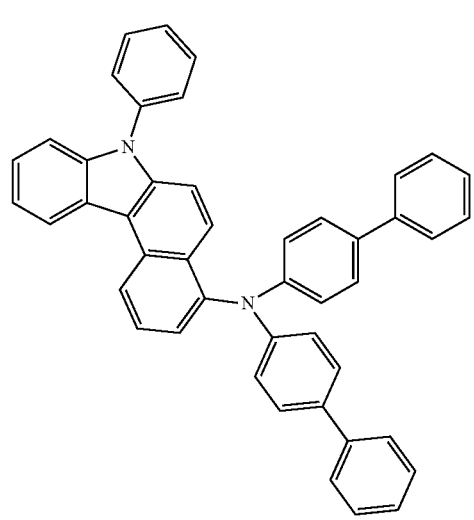
[C-69]
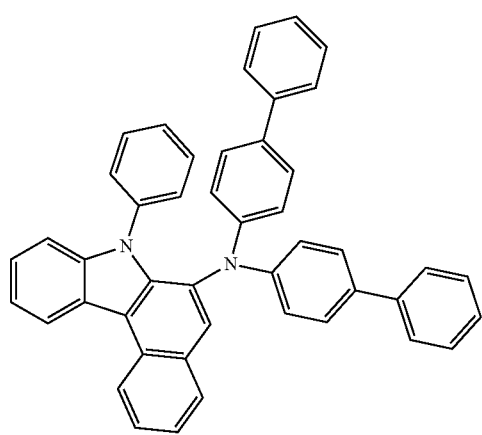
[C-72]
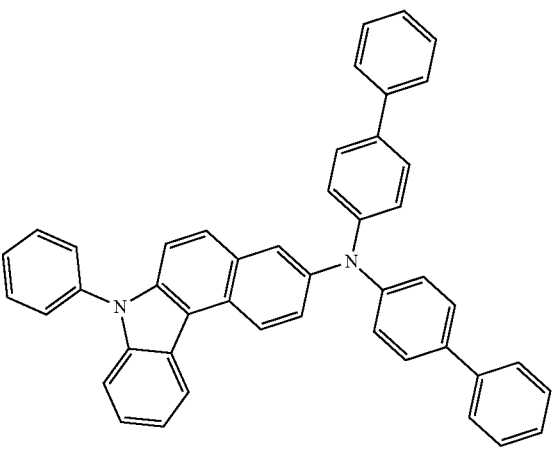

[C-73]
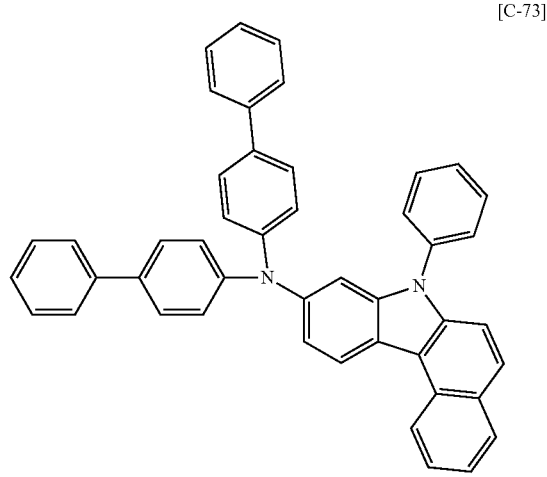
[C-74]
[C-75]
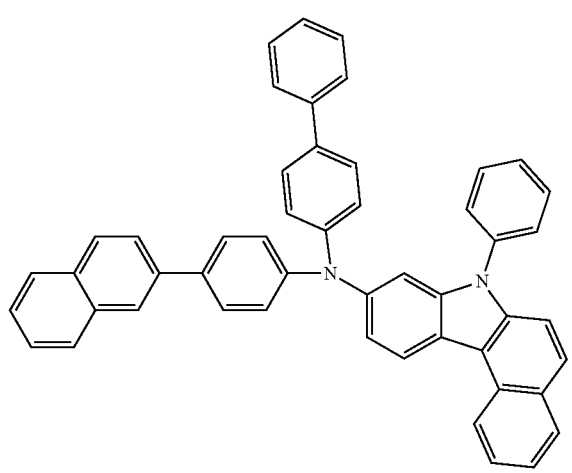
[C-76]
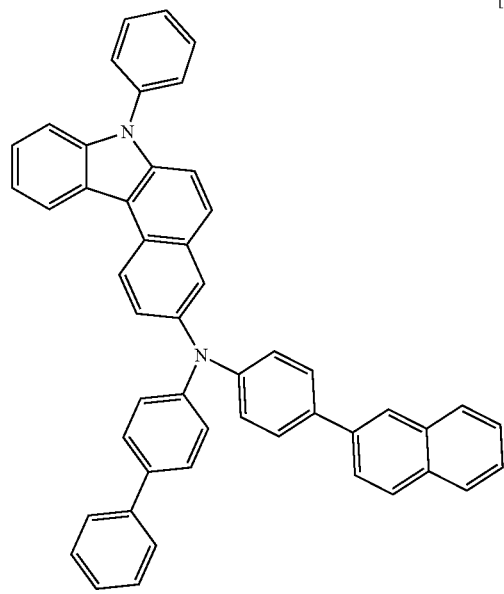
[D-1]
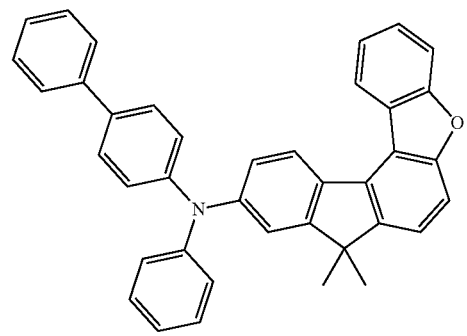
[D-2]
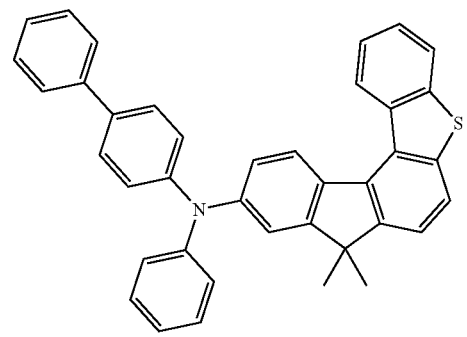
[D-3]
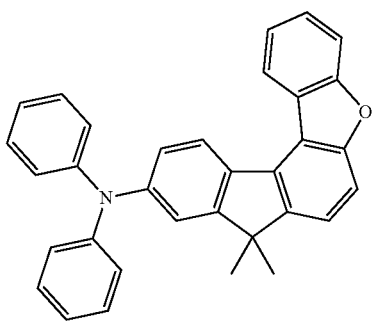

[D-4]
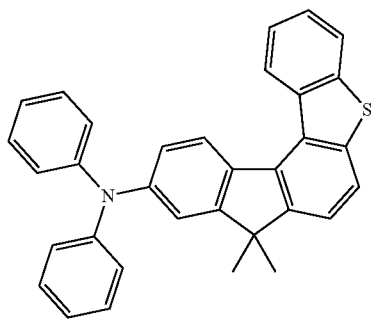
[D-5]
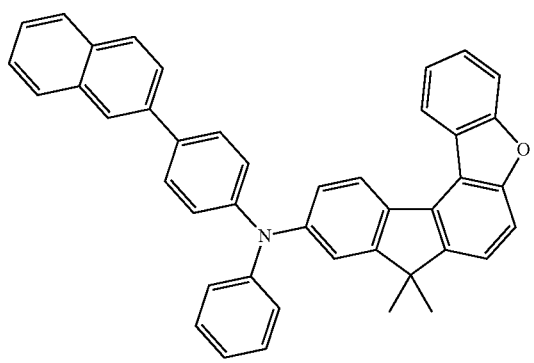
[D-6]
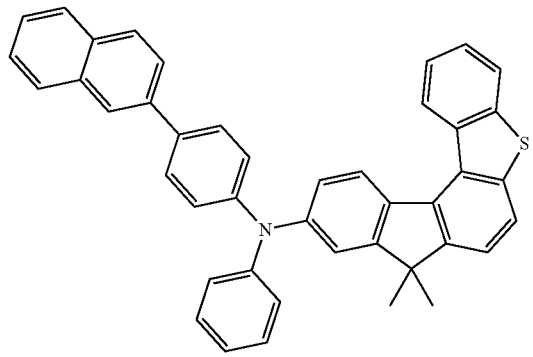
[D-7]
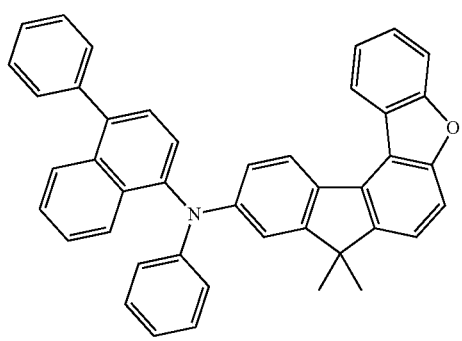
[D-8]
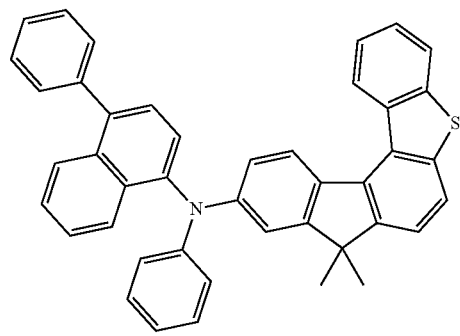
[D-9]
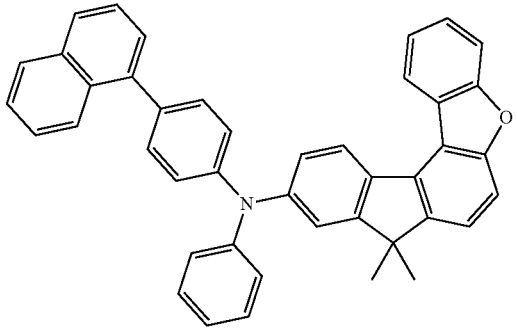
[D-10]
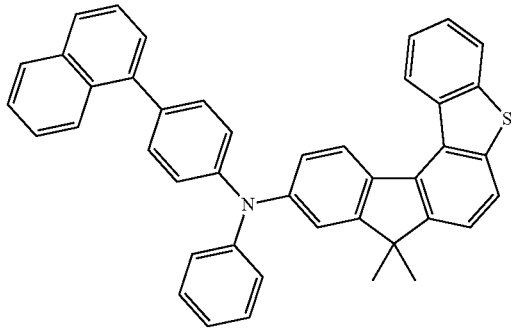
[D-11]
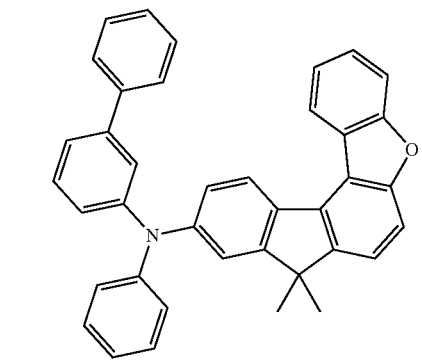

[D-12]
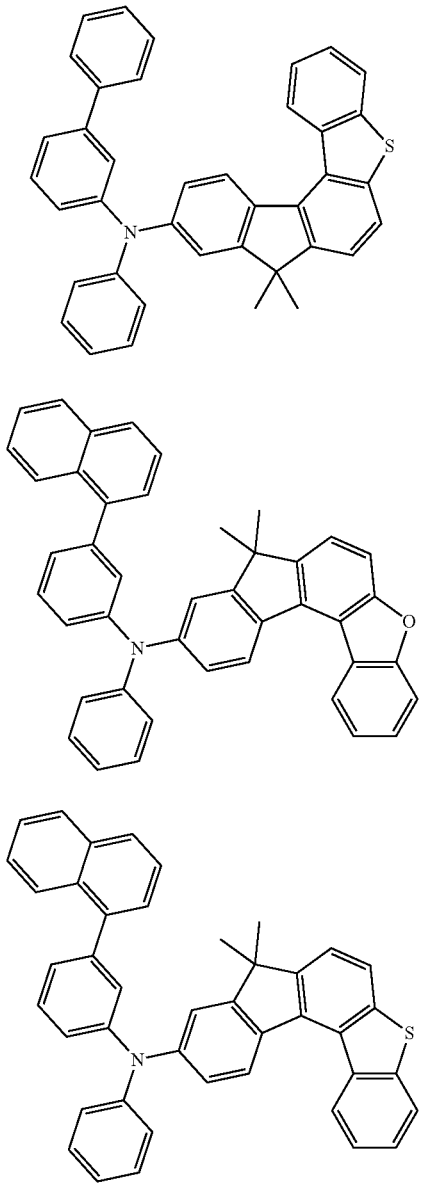
[D-13]
[D-14]
[D-15]
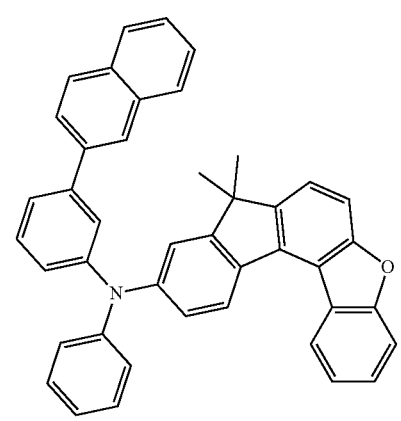
[D-16]
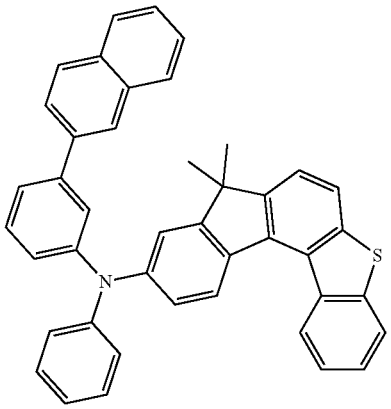
[D-17]
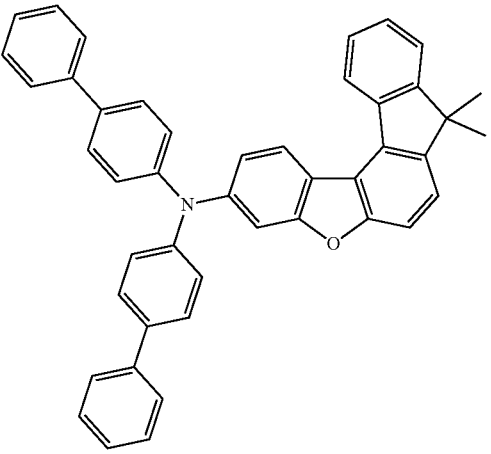
[D-18]
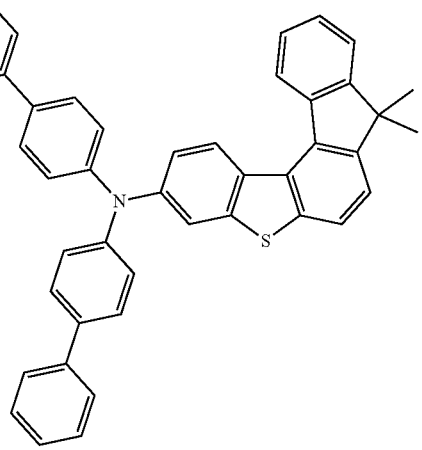

[D-19]
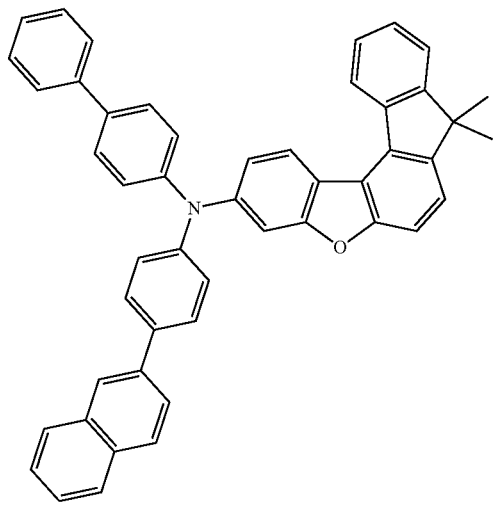
[D-22]
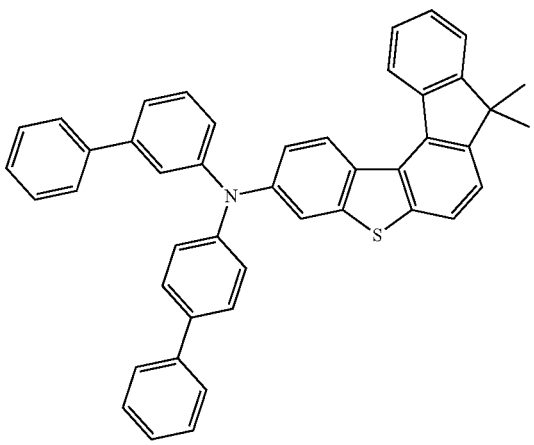
[D-20]
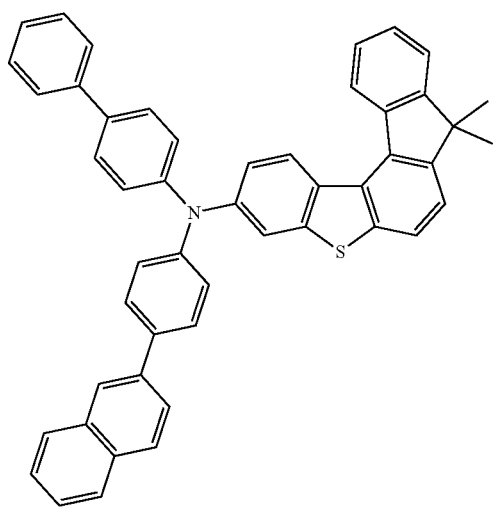
[D-23]
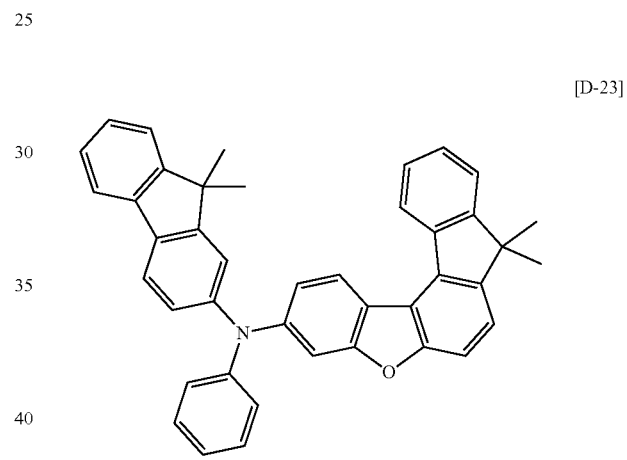
[D-21]
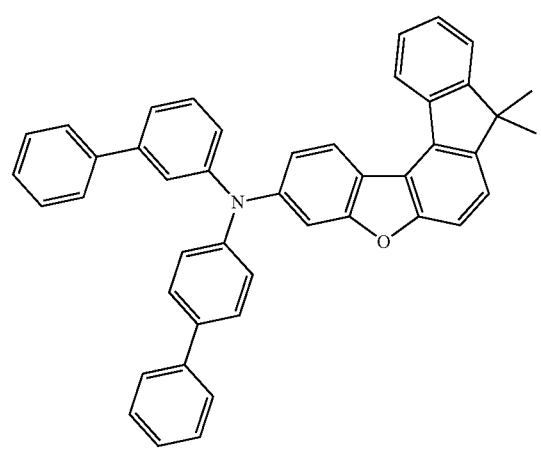
[D-24]
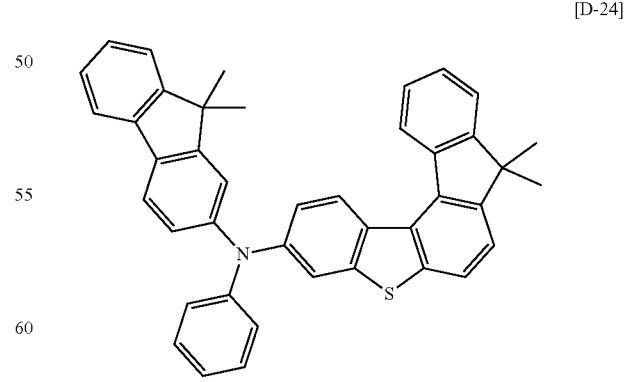

[D-25]
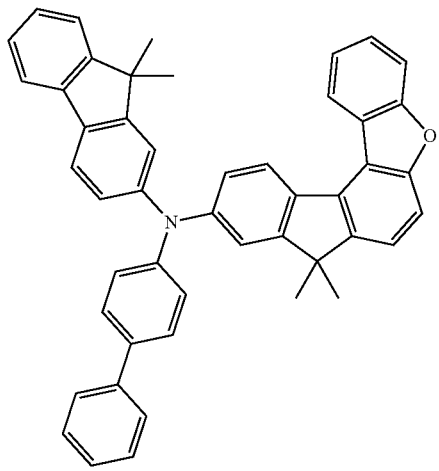
[D-26]
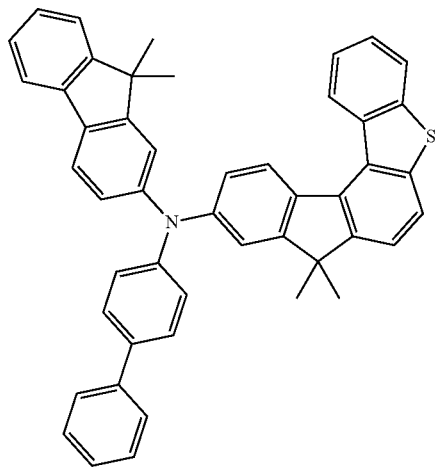
[D-27]
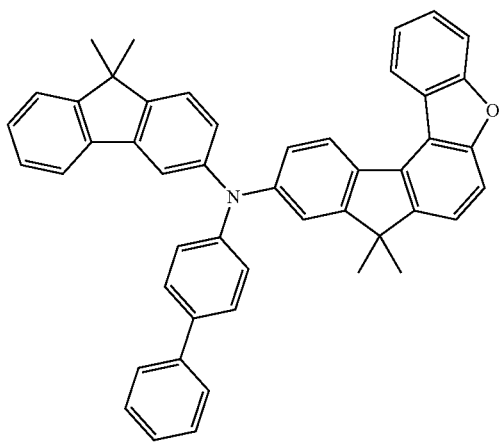
[D-28]
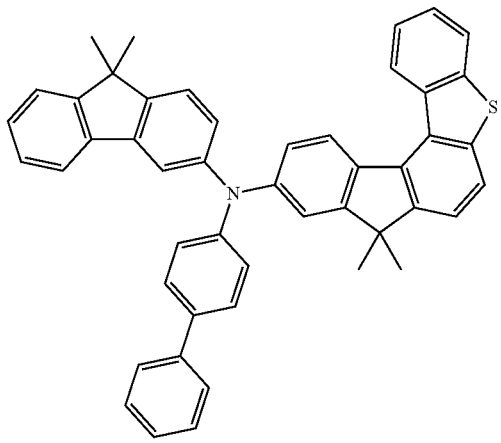
[D-29]
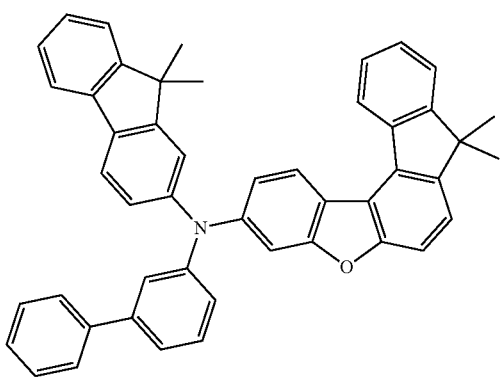
[D-30]
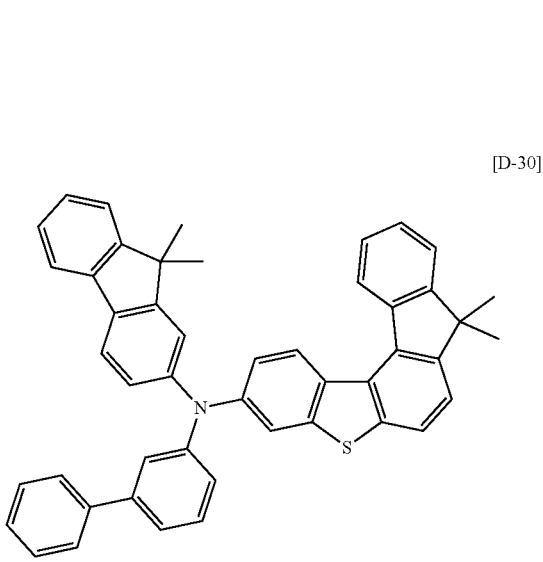

[D-31]
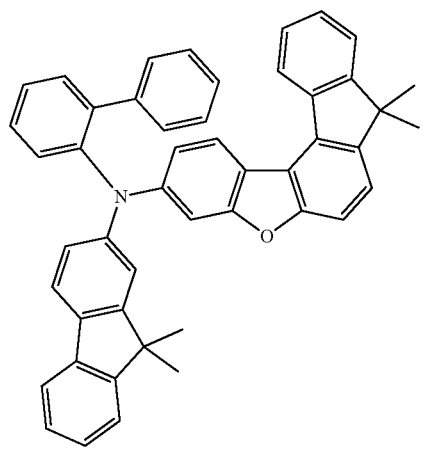
[D-34]
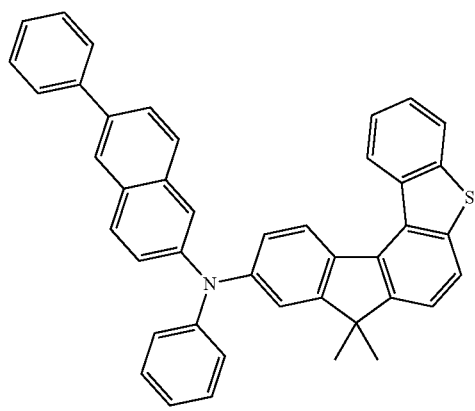
[D-32]
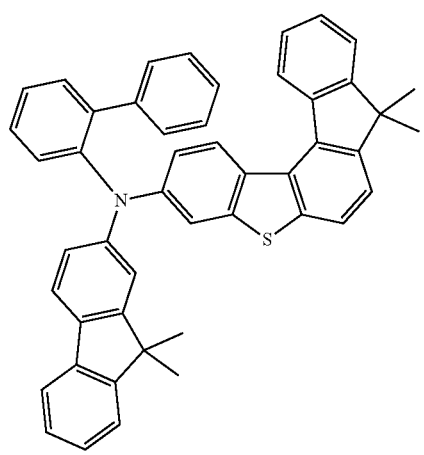
[D-35]
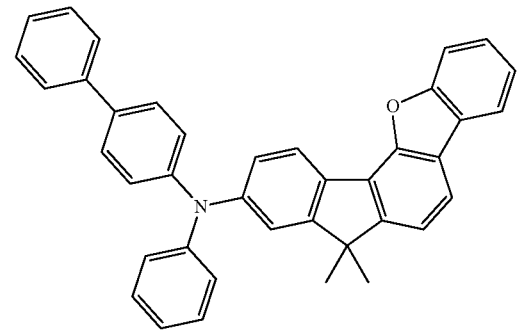
[D-36]
[D-33]
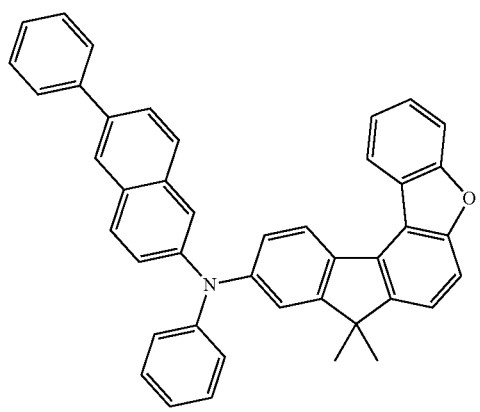
[D-37]
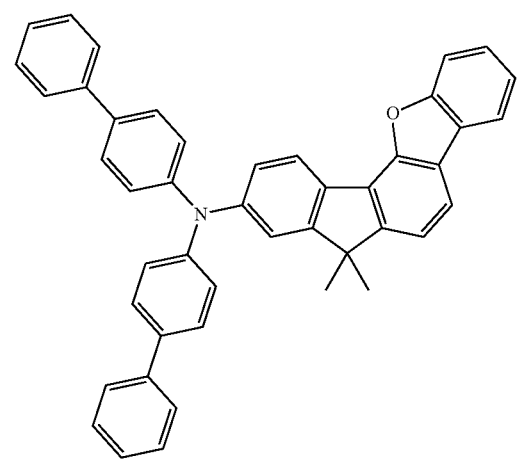

[D-38]
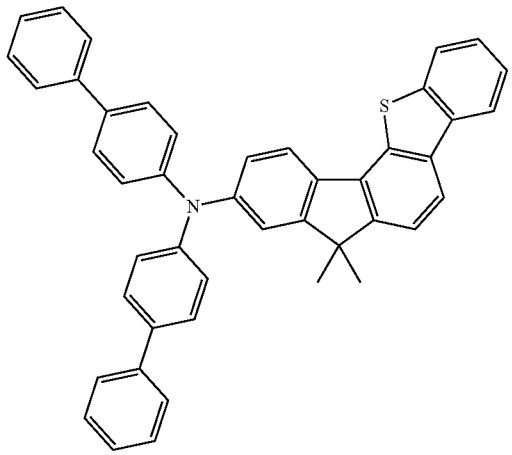
[D-39]
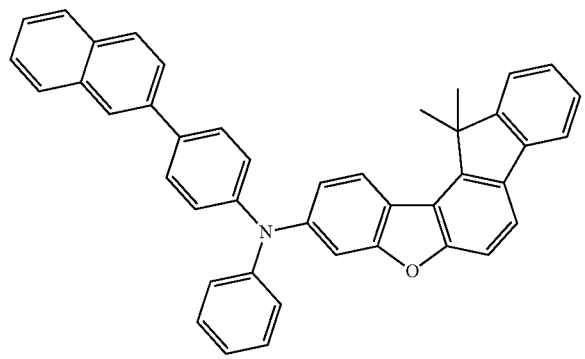
[D-40]
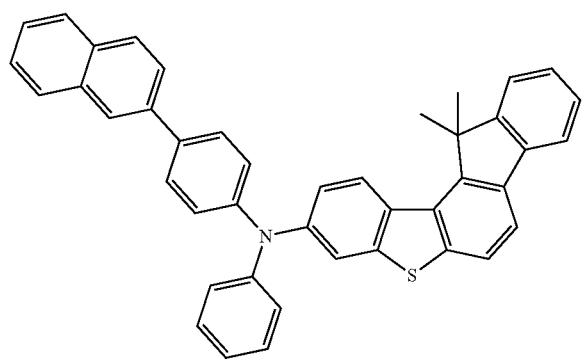
[D-41]
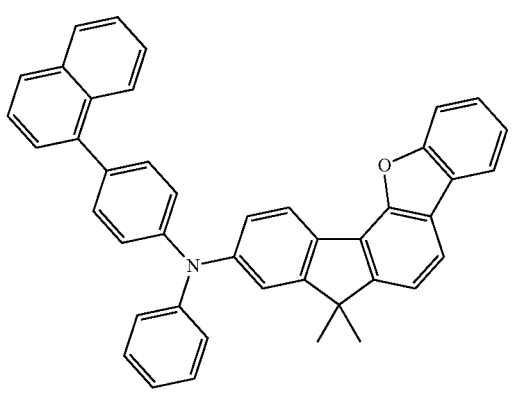
[D-42]
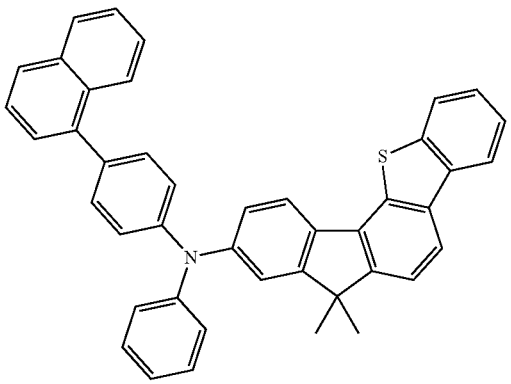
[D-43]
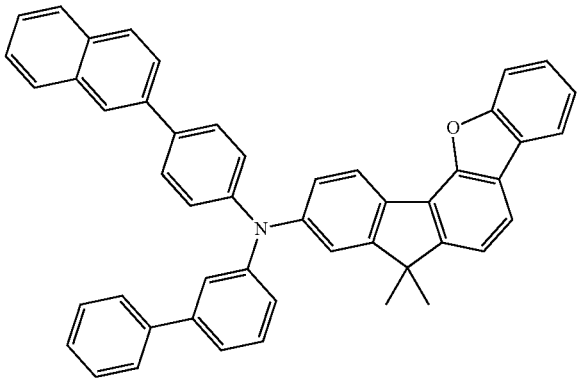
[D-43]
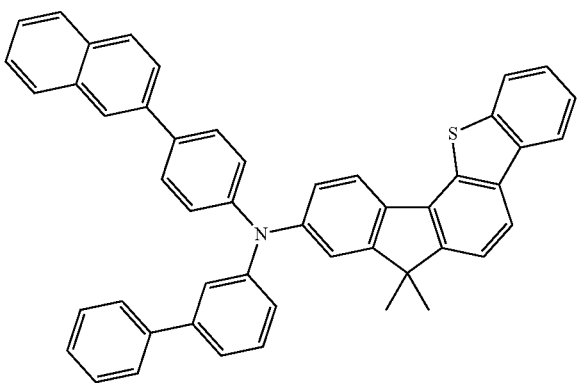

[D-45]
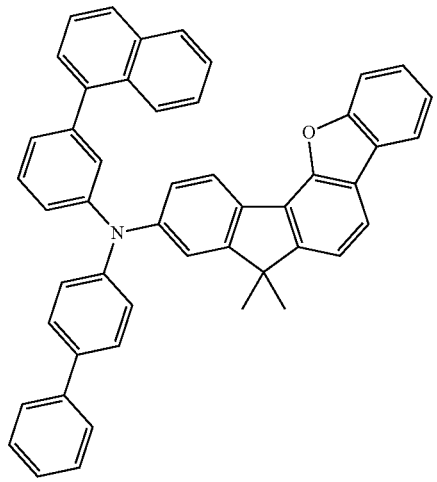
[D-46]
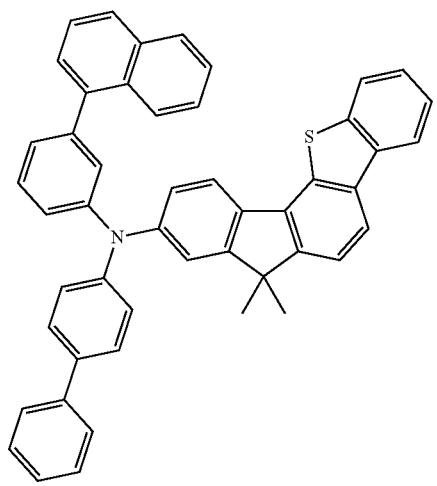
[D-47]
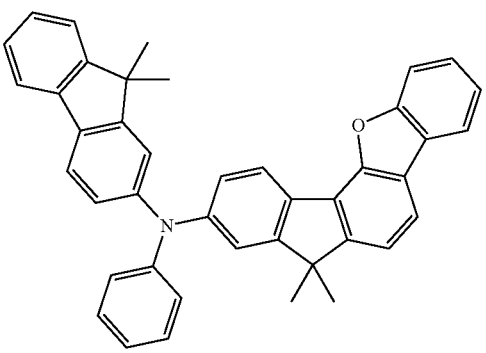
[D-48]
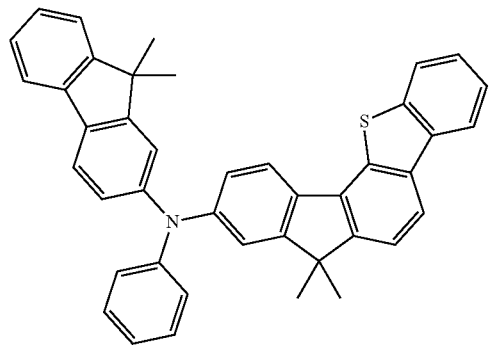
[D-49]
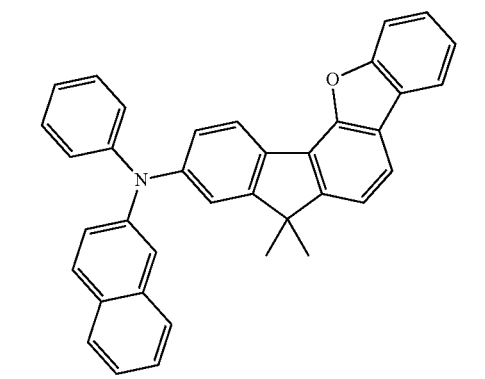
[D-50]
[D-51]
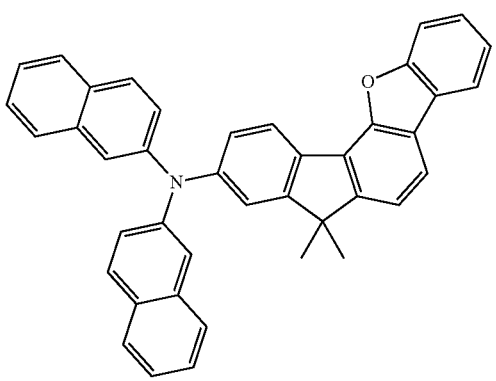

[D-52]
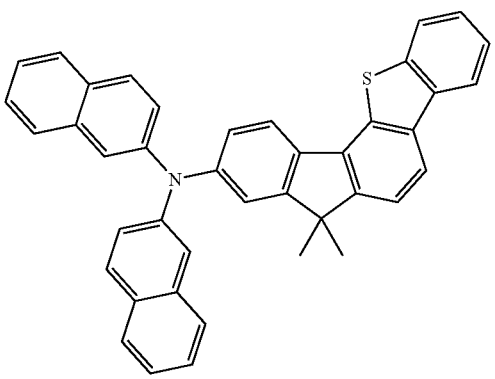

[D-53]
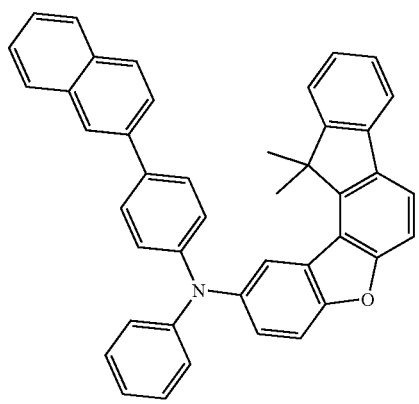

[D-54]
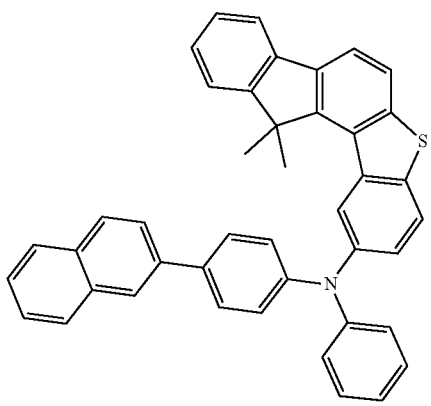

[D-55]
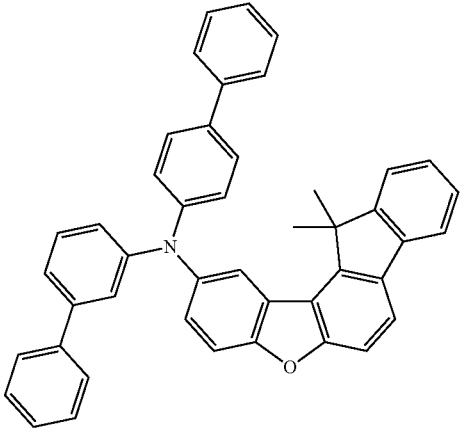

[D-56]
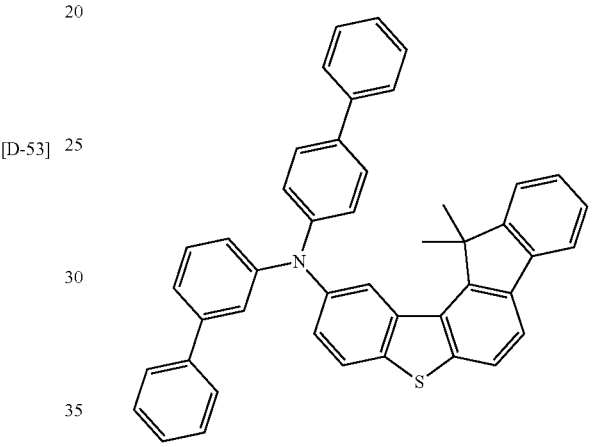

The first compound and the second compound may be, e.g., included in a weight ratio of about 1:99 to about 99:1. Within the range, bipolar characteristics may be implemented to improve efficiency and life-span by adjusting an appropriate weight ratio using the electron transport capability of the first compound and the hole transport capability of the second compound. Within the range, they may be, e.g., included in a weight ratio of about 10:90 to about 90:10, about 20:80 to about 80:20, e.g. about 20:80 to about 70:30, about 20:80 to about 60:40, and about 30:70 to about 60:40. In an implementation, they may be included in a weight ratio of about 40:60, about 50:50, or about 60:40.

In addition to the aforementioned first compound and second compound, one or more compounds may be further included.

The aforementioned compound for the organic optoelectronic device or composition for the organic optoelectronic device may be a composition further including a dopant.

The dopant may be, e.g., a phosphorescent dopant. In an implementation, the dopant may be, e.g., a red, green, or blue phosphorescent dopant. In an implementation, the dopant may be, e.g., a red or green phosphorescent dopant.

The dopant is a material mixed with the compound or the composition for an organic optoelectronic device in a small amount to facilitate light emission, and may be a material such as a metal complex that emits light by multiple excitation into a triplet or more. The dopant may be, e.g., an inorganic, organic, or organic/inorganic compound, and one or more types thereof may be used.

The dopant may be, e.g., a phosphorescent dopant and examples of the phosphorescent dopant may include organometallic compounds including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$$L^{15}MX^2 \qquad \text{[Chemical Formula Z]}$$

In Chemical Formula Z, M may be a metal, and $L^{15}$ and $X^2$ may each independently be ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and $L^{15}$ and $X^2$ may be, e.g., a bidentate ligand.

The aforementioned compound for the organic optoelectronic device or composition for the organic optoelectronic device described above may be formed by a dry film forming method such as chemical vapor deposition.

Hereinafter, an organic optoelectronic device including the aforementioned compound for the organic optoelectronic device or composition for the organic optoelectronic device is described.

The organic optoelectronic device may be a suitable device to convert electrical energy into photoenergy and vice versa, e.g., an organic photoelectric device, an organic light emitting diode, an organic solar cell, and an organic photoconductor drum.

Herein, an organic light emitting diode as one example of an organic optoelectronic device is described referring to drawings.

Figure 2:
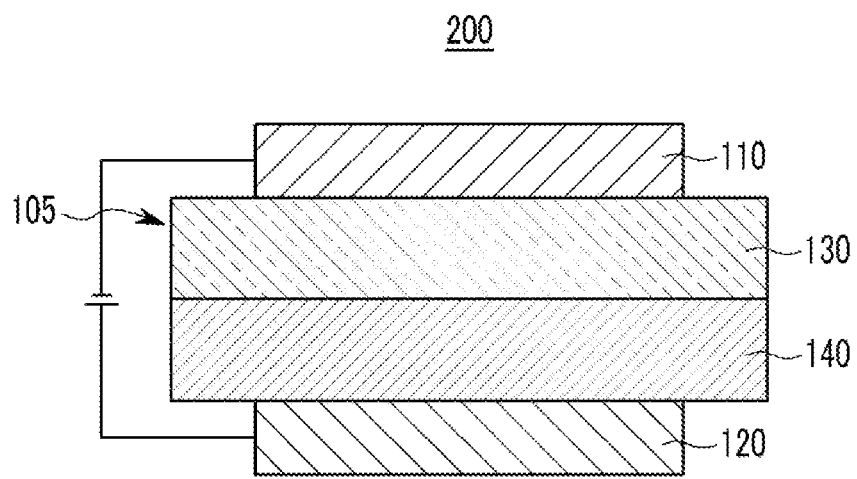

FIGS. 1 and 2 are cross-sectional views of an organic light emitting diode according to embodiments.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to facilitate hole injection, and may be, e.g., a metal, a metal oxide and/or a conductive polymer. The anode 120 may be, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy) thiophene) (PEDOT), polypyrrole, and polyaniline.

The cathode 110 may be made of a conductor having a small work function to facilitate electron injection, and may be, e.g., a metal, a metal oxide and/or a conductive polymer. The cathode 110 may be, e.g., a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca.

The organic layer 105 may include the aforementioned compound for the organic optoelectronic device or composition for the organic optoelectronic device.

The organic layer 105 may include the light emitting layer 130, and the light emitting layer 130 may include the aforementioned compound for the organic optoelectronic device or composition for the organic optoelectronic device.

The composition for the organic optoelectronic device further including a dopant may be, e.g., a red light emitting composition.

The light emitting layer 130 may include, e.g., the aforementioned first compound for the organic optoelectronic device and compound for the second organic optoelectronic device, respectively, as phosphorescent hosts.

The organic layer may further include an auxiliary layer in addition to the light emitting layer.

The auxiliary layer may be, e.g., a hole auxiliary layer 140.

Referring to FIG. 2, the organic light emitting diode 200 may further include a hole auxiliary layer 140 in addition to the light emitting layer 130. The hole auxiliary layer 140 may help increase hole injection and/or hole mobility and block electrons between the anode 120 and the light emitting layer 130.

The hole auxiliary layer 140 may include, e.g., a compound of Group E.

In an implementation, the hole auxiliary layer 140 may include a hole transport layer between the anode 120 and the light emitting layer 130, and a hole transport auxiliary layer between the light emitting layer 130 and the hole transport layer. In an implementation, at least one of the compounds of Group E may be included in the hole transport auxiliary layer.

[Group E]

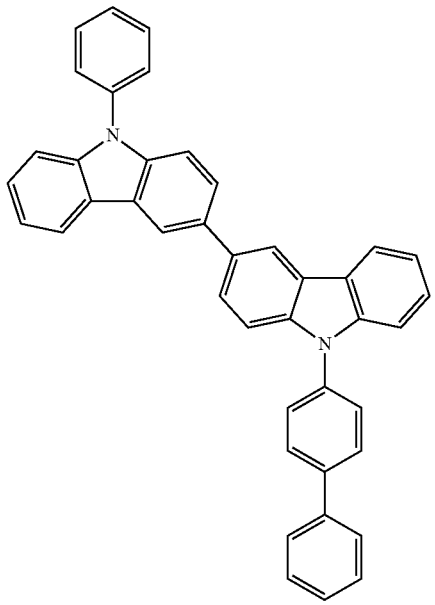

149
-continued
150
-continued
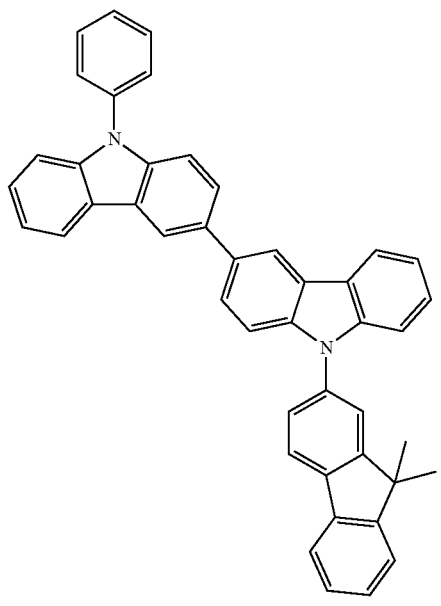
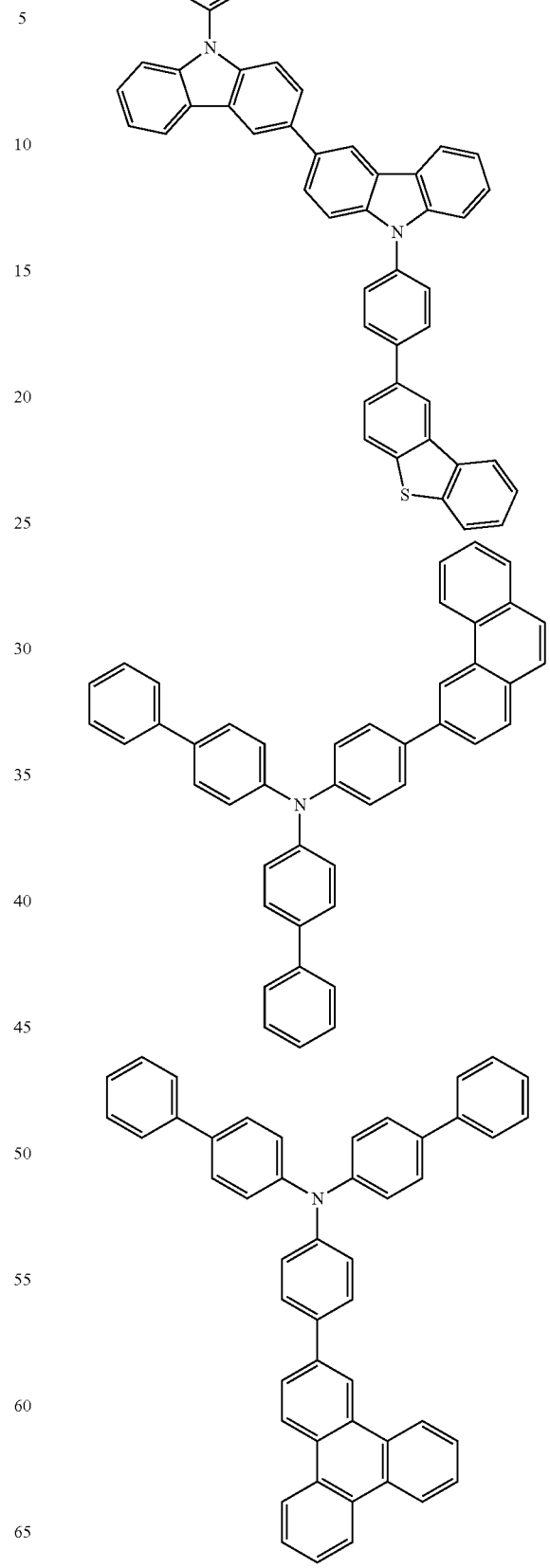

151
-continued
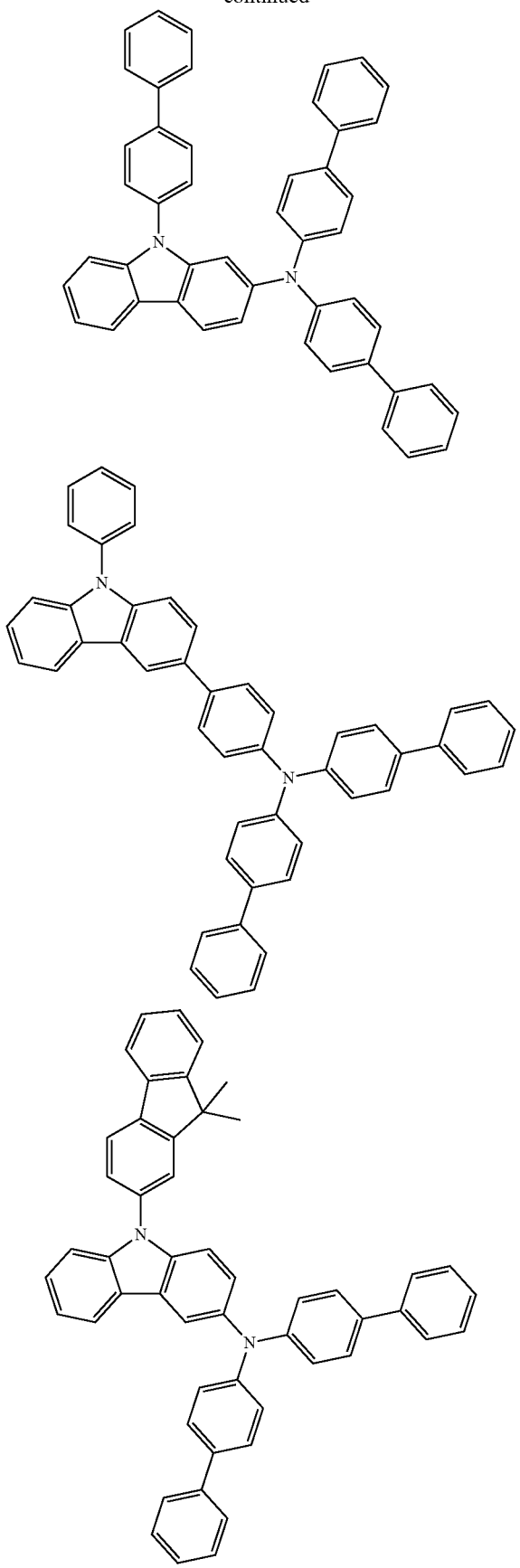
152
-continued
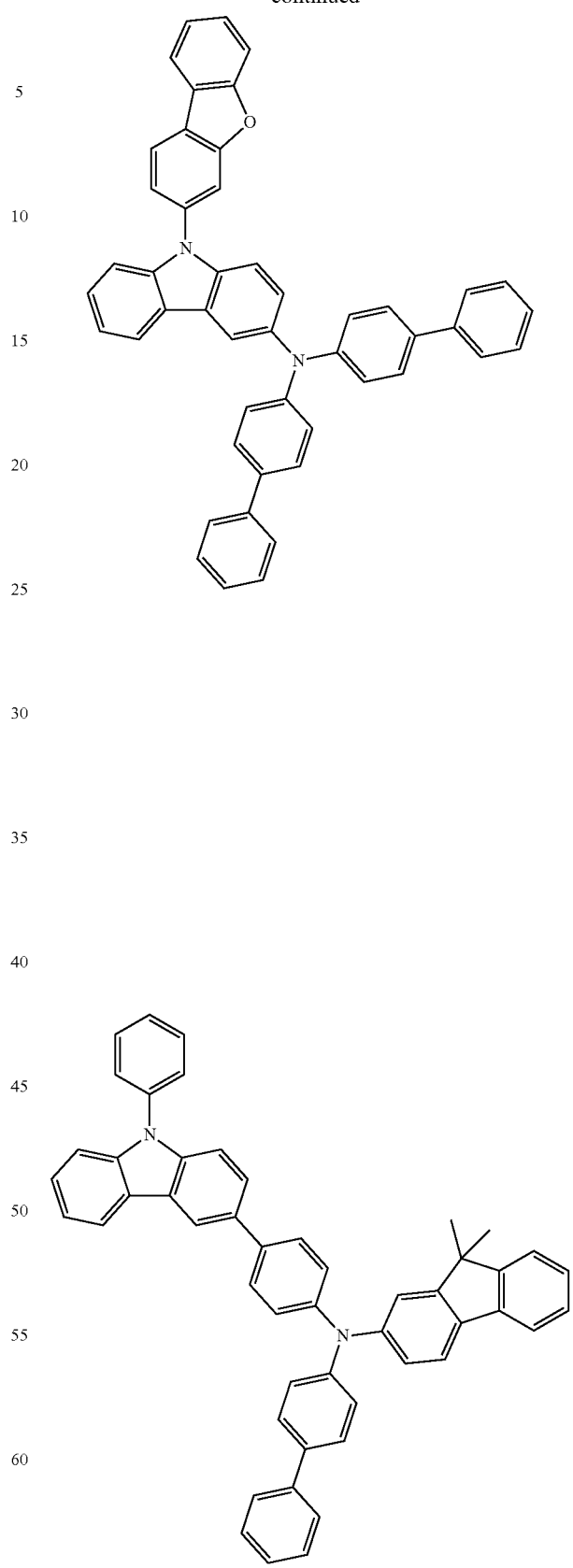

153
-continued
154
-continued
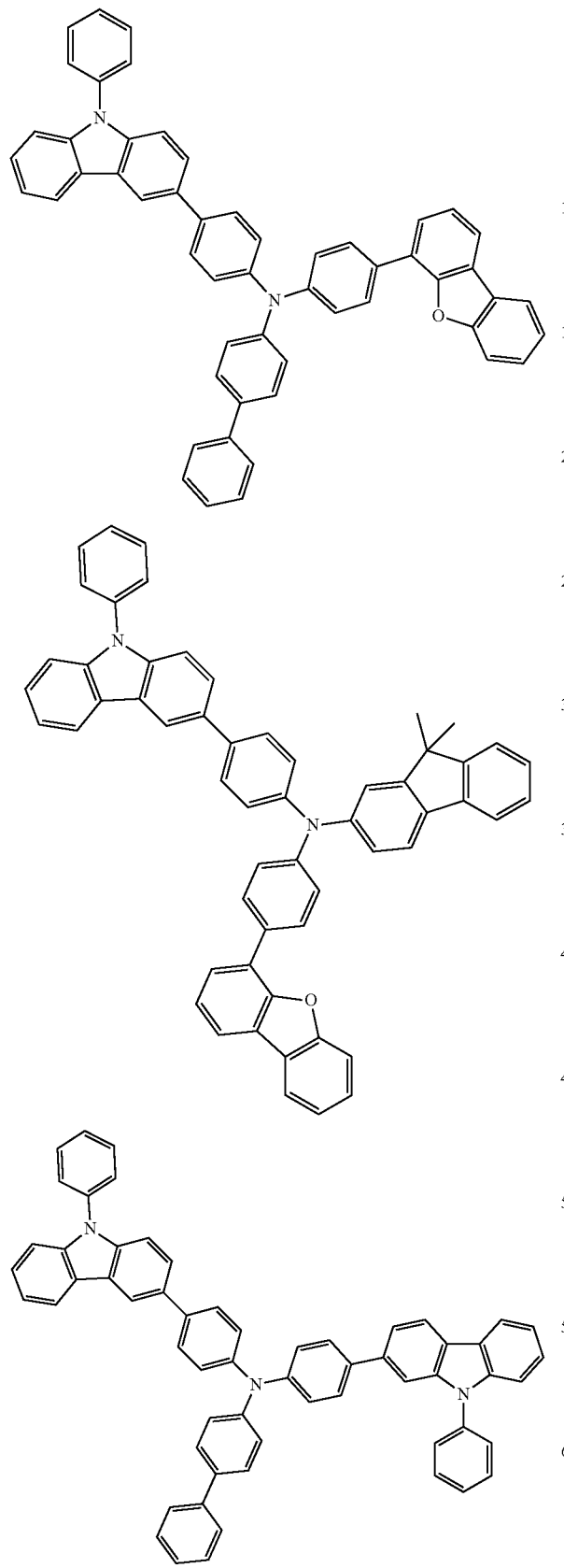
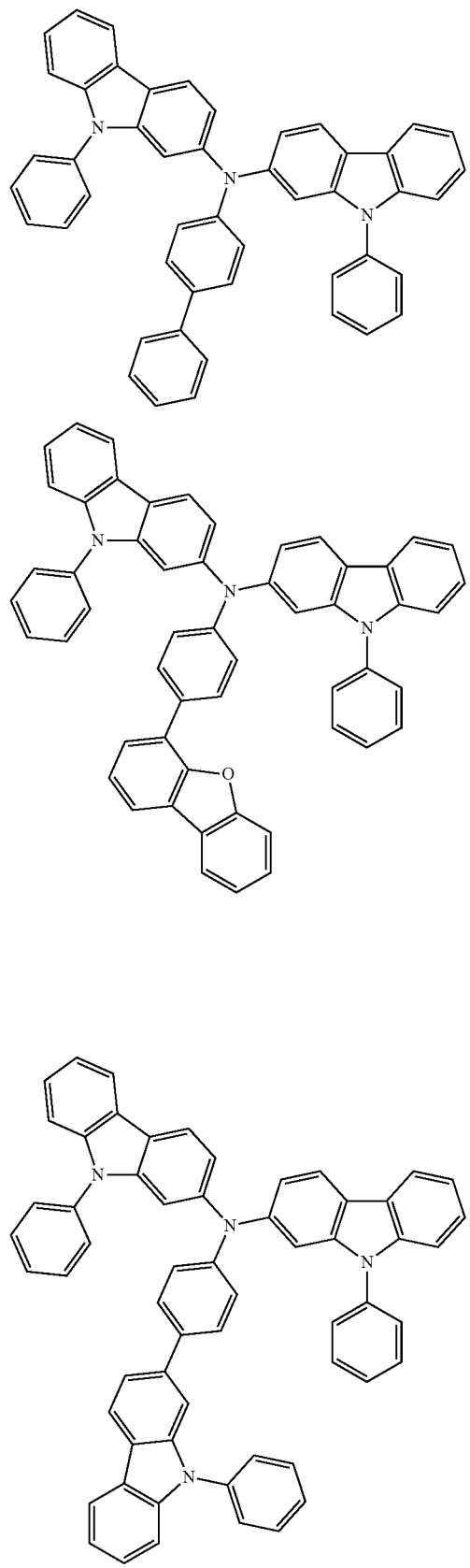

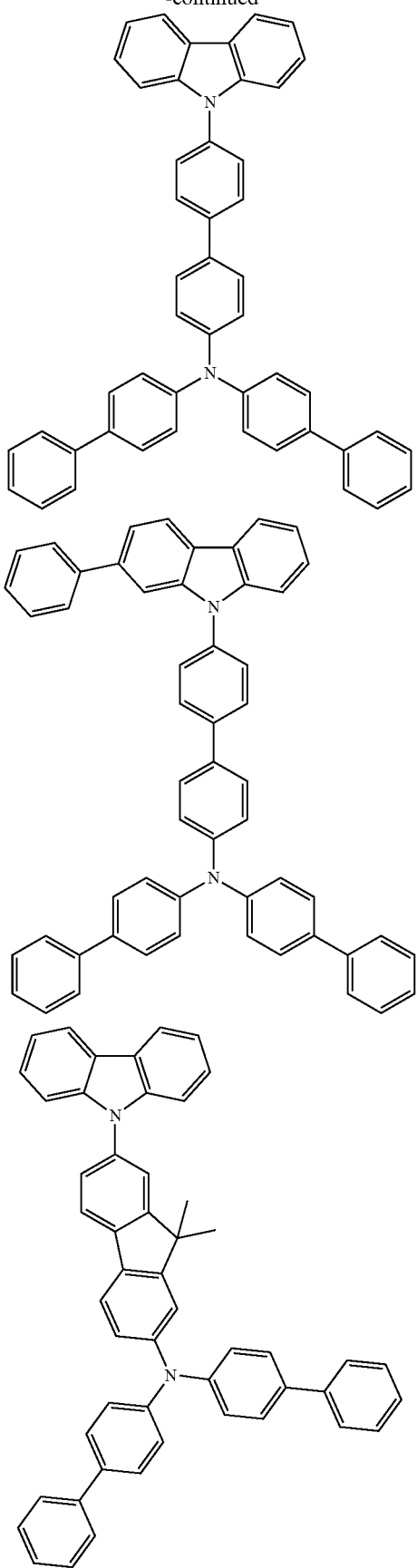
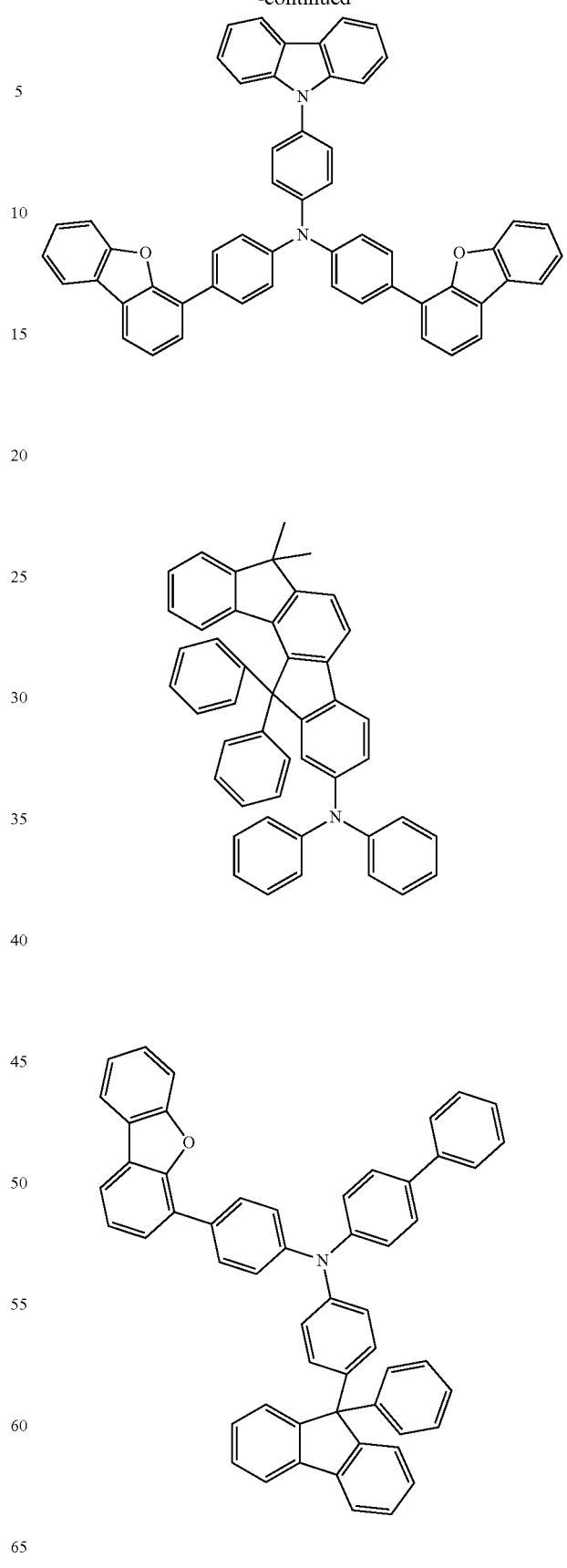

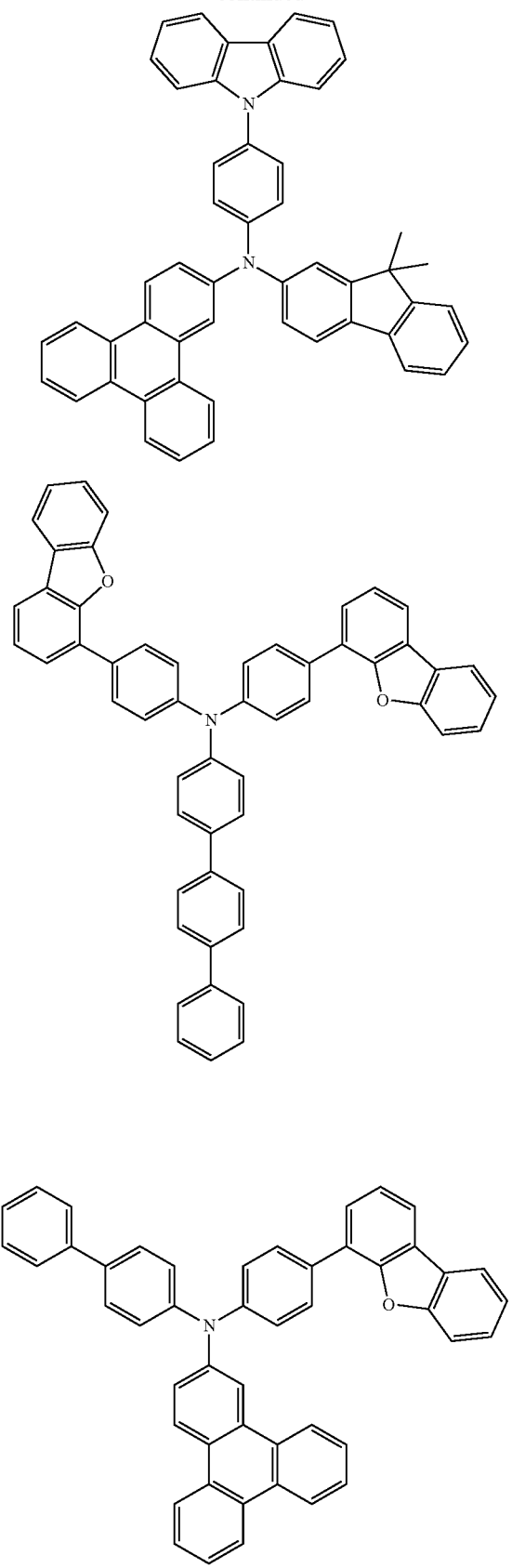
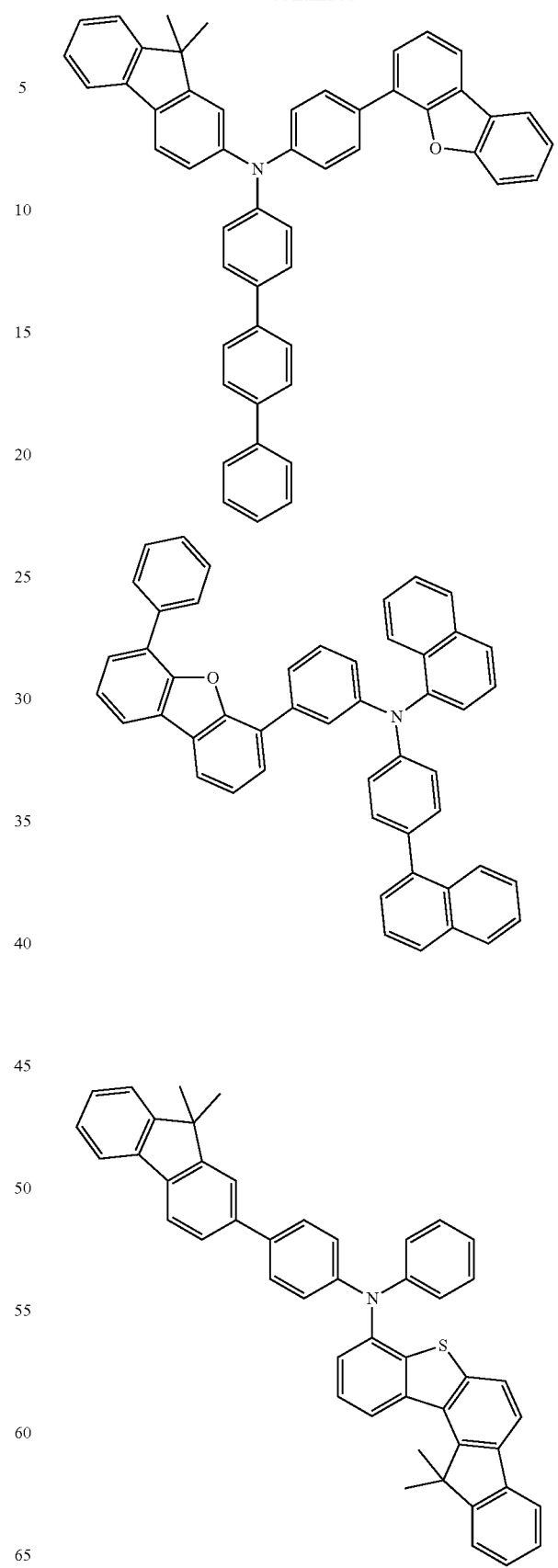

159
-continued
160
-continued
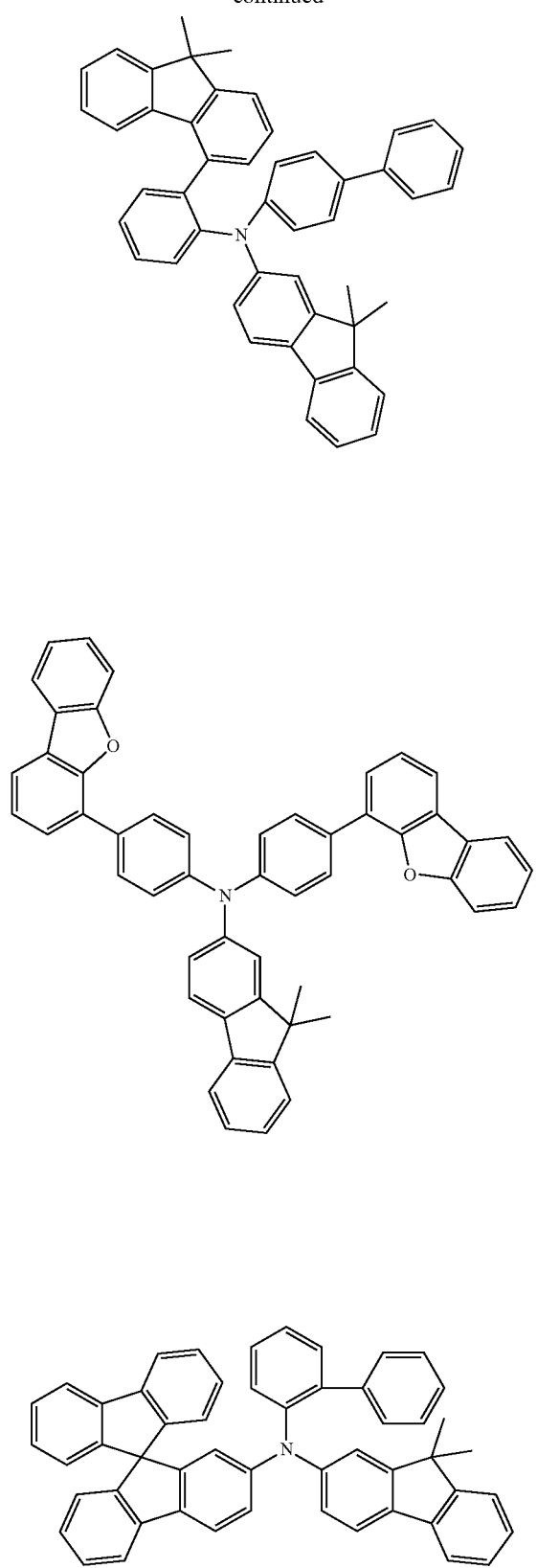
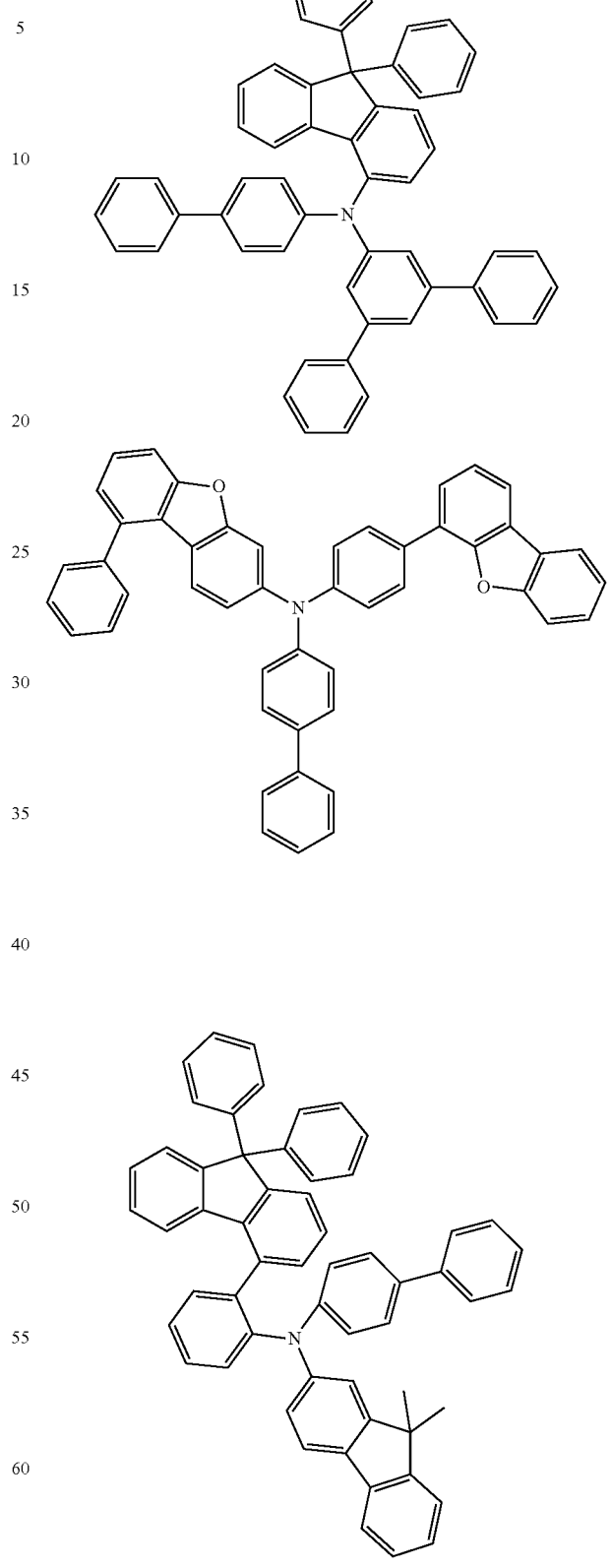

161
-continued
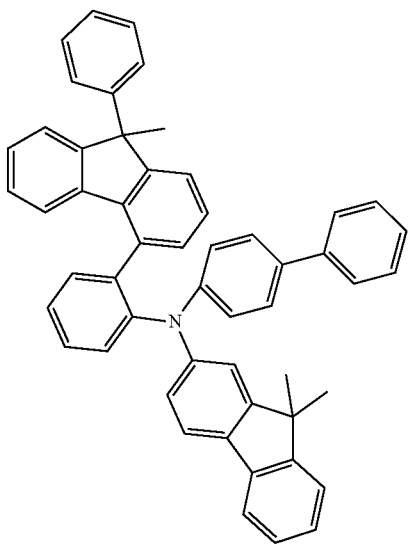
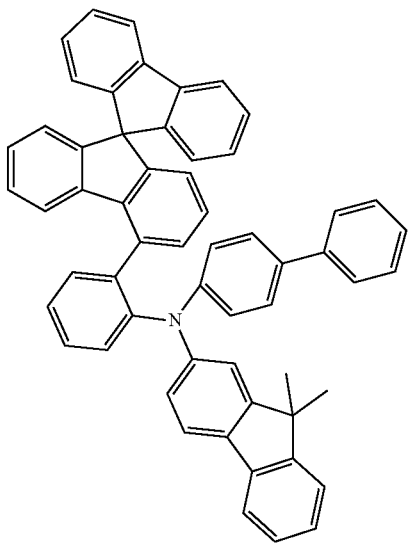
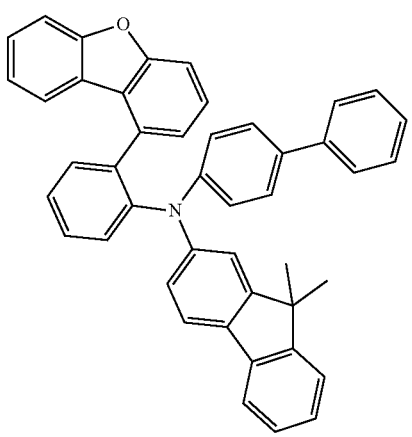
162
-continued
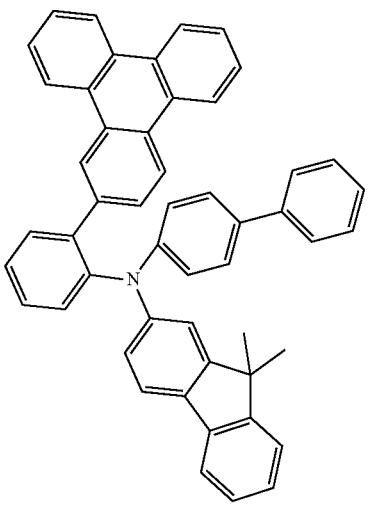
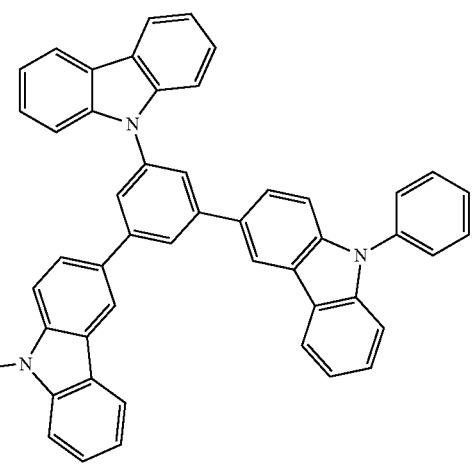
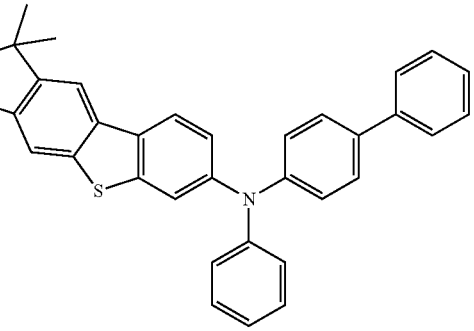

-continued
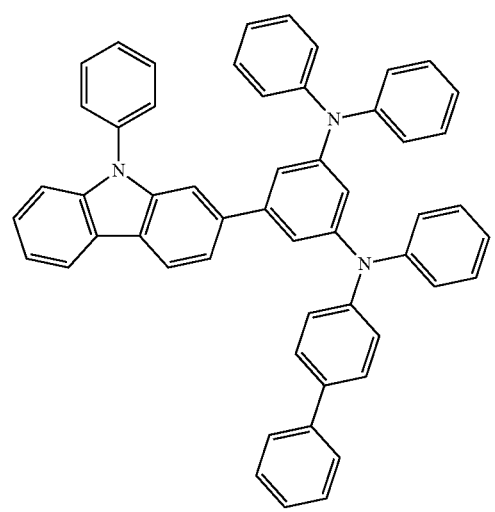
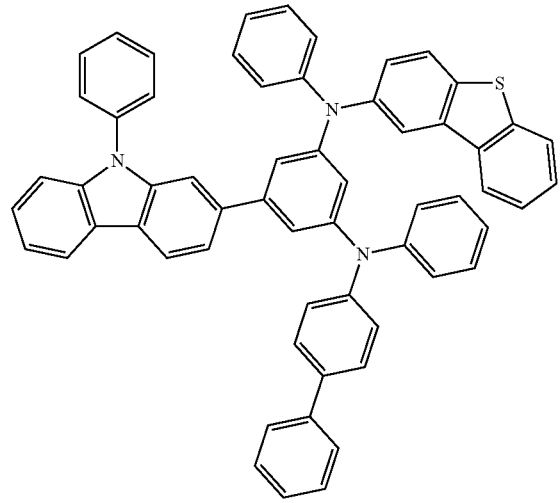
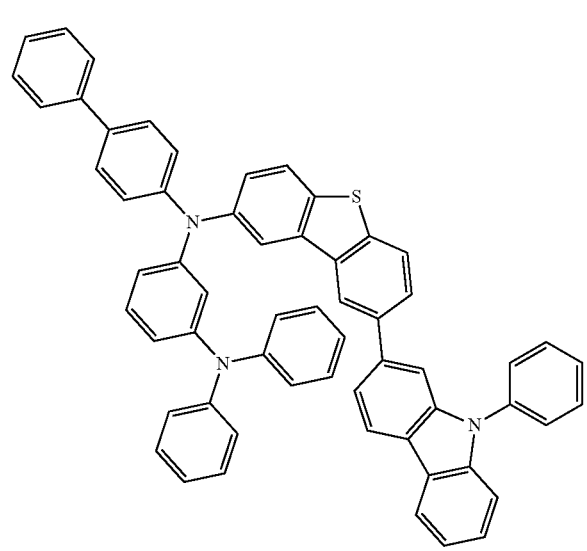
-continued
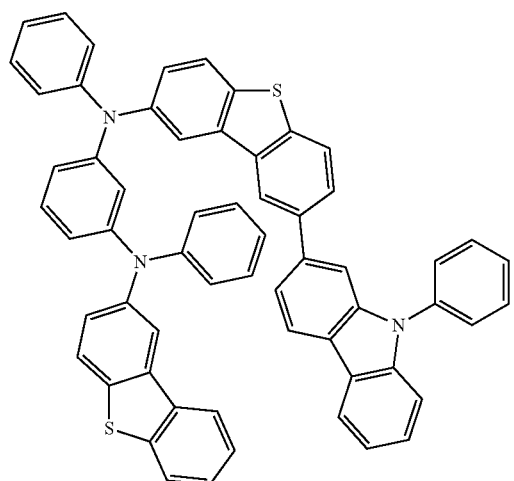
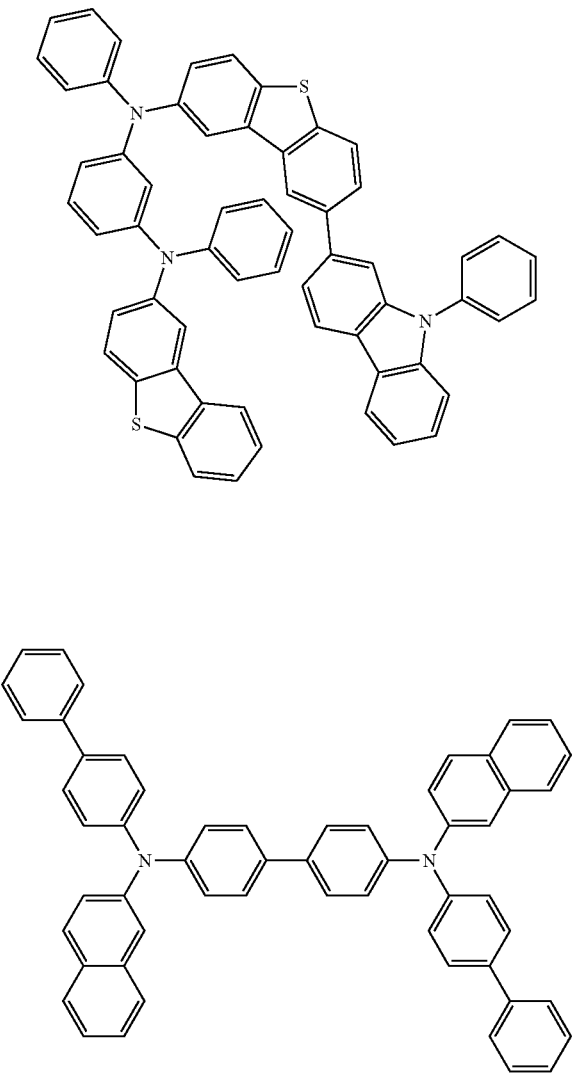
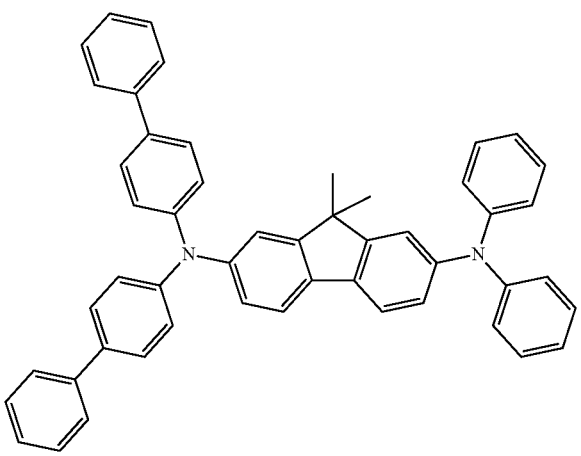

165
-continued
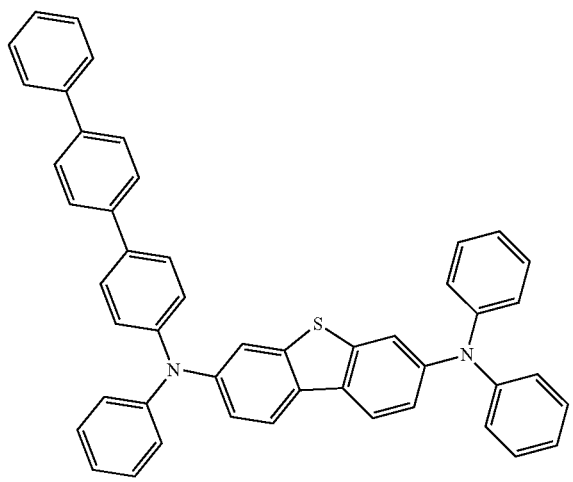
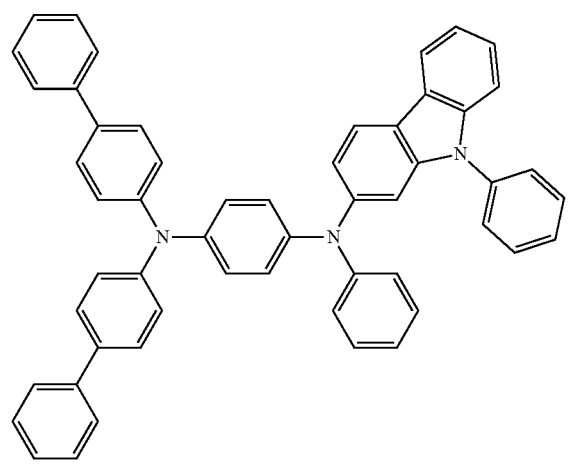
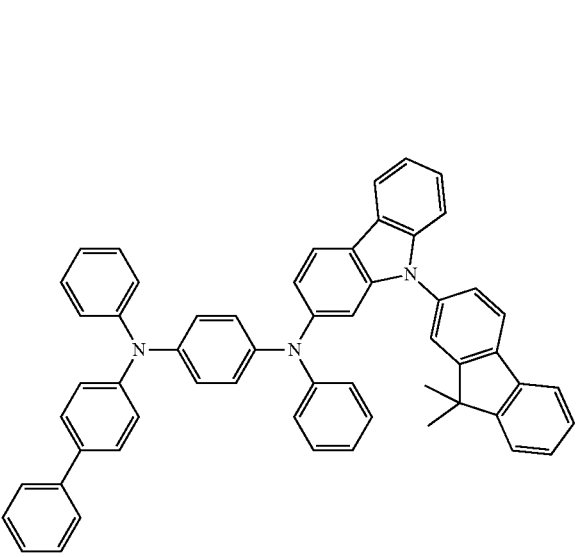
166
-continued
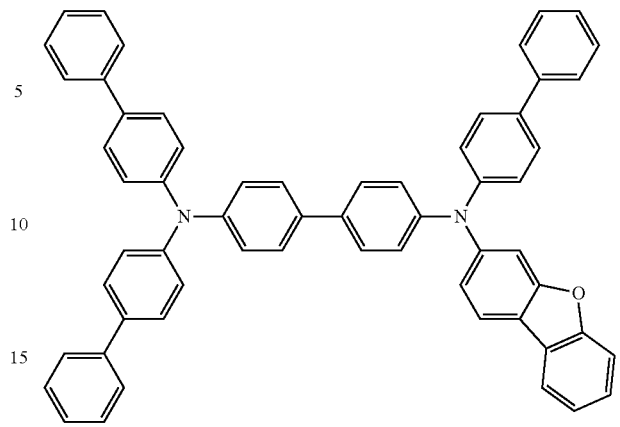
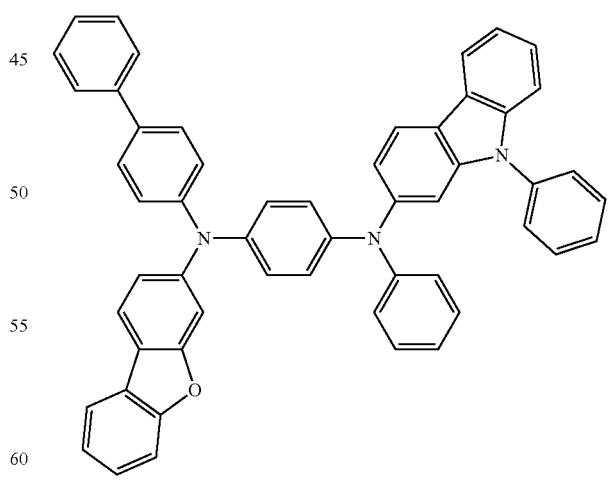

167
-continued
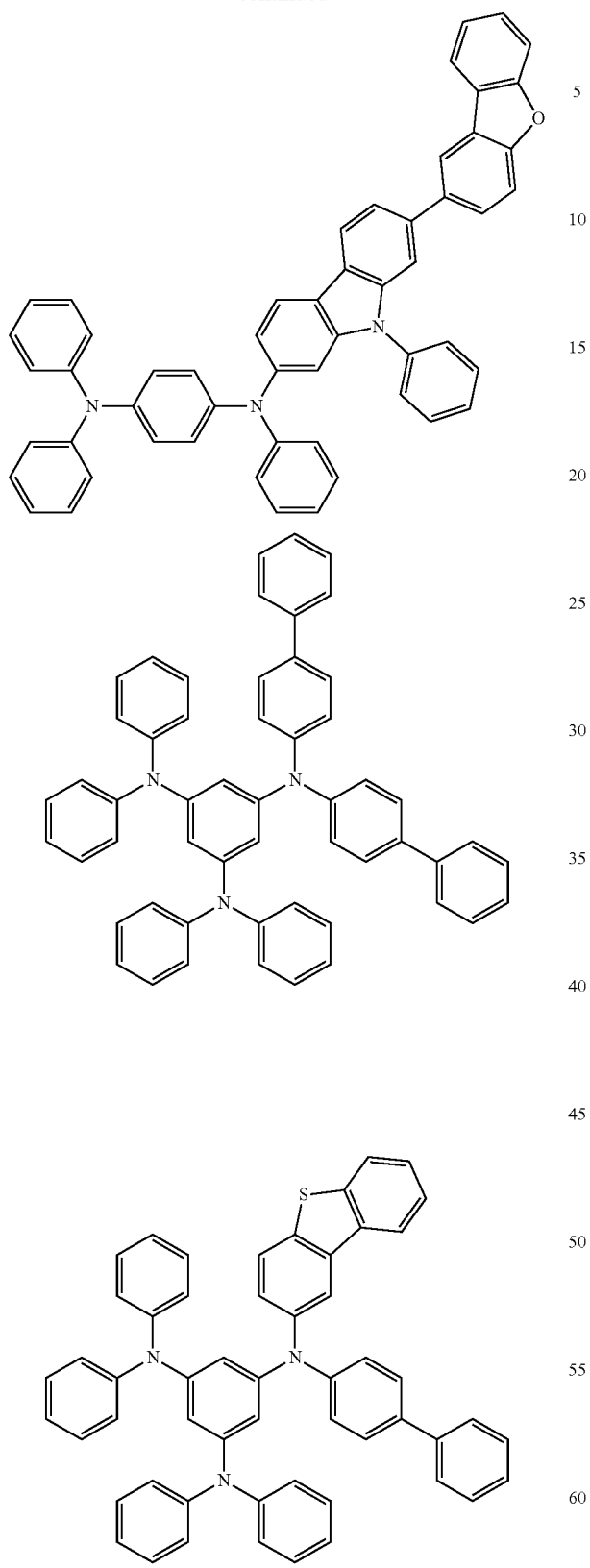
168
-continued
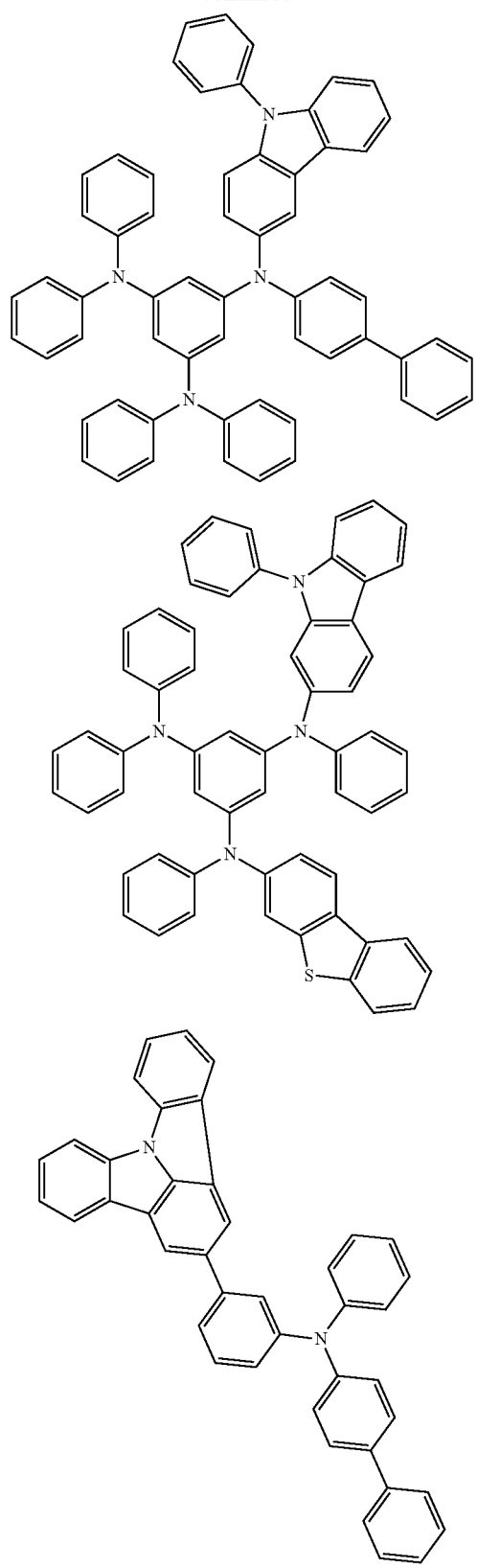

169
-continued
170
-continued
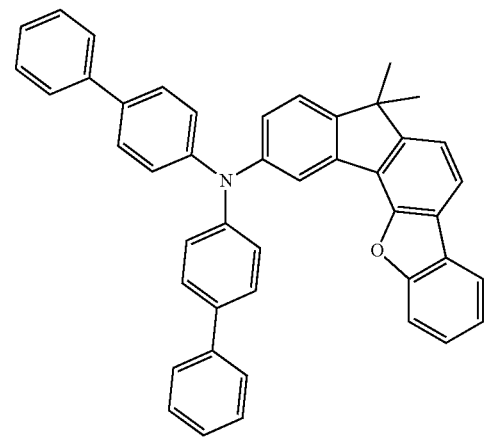
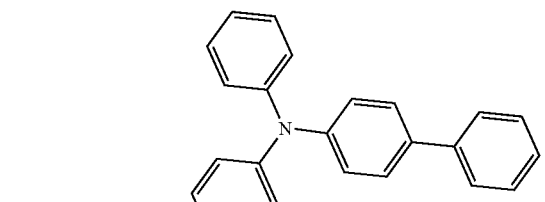
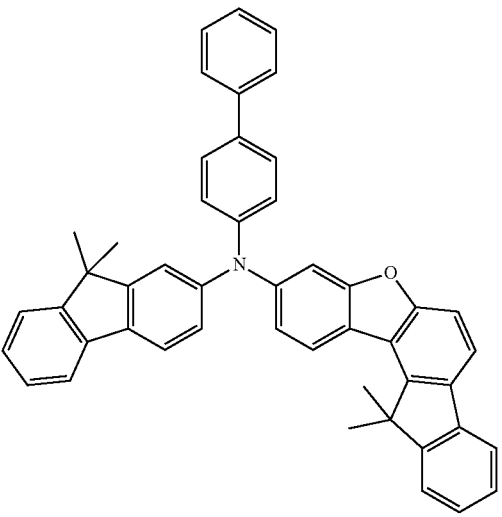
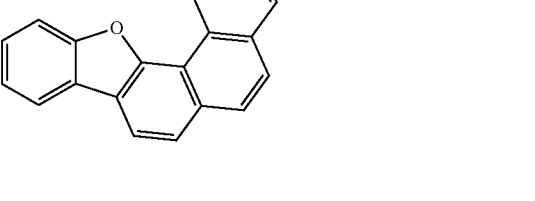
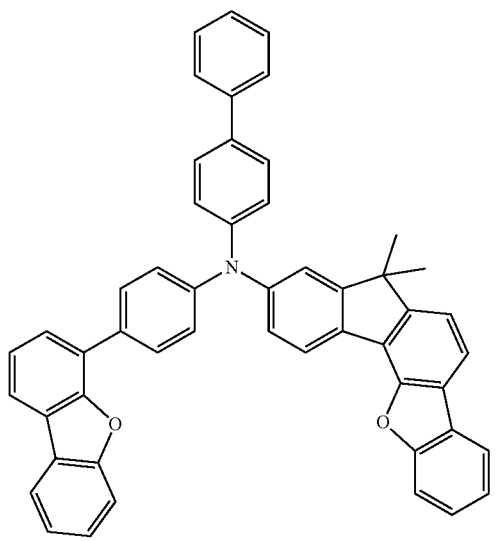
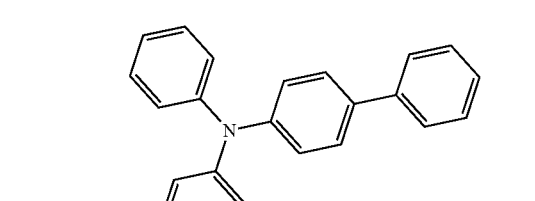
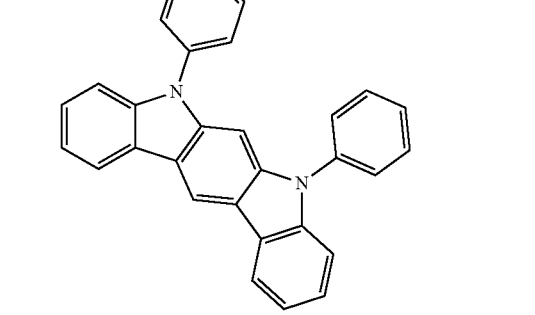

-continued

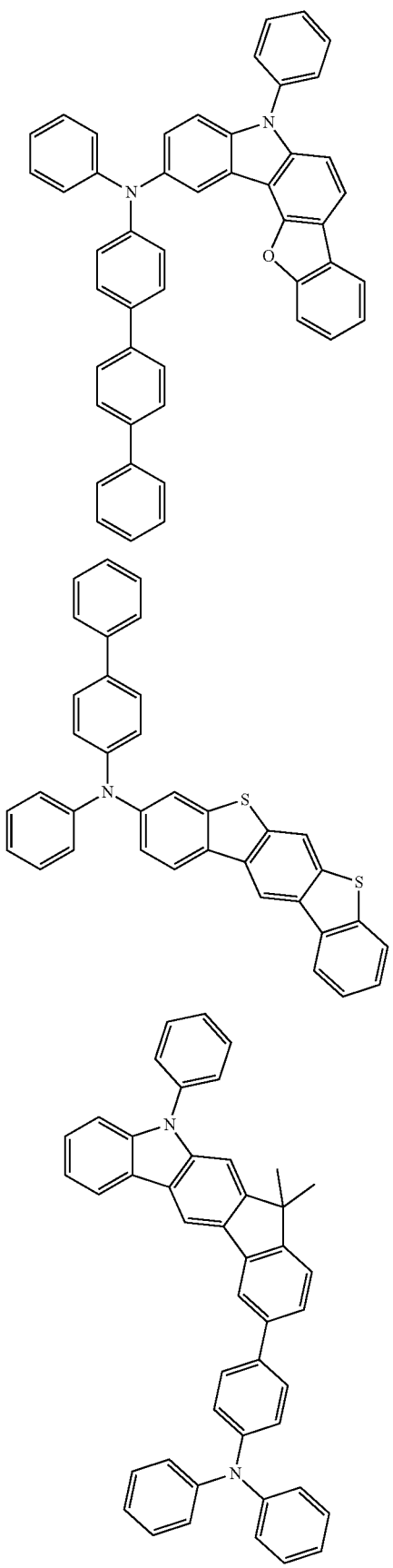

-continued

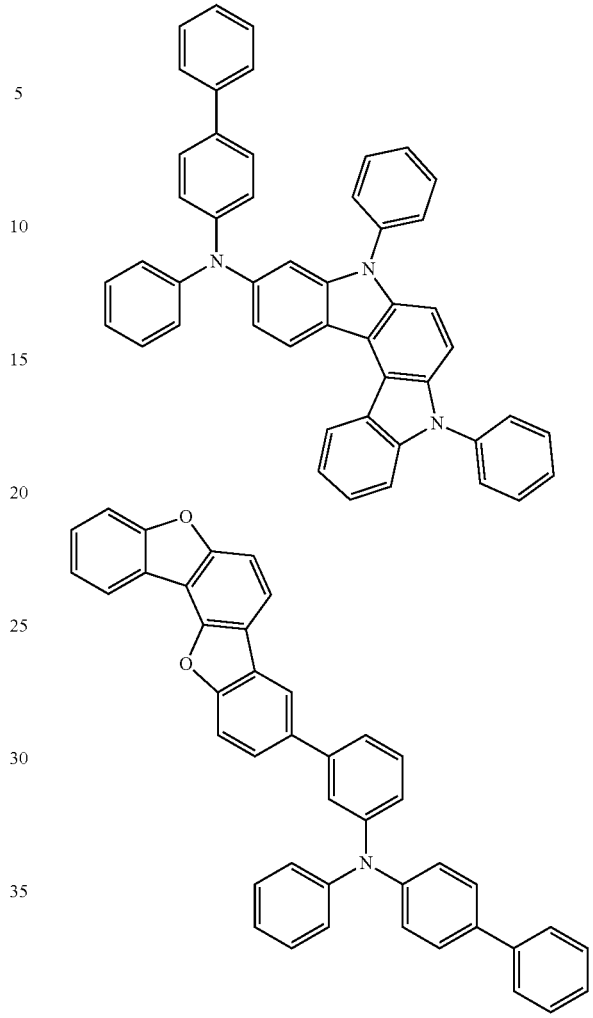

In addition to the above-described compounds, compounds disclosed in U.S. Pat. No. 5,061,569A, JP1993-009471A, WO1995-009147A1, JP1995-126615A, JP1998-095973A, and compounds having similar structures may also be used for the hole transport auxiliary layer.

In addition, in an embodiment, it may be an organic light emitting diode that further includes an electron transport layer, an electron injection layer, and a hole injection layer, as the organic layer 105 in FIG. 1 or 2.

The organic light-emitting devices 100 and 200 may be manufactured by forming an anode or a cathode on a substrate, forming an organic layer by a dry film method such as evaporation, sputtering, plasma plating and ion plating, and then forming a cathode or an anode.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd., TCI Inc., Tokyo chemical industry or P&H tech as far as there in no particular comment or were synthesized by suitable methods.

(Preparation of Compound for Organic Optoelectronic Device)

The compound as one specific examples was synthesized through the following steps.

Synthesis Example 1: Synthesis of Compound 20

[Reaction Scheme 1]

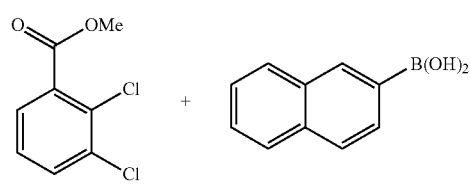

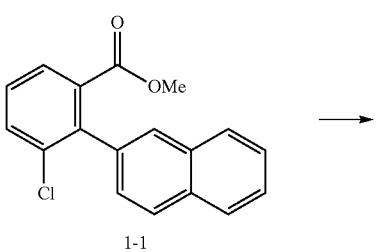

1-1

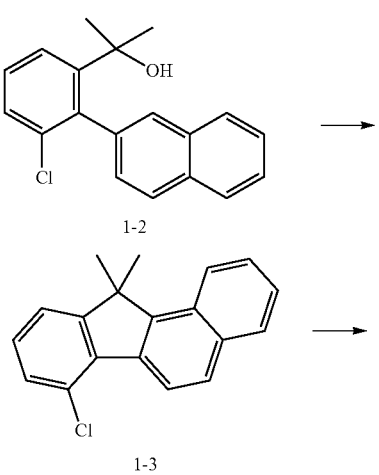

1-2

1-3

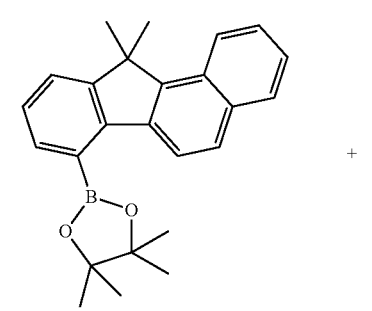

1-4

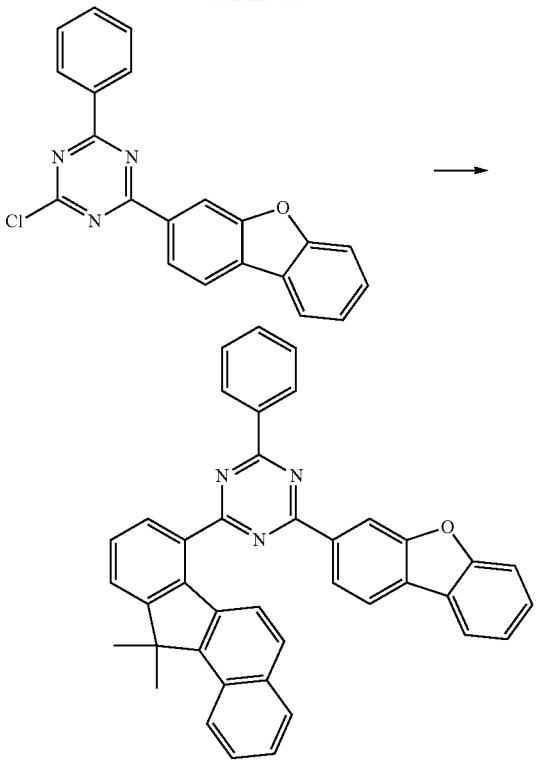

20

Synthesis Example 1-a: Synthesis of Compound 1-1

45.5 g (222 mmol) of methyl 2,3-dichlorobenzoate was put in 500 ml of toluene and 200 ml of distilled water, and 1 equivalent of 2-naphthaleneboronic acid, 0.05 equivalent of dichlorodiphenylphosphinoferrocene palladium, and 2.5 equivalent of potassium carbonate were added thereto and then, heated and refluxed under a nitrogen atmosphere. After 6 hours, the reaction solution was cooled down, and after removing an aqueous layer, an organic layer obtained therefrom was treated and dried with magnesium sulfate and purified through column chromatography to obtain a white solid of Compound 1-1 (30.6 g, 46%).

Synthesis Example 1-b: Synthesis of Compound 1-2

Compound 1-1 was put in 300 ml of anhydrous tetrahydrofuran and then, cooled down to 0° C., and 2.5 equivalent of methyl magnesium bromide was slowly injected thereinto under a nitrogen atmosphere. The mixture was reacted until the temperature naturally reached ambient temperature, and 4 hours later, water was used to terminate the reaction. An organic layer obtained by removing an aqueous layer was dried to obtain Compound 1-2 (30 g, 98%).

Synthesis Example 1-c: Synthesis of Compound 1-3

Compound 1-2 was put in 300 ml of dichloromethane, and after decreasing the temperature down to 0° C., 2.5 equivalent of boron trifluoride etherate was slowly injected thereinto under a nitrogen atmosphere. The mixture was reacted, until the temperature naturally reached ambient temperature, and 4 hours later, the reaction was terminated with water. An organic layer obtained by removing an aqueous layer was dried and then, purified through column chromatography to obtain a white solid of Compound 1-3 (21 g, 76%).

Synthesis Example 1-d: Synthesis of Compound 1-4

Compound 1-3 was put in 250 ml of xylene, and 0.05 equivalent of dichlorodiphenyl-phosphinoferrocene palladium, 1.2 equivalent of bis(pinacolato)diboron, and 2 equivalent of potassium acetate were added thereto and then, heated and refluxed under a nitrogen atmosphere for 16 hours. The reaction solution was passed through a silica pad to quantitatively obtain Compound 1-4.

Synthesis Example 1-e: Synthesis of Compound 20

Compound 1-4 was put in 200 ml of 1,4-dioxane and 100 ml of distilled water, and 1 equivalent of 2-chloro-4-(3-dibenzofuranyl)-6-phenyl-1,3,5-triazine, 0.03 equivalent of tetrakis(triphenylphosphine)palladium, and 2 equivalent of potassium carbonate were added thereto and then, heated and refluxed under a nitrogen atmosphere. After 18 hours, the reaction solution was cooled down, and after removing an aqueous layer therefrom, a solid extracted therein was filtered, washed with methanol, and recrystallized with toluene to obtain Compound 20 (31 g, 73%).

LC/MS [M+H] 566.22

Synthesis Example 2: Synthesis of Compound 6

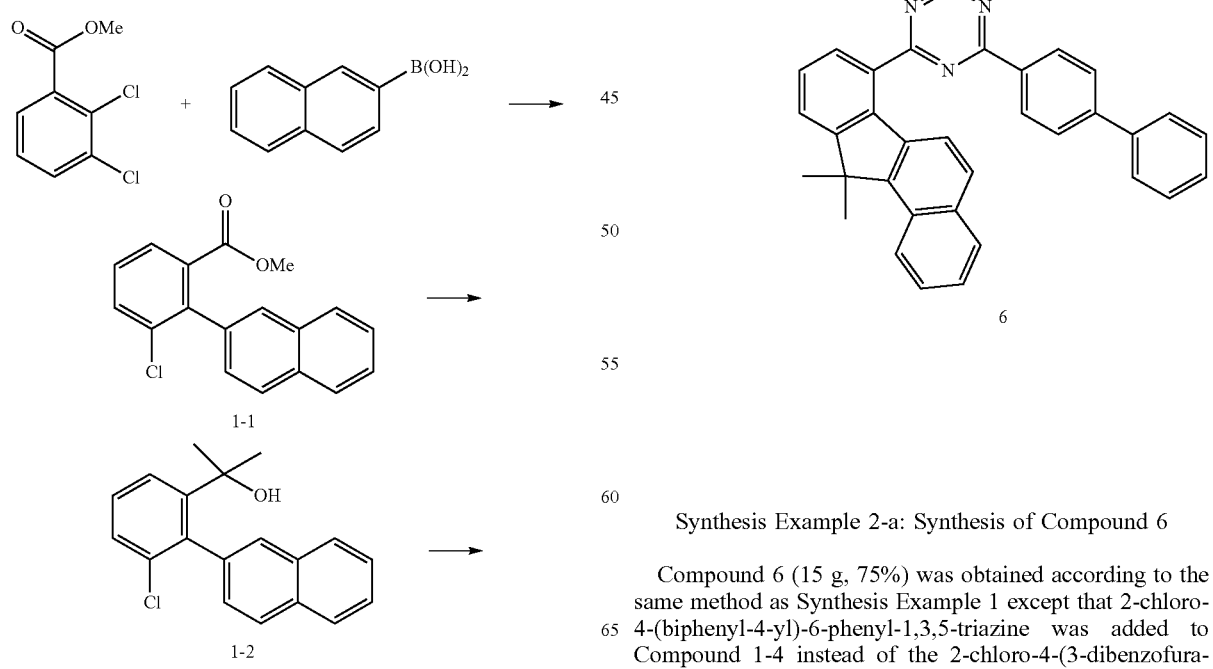

Synthesis Example 2-a: Synthesis of Compound 6

Compound 6 (15 g, 75%) was obtained according to the same method as Synthesis Example 1 except that 2-chloro-4-(biphenyl-4-yl)-6-phenyl-1,3,5-triazine was added to Compound 1-4 instead of the 2-chloro-4-(3-dibenzofuranyl)-6-phenyl-1,3,5-triazine. LC/MS [M+H] 552.19

Synthesis Example 3: Synthesis of Compound 10

[Reaction Scheme 3]

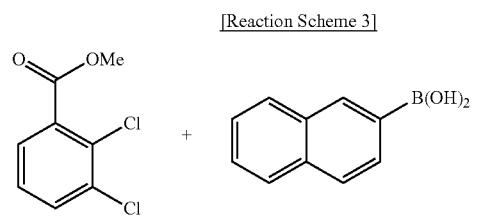

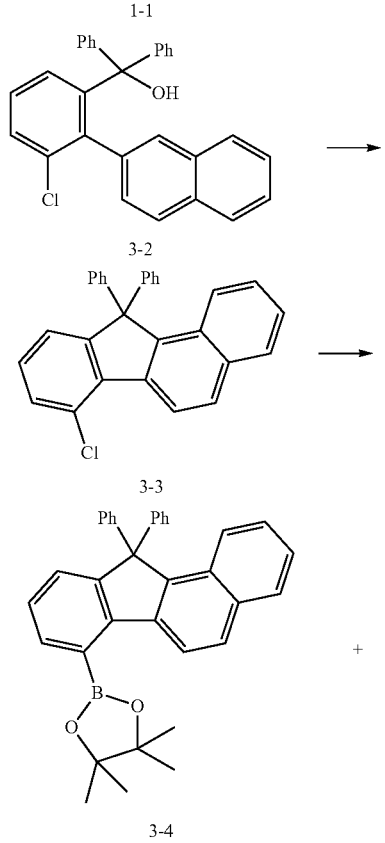

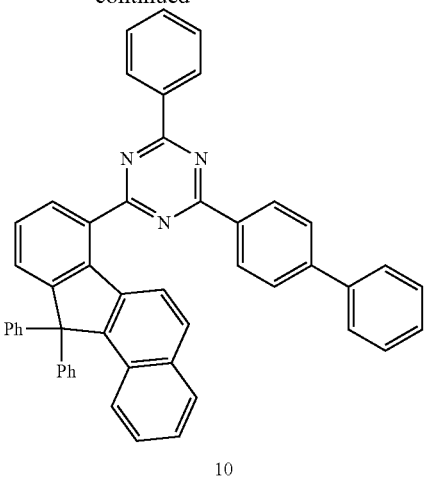

10

Synthesis Example 3-a: Synthesis of Compound 3-2

Compound 3-2 was obtained according to the same method as Synthesis Example 2 except that phenylmagnesium bromide was added to Compound 1-1 instead of the methylmagnesium bromide.

Synthesis Example 3-b: Synthesis of Compound 3-3

The reaction was performed according to the same method as Synthesis Example 1-c, except that Intermediate 3-2 was used instead of Compound 1-2. An organic layer obtained after removing an aqueous layer therefrom was dried and then, recrystallized with methanol to obtain a white solid of Compound 3-3.

Synthesis Example 3-c: Synthesis of Compound 3-4

Compound 3-4 was obtained according to the same method as Synthesis Example 1-d, except that Intermediate 3-3 was used instead of Compound 1-3.

Synthesis Example 3-d: Synthesis of Compound 10

Compound 10 (17.3 g, 68%) was obtained according to the same method as Synthesis Example 1-e except that Intermediate 3-4 was used instead of Compound 1-4.
LC/MS [M+H] 676.24

Synthesis Example 4: Synthesis of Compound 5

[Reaction Scheme 4]

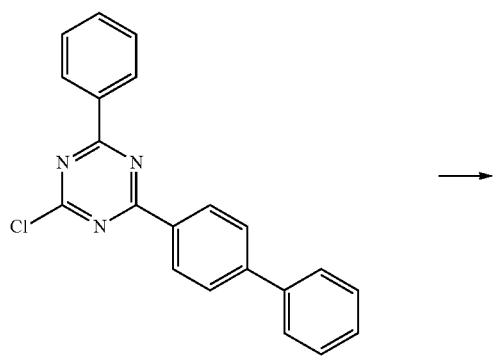

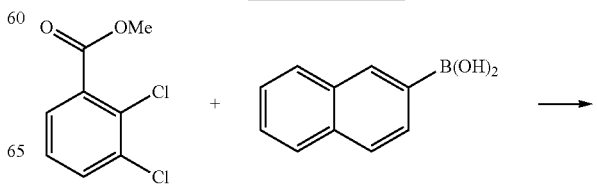

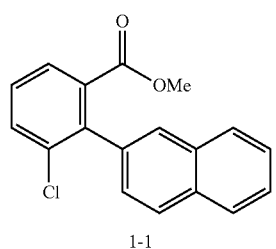
1-1
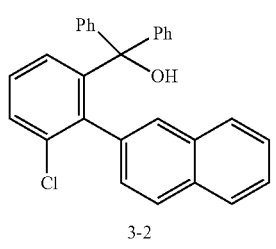
3-2
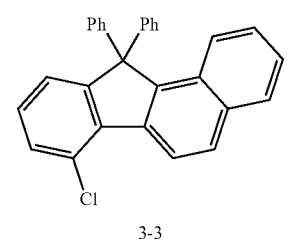
3-3
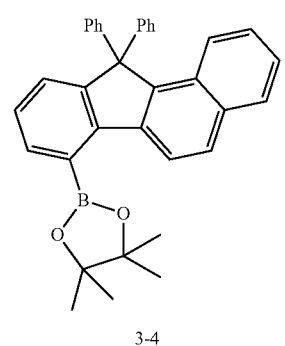
3-4
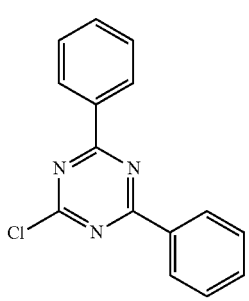
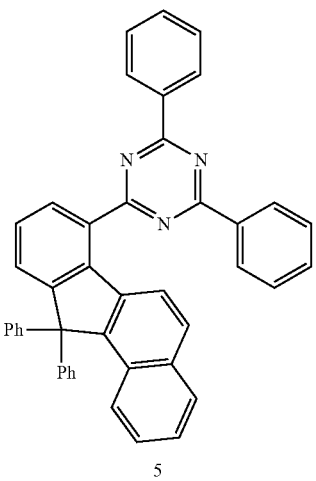
5
Synthesis Example 4-a: Synthesis of Compound 5
Compound 5 (12.3 g, 62%) was obtained according to the same method as Synthesis Example 3 except that 2-chloro-4,6-diphenyl-1,3,5-triazine was added to Compound 3-4 instead of the 2-chloro-4-(biphenyl-4-yl)-6-phenyl-1,3,5-triazine.
LC/MS [M+H] 600.07
Synthesis Example 5: Synthesis of Compound 51
[Reaction Scheme 5]
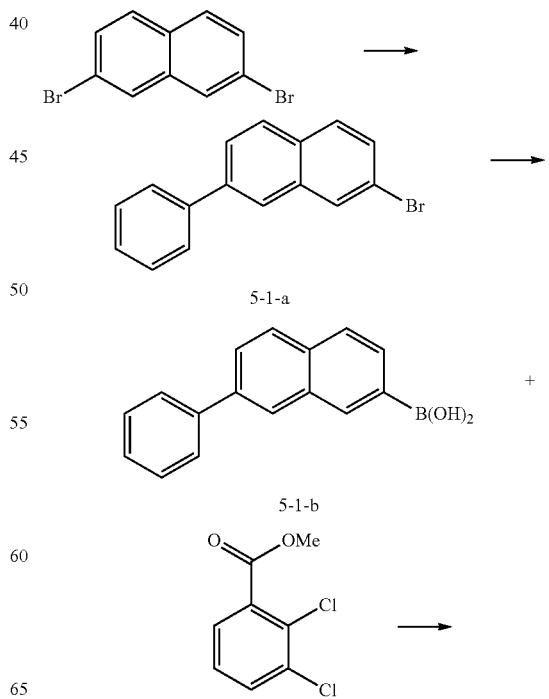

-continued

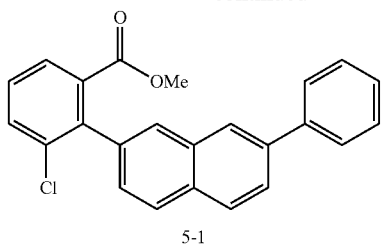

5-1

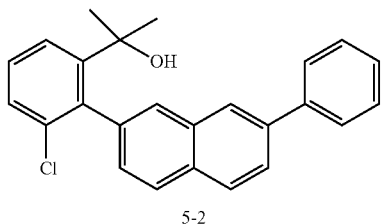

5-2

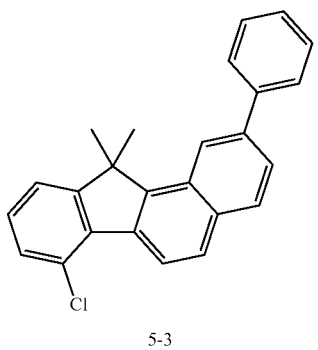

5-3

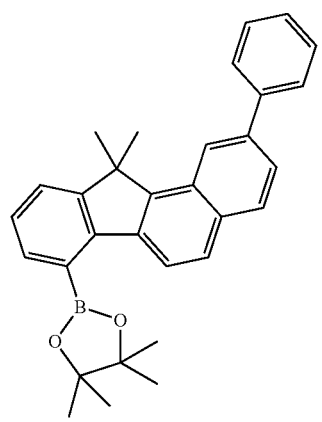

5-4

-continued

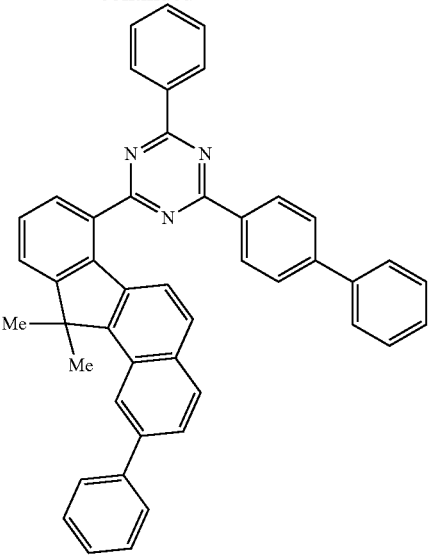

51

Synthesis Example 5-a: Synthesis of Compound 5-1-a 28.6 g of 2,7-dibromonaphthalene and 1.1 equivalent of phenylboronic acid were dissolved in 400 ml of 1,4-dioxane, and 0.05 equivalent of dichlorodiphenylphosphinoferrocene palladium and an excess of a Ba(OH)$_2$ aqueous solution were added thereto and then, heated and refluxed under a nitrogen atmosphere. When a reaction was terminated, an organic layer extracted by using an ammonium chloride aqueous solution and dichloromethane was dried and column-purified to obtain white Compound 5-1-a (14.4 g, 51%).

Synthesis Example 5-b: Synthesis of Compound 5-1-b

Compound 5-1-b was obtained according to the same method as Synthesis Example 1-d except that Compound 5-1-a was used instead of Compound 1-3.

Synthesis Example 5-c: Synthesis of Compound 5-1

Compound 5-1 (6 g, 32%) was obtained according to the same method as Synthesis Example 1-a except that Compound 5-1-b was used instead of the 2-naphthaleneboronic acid.

Synthesis Example 5-d: Synthesis of Compound 5-2

Compound 5-2 was obtained according to the same method as Synthesis Example 1-b except that Compound 5-1 was used instead of Compound 1-1.

Synthesis Example 5-e: Synthesis of Compound 5-3

Compound 5-3 (4 g, 68%) was obtained according to the same method as Synthesis Example 1-c except that Compound 5-2 was used instead of Compound 1-2.

Synthesis Example 5-f: Synthesis of Compound 5-4

Compound 5-4 was obtained according to the same method as Synthesis Example 1-d except that Compound 5-3 was used instead of Compound 1-3.

Synthesis Example 5-g: Synthesis of Compound 51

Compound 51 (5 g, 72%) was obtained according to the same method as Synthesis Example 1-e except that Intermediate 5-4 was used instead of Intermediate 1-4.

LC/MS [M+H] 627.99

Comparative Synthesis Example 1: Synthesis of Compound a

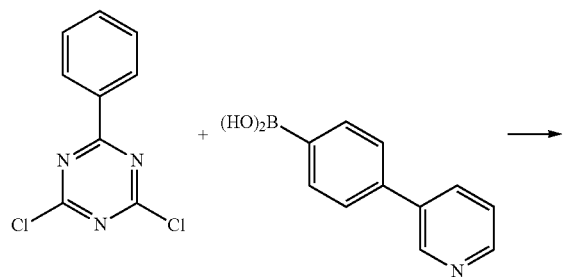

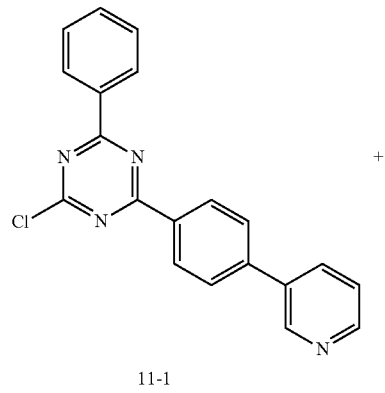

11-1

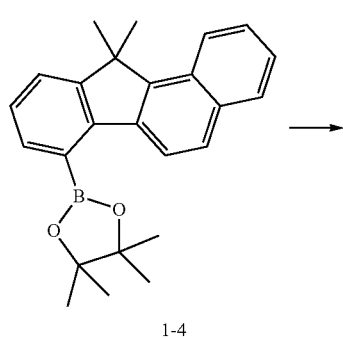

1-4

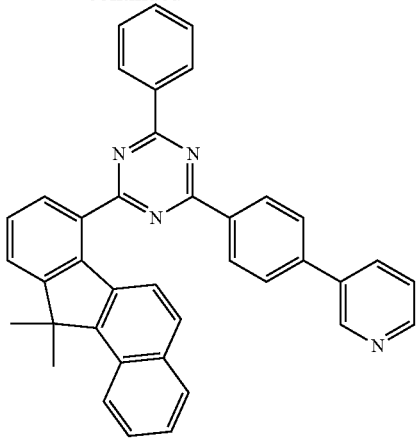

a 2,4-dichloro-6-phenyl-1,3,5-triazine, 0.6 equivalent of (4-(pyridin-3-yl)phenyl) boronic acid, 0.05 equivalent of tetrakis(triphenylphosphine)palladium (0), and 2.5 equivalent of potassium carbonate were put in 200 ml of toluene and 100 ml of water and then, refluxed and stirred for 2 hours. When a reaction was terminated, the solution was transferred to a separatory funnel and extracted with dichloromethane, and an organic layer therefrom was dried with magnesium sulfate and purified through column chromatography to obtain Intermediate 11-1 (50%).

Compound a was obtained according to the same method as Step 4 of Synthesis Example 1 except that Intermediate 11-1 was used instead of the 2-chloro-4-(biphenyl-4-yl)-6-phenyl-1,3,5-triazine.

LC/MS [M+H] 553.72

Comparative Synthesis Example 2: Synthesis of Compound b

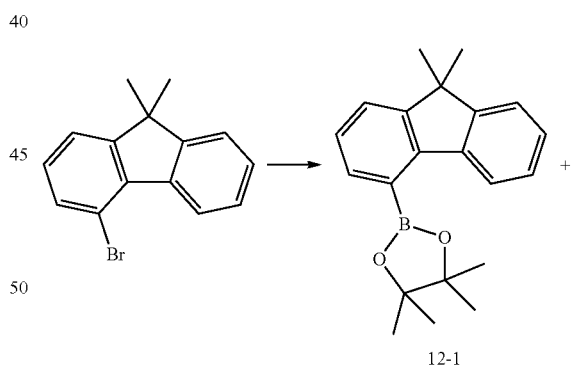

12-1

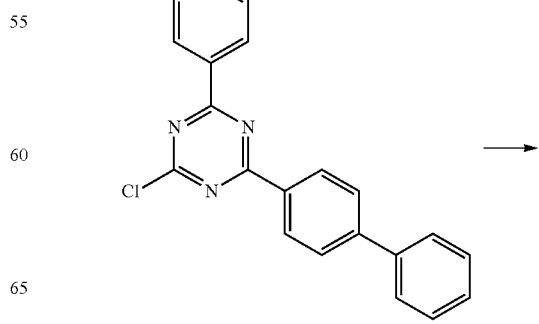

b

Compound b was obtained according to the same method as Step 4 of Synthesis Example 1 except that 12 g (44 mmol) of 4-bromo-9,9-dimethylfluorene was used instead of Intermediate 1-3.

LC/MS [M+H] 502.21

Comparative Synthesis Example 3: Synthesis of Compound c

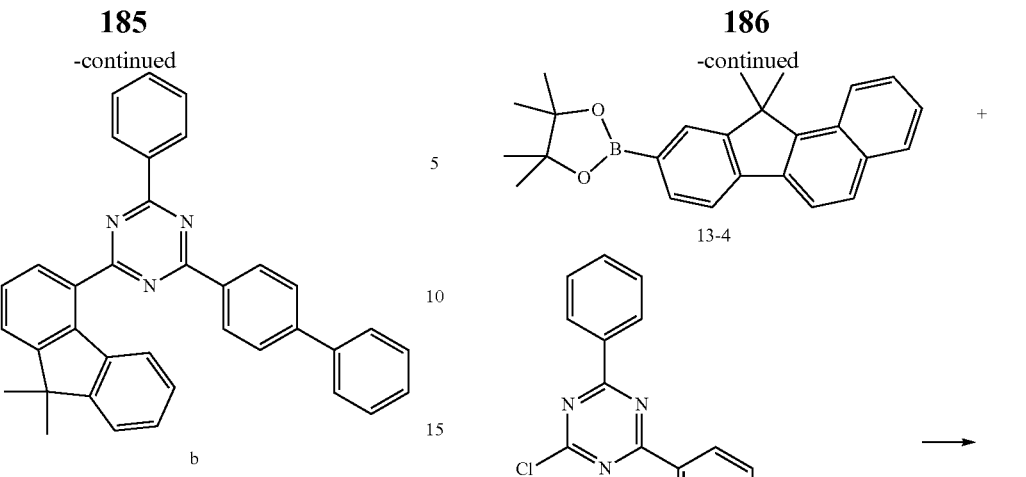

Compound c was obtained according to the same method as Synthesis Example 1 except that methyl 2-bromo-5-chlorobenzoate was used instead of the methyl 2,3-dichlorobenzoate as a starting material.

LC/MS [M+H] 552.27

(Manufacture of Organic Light Emitting Diode)

Example 1

A glass substrate coated with ITO (Indium tin oxide) with a thickness of 1,500 Å was washed with distilled water. After washing with the distilled water, the glass substrate was ultrasonically washed with isopropyl alcohol, acetone, or methanol, and dried and then, moved to a plasma cleaner, cleaned using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1,020 Å-thick to form a hole transport layer. On the hole transport layer, 400 Å-thick light emitting layer was formed by using Compound 20 of Synthesis Example 1 as a host and doping 2 wt % of [Ir(piq)$_2$acac] as a dopant by a vacuum-deposition. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer with the following structure.

ITO/Compound A (700 Å)/Compound B (50 Å)/Compound C (1,020 Å)/EML [Compound 20: [Ir(piq)$_2$acac] (2 wt %)] (400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl) quinoline Liq: 8-hydroxy-quinolinato lithium Examples 2 to 7 and Comparative Examples 1 to 3

Diodes of Examples 2 to 7, Comparative Examples 1 to 3 were manufactured in the same manner as in Example 1, except that the hosts and ratios thereof were changed as described in Tables 1 and 2.

Evaluation: Life-Span Increase Effect

Luminous efficiency and life-span characteristics of the organic light emitting diodes according to Example 1 to Example 7 and Comparative Example 1 to Comparative Example 3 were evaluated. Specific measurement methods were as follows, and the results are shown in Tables 1 and 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to obtain the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T95 life-spans of the organic light emitting diodes according to Examples 1 to 7 and Comparative Examples 1 to 3 were measured as a time when their luminance decreased down to 95% relative to the initial luminance (cd/m$^2$) after emitting light at 6,000 cd/m$^2$ as the initial luminance (cd/m$^2$) and measuring their luminance decrease depending on a time with a Polanonix life-span measurement system.

(5) Calculation of Life-Span Ratio (%)

The life-span ratio of a single host evaluation or a mixed host to which the same second host was applied was compared and evaluated based on Example 1 and Example 3, respectively (e.g., Example 1 and Example 3 were reference examples with a life-span ratio of 100%, and the life-span ratios of the other Examples and Comparative Examples are shown relative to the 100% value of Example 1 and Example 3).

TABLE 1

|  | Single host | T95 (%) |
| --- | --- | --- |
| Example 1 | Compound 20 | 100% |
| Example 2 | Compound 6 | 120% |
| Comparative Example 1 | Compound a | 11% |

TABLE 2

|  | Host | | Ratio of First and second hosts | T95 (%) | Efficiency (%) |
| --- | --- | --- | --- | --- | --- |
|  | First | Second | | | |
| Example 3 | Compound 6 | B-23 | 5:5 | 164% | 112% |
| Example 4 | Compound 6 | C-2 | 5:5 | 193% | 117% |
| Example 5 | Compound 6 | D-41 | 5:5 | 190% | 118% |
| Example 6 | Compound 10 | C-2 | 5:5 | 105% | 111% |
| Example 7 | Compound 5 | C-2 | 5:5 | 118% | 115% |
| Comparative Example 2 | Compound b | C-2 | 5:5 | 43% | 97% |
| Comparative Example 3 | Compound c | C-2 | 5:5 | 100% | 100% |

Referring to Tables 1 and 2, the compounds of the Examples had significantly improved life-span and efficiency compared with the Comparative Examples.

One or more embodiments may provide a compound for an organic optoelectronic device capable of realizing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

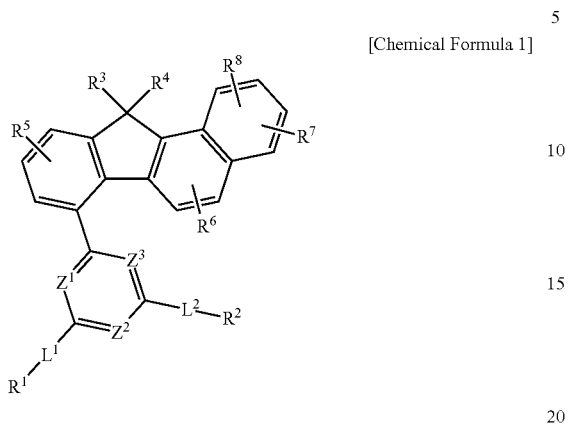

wherein, in Chemical Formula 1,
$Z^1$ to $Z^3$ are each N,
$L^1$ and $L^2$ are independently a single bond or a substituted or unsubstituted phenylene group,
$R^1$ and $R^2$ are independently an unsubstituted C6 aryl group or a substituted or unsubstituted biphenyl group,
$R^3$ and $R^4$ are independently a substituted or unsubstituted methyl group, a substituted or unsubstituted ethyl group, or a substituted or unsubstituted phenyl group,
$R^5$ to $R^8$ are independently hydrogen or deuterium, and
"substituted" refers to replacement at least one hydrogen of a substituent or a compound by deuterium, a C1 to C5 alkyl group, a C6 to C18 aryl group, or a cyano group.

2. The compound as claimed in claim 1, wherein moieties *-$L^1$-$R^1$ and *-$L^2$-$R^2$ of Chemical Formula 1 are independently a moiety of Group I:

[Group I]

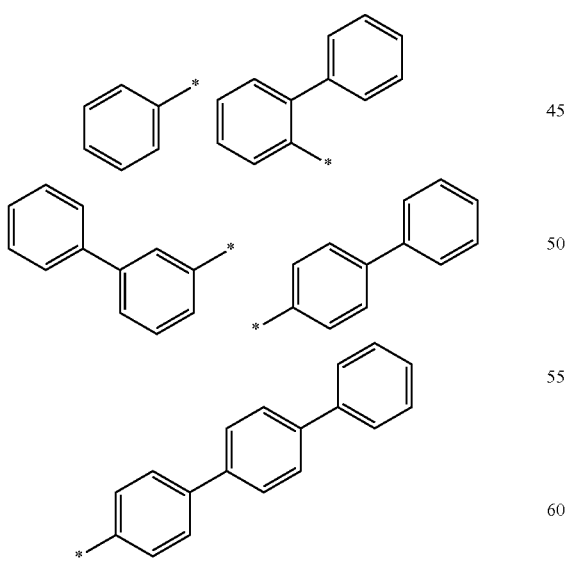

wherein, in Group I, * is a linking point with the $Z^1$ to $Z^3$-containing six-membered ring.

3. The compound as claimed in claim 1, wherein the compound is a compound of Group 1:

[Group 1]

[1]

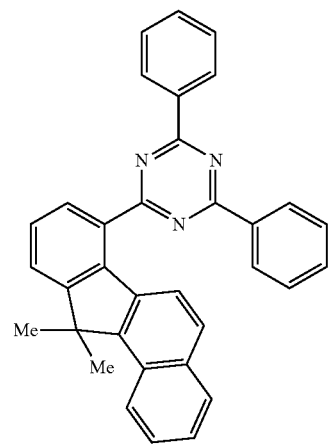

[2]

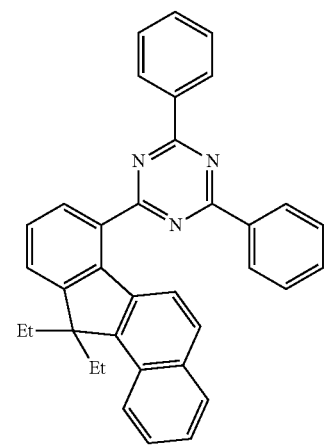

[4]

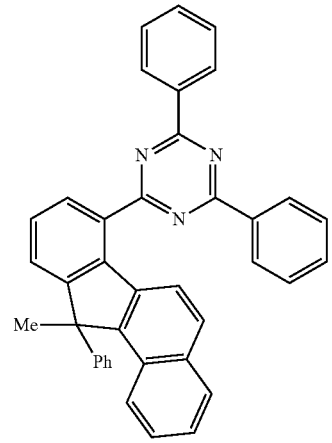

-continued
[5]
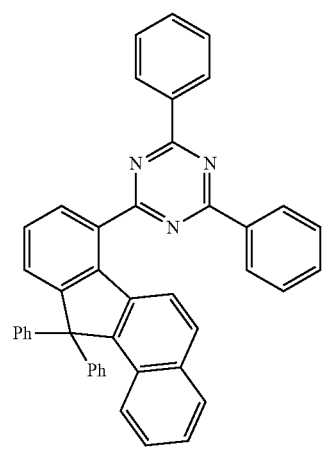
[6]
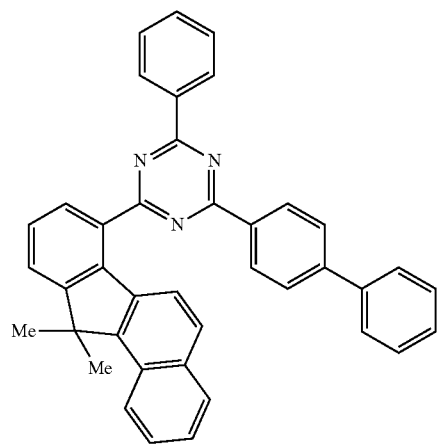
[7]
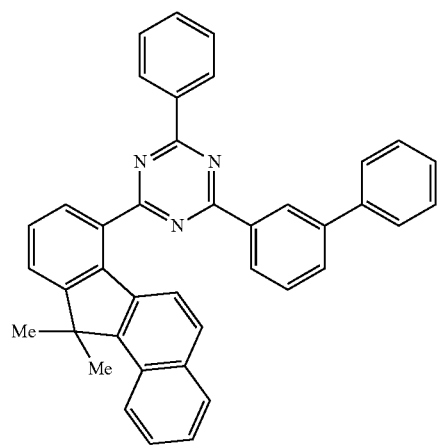
-continued
[10]
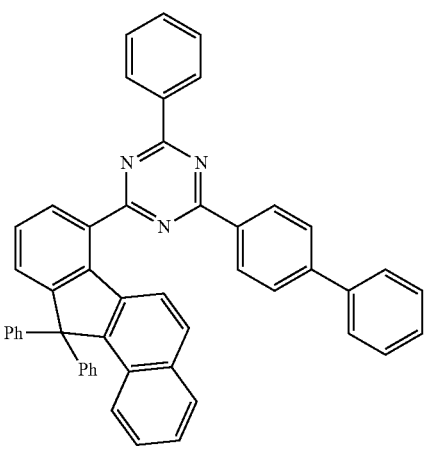
[11]
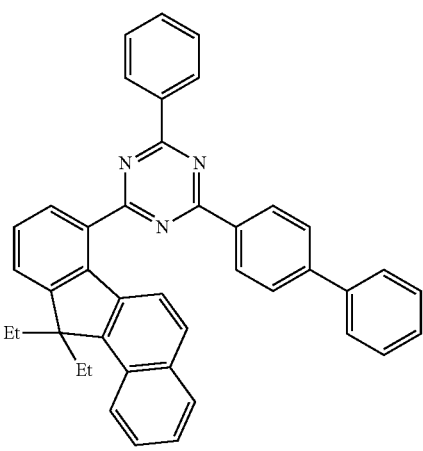
[12]
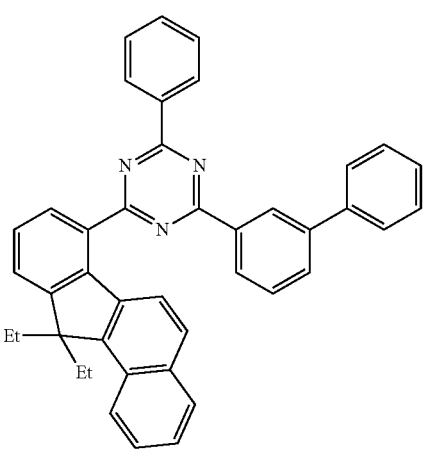

-continued

[13]

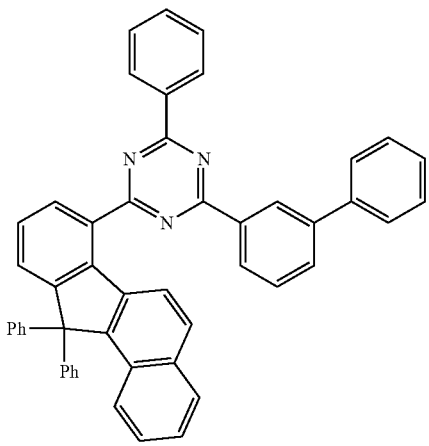

[14]

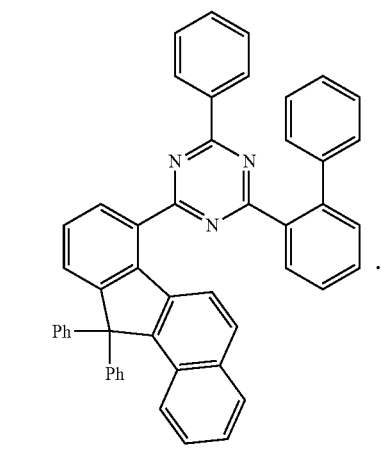

4. A composition for an organic optoelectronic device, the composition comprising:
   a first compound for an organic optoelectronic device; and
   a second compound for an organic optoelectronic device,
   wherein:
   the first compound is the compound for an organic optoelectronic device as claimed in claim 1, and
   the second compound is represented by:
   a combination of Chemical Formula 3 and Chemical Formula 4;
   a combination of Chemical Formula 5 and Chemical Formula 6; or
   a combination of Chemical Formula 7 and Chemical Formula 8,

[Chemical Formula 3]

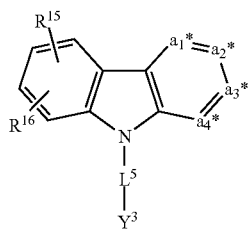

-continued

[Chemical Formula 4]

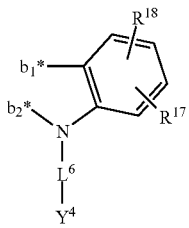

in Chemical Formulae 3 and 4,
$Y^3$ and $Y^4$ are independently a substituted or unsubstituted phenyl group, a substituted or unsubstituted naphthyl group, or a substituted or unsubstituted biphenyl group,
adjacent two of $a_1^*$ to $a_4^*$ are linked to $b_1^*$ and $b_2^*$, respectively,
remaining two of $a_1^*$ to $a_4^*$ not linked to $b_1^*$ and $b_2^*$ are independently $C-L^a-R^c$,
$L^a$, $L^5$, and $L^6$ are independently a single bond, or a substituted or unsubstituted phenylene group, and
$R^c$ and $R^{15}$ to $R^{18}$ are independently hydrogen or deuterium;

[Chemical Formula 5]

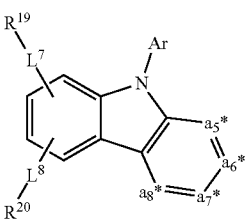

[Chemical Formula 6]

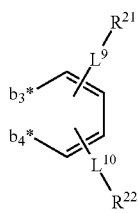

in Chemical Formulae 5 and 6,
Ar is a substituted or unsubstituted C6 to C12 aryl group,
adjacent two of $a_5^*$ to $a_8^*$ are linked to $b_3^*$ and $b_4^*$, respectively,
remaining two of $a_5^*$ to $a_8^*$ not linked to $b_3^*$ and $b_4^*$ are independently $C-L^b-R^d$,
$L^b$ and $L^7$ to $L^{10}$ are independently a single bond,
$R^d$ and $R^{19}$ to $R^{22}$ are independently hydrogen or deuterium, and
at least one of $R^d$ and $R^{19}$ to $R^{22}$ is a group represented by Chemical Formula A,

[Chemical Formula A]

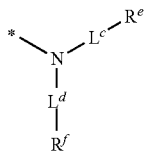

in Chemical Formula A, $L^e$ and $L^d$ are independently a single bond or a substituted or unsubstituted C6 to C12 arylene group, $R^e$ and $R^f$ are independently a substituted or unsubstituted phenyl group or a substituted or unsubstituted biphenyl group, and

* is a linking point with one of $L^b$ and $L^7$ to $L^{10}$;

[Chemical Formula 7]

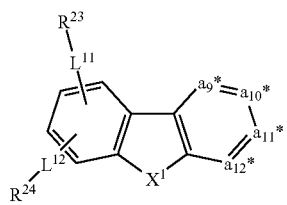

[Chemical Formula 8]

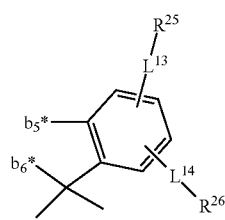

in Chemical Formulae 7 and 8, $X^1$ is O or S, adjacent two of $a_9^*$ to $a_{12}^*$ are linked to $b_5^*$ and $b_6^*$, respectively, remaining two of $a_9^*$ to $a_{12}^*$ not linked to $b_5^*$ and $b_6^*$ are independently $C-L^e-R^g$, $L^e$, and $L^{11}$ to $L^{14}$ are independently a single bond, $R^g$ and $R^{23}$ to $R^{26}$ are independently hydrogen or deuterium, and at least one of $R^g$ and $R^{23}$ to $R^{26}$ is a group represented by Chemical Formula B,

[Chemical Formula B]

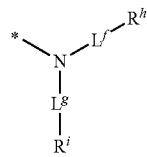

in Chemical Formula B, $L^f$ and $L^g$ are independently a single bond or a substituted or unsubstituted C6 to C12 arylene group, $R^h$ and $R^i$ are independently a substituted or unsubstituted phenyl group, a substituted or unsubstituted biphenyl group, or a substituted or unsubstituted naphthyl group, and

* is a linking point with one of $L^e$ and $L^{11}$ to $L^{14}$.

5. The composition as claimed in claim 4, wherein:

the second compound is represented by the combination of Chemical Formulae 3 and 4, and the combination of Chemical Formulae 3 and 4 is represented by Chemical Formula 3C:

[Chemical Formula 3C]

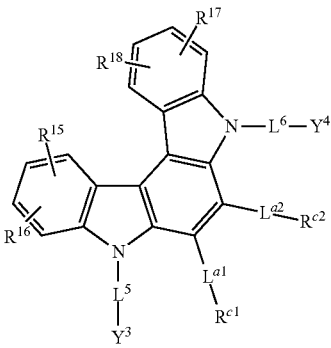

in Chemical Formula 3C, $L^{a1}$ and $L^{a2}$ are each a single bond, $L^5$ and $L^6$ are independently a single bond or a substituted or unsubstituted phenylene group, $R^{15}$ to $R^{18}$, $R^{c1}$, and $R^{c2}$ are each independently hydrogen or deuterium, and $Y^3$ and $Y^4$ are independently a substituted or unsubstituted phenyl group, a substituted or unsubstituted naphthyl group, or a substituted or unsubstituted biphenyl group.

6. The composition as claimed in claim 4, wherein:

the second compound is represented by the combination of Chemical Formulae 5 and 6, the combination of Chemical Formulae 5 and 6 is represented by Chemical Formula 5A-2:

[Chemical Formula 5A-2]

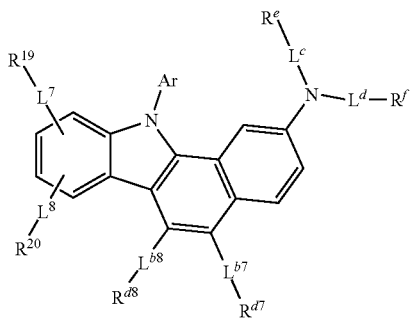

in Chemical Formula 5A-2,

Ar is a substituted or unsubstituted C6 to C12 aryl group, $L^7$, $L^8$, $L^{b7}$, and $L^{b8}$ are each a single bond, $L^c$ and $L^d$ are independently a single bond or a substituted or unsubstituted C6 to C12 arylene group, $R^{19}$, $R^{20}$, $R^{d7}$, and $R^{d8}$ are each independently hydrogen or deuterium, and $R^e$ and $R^f$ are independently a substituted or unsubstituted phenyl group or a substituted or unsubstituted biphenyl group.

7. The composition as claimed in claim 4, wherein:

the second compound is represented by the combination of Chemical Formulae 7 and 8, the combination of Chemical Formulae 7 and 8 is represented by Chemical Formula 7F-2:

[Chemical Formula 7F-2]

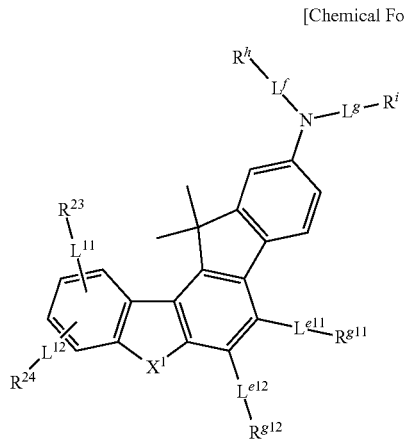

in Chemical Formula 7F-2,
$X^1$ is O or S,
$L^{11}$, $L^{12}$, $L^{e11}$, and $L^{e12}$ are each a single bond,
$L^g$ and $L^f$ are independently a single bond or a substituted or unsubstituted C6 to C12 arylene group,
$R^{23}$, $R^{24}$, $R^{g11}$, and $R^{g12}$ are each independently hydrogen or deuterium, and
$R^h$ and $R^i$ are independently a substituted or unsubstituted phenyl group, a substituted or unsubstituted biphenyl group or a substituted or unsubstituted naphthyl group.

8. An organic optoelectronic device, comprising:
an anode and a cathode facing each other; and
at least one organic layer between the anode and the cathode,
wherein the at least one organic layer includes the compound for an organic optoelectronic device as claimed in claim 1.

9. The organic optoelectronic device as claimed in claim 8, wherein:
the at least one organic layer includes a light emitting layer, and
the light emitting layer includes the compound.

10. A display device comprising the organic optoelectronic device as claimed in claim 8.

11. An organic optoelectronic device, comprising:
an anode and a cathode facing each other; and
at least one organic layer between the anode and the cathode,
wherein the at least one organic layer includes the composition for an organic optoelectronic device as claimed in claim 4.

12. The organic optoelectronic device as claimed in claim 11, wherein:
the at least one organic layer includes a light emitting layer, and
the light emitting layer includes the composition.

13. A display device comprising the organic optoelectronic device as claimed in claim 11.

14. The organic optoelectronic device as claimed in claim 12, wherein:
the first compound of the composition is Compound 6,

[Compound 6]

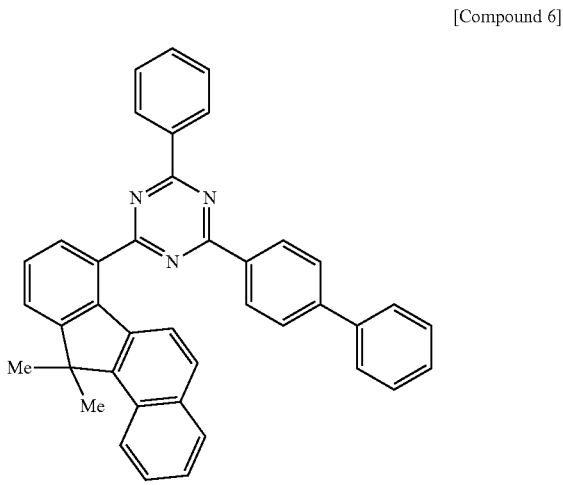 [SMILES: CC1(C)c2cccc(-c3nc(-c4ccccc4)nc(-c4ccc(-c5ccccc5)cc4)n3)c2-c2ccc3ccccc3c21]

the second compound of the composition is C-2,

[C-2]

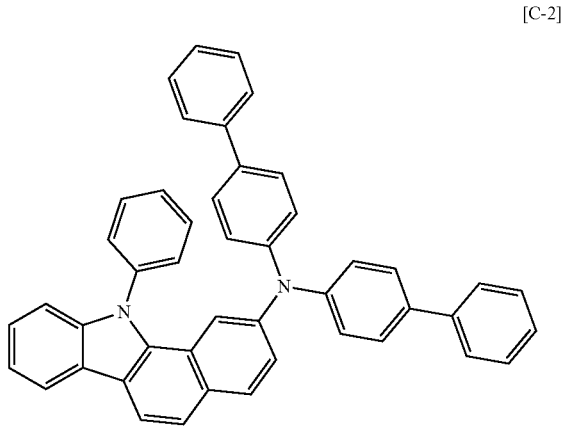 [SMILES: c1ccc(-c2ccc(N(c3ccc(-c4ccccc4)cc3)c3ccc4ccc5c6ccccc6n(-c6ccccc6)c5c4c3)cc2)cc1]

the weight ratio of the first compound to the second compound is 5:5,
the light emitting layer includes a dopant, and
the dopant is [Ir(piq)$_2$acac].

* * * * *